US011608570B2

United States Patent
Ng et al.

(10) Patent No.: US 11,608,570 B2
(45) Date of Patent: Mar. 21, 2023

(54) TARGETED IN SITU PROTEIN DIVERSIFICATION BY SITE DIRECTED DNA CLEAVAGE AND REPAIR

(71) Applicant: Max-Planck-Gesellschaft zur Förderung der Wissenschaften E.V., Munich (DE)

(72) Inventors: David Ng, Eurasburg (DE); Oliver Griesbeck, Munich (DE); Mutlu Erdogan, Gräfelfing (DE)

(73) Assignee: Max-Planck-Gesellschaft zur Förderung der Wissenschaften E.V., Munich (DE)

( * ) Notice: Subject to any disclaimer, the term of this patent is extended or adjusted under 35 U.S.C. 154(b) by 989 days.

(21) Appl. No.: 16/321,027

(22) PCT Filed: Jul. 31, 2017

(86) PCT No.: PCT/EP2017/069271
§ 371 (c)(1),
(2) Date: Jan. 27, 2019

(87) PCT Pub. No.: WO2018/020050
PCT Pub. Date: Feb. 1, 2018

(65) Prior Publication Data
US 2019/0144853 A1 May 16, 2019

(30) Foreign Application Priority Data
Jul. 29, 2016 (EP) ..................................... 16181872

(51) Int. Cl.
*C40B 30/06* (2006.01)
*C12N 15/90* (2006.01)
(Continued)

(52) U.S. Cl.
CPC ................ *C40B 30/06* (2013.01); *C12N 9/22* (2013.01); *C12N 15/102* (2013.01);
(Continued)

(58) Field of Classification Search
None
See application file for complete search history.

(56) References Cited

U.S. PATENT DOCUMENTS

| 2004/0087014 | A1 | 5/2004 | Huse |
| 2011/0023149 | A1 | 1/2011 | Weinstein et al. |
| 2012/0264616 | A1* | 10/2012 | Negroni ............... C12N 9/1205 435/235.1 |

FOREIGN PATENT DOCUMENTS

| WO | 2005080552 A1 | 9/2005 |
| WO | 2009061369 A2 | 5/2009 |

OTHER PUBLICATIONS

European Search Report dated Jan. 18, 2017, received in EP 16 181872.9.
(Continued)

*Primary Examiner* — Christian C Boesen
(74) *Attorney, Agent, or Firm* — Michele M. Wales; InHouse Patent Counsel, LLC

(57) ABSTRACT

The present invention relates to a method for producing a panel of cells (i.e. a cell library) expressing various different mutant variants of a protein of interest, wherein only one of said mutant variants is expressed per cell from a single gene copy. The present invention also relates to a method or cell library for identifying a mutant variant of a protein of interest having a different or modified biological activity as compared to the corresponding wild-type protein of interest. According to the present invention the identified mutant
(Continued)

Figure 1:
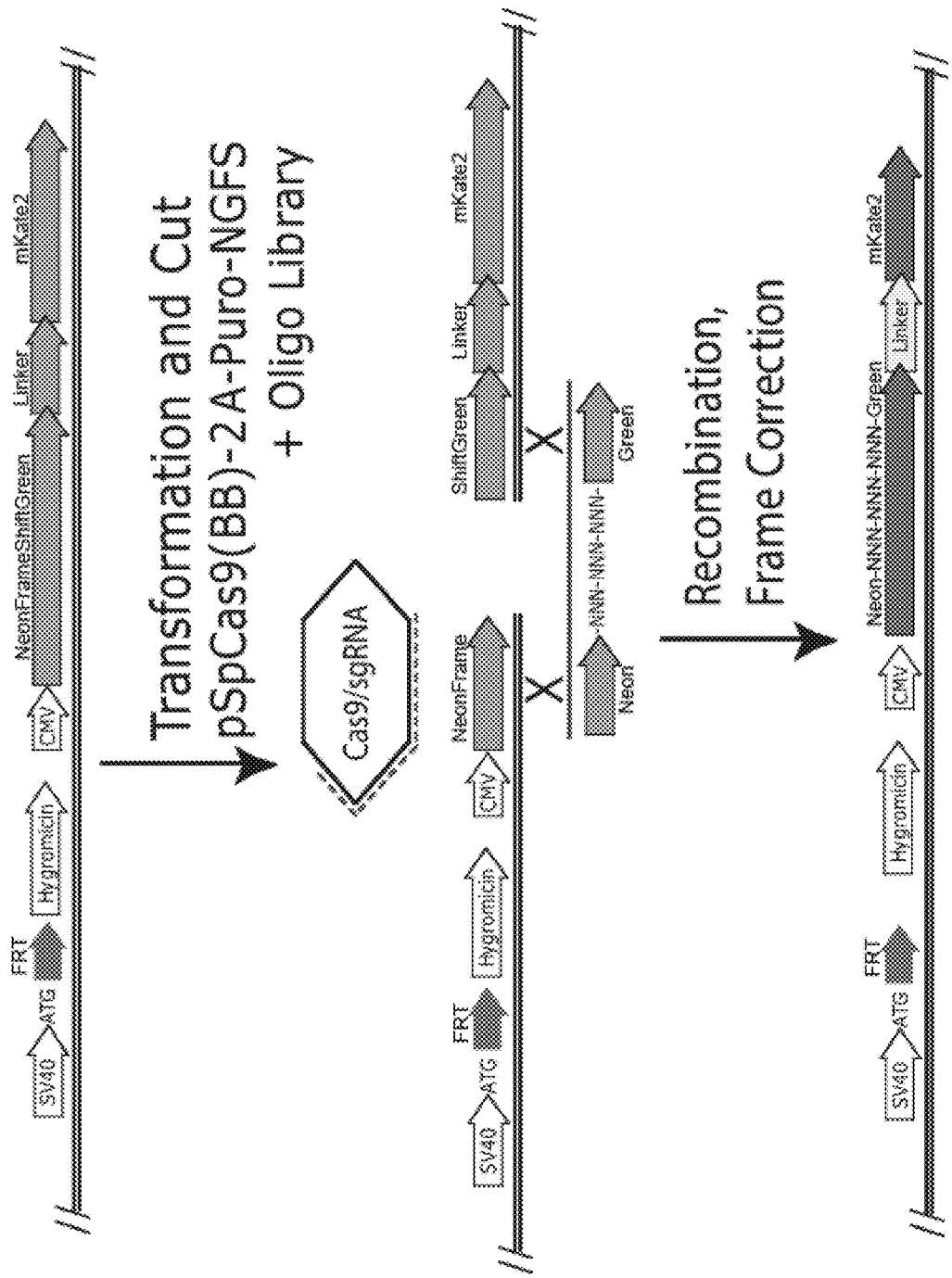

variant of a protein of interest may be applied for white biotechnology.

14 Claims, 19 Drawing Sheets

Specification includes a Sequence Listing.

(51) Int. Cl.
*C12N 15/10* (2006.01)
*C12N 9/22* (2006.01)
*C40B 20/04* (2006.01)
*C40B 50/06* (2006.01)
*C40B 70/00* (2006.01)

(52) U.S. Cl.
CPC ..... *C12N 15/1037* (2013.01); *C12N 15/1058* (2013.01); *C12N 15/902* (2013.01); *C40B 20/04* (2013.01); *C40B 50/06* (2013.01); *C40B 70/00* (2013.01)

(56) References Cited

OTHER PUBLICATIONS

International Search Report and Written Opinion dated Oct. 18, 2017 in PCT/EP2017/069271.
Jiang et al., "RNA-Guided Editing of Bacterial Genomes Using CRISPR-Cas Systems", Nature Biotechnology, vol. 31, No. 3, pp. 233-239, (2013).
Ran et al., "Genome Engineering Using the CRISPR-Cas9 System", Nature Protocols, vol. 8, No. 11, pp. 2281-2308, (2013).
Wong et al., "A Statistical Analysis of Random Mutagenesis Methods Used for Directed Protein Evolution", Journal of Molecular Biology, vol. 355, No. 4, pp. 858-871, (2006).
Xu et al., "Efficient Genome Editing in Clostridium Cellulolyticum via CRISPR-Cas9 Nickase", Applied and Environmental Microbiology, vol. 81, No. 13, pp. 4423-4431, (2015).
Xu Tao et al., "Supplementary Data for Efficient Genome Editing in Clostridium Cellulolyticum via CRISPR-Cas9 Nickase", Applied and Environmental Microbiology, pp. 1-13, (2015).
International Preliminary Report of Patentability and Written Opinion dated Feb. 7, 2019 and received in PCT/EP2017/069271.
EPO Office Action dated Mar. 24, 2020 received in corresponding EP Application 17 754 625.6.
Zou et al., "Gene Targeting of a Disease-Related Gene in Human Induced Pluripotent Stem and Embryonic Stem Cells", Cell Stem Cell, vol. 5, pp. 97-110 (2009).
Chinese Office Action (along with English Translation) dated Nov. 22, 2022, in corresponding Chinese Application.

\* cited by examiner

Figure 3
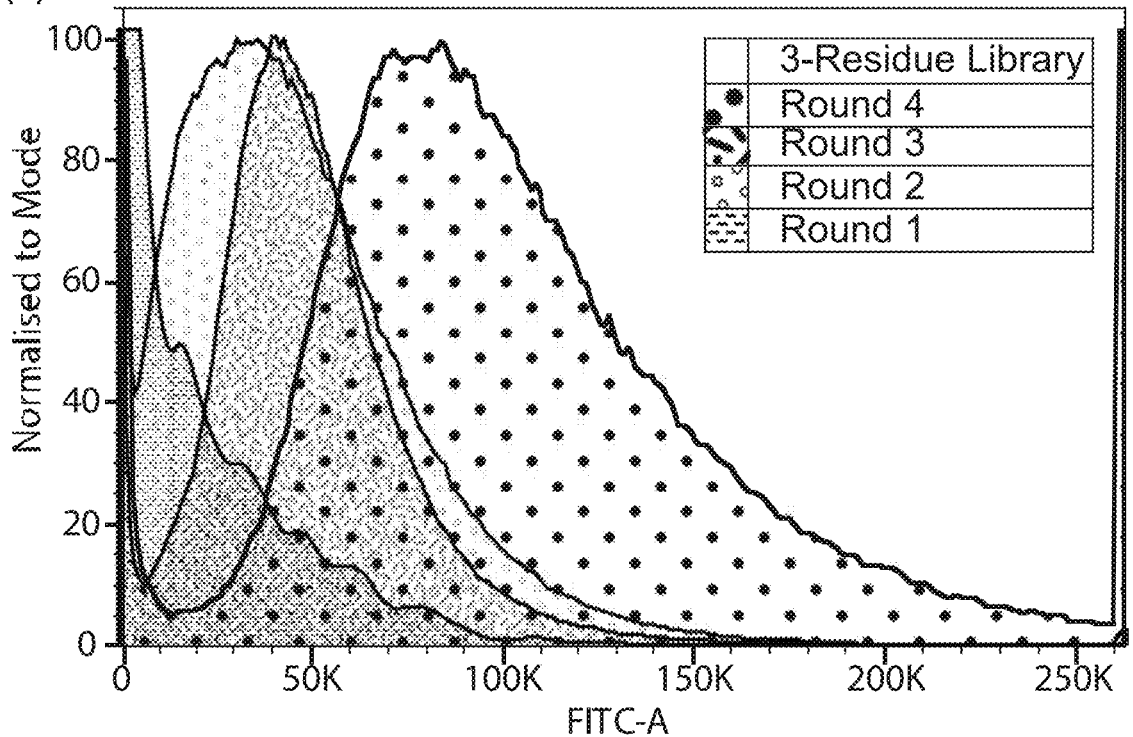
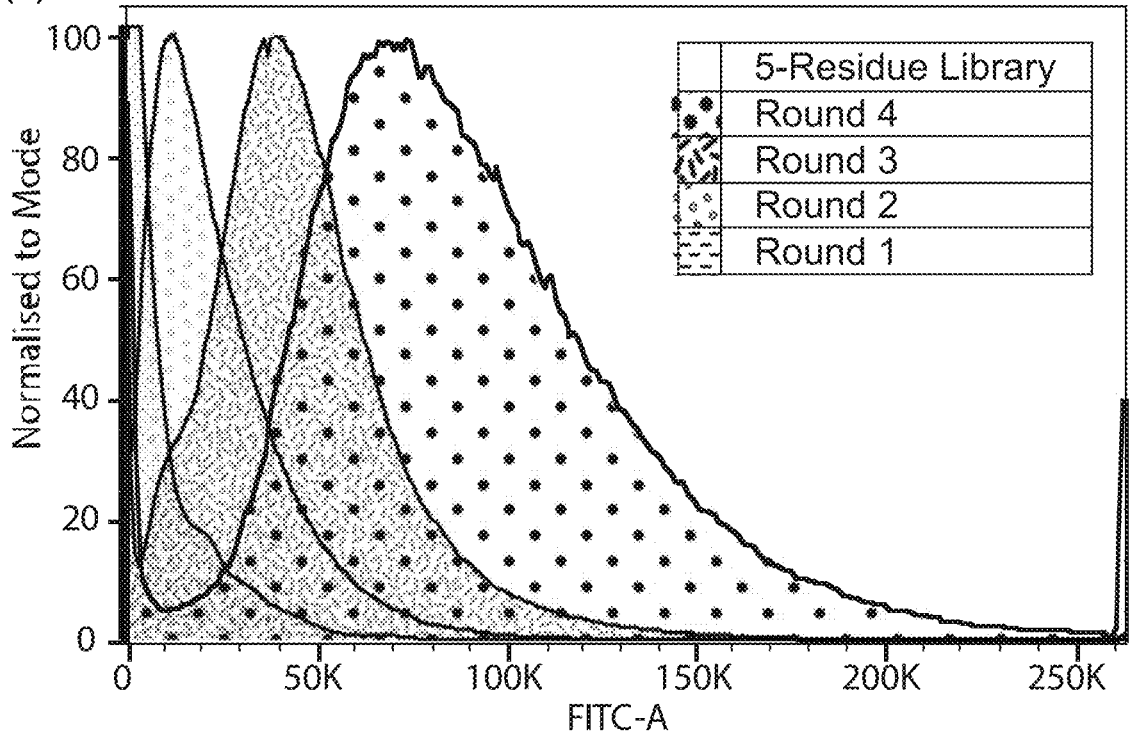

Figure 5

Figure 6

| DNA Sequence | Translation |
|---|---|
| TCGCTGACCGCTGCG-GGCAGTCGC-AGGTCGAAGAAGACT | SLTAA-GSR-RSKKT |
| TCGCTGACCGCTGCG-AGTGTGTCC-AGGTCGAAGAAGACT | SLTAA-SVS-RSKKT |
| TCGCTGACCGCTGCG-GGGTGTTGT-AGGTCGAAGAAGACT | SLTAA-GCC-RSKKT |
| TCGCTGACCGCTGCG-ATGATGGGC-AGGTCGAAGAAGACT | SLTAA-MMG-RSKKT |
| TCGCTGACCGCTGCG-TGTGTCTCG-AGGTCGAAGAAGACT | SLTAA-CVS-RSKKT |
| TCGCTGACCGCTGCG-GGCGCCACC-AGGTCGAAGAAGACT | SLTAA-GAT-RSKKT |
| TCGCTGACCGCTGCG-AAGTTCTCT-AGGTCGAAGAAGACT | SLTAA-KFS-RSKKT |
| TCGCTGACCGCTGCG-TCGCTTATG-AGGTCGAAGAAGACT | SLTAA-SLM-RSKKT |
| TCGCTGACCGCTGCG-AGTAAGCGC-AGGTCGAAGAAGACT | SLTAA-SKR-RSKKT |
| TCGCTGACCGCTGCG-CAGGCTACT-AGGTCGAAGAAGACT | SLTAA-QAT-RSKKT |
| TCGCTGACCGCTGCG-TGCGTGTGT-AGGTCGAAGAAGACT | SLTAA-CVC-RSKKT |
| TCGCTGACCGCTGCG-CGGATGGGG-AGGTCGAAGAAGACT | SLTAA-RMG-RSKKT |
| TCGCTGACCGCTGCG-ATTTGGACG-AGGTCGAAGAAGACT | SLTAA-IWT-RSKKT |

Characterization of mNeonGreen2

Figure 8

Diversification of mNeonGreen

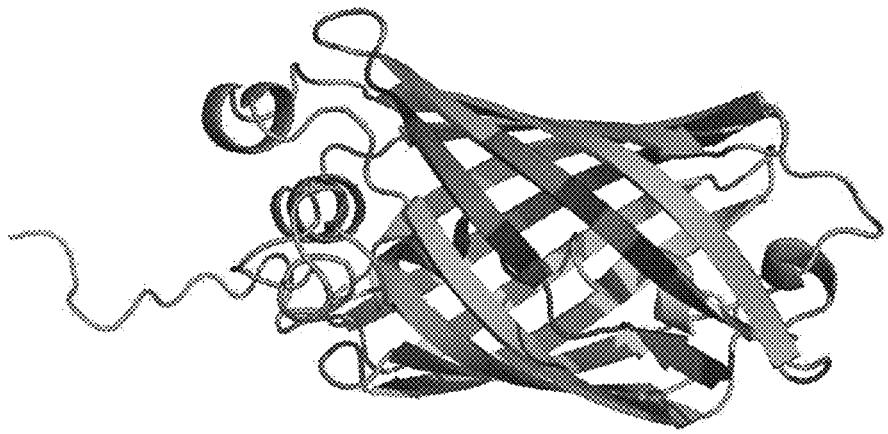

```
LanYFP      ---------------MSLPATHELHIFGSFNGVDFDMVGRGTGNPNDGYEELNLKSTKGALQFSP
dLanYFP     MVSKGEEDNMASLPATHELHIFGSFNGVDFDMVGRGTGNPNDGYEELNLKSTKGDLQFSP
mNeonGreen  MVSKGEEDNMASLPATHELHIFGSINGVDFDMVGQGTGNPNDGYEELNLKSTKGDLQFSP LanYFP      WILVPQIGYGFHQYLPFPDGMSPFQAAMKDGSGYQVHRTMQFEDGASLTSNYRYTYEGSH
dLanYFP     WILVPQIGYGFHQYLPFPDGMSPFQAAMKDGSGYQVHRTMQFEDGASLTSNYRYTYEGSH
mNeonGreen  WILVPHIGYGFHQYLPYPDGMSPFQAAMVDGSGYQVHRTMQFEDGASLTVNYRYTYEGSH
                                        4

LanYFP      IKGEFQVIGTGFPADGPVMTNSLTAADWCVTKMLYPNDKTIISTFDWTYTTGSGKRYQST
dLanYFP     IKGEFQVIGTGFPADGPVMTNSLTAADWCVTKMLYPNDKTIISTFDWTYTTGNGKRYQST
mNeonGreen  IKGEFQVIGTGFPADGPVMTNSLTAADWCSKKIYPNDKTIISTFDIYYTTGNGKRYRIT
                  3              5    2                 1

LanYFP      VRTNYTFAKPMAANILKNQPMFVFRKTELKHSKTELNFKEWQKAFTDVM----------
dLanYFP     ARTIYTFAKPMAANILKNQPMFVFRKTELKHSKTELNFKEWQKAFTDVMGMDELYK
mNeonGreen  ARTIYTFAKPMAANYLKNQPMYVFRKTELKHSKTELNFKEWQKAFTDVMGMDELYK
```

Figure 9

| | |
|---|---|
| 1.F | 5' – CACCGCATCATCAGTACCTTTAAG – 3' |
| 1.R | 3' – CGTAGTAGTCATGGAAATTCCAAA – 5' |
| | |
| 2.F | 5' – GTGGCCTGGCGACGCCTGACCACG – 3' |
| 2.R | 3' – GGACCGCTGCGGACTGGTGCCAAA – 5' |
| | |
| 3.F | 5' – CACCGAAAGGAGAGGCCCAGGTGA – 3' |
| 3.R | 3' – CTTTCCTCTCCGGGTCCACTCAAA – 5' |
| | |
| 4.F | 5' – CACCGTGGTCCCTCATATCGGGTA – 3' |
| 4.R | 3' – CACCAGGGAGTATAGCCCATCAAA – 5' |
| | |
| 5.F | 5' – CACCGCGCTGACCGCTGCGGACGC – 3' |
| 5.R | 3' – CGCGACTGGCGACGCCTGCGCAAA – 5' |

Figure 15
a
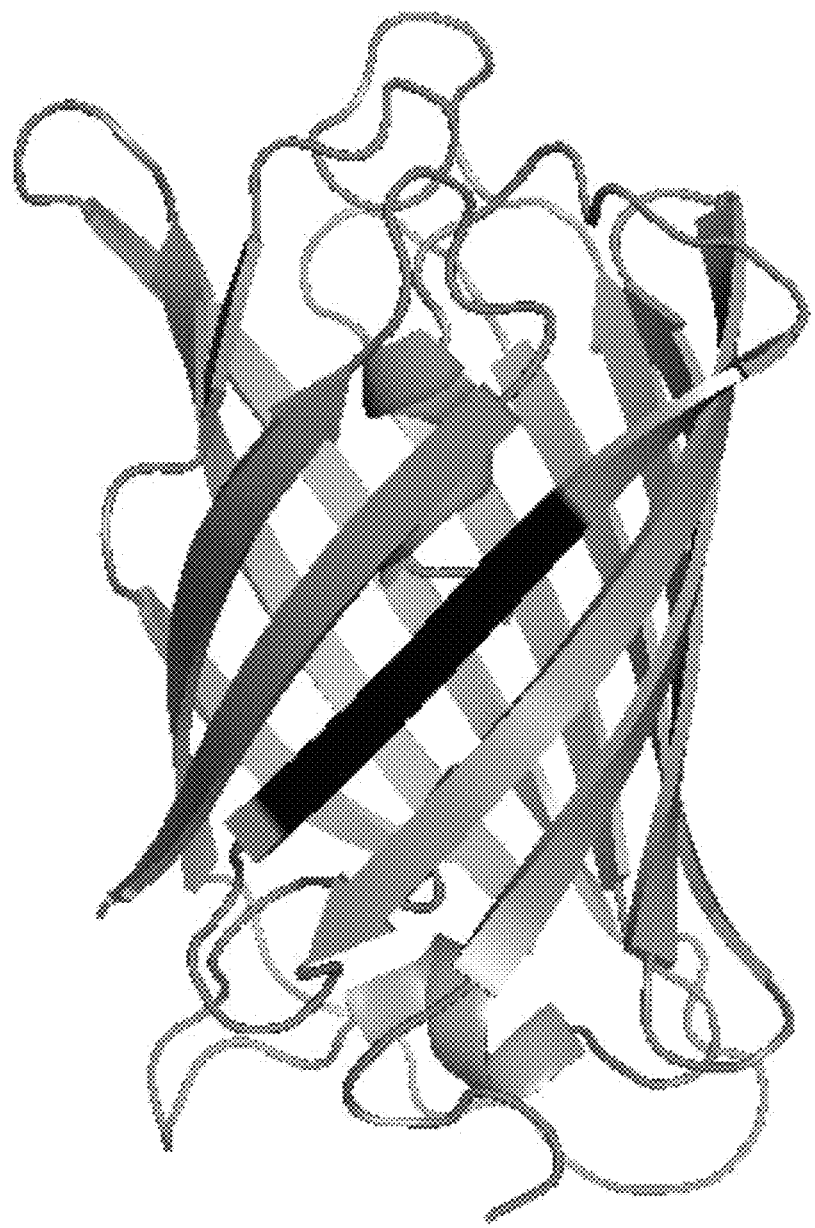
b
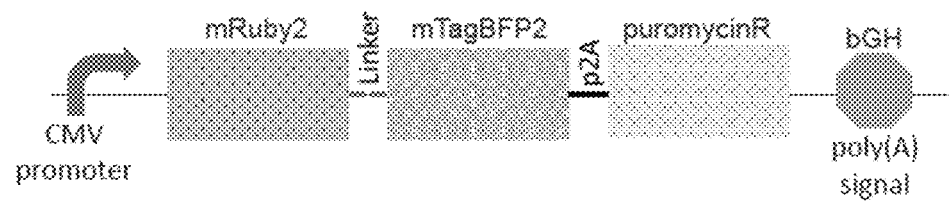

Figure 19

|  | 5 a.a. modified region | Silent mutation for sgRNA binding |  |
|---|---|---|---|
| mRuby2 | act Caa ACC ATG AGG ATC | AAA gtc | t-QTMRI-Kv |
| 1 | act CAG ATT ATG TGG CTT | AAG gtc | t-QIMWL-Kv |
| 2 | act CAG ATT ATG TTT ATT | AAG gtc | t-QIMFI-Kv |
| 3 | act CAG GTG ATG CAC TGC | AAA gtc | t-QVMHC-Kv |
| 4 | act CAG CGG ATG TGC ATC | AAG gtc | t-QRMCI-Kv |
| 5 | act CAG CGC ATG TCG ATC | AAA gtc | t-QRMSI-Kv |
| 6 | act CAG GTT GCG TAC CTC | AAG gtc | t-QVAYL-Kv |
| 7 | act CAG CGG GCC ATT ATT | AAG gtc | t-QRAII-Kv |

Figure 20

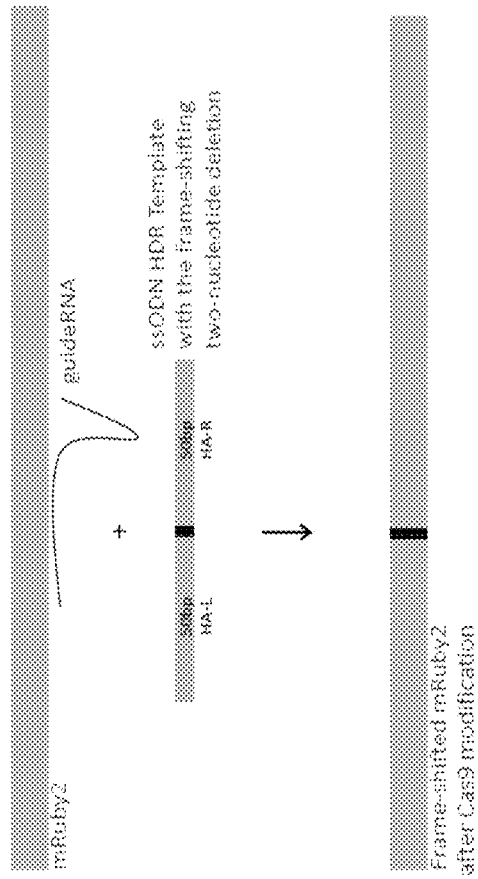

b

SEQUENCE LISTING

<160> NUMBER OF SEQ ID NOS: 95

<210> SEQ ID NO 1
<211> LENGTH: 18
<212> TYPE: PRT
<213> ORGANISM: Artificial Sequence
<220> FEATURE:
<223> OTHER INFORMATION: 2A peptide T2A

<400> SEQUENCE: 1

Glu Gly Arg Gly Ser Leu Leu Thr Cys Gly Asp Val Glu Glu Asn Pro
1               5                   10                  15

Gly Pro

<210> SEQ ID NO 2
<211> LENGTH: 19
<212> TYPE: PRT
<213> ORGANISM: Artificial Sequence
<220> FEATURE:
<223> OTHER INFORMATION: 2A peptide P2A

<400> SEQUENCE: 2

Ala Thr Asn Phe Ser Leu Leu Lys Gln Ala Gly Asp Val Glu Glu Asn
1               5                   10                  15

Pro Gly Pro

<210> SEQ ID NO 3
<211> LENGTH: 20
<212> TYPE: PRT
<213> ORGANISM: Artificial Sequence
<220> FEATURE:
<223> OTHER INFORMATION: 2A peptide E2A

<400> SEQUENCE: 3

Gln Cys Thr Asn Tyr Ala Leu Leu Lys Leu Ala Gly Asp Val Glu Ser

```
1               5                   10                  15

Asn Pro Gly Pro
            20

<210> SEQ ID NO 4
<211> LENGTH: 22
<212> TYPE: PRT
<213> ORGANISM: Artificial Sequence
<220> FEATURE:
<223> OTHER INFORMATION: 2A peptide F2A

<400> SEQUENCE: 4

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 5
<211> LENGTH: 7
<212> TYPE: PRT
<213> ORGANISM: Artificial Sequence
<220> FEATURE:
<223> OTHER INFORMATION: Target site of TEV protease
<220> FEATURE:
<221> NAME/KEY: UNSURE
<222> LOCATION: (2)..(2)
<223> OTHER INFORMATION: note: Xaa = any amino acid
<220> FEATURE:
<221> NAME/KEY: UNSURE
<222> LOCATION: (3)..(3)
<223> OTHER INFORMATION: note: Xaa = any amino acid
<220> FEATURE:
<221> NAME/KEY: UNSURE
<222> LOCATION: (5)..(5)
<223> OTHER INFORMATION: note: Xaa = any amino acid
<220> FEATURE:
<221> NAME/KEY: VARIANT
<222> LOCATION: (7)..(7)
<223> OTHER INFORMATION: Replace: Ser

<400> SEQUENCE: 5

Glu Xaa Xaa Tyr Xaa Gln Gly
1               5

<210> SEQ ID NO 6
<211> LENGTH: 6
<212> TYPE: PRT
<213> ORGANISM: Artificial Sequence
<220> FEATURE:
<223> OTHER INFORMATION: Target Site of Genenase I

<400> SEQUENCE: 6

Pro Gly Ala Ala His Tyr
1               5

<210> SEQ ID NO 7
<211> LENGTH: 5
<212> TYPE: PRT
<213> ORGANISM: Artificial Sequence
<220> FEATURE:
<223> OTHER INFORMATION: Target site of Enterokinase

<400> SEQUENCE: 7

Asp Asp Asp Asp Lys
1               5

<210> SEQ ID NO 8
<211> LENGTH: 8
```

```
<212> TYPE: PRT
<213> ORGANISM: Artificial Sequence
<220> FEATURE:
<223> OTHER INFORMATION: Target site of Human Rhinovirus (HRV) 3C
      Protease

<400> SEQUENCE: 8

Leu Glu Val Leu Phe Gln Gly Pro
1               5

<210> SEQ ID NO 9
<211> LENGTH: 4
<212> TYPE: PRT
<213> ORGANISM: Artificial Sequence
<220> FEATURE:
<223> OTHER INFORMATION: Target site of Factor Xa
<220> FEATURE:
<221> NAME/KEY: VARIANT
<222> LOCATION: (2)..(2)
<223> OTHER INFORMATION: Replace: Asp

<400> SEQUENCE: 9

Ile Glu Gly Arg
1

<210> SEQ ID NO 10
<211> LENGTH: 6
<212> TYPE: PRT
<213> ORGANISM: Artificial Sequence
<220> FEATURE:
<223> OTHER INFORMATION: Target site of Thrombin

<400> SEQUENCE: 10

Leu Val Pro Arg Gly Ser
1               5

<210> SEQ ID NO 11
<211> LENGTH: 12
<212> TYPE: DNA
<213> ORGANISM: Artificial Sequence
<220> FEATURE:
<223> OTHER INFORMATION: Preferred direct repeat (DR) sequence for use
      with SpCas9 or SaCas9 nuclease

<400> SEQUENCE: 11
gttttagagc ta                                                          12

<210> SEQ ID NO 12
<211> LENGTH: 31
<212> TYPE: DNA
<213> ORGANISM: Artificial Sequence
<220> FEATURE:
<223> OTHER INFORMATION: Preferred tracrRNA sequence for use with the
      SpCas9 or SaCas9 nuclease

<400> SEQUENCE: 12
tagcaagtta aaataaggct agtccgtttt t                                     31

<210> SEQ ID NO 13
<211> LENGTH: 39
<212> TYPE: DNA
<213> ORGANISM: Artificial Sequence
<220> FEATURE:
<223> OTHER INFORMATION: Forward primer for site-directed mutagenesis

<400> SEQUENCE: 13
tcgctgaccg ctgcggacgc aggtcgaaga agacttacc                             39
```

<210> SEQ ID NO 14
<211> LENGTH: 25
<212> TYPE: DNA
<213> ORGANISM: Artificial Sequence
<220> FEATURE:
<223> OTHER INFORMATION: Reverse primer for site-directed mutagenesis

<400> SEQUENCE: 14
gtccgcagcg gtcagcgagt tggtc                                    25

<210> SEQ ID NO 15
<211> LENGTH: 39
<212> TYPE: DNA
<213> ORGANISM: Artificial Sequence
<220> FEATURE:
<223> OTHER INFORMATION: Forward amplification primer

<400> SEQUENCE: 15
tcgctgaccg ctgcggacgc aggtcgaaga agacttacc                     39

<210> SEQ ID NO 16
<211> LENGTH: 49
<212> TYPE: DNA
<213> ORGANISM: Artificial Sequence
<220> FEATURE:
<223> OTHER INFORMATION: Reverse amplification primer

<400> SEQUENCE: 16
cggccgccac tgtgctggat ctattatcac ttgtacagct cgtccatgc           49

<210> SEQ ID NO 17
<211> LENGTH: 24
<212> TYPE: DNA
<213> ORGANISM: Artificial Sequence
<220> FEATURE:
<223> OTHER INFORMATION: Pre-annealed forward primer

<400> SEQUENCE: 17
caccgcgctg accgctgcgg acgc                                     24

<210> SEQ ID NO 18
<211> LENGTH: 24
<212> TYPE: DNA
<213> ORGANISM: Artificial Sequence
<220> FEATURE:
<223> OTHER INFORMATION: Pre-annealed reverse primer

<400> SEQUENCE: 18
aaacgcgtcc gcagcggtca gcgc                                     24

<210> SEQ ID NO 19
<211> LENGTH: 198
<212> TYPE: PRT
<213> ORGANISM: Artificial Sequence
<220> FEATURE:
<223> OTHER INFORMATION: FokI nuclease

<400> SEQUENCE: 19

Gly Ser Gln Leu Val Lys Ser Glu Leu Glu Glu Lys Lys Ser Glu Leu
1               5                   10                  15

Arg His Lys Leu Lys Tyr Val Pro His Glu Tyr Ile Glu Leu Ile Glu
                20                  25                  30

Ile Ala Arg Asn Ser Thr Gln Asp Arg Ile Leu Glu Met Lys Val Met
        35                  40                  45

```
Glu Phe Phe Met Lys Val Tyr Gly Tyr Arg Gly Lys His Leu Gly Gly
        50                  55                  60

Ser Arg Lys Pro Asp Gly Ala Ile Tyr Thr Val Gly Ser Pro Ile Asp
 65                  70                  75                  80

Tyr Gly Val Ile Val Asp Thr Lys Ala Tyr Ser Gly Gly Tyr Asn Leu
                 85                  90                  95

Pro Ile Gly Gln Ala Asp Glu Met Gln Arg Tyr Val Glu Glu Asn Gln
                100                 105                 110

Thr Arg Asn Lys His Ile Asn Pro Asn Glu Trp Trp Lys Val Tyr Pro
            115                 120                 125

Ser Ser Val Thr Glu Phe Lys Phe Leu Phe Val Ser Gly His Phe Lys
130                 135                 140

Gly Asn Tyr Lys Ala Gln Leu Thr Arg Leu Asn His Ile Thr Asn Cys
145                 150                 155                 160

Asn Gly Ala Val Leu Ser Val Glu Glu Leu Leu Ile Gly Gly Glu Met
                165                 170                 175

Ile Lys Ala Gly Thr Leu Thr Leu Glu Glu Val Arg Arg Lys Phe Asn
                180                 185                 190

Asn Gly Glu Ile Asn Phe
            195
```

<210> SEQ ID NO 20
<211> LENGTH: 1022
<212> TYPE: PRT
<213> ORGANISM: Artificial Sequence
<220> FEATURE:
<223> OTHER INFORMATION: megaTAL endonuclease

<400> SEQUENCE: 20

```
Val Asp Leu Arg Thr Leu Gly Tyr Ser Gln Gln Gln Gln Glu Lys Ile
  1               5                  10                  15

Lys Pro Lys Val Arg Ser Thr Val Ala Gln His His Glu Ala Leu Val
                 20                  25                  30

Gly His Gly Phe Thr His Ala His Ile Val Ala Leu Ser Gln His Pro
            35                  40                  45

Ala Ala Leu Gly Thr Val Ala Val Thr Tyr Gln His Ile Ile Thr Ala
 50                  55                  60

Leu Pro Glu Ala Thr His Glu Asp Ile Val Gly Val Gly Lys Gln Trp
 65                  70                  75                  80

Ser Gly Ala Arg Ala Leu Glu Ala Leu Leu Thr Asp Ala Gly Glu Leu
                 85                  90                  95

Arg Gly Pro Pro Leu Gln Leu Asp Thr Gly Gln Leu Val Lys Ile Ala
                100                 105                 110

Lys Arg Gly Gly Val Thr Ala Met Glu Ala Val His Ala Ser Arg Asn
            115                 120                 125

Ala Leu Thr Gly Ala Pro Leu Asn Leu Thr Pro Asp Gln Val Val Ala
130                 135                 140

Ile Ala Ser Asn Gly Gly Gly Lys Gln Ala Leu Glu Thr Val Gln Arg
145                 150                 155                 160

Leu Leu Pro Val Leu Cys Gln Asp His Gly Leu Thr Pro Asp Gln Val
                165                 170                 175

Val Ala Ile Ala Ser His Asp Gly Gly Lys Gln Ala Leu Glu Thr Val
                180                 185                 190

Gln Arg Leu Leu Pro Val Leu Cys Gln Asp His Gly Leu Thr Pro Asp
            195                 200                 205
```

```
Gln Val Val Ala Ile Ala Ser Asn Ile Gly Gly Lys Gln Ala Leu Glu
    210                 215                 220

Thr Val Gln Arg Leu Leu Pro Val Leu Cys Gln Asp His Gly Leu Thr
225                 230                 235                 240

Pro Asp Gln Val Val Ala Ile Ala Ser Asn Gly Gly Lys Gln Ala
                245                 250                 255

Leu Glu Thr Val Gln Arg Leu Leu Pro Val Leu Cys Gln Asp His Gly
            260                 265                 270

Leu Thr Pro Asp Gln Val Val Ala Ile Ala Ser Asn Gly Gly Lys
        275                 280                 285

Gln Ala Leu Glu Thr Val Gln Arg Leu Leu Pro Val Leu Cys Gln Asp
    290                 295                 300

His Gly Leu Thr Pro Asp Gln Val Val Ala Ile Ala Ser Asn Ile Gly
305                 310                 315                 320

Gly Lys Gln Ala Leu Glu Thr Val Gln Arg Leu Leu Pro Val Leu Cys
                325                 330                 335

Gln Asp His Gly Leu Thr Pro Asp Gln Val Val Ala Ile Ala Ser His
            340                 345                 350

Asp Gly Gly Lys Gln Ala Leu Glu Thr Val Gln Arg Leu Leu Pro Val
        355                 360                 365

Leu Cys Gln Asp His Gly Leu Thr Pro Asp Gln Val Val Ala Ile Ala
    370                 375                 380

Ser Asn Ile Gly Gly Lys Gln Ala Leu Glu Thr Val Gln Arg Leu Leu
385                 390                 395                 400

Pro Val Leu Cys Gln Asp His Gly Leu Thr Pro Asp Gln Val Val Ala
                405                 410                 415

Ile Ala Ser His Asp Gly Gly Lys Gln Ala Leu Glu Thr Val Gln Arg
            420                 425                 430

Leu Leu Pro Val Leu Cys Gln Asp His Gly Leu Thr Pro Asp Gln Val
        435                 440                 445

Val Ala Ile Ala Ser His Asp Gly Gly Lys Gln Ala Leu Glu Thr Val
    450                 455                 460

Gln Arg Leu Leu Pro Val Leu Cys Gln Asp His Gly Leu Thr Pro Asp
465                 470                 475                 480

Gln Val Val Ala Ile Ala Ser Asn Gly Gly Lys Gln Ala Leu Glu
                485                 490                 495

Thr Val Gln Arg Leu Leu Pro Val Leu Cys Gln Asp His Gly Leu Thr
            500                 505                 510

Pro Asp Gln Val Val Ala Ile Ala Ser Asn Asn Gly Gly Lys Gln Ala
        515                 520                 525

Leu Glu Thr Val Gln Arg Leu Leu Pro Val Leu Cys Gln Asp His Gly
    530                 535                 540

Leu Thr Pro Asp Gln Val Val Ala Ile Ala Ser His Asp Gly Gly Lys
545                 550                 555                 560

Gln Ala Leu Glu Thr Val Gln Arg Leu Leu Pro Val Leu Cys Gln Asp
                565                 570                 575

His Gly Leu Thr Pro Asp Gln Val Val Ala Ile Ala Ser Asn Ile Gly
            580                 585                 590

Gly Lys Gln Ala Leu Glu Thr Val Gln Arg Leu Leu Pro Val Leu Cys
        595                 600                 605

Gln Asp His Gly Leu Thr Pro Asp Gln Val Val Ala Ile Ala Ser Asn
    610                 615                 620

Asn Gly Gly Lys Gln Ala Leu Glu Thr Val Gln Arg Leu Leu Pro Val
```

-continued

```
               625                 630                 635                 640

Leu Cys Gln Asp His Gly Leu Thr Pro Asp Gln Val Val Ala Ile Ala
                645                 650                 655

Ser His Asp Gly Gly Lys Gln Ala Leu Glu Thr Val Gln Arg Leu Leu
                660                 665                 670

Pro Val Leu Cys Gln Asp His Gly Leu Thr Pro Asp Gln Val Val Ala
                675                 680                 685

Ile Ala Ser Asn Gly Gly Lys Gln Ala Leu Glu Ser Ile Val Ala
690                 695                 700

Gln Leu Ser Arg Pro Asp Pro Ala Leu Ala Ala Leu Thr Asn Asp His
705                 710                 715                 720

Leu Val Ala Leu Ala Cys Leu Gly Gly Arg Pro Ala Met Asp Ala Val
                725                 730                 735

Lys Lys Gly Leu Pro His Ala Pro Glu Leu Ile Arg Arg Val Asn Arg
                740                 745                 750

Arg Ile Gly Glu Arg Thr Ser His Arg Val Ala Ile Ser Arg Val Gly
                755                 760                 765

Gly Ser Asp Leu Thr Tyr Ala Tyr Leu Val Gly Leu Tyr Glu Gly Asp
                770                 775                 780

Gly Tyr Phe Ser Ile Thr Lys Lys Gly Lys Tyr Leu Thr Tyr Glu Leu
785                 790                 795                 800

Gly Ile Glu Leu Ser Ile Lys Asp Val Gln Leu Ile Tyr Lys Ile Lys
                805                 810                 815

Lys Ile Leu Gly Ile Gly Ile Val Ser Phe Arg Lys Asn Glu Ile
                820                 825                 830

Glu Met Val Ala Leu Arg Ile Arg Asp Lys Asn His Leu Lys Ser Lys
                835                 840                 845

Ile Leu Pro Ile Phe Glu Lys Tyr Pro Met Phe Ser Asn Lys Gln Tyr
                850                 855                 860

Asp Tyr Leu Arg Phe Arg Asn Ala Leu Leu Ser Gly Ile Ile Tyr Leu
865                 870                 875                 880

Glu Asp Leu Pro Asp Tyr Thr Arg Ser Asp Glu Pro Leu Asn Ser Ile
                885                 890                 895

Glu Ser Ile Ile Asn Thr Ser Tyr Phe Ser Ala Trp Leu Val Gly Phe
                900                 905                 910

Ile Glu Ala Glu Gly Cys Phe Ser Val Tyr Lys Leu Asn Lys Asp Asp
                915                 920                 925

Asp Tyr Leu Ile Ala Ser Phe Asp Ile Ala Gln Arg Asp Gly Asp Ile
                930                 935                 940

Leu Ile Ser Ala Ile Arg Lys Tyr Leu Ser Phe Thr Thr Lys Val Tyr
945                 950                 955                 960

Leu Asp Lys Thr Asn Cys Ser Lys Leu Lys Val Thr Ser Val Arg Ser
                965                 970                 975

Val Glu Asn Ile Ile Lys Phe Leu Gln Asn Ala Pro Val Lys Leu Leu
                980                 985                 990

Gly Asn Lys Lys Leu Gln Tyr Lys Leu Trp Leu Lys Gln Leu Arg Lys
                995                 1000                1005

Ile Ser Arg Tyr Ser Glu Lys Ile Lys Ile Pro Ser Asn Tyr
                1010                1015                1020

<210> SEQ ID NO 21
<211> LENGTH: 1307
<212> TYPE: PRT
<213> ORGANISM: Artificial Sequence
```

<220> FEATURE:
<223> OTHER INFORMATION: AsCpf1

<400> SEQUENCE: 21

| Met | Thr | Gln | Phe | Glu | Gly | Phe | Thr | Asn | Leu | Tyr | Gln | Val | Ser | Lys | Thr |
|---|---|---|---|---|---|---|---|---|---|---|---|---|---|---|---|
| 1 | | | | 5 | | | | | 10 | | | | | 15 | |

| Leu | Arg | Phe | Glu | Leu | Ile | Pro | Gln | Gly | Lys | Thr | Leu | Lys | His | Ile | Gln |
| | | | 20 | | | | | 25 | | | | | 30 | | |

| Glu | Gln | Gly | Phe | Ile | Glu | Glu | Asp | Lys | Ala | Arg | Asn | Asp | His | Tyr | Lys |
| | | 35 | | | | 40 | | | | | 45 | | | | |

| Glu | Leu | Lys | Pro | Ile | Ile | Asp | Arg | Ile | Tyr | Lys | Thr | Tyr | Ala | Asp | Gln |
| | 50 | | | | | 55 | | | | | 60 | | | | |

| Cys | Leu | Gln | Leu | Val | Gln | Leu | Asp | Trp | Glu | Asn | Leu | Ser | Ala | Ala | Ile |
| 65 | | | | | 70 | | | | 75 | | | | | | 80 |

| Asp | Ser | Tyr | Arg | Lys | Glu | Lys | Thr | Glu | Glu | Thr | Arg | Asn | Ala | Leu | Ile |
| | | | | 85 | | | | | 90 | | | | | 95 | |

| Glu | Glu | Gln | Ala | Thr | Tyr | Arg | Asn | Ala | Ile | His | Asp | Tyr | Phe | Ile | Gly |
| | | | 100 | | | | | 105 | | | | | 110 | | |

| Arg | Thr | Asp | Asn | Leu | Thr | Asp | Ala | Ile | Asn | Lys | Arg | His | Ala | Glu | Ile |
| | | 115 | | | | | 120 | | | | | 125 | | | |

| Tyr | Lys | Gly | Leu | Phe | Lys | Ala | Glu | Leu | Phe | Asn | Gly | Lys | Val | Leu | Lys |
| | 130 | | | | | 135 | | | | | 140 | | | | |

| Gln | Leu | Gly | Thr | Val | Thr | Thr | Thr | Glu | His | Glu | Asn | Ala | Leu | Leu | Arg |
| 145 | | | | | 150 | | | | 155 | | | | | | 160 |

| Ser | Phe | Asp | Lys | Phe | Thr | Thr | Tyr | Phe | Ser | Gly | Phe | Tyr | Glu | Asn | Arg |
| | | | | 165 | | | | | 170 | | | | | 175 | |

| Lys | Asn | Val | Phe | Ser | Ala | Glu | Asp | Ile | Ser | Thr | Ala | Ile | Pro | His | Arg |
| | | | 180 | | | | | 185 | | | | | 190 | | |

| Ile | Val | Gln | Asp | Asn | Phe | Pro | Lys | Phe | Lys | Glu | Asn | Cys | His | Ile | Phe |
| | | | | 195 | | | | | 200 | | | | | 205 | |

| Thr | Arg | Leu | Ile | Thr | Ala | Val | Pro | Ser | Leu | Arg | Glu | His | Phe | Glu | Asn |
| | | | 210 | | | | | 215 | | | | | 220 | | |

| Val | Lys | Lys | Ala | Ile | Gly | Ile | Phe | Val | Ser | Thr | Ser | Ile | Glu | Glu | Val |
| 225 | | | | | 230 | | | | | 235 | | | | | 240 |

| Phe | Ser | Phe | Pro | Phe | Tyr | Asn | Gln | Leu | Leu | Thr | Gln | Thr | Gln | Ile | Asp |
| | | | | 245 | | | | | 250 | | | | | 255 | |

| Leu | Tyr | Asn | Gln | Leu | Leu | Gly | Gly | Ile | Ser | Arg | Glu | Ala | Gly | Thr | Glu |
| | | | 260 | | | | | 265 | | | | | 270 | | |

| Lys | Ile | Lys | Gly | Leu | Asn | Glu | Val | Leu | Asn | Leu | Ala | Ile | Gln | Lys | Asn |
| | | 275 | | | | | 280 | | | | | 285 | | | |

| Asp | Glu | Thr | Ala | His | Ile | Ile | Ala | Ser | Leu | Pro | His | Arg | Phe | Ile | Pro |
| | 290 | | | | | 295 | | | | | 300 | | | | |

| Leu | Phe | Lys | Gln | Ile | Leu | Ser | Asp | Arg | Asn | Thr | Leu | Ser | Phe | Ile | Leu |
| 305 | | | | | 310 | | | | | 315 | | | | | 320 |

| Glu | Glu | Phe | Lys | Ser | Asp | Glu | Glu | Val | Ile | Gln | Ser | Phe | Cys | Lys | Tyr |
| | | | | 325 | | | | | 330 | | | | | 335 | |

| Lys | Thr | Leu | Leu | Arg | Asn | Glu | Asn | Val | Leu | Glu | Thr | Ala | Glu | Ala | Leu |
| | | | 340 | | | | | 345 | | | | | 350 | | |

| Phe | Asn | Glu | Leu | Asn | Ser | Ile | Asp | Leu | Thr | His | Ile | Phe | Ile | Ser | His |
| | | | | 355 | | | | | 360 | | | | | 365 | |

| Lys | Lys | Leu | Glu | Thr | Ile | Ser | Ser | Ala | Leu | Cys | Asp | His | Trp | Asp | Thr |
| | | | 370 | | | | | 375 | | | | | 380 | | |

| Leu | Arg | Asn | Ala | Leu | Tyr | Glu | Arg | Arg | Ile | Ser | Glu | Leu | Thr | Gly | Lys |
| 385 | | | | | 390 | | | | | 395 | | | | | 400 |

```
Ile Thr Lys Ser Ala Lys Glu Lys Val Gln Arg Ser Leu Lys His Glu
            405                 410                 415

Asp Ile Asn Leu Gln Glu Ile Ile Ser Ala Ala Gly Lys Glu Leu Ser
        420                 425                 430

Glu Ala Phe Lys Gln Lys Thr Ser Glu Ile Leu Ser His Ala His Ala
            435                 440                 445

Ala Leu Asp Gln Pro Leu Pro Thr Thr Leu Lys Lys Gln Glu Glu Lys
        450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
        515                 520                 525

Glu Lys Phe Lys Leu Asn Phe Gln Met Pro Thr Leu Ala Ser Gly Trp
        530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
        595                 600                 605

Ser Thr Gln Leu Lys Ala Val Thr Ala His Phe Gln Thr His Thr Thr
        610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
        675                 680                 685

Lys Thr Thr Ser Ile Asp Leu Ser Ser Leu Arg Pro Ser Ser Gln Tyr
        690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
        755                 760                 765

Phe Ser Pro Glu Asn Leu Ala Lys Thr Ser Ile Lys Leu Asn Gly Gln
        770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815
```

```
Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
        835                 840                 845

Val Ile Thr Lys Glu Val Ser His Glu Ile Ile Lys Asp Arg Arg Phe
    850                 855                 860

Thr Ser Asp Lys Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
        915                 920                 925

Gln Arg Ser Leu Asn Thr Ile Gln Gln Phe Asp Tyr Gln Lys Lys Leu
    930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
            980                 985                 990

Glu Asn Leu Asn Phe Gly Phe Lys  Ser Lys Arg Thr Gly  Ile Ala Glu
            995                 1000                1005

Lys Ala Val Tyr Gln Gln Phe  Glu Lys Met Leu Ile  Asp Lys Leu
    1010                1015                1020

Asn Cys Leu Val Leu Lys Asp  Tyr Pro Ala Glu Lys  Val Gly Gly
    1025                1030                1035

Val Leu Asn Pro Tyr Gln Leu  Thr Asp Gln Phe Thr  Ser Phe Ala
    1040                1045                1050

Lys Met Gly Thr Gln Ser Gly  Phe Leu Phe Tyr Val  Pro Ala Pro
    1055                1060                1065

Tyr Thr Ser Lys Ile Asp Pro  Leu Thr Gly Phe Val  Asp Pro Phe
    1070                1075                1080

Val Trp Lys Thr Ile Lys Asn  His Glu Ser Arg Lys  His Phe Leu
    1085                1090                1095

Glu Gly Phe Asp Phe Leu His  Tyr Asp Val Lys Thr  Gly Asp Phe
    1100                1105                1110

Ile Leu His Phe Lys Met Asn  Arg Asn Leu Ser Phe  Gln Arg Gly
    1115                1120                1125

Leu Pro Gly Phe Met Pro Ala  Trp Asp Ile Val Phe  Glu Lys Asn
    1130                1135                1140

Glu Thr Gln Phe Asp Ala Lys  Gly Thr Pro Phe Ile  Ala Gly Lys
    1145                1150                1155

Arg Ile Val Pro Val Ile Glu  Asn His Arg Phe Thr  Gly Arg Tyr
    1160                1165                1170

Arg Asp Leu Tyr Pro Ala Asn  Glu Leu Ile Ala Leu  Leu Glu Glu
    1175                1180                1185

Lys Gly Ile Val Phe Arg Asp  Gly Ser Asn Ile Leu  Pro Lys Leu
    1190                1195                1200

Leu Glu Asn Asp Asp Ser His  Ala Ile Asp Thr Met  Val Ala Leu
    1205                1210                1215

Ile Arg Ser Val Leu Gln Met  Arg Asn Ser Asn Ala  Ala Thr Gly
```

```
         1220                1225                1230

Glu Asp Tyr Ile Asn Ser Pro Val Arg Asp Leu Asn Gly Val Cys
         1235                1240                1245

Phe Asp Ser Arg Phe Gln Asn Pro Glu Trp Pro Met Asp Ala Asp
         1250                1255                1260

Ala Asn Gly Ala Tyr His Ile Ala Leu Lys Gly Gln Leu Leu Leu
         1265                1270                1275

Asn His Leu Lys Glu Ser Lys Asp Leu Lys Leu Gln Asn Gly Ile
         1280                1285                1290

Ser Asn Gln Asp Trp Leu Ala Tyr Ile Gln Glu Leu Arg Asn
         1295                1300                1305

<210> SEQ ID NO 22
<211> LENGTH: 1228
<212> TYPE: PRT
<213> ORGANISM: Artificial Sequence
<220> FEATURE:
<223> OTHER INFORMATION: LbCpf1

<400> SEQUENCE: 22

Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
                20                  25                  30

Asn Lys Arg Leu Leu Val Glu Asp Glu Lys Arg Ala Glu Asp Tyr Lys
            35                  40                  45

Gly Val Lys Lys Leu Leu Asp Arg Tyr Tyr Leu Ser Phe Ile Asn Asp
        50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
                100                 105                 110

Glu Gly Tyr Lys Ser Leu Phe Lys Lys Asp Ile Ile Glu Thr Ile Leu
                115                 120                 125

Pro Glu Phe Leu Asp Asp Lys Asp Glu Ile Ala Leu Val Asn Ser Phe
            130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
                180                 185                 190

Val Asp Ala Ile Phe Asp Lys His Glu Val Gln Glu Ile Lys Glu Lys
                195                 200                 205

Ile Leu Asn Ser Asp Tyr Asp Val Glu Asp Phe Phe Glu Gly Glu Phe
            210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
                260                 265                 270

Phe Lys Pro Leu Tyr Lys Gln Val Leu Ser Asp Arg Glu Ser Leu Ser
```

```
              275                 280                 285
Phe Tyr Gly Glu Gly Tyr Thr Ser Asp Glu Glu Val Leu Glu Val Phe
290                 295                 300
Arg Asn Thr Leu Asn Lys Asn Ser Glu Ile Phe Ser Ser Ile Lys Lys
305                 310                 315                 320
Leu Glu Lys Leu Phe Lys Asn Phe Asp Glu Tyr Ser Ser Ala Gly Ile
                325                 330                 335
Phe Val Lys Asn Gly Pro Ala Ile Ser Thr Ile Ser Lys Asp Ile Phe
                340                 345                 350
Gly Glu Trp Asn Val Ile Arg Asp Lys Trp Asn Ala Glu Tyr Asp Asp
                355                 360                 365
Ile His Leu Lys Lys Lys Ala Val Val Thr Glu Lys Tyr Glu Asp Asp
    370                 375                 380
Arg Arg Lys Ser Phe Lys Lys Ile Gly Ser Phe Ser Leu Glu Gln Leu
385                 390                 395                 400
Gln Glu Tyr Ala Asp Ala Asp Leu Ser Val Val Glu Lys Leu Lys Glu
                405                 410                 415
Ile Ile Ile Gln Lys Val Asp Glu Ile Tyr Lys Val Tyr Gly Ser Ser
                420                 425                 430
Glu Lys Leu Phe Asp Ala Asp Phe Val Leu Glu Lys Ser Leu Lys Lys
            435                 440                 445
Asn Asp Ala Val Val Ala Ile Met Lys Asp Leu Leu Asp Ser Val Lys
450                 455                 460
Ser Phe Glu Asn Tyr Ile Lys Ala Phe Phe Gly Glu Gly Lys Glu Thr
465                 470                 475                 480
Asn Arg Asp Glu Ser Phe Tyr Gly Asp Phe Val Leu Ala Tyr Asp Ile
                485                 490                 495
Leu Leu Lys Val Asp His Ile Tyr Asp Ala Ile Arg Asn Tyr Val Thr
                500                 505                 510
Gln Lys Pro Tyr Ser Lys Asp Lys Phe Lys Leu Tyr Phe Gln Asn Pro
            515                 520                 525
Gln Phe Met Gly Gly Trp Asp Lys Asp Lys Glu Thr Asp Tyr Arg Ala
    530                 535                 540
Thr Ile Leu Arg Tyr Gly Ser Lys Tyr Tyr Leu Ala Ile Met Asp Lys
545                 550                 555                 560
Lys Tyr Ala Lys Cys Leu Gln Lys Ile Asp Lys Asp Asp Val Asn Gly
                565                 570                 575
Asn Tyr Glu Lys Ile Asn Tyr Lys Leu Leu Pro Gly Pro Asn Lys Met
                580                 585                 590
Leu Pro Lys Val Phe Phe Ser Lys Lys Trp Met Ala Tyr Tyr Asn Pro
            595                 600                 605
Ser Glu Asp Ile Gln Lys Ile Tyr Lys Asn Gly Thr Phe Lys Lys Gly
    610                 615                 620
Asp Met Phe Asn Leu Asn Asp Cys His Lys Leu Ile Asp Phe Phe Lys
625                 630                 635                 640
Asp Ser Ile Ser Arg Tyr Pro Lys Trp Ser Asn Ala Tyr Asp Phe Asn
                645                 650                 655
Phe Ser Glu Thr Glu Lys Tyr Lys Asp Ile Ala Gly Phe Tyr Arg Glu
                660                 665                 670
Val Glu Glu Gln Gly Tyr Lys Val Ser Phe Glu Ser Ala Ser Lys Lys
            675                 680                 685
Glu Val Asp Lys Leu Val Glu Glu Gly Lys Leu Tyr Met Phe Gln Ile
    690                 695                 700
```

-continued

```
Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
            740                 745                 750

Lys Glu Glu Leu Val Val His Pro Ala Asn Ser Pro Ile Ala Asn Lys
                755                 760                 765

Asn Pro Asp Asn Pro Lys Lys Thr Thr Thr Leu Ser Tyr Asp Val Tyr
770                 775                 780

Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
                805                 810                 815

Arg Val Leu Leu Lys His Asp Asp Asn Pro Tyr Val Ile Gly Ile Asp
                820                 825                 830

Arg Gly Glu Arg Asn Leu Leu Tyr Ile Val Val Val Asp Gly Lys Gly
            835                 840                 845

Asn Ile Val Glu Gln Tyr Ser Leu Asn Glu Ile Ile Asn Asn Phe Asn
850                 855                 860

Gly Ile Arg Ile Lys Thr Asp Tyr His Ser Leu Leu Asp Lys Lys Glu
865                 870                 875                 880

Lys Glu Arg Phe Glu Ala Arg Gln Asn Trp Thr Ser Ile Glu Asn Ile
                885                 890                 895

Lys Glu Leu Lys Ala Gly Tyr Ile Ser Gln Val Val His Lys Ile Cys
                900                 905                 910

Glu Leu Val Glu Lys Tyr Asp Ala Val Ile Ala Leu Glu Asp Leu Asn
                915                 920                 925

Ser Gly Phe Lys Asn Ser Arg Val Lys Val Glu Lys Gln Val Tyr Gln
930                 935                 940

Lys Phe Glu Lys Met Leu Ile Asp Lys Leu Asn Tyr Met Val Asp Lys
945                 950                 955                 960

Lys Ser Asn Pro Cys Ala Thr Gly Gly Ala Leu Lys Gly Tyr Gln Ile
                965                 970                 975

Thr Asn Lys Phe Glu Ser Phe Lys Ser Met Ser Thr Gln Asn Gly Phe
                980                 985                 990

Ile Phe Tyr Ile Pro Ala Trp Leu Thr Ser Lys Ile Asp Pro Ser Thr
            995                 1000                1005

Gly Phe Val Asn Leu Leu Lys Thr Lys Tyr Thr Ser Ile Ala Asp
    1010                1015                1020

Ser Lys Lys Phe Ile Ser Ser Phe Asp Arg Ile Met Tyr Val Pro
    1025                1030                1035

Glu Glu Asp Leu Phe Glu Phe Ala Leu Asp Tyr Lys Asn Phe Ser
    1040                1045                1050

Arg Thr Asp Ala Asp Tyr Ile Lys Lys Trp Lys Leu Tyr Ser Tyr
    1055                1060                1065

Gly Asn Arg Ile Arg Ile Phe Arg Asn Pro Lys Lys Asn Asn Val
    1070                1075                1080

Phe Asp Trp Glu Glu Val Cys Leu Thr Ser Ala Tyr Lys Glu Leu
    1085                1090                1095

Phe Asn Lys Tyr Gly Ile Asn Tyr Gln Gln Gly Asp Ile Arg Ala
    1100                1105                1110
```

```
Leu Leu Cys Glu Gln Ser Asp Lys Ala Phe Tyr Ser Ser Phe Met
    1115                1120                1125

Ala Leu Met Ser Leu Met Leu Gln Met Arg Asn Ser Ile Thr Gly
    1130                1135                1140

Arg Thr Asp Val Asp Phe Leu Ile Ser Pro Val Lys Asn Ser Asp
    1145                1150                1155

Gly Ile Phe Tyr Asp Ser Arg Asn Tyr Glu Ala Gln Glu Asn Ala
    1160                1165                1170

Ile Leu Pro Lys Asn Ala Asp Ala Asn Gly Ala Tyr Asn Ile Ala
    1175                1180                1185

Arg Lys Val Leu Trp Ala Ile Gly Gln Phe Lys Lys Ala Glu Asp
    1190                1195                1200

Glu Lys Leu Asp Lys Val Lys Ile Ala Ile Ser Asn Lys Glu Trp
    1205                1210                1215

Leu Glu Tyr Ala Gln Thr Ser Val Lys His
    1220                1225
```

```
<210> SEQ ID NO 23
<211> LENGTH: 1368
<212> TYPE: PRT
<213> ORGANISM: Artificial Sequence
<220> FEATURE:
<223> OTHER INFORMATION: SpCas9

<400> SEQUENCE: 23
```

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240
```

Leu Ile Ala Leu Ser Leu Gly Leu Thr Pro Asn Phe Lys Ser Asn Phe
            245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
            290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
            325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
            370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
            405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
            485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
            565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
            645                 650                 655

Thr Gly Trp Gly Arg Leu Ser Arg Lys Leu Ile Asn Gly Ile Arg Asp

-continued

```
                660                 665                 670
Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080
```

Arg Lys Val Leu Ser Met Pro Gln Val Asn Ile Val Lys Lys Thr
              1085            1090            1095

Glu Val Gln Thr Gly Gly Phe Ser Lys Glu Ser Ile Leu Pro Lys
     1100            1105            1110

Arg Asn Ser Asp Lys Leu Ile Ala Arg Lys Lys Asp Trp Asp Pro
        1115            1120            1125

Lys Lys Tyr Gly Gly Phe Asp Ser Pro Thr Val Ala Tyr Ser Val
        1130            1135            1140

Leu Val Val Ala Lys Val Glu Lys Gly Lys Ser Lys Lys Leu Lys
        1145            1150            1155

Ser Val Lys Glu Leu Leu Gly Ile Thr Ile Met Glu Arg Ser Ser
        1160            1165            1170

Phe Glu Lys Asn Pro Ile Asp Phe Leu Glu Ala Lys Gly Tyr Lys
        1175            1180            1185

Glu Val Lys Lys Asp Leu Ile Ile Lys Leu Pro Lys Tyr Ser Leu
        1190            1195            1200

Phe Glu Leu Glu Asn Gly Arg Lys Arg Met Leu Ala Ser Ala Gly
        1205            1210            1215

Glu Leu Gln Lys Gly Asn Glu Leu Ala Leu Pro Ser Lys Tyr Val
        1220            1225            1230

Asn Phe Leu Tyr Leu Ala Ser His Tyr Glu Lys Leu Lys Gly Ser
        1235            1240            1245

Pro Glu Asp Asn Glu Gln Lys Gln Leu Phe Val Glu Gln His Lys
        1250            1255            1260

His Tyr Leu Asp Glu Ile Ile Glu Gln Ile Ser Glu Phe Ser Lys
        1265            1270            1275

Arg Val Ile Leu Ala Asp Ala Asn Leu Asp Lys Val Leu Ser Ala
        1280            1285            1290

Tyr Asn Lys His Arg Asp Lys Pro Ile Arg Glu Gln Ala Glu Asn
        1295            1300            1305

Ile Ile His Leu Phe Thr Leu Thr Asn Leu Gly Ala Pro Ala Ala
        1310            1315            1320

Phe Lys Tyr Phe Asp Thr Thr Ile Asp Arg Lys Arg Tyr Thr Ser
        1325            1330            1335

Thr Lys Glu Val Leu Asp Ala Thr Leu Ile His Gln Ser Ile Thr
        1340            1345            1350

Gly Leu Tyr Glu Thr Arg Ile Asp Leu Ser Gln Leu Gly Gly Asp
        1355            1360            1365

<210> SEQ ID NO 24
<211> LENGTH: 1121
<212> TYPE: PRT
<213> ORGANISM: Artificial Sequence
<220> FEATURE:
<223> OTHER INFORMATION: St1Cas9

<400> SEQUENCE: 24

Met Ser Asp Leu Val Leu Gly Leu Asp Ile Gly Ile Gly Ser Val Gly
1               5                   10                  15

Val Gly Ile Leu Asn Lys Val Thr Gly Glu Ile Ile His Lys Asn Ser
            20                  25                  30

Arg Ile Phe Pro Ala Ala Gln Ala Glu Asn Asn Leu Val Arg Arg Thr
        35                  40                  45

Asn Arg Gln Gly Arg Arg Leu Ala Arg Arg Lys Lys His Arg Arg Val
    50                  55                  60

```
Arg Leu Asn Arg Leu Phe Glu Glu Ser Gly Leu Ile Thr Asp Phe Thr
 65                  70                  75                  80

Lys Ile Ser Ile Asn Leu Asn Pro Tyr Gln Leu Arg Val Lys Gly Leu
                 85                  90                  95

Thr Asp Glu Leu Ser Asn Glu Glu Leu Phe Ile Ala Leu Lys Asn Met
            100                 105                 110

Val Lys His Arg Gly Ile Ser Tyr Leu Asp Asp Ala Ser Asp Asp Gly
        115                 120                 125

Asn Ser Ser Val Gly Asp Tyr Ala Gln Ile Val Lys Glu Asn Ser Lys
    130                 135                 140

Gln Leu Glu Thr Lys Thr Pro Gly Gln Ile Gln Leu Glu Arg Tyr Gln
145                 150                 155                 160

Thr Tyr Gly Gln Leu Arg Gly Asp Phe Thr Val Glu Lys Asp Gly Lys
                165                 170                 175

Lys His Arg Leu Ile Asn Val Phe Pro Thr Ser Ala Tyr Arg Ser Glu
            180                 185                 190

Ala Leu Arg Ile Leu Gln Thr Gln Gln Glu Phe Asn Pro Gln Ile Thr
        195                 200                 205

Asp Glu Phe Ile Asn Arg Tyr Leu Glu Ile Leu Thr Gly Lys Arg Lys
    210                 215                 220

Tyr Tyr His Gly Pro Gly Asn Glu Lys Ser Arg Thr Asp Tyr Gly Arg
225                 230                 235                 240

Tyr Arg Thr Ser Gly Glu Thr Leu Asp Asn Ile Phe Gly Ile Leu Ile
                245                 250                 255

Gly Lys Cys Thr Phe Tyr Pro Asp Glu Phe Arg Ala Ala Lys Ala Ser
            260                 265                 270

Tyr Thr Ala Gln Glu Phe Asn Leu Leu Asn Asp Leu Asn Asn Leu Thr
        275                 280                 285

Val Pro Thr Glu Thr Lys Lys Leu Ser Lys Glu Gln Lys Asn Gln Ile
    290                 295                 300

Ile Asn Tyr Val Lys Asn Glu Lys Ala Met Gly Pro Ala Lys Leu Phe
305                 310                 315                 320

Lys Tyr Ile Ala Lys Leu Leu Ser Cys Asp Val Ala Asp Ile Lys Gly
                325                 330                 335

Tyr Arg Ile Asp Lys Ser Gly Lys Ala Glu Ile His Thr Phe Glu Ala
            340                 345                 350

Tyr Arg Lys Met Lys Thr Leu Glu Thr Leu Asp Ile Glu Gln Met Asp
        355                 360                 365

Arg Glu Thr Leu Asp Lys Leu Ala Tyr Val Leu Thr Leu Asn Thr Glu
    370                 375                 380

Arg Glu Gly Ile Gln Glu Ala Leu Glu His Glu Phe Ala Asp Gly Ser
385                 390                 395                 400

Phe Ser Gln Lys Gln Val Asp Glu Leu Val Gln Phe Arg Lys Ala Asn
                405                 410                 415

Ser Ser Ile Phe Gly Lys Gly Trp His Asn Phe Ser Val Lys Leu Met
            420                 425                 430

Met Glu Leu Ile Pro Glu Leu Tyr Glu Thr Ser Glu Glu Gln Met Thr
        435                 440                 445

Ile Leu Thr Arg Leu Gly Lys Gln Lys Thr Thr Ser Ser Ser Asn Lys
    450                 455                 460

Thr Lys Tyr Ile Asp Glu Lys Leu Leu Thr Glu Glu Ile Tyr Asn Pro
465                 470                 475                 480
```

```
Val Val Ala Lys Ser Val Arg Gln Ala Ile Lys Ile Val Asn Ala Ala
            485                 490                 495

Ile Lys Glu Tyr Gly Asp Phe Asp Asn Ile Val Ile Glu Met Ala Arg
            500                 505                 510

Glu Thr Asn Glu Asp Asp Glu Lys Lys Ala Ile Gln Lys Ile Gln Lys
            515                 520                 525

Ala Asn Lys Asp Glu Lys Asp Ala Ala Met Leu Lys Ala Ala Asn Gln
            530                 535                 540

Tyr Asn Gly Lys Ala Glu Leu Pro His Ser Val Phe His Gly His Lys
545                 550                 555                 560

Gln Leu Ala Thr Lys Ile Arg Leu Trp His Gln Gln Gly Glu Arg Cys
                565                 570                 575

Leu Tyr Thr Gly Lys Thr Ile Ser Ile His Asp Leu Ile Asn Asn Ser
                580                 585                 590

Asn Gln Phe Glu Val Asp His Ile Leu Pro Leu Ser Ile Thr Phe Asp
                595                 600                 605

Asp Ser Leu Ala Asn Lys Val Leu Val Tyr Ala Thr Ala Asn Gln Glu
                610                 615                 620

Lys Gly Gln Arg Thr Pro Tyr Gln Ala Leu Asp Ser Met Asp Asp Ala
625                 630                 635                 640

Trp Ser Phe Arg Glu Leu Lys Ala Phe Val Arg Glu Ser Lys Thr Leu
                645                 650                 655

Ser Asn Lys Lys Lys Glu Tyr Leu Leu Thr Glu Glu Asp Ile Ser Lys
                660                 665                 670

Phe Asp Val Arg Lys Lys Phe Ile Glu Arg Asn Leu Val Asp Thr Arg
                675                 680                 685

Tyr Ala Ser Arg Val Val Leu Asn Ala Leu Gln Glu His Phe Arg Ala
690                 695                 700

His Lys Ile Asp Thr Lys Val Ser Val Val Arg Gly Gln Phe Thr Ser
705                 710                 715                 720

Gln Leu Arg Arg His Trp Gly Ile Glu Lys Thr Arg Asp Thr Tyr His
                725                 730                 735

His His Ala Val Asp Ala Leu Ile Ile Ala Ala Ser Ser Gln Leu Asn
                740                 745                 750

Leu Trp Lys Lys Gln Lys Asn Thr Leu Val Ser Tyr Ser Glu Asp Gln
                755                 760                 765

Leu Leu Asp Ile Glu Thr Gly Glu Leu Ile Ser Asp Asp Glu Tyr Lys
                770                 775                 780

Glu Ser Val Phe Lys Ala Pro Tyr Gln His Phe Val Asp Thr Leu Lys
785                 790                 795                 800

Ser Lys Glu Phe Glu Asp Ser Ile Leu Phe Ser Tyr Gln Val Asp Ser
                805                 810                 815

Lys Phe Asn Arg Lys Ile Ser Asp Ala Thr Ile Tyr Ala Thr Arg Gln
                820                 825                 830

Ala Lys Val Gly Lys Asp Lys Ala Asp Glu Thr Tyr Val Leu Gly Lys
                835                 840                 845

Ile Lys Asp Ile Tyr Thr Gln Asp Gly Tyr Asp Ala Phe Met Lys Ile
                850                 855                 860

Tyr Lys Lys Asp Lys Ser Lys Phe Leu Met Tyr Arg His Asp Pro Gln
865                 870                 875                 880

Thr Phe Glu Lys Val Ile Glu Pro Ile Leu Glu Asn Tyr Pro Asn Lys
                885                 890                 895

Gln Ile Asn Glu Lys Gly Lys Glu Val Pro Cys Asn Pro Phe Leu Lys
```

Tyr Lys Glu Glu His Gly Tyr Ile Arg Lys Tyr Ser Lys Lys Gly Asn
            900                 905                 910

Gly Pro Glu Ile Lys Ser Leu Lys Tyr Tyr Asp Ser Lys Leu Gly Asn
        915                 920                 925

His Ile Asp Ile Thr Pro Lys Asp Ser Asn Asn Lys Val Val Leu Gln
945                 950                 955                 960

Ser Val Ser Pro Trp Arg Ala Asp Val Tyr Phe Asn Lys Thr Thr Gly
                965                 970                 975

Lys Tyr Glu Ile Leu Gly Leu Lys Tyr Ala Asp Leu Gln Phe Glu Lys
            980                 985                 990

Gly Thr Gly Thr Tyr Lys Ile Ser Gln Glu Lys Tyr Asn Asp Ile Lys
        995                 1000                1005

Lys Lys Glu Gly Val Asp Ser Asp Ser Glu Phe Lys Phe Thr Leu
    1010                1015                1020

Tyr Lys Asn Asp Leu Leu Leu Val Lys Asp Thr Glu Thr Lys Glu
    1025                1030                1035

Gln Gln Leu Phe Arg Phe Leu Ser Arg Thr Met Pro Lys Gln Lys
    1040                1045                1050

His Tyr Val Glu Leu Lys Pro Tyr Asp Lys Gln Lys Phe Glu Gly
    1055                1060                1065

Gly Glu Ala Leu Ile Lys Val Leu Gly Asn Val Ala Asn Ser Gly
    1070                1075                1080

Gln Cys Lys Lys Gly Leu Gly Lys Ser Asn Ile Ser Ile Tyr Lys
    1085                1090                1095

Val Arg Thr Asp Val Leu Gly Asn Gln His Ile Ile Lys Asn Glu
    1100                1105                1110

Gly Asp Lys Pro Lys Leu Asp Phe
    1115                1120

<210> SEQ ID NO 25
<211> LENGTH: 1053
<212> TYPE: PRT
<213> ORGANISM: Artificial Sequence
<220> FEATURE:
<223> OTHER INFORMATION: SaCas9

<400> SEQUENCE: 25

Met Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
            20                  25                  30

Val Arg Leu Phe Lys Glu Ala Asn Val Glu Asn Asn Glu Gly Arg Arg
        35                  40                  45

Ser Lys Arg Gly Ala Arg Arg Leu Lys Arg Arg Arg His Arg Ile
    50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala

```
            130                 135                 140
Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
        195                 200                 205

Arg Thr Tyr Tyr Glu Gly Pro Gly Glu Gly Ser Pro Phe Gly Trp Lys
    210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
        275                 280                 285

Lys Gln Lys Lys Lys Pro Thr Leu Lys Gln Ile Ala Lys Glu Ile Leu
    290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
            340                 345                 350

Lys Ile Leu Thr Ile Tyr Gln Ser Ser Glu Asp Ile Gln Glu Glu Leu
        355                 360                 365

Thr Asn Leu Asn Ser Glu Leu Thr Gln Glu Glu Ile Glu Gln Ile Ser
    370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                405                 410                 415

Ile Phe Asn Arg Leu Lys Leu Val Pro Lys Lys Val Asp Leu Ser Gln
            420                 425                 430

Gln Lys Glu Ile Pro Thr Thr Leu Val Asp Asp Phe Ile Leu Ser Pro
        435                 440                 445

Val Val Lys Arg Ser Phe Ile Gln Ser Ile Lys Val Ile Asn Ala Ile
    450                 455                 460

Ile Lys Lys Tyr Gly Leu Pro Asn Asp Ile Ile Ile Glu Leu Ala Arg
465                 470                 475                 480

Glu Lys Asn Ser Lys Asp Ala Gln Lys Met Ile Asn Glu Met Gln Lys
                485                 490                 495

Arg Asn Arg Gln Thr Asn Glu Arg Ile Glu Glu Ile Ile Arg Thr Thr
            500                 505                 510

Gly Lys Glu Asn Ala Lys Tyr Leu Ile Glu Lys Ile Lys Leu His Asp
        515                 520                 525

Met Gln Glu Gly Lys Cys Leu Tyr Ser Leu Glu Ala Ile Pro Leu Glu
    530                 535                 540

Asp Leu Leu Asn Asn Pro Phe Asn Tyr Glu Val Asp His Ile Ile Pro
545                 550                 555                 560
```

```
Arg Ser Val Ser Phe Asp Asn Ser Phe Asn Asn Lys Val Leu Val Lys
            565                 570                 575

Gln Glu Glu Asn Ser Lys Lys Gly Asn Arg Thr Pro Phe Gln Tyr Leu
            580                 585                 590

Ser Ser Ser Asp Ser Lys Ile Ser Tyr Glu Thr Phe Lys Lys His Ile
            595                 600                 605

Leu Asn Leu Ala Lys Gly Lys Gly Arg Ile Ser Lys Thr Lys Lys Glu
            610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
            645                 650                 655

Met Asn Leu Leu Arg Ser Tyr Phe Arg Val Asn Asn Leu Asp Val Lys
            660                 665                 670

Val Lys Ser Ile Asn Gly Gly Phe Thr Ser Phe Leu Arg Arg Lys Trp
            675                 680                 685

Lys Phe Lys Lys Glu Arg Asn Lys Gly Tyr Lys His His Ala Glu Asp
            690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
            725                 730                 735

Gln Ala Glu Ser Met Pro Glu Ile Glu Thr Glu Gln Glu Tyr Lys Glu
            740                 745                 750

Ile Phe Ile Thr Pro His Gln Ile Lys His Ile Lys Asp Phe Lys Asp
            755                 760                 765

Tyr Lys Tyr Ser His Arg Val Asp Lys Lys Pro Asn Arg Glu Leu Ile
770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
            805                 810                 815

Lys Lys Leu Ile Asn Lys Ser Pro Glu Lys Leu Leu Met Tyr His His
            820                 825                 830

Asp Pro Gln Thr Tyr Gln Lys Leu Lys Leu Ile Met Glu Gln Tyr Gly
            835                 840                 845

Asp Glu Lys Asn Pro Leu Tyr Lys Tyr Tyr Glu Glu Thr Gly Asn Tyr
850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
            885                 890                 895

Tyr Pro Asn Ser Arg Asn Lys Val Val Lys Leu Ser Leu Lys Pro Tyr
            900                 905                 910

Arg Phe Asp Val Tyr Leu Asp Asn Gly Val Tyr Lys Phe Val Thr Val
            915                 920                 925

Lys Asn Leu Asp Val Ile Lys Lys Glu Asn Tyr Glu Val Asn Ser
            930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
            965                 970                 975
```

Glu Leu Tyr Arg Val Ile Gly Val Asn Asn Asp Leu Leu Asn Arg Ile
            980                 985                 990

Glu Val Asn Met Ile Asp Ile Thr Tyr Arg Glu Tyr Leu Glu Asn Met
        995                 1000                1005

Asn Asp Lys Arg Pro Pro Arg Ile Ile Lys Thr Ile Ala Ser Lys
    1010                1015                1020

Thr Gln Ser Ile Lys Lys Tyr Ser Thr Asp Ile Leu Gly Asn Leu
    1025                1030                1035

Tyr Glu Val Lys Ser Lys Lys His Pro Gln Ile Ile Lys Lys Gly
    1040                1045                1050

<210> SEQ ID NO 26
<211> LENGTH: 704
<212> TYPE: DNA
<213> ORGANISM: Artificial Sequence
<220> FEATURE:
<223> OTHER INFORMATION: frame-shift version of mNeonGreen

<400> SEQUENCE: 26
atggtgagca agggcgagga ggataacatg cctctctcc cagcgacaca tgagttacac      60
atctttggct ccatcaacgg tgtggacttt gacatggtgg gtcagggcac cggcaatcca     120
aatgatggtt atgaggagtt aaacctgaag tccaccaagg gtgacctcca gttctccccc    180
tggattctgg tccctcatat cgggtatggc ttccatcagt acctgcccta ccctgacggg     240
atgtcgcctt ccaggccgc catggtagat ggctccggat accaagtcca tcgcacaatg      300
cagtttgaag atggtgcctc ccttactgtt aactaccgct acacctacga ggaagccac     360 atcaaaggag aggcccaggt gaaggggact ggtttccctg ctgacggtcc tgtgatgacc     420
aactcgctga ccgctgcgga cgcaggtcga agaagactta ccccaacgac aaaaccatca    480
tcagtacctt taagtggagt acaccactg gaaatggcaa gcgctaccgg agcactgcgc      540
ggaccaccta ccctttgcc aagccaatgg cggctaacta tctgaagaac cagccgatgt      600
acgtgttccg taagacggag ctcaagcact ccaagaccga gctcaacttc aaggagtggc     660
aaaaggcctt taccgatgtg atgggcatgg acgagctgta caag                     704

<210> SEQ ID NO 27
<211> LENGTH: 708
<212> TYPE: DNA
<213> ORGANISM: Artificial Sequence
<220> FEATURE:
<223> OTHER INFORMATION: Coding region of mNeonGreen

<400> SEQUENCE: 27
atggtgagca agggcgagga ggataacatg gcctctctcc cagcgacaca tgagttacac      60
atctttggct ccatcaacgg tgtggacttt gacatggtgg gtcagggcac cggcaatcca     120
aatgatggtt atgaggagtt aaacctgaag tccaccaagg gtgacctcca gttctccccc    180
tggattctgg tccctcatat cgggtatggc ttccatcagt acctgcccta ccctgacggg     240
atgtcgcctt ccaggccgc catggtagat ggctccggat accaagtcca tcgcacaatg      300
cagtttgaag atggtgcctc ccttactgtt aactaccgct acacctacga ggaagccac     360 atcaaaggag aggcccaggt gaaggggact ggtttccctg ctgacggtcc tgtgatgacc     420
aactcgctga ccgctgcgga ctggtgcagg tcgaagaaga cttaccccaa cgacaaaacc    480
atcatcagta cctttaagtg gagttacacc actggaaatg gcaagcgcta ccggagcact    540
gcgcggacca cctacacctt tgccaagcca atggcggcta actatctgaa gaaccagccg    600

```
atgtacgtgt tccgtaagac ggagctcaag cactccaaga ccgagctcaa cttcaaggag    660
tggcaaaagg cctttaccga tgtgatgggc atggacgagc tgtacaag              708
```

<210> SEQ ID NO 28
<211> LENGTH: 236
<212> TYPE: PRT
<213> ORGANISM: Artificial Sequence
<220> FEATURE:
<223> OTHER INFORMATION: mNeon Green

<400> SEQUENCE: 28

```
Met Val Ser Lys Gly Glu Glu Asp Asn Met Ala Ser Leu Pro Ala Thr
1               5                   10                  15

His Glu Leu His Ile Phe Gly Ser Ile Asn Gly Val Asp Phe Asp Met
            20                  25                  30

Val Gly Gln Gly Thr Gly Asn Pro Asn Asp Gly Tyr Glu Glu Leu Asn
        35                  40                  45

Leu Lys Ser Thr Lys Gly Asp Leu Gln Phe Ser Pro Trp Ile Leu Val
    50                  55                  60

Pro His Ile Gly Tyr Gly Phe His Gln Tyr Leu Pro Tyr Pro Asp Gly
65                  70                  75                  80

Met Ser Pro Phe Gln Ala Ala Met Val Asp Gly Ser Gly Tyr Gln Val
                85                  90                  95

His Arg Thr Met Gln Phe Glu Asp Gly Ala Ser Leu Thr Val Asn Tyr
            100                 105                 110

Arg Tyr Thr Tyr Glu Gly Ser His Ile Lys Gly Glu Ala Gln Val Lys
        115                 120                 125

Gly Thr Gly Phe Pro Ala Asp Gly Pro Val Met Thr Asn Ser Leu Thr
    130                 135                 140

Ala Ala Asp Trp Cys Arg Ser Lys Lys Thr Tyr Pro Asn Asp Lys Thr
145                 150                 155                 160

Ile Ile Ser Thr Phe Lys Trp Ser Tyr Thr Thr Gly Asn Gly Lys Arg
                165                 170                 175

Tyr Arg Ser Thr Ala Arg Thr Thr Tyr Thr Phe Ala Lys Pro Met Ala
            180                 185                 190

Ala Asn Tyr Leu Lys Asn Gln Pro Met Tyr Val Phe Arg Lys Thr Glu
        195                 200                 205

Leu Lys His Ser Lys Thr Glu Leu Asn Phe Lys Glu Trp Gln Lys Ala
    210                 215                 220

Phe Thr Asp Val Met Gly Met Asp Glu Leu Tyr Lys
225                 230                 235
```

<210> SEQ ID NO 29
<211> LENGTH: 704
<212> TYPE: DNA
<213> ORGANISM: Artificial Sequence
<220> FEATURE:
<223> OTHER INFORMATION: mutated coding region of mNeonGreen

<400> SEQUENCE: 29

```
atggtgagca agggcgagga ggataacatg gcctctctcc cagcgacaca tgagttacac    60
atctttggct ccatcaacgg tgtggacttt gacatggtgg tcagggcac cggcaatcca    120 aatgatggtt atgaggagtt aaacctgaag tccaccaagg gtgacctcca gttctccccc    180
tggattctgg tccctcatat cgggtatggc ttccatcagt acctgcccta ccctgacggg    240
atgtcgcctt tccaggccgc catggtagat ggctccggat accaagtcca tcgcacaatg    300
```

```
cagtttgaag atggtgcctc ccttactgtt aactaccgct acacctacga gggaagccac    360
atcaaaggag aggcccaggt gaagggggact ggtttccctg ctgacggtcc tgtgatgacc   420
aactcgctga ccgctgcgga cgcaggtcga agaagactta ccccaacgac aaaaccatca    480
tcagtaccct taagtggagt tacaccactg gaaatggcaa cgctaccgg agcactgcgc     540 ggaccaccta cacctttgcc aagccaatgg cggctaacta tctgaagaac cagccgatgt    600
acgtgttccg taagacggag ctcaagcact ccaagaccga gctcaacttc aaggagtggc    660
aaaaggcctt taccgatgtg atgggcatgg acgagctgta caag                     704
```

<210> SEQ ID NO 30
<211> LENGTH: 105
<212> TYPE: DNA
<213> ORGANISM: Artificial Sequence
<220> FEATURE:
<223> OTHER INFORMATION: Donor template NSFS-R

<400> SEQUENCE: 30

```
ggtttccctg ctgacggtcc tgtgatgacc aactcgctga ccgctgcgga ctggtgcagg    60
tcgaagaaga cttaccccaa cgacaaaacc atcatcagta ccttt                    105
```

<210> SEQ ID NO 31
<211> LENGTH: 237
<212> TYPE: PRT
<213> ORGANISM: Artificial Sequence
<220> FEATURE:
<223> OTHER INFORMATION: mRuby2

<400> SEQUENCE: 31

```
Met Val Ser Lys Gly Glu Glu Leu Ile Lys Glu Asn Met Arg Met Lys
1               5                   10                  15

Val Val Met Glu Gly Ser Val Asn Gly His Gln Phe Lys Cys Thr Gly
            20                  25                  30

Glu Gly Glu Gly Asn Pro Tyr Met Gly Thr Gln Thr Met Arg Ile Lys
        35                  40                  45

Val Ile Glu Gly Gly Pro Leu Pro Phe Ala Phe Asp Ile Leu Ala Thr
    50                  55                  60

Ser Phe Met Tyr Gly Ser Arg Thr Phe Ile Lys Tyr Pro Lys Gly Ile
65                  70                  75                  80

Pro Asp Phe Phe Lys Gln Ser Phe Pro Glu Gly Phe Thr Trp Glu Arg
                85                  90                  95

Val Thr Arg Tyr Glu Asp Gly Gly Val Val Thr Val Met Gln Asp Thr
            100                 105                 110

Ser Leu Glu Asp Gly Cys Leu Val Tyr His Val Gln Val Arg Gly Val
        115                 120                 125

Asn Phe Pro Ser Asn Gly Pro Val Met Gln Lys Lys Thr Lys Gly Trp
    130                 135                 140

Glu Pro Asn Thr Glu Met Met Tyr Pro Ala Asp Gly Gly Leu Arg Gly
145                 150                 155                 160

Tyr Thr His Met Ala Leu Lys Val Asp Gly Gly His Leu Ser Cys
                165                 170                 175

Ser Phe Val Thr Thr Tyr Arg Ser Lys Lys Thr Val Gly Asn Ile Lys
            180                 185                 190

Met Pro Gly Ile His Ala Val Asp His Arg Leu Glu Arg Leu Glu Glu
        195                 200                 205

Ser Asp Asn Glu Met Phe Val Val Gln Arg Glu His Ala Val Ala Lys
    210                 215                 220
```

```
Phe Ala Gly Leu Gly Gly Gly Met Asp Glu Leu Tyr Lys
225                 230                 235

<210> SEQ ID NO 32
<211> LENGTH: 199
<212> TYPE: PRT
<213> ORGANISM: Artificial Sequence
<220> FEATURE:
<223> OTHER INFORMATION: Puromycin Resistance gene

<400> SEQUENCE: 32

Met Thr Glu Tyr Lys Pro Thr Val Arg Leu Ala Thr Arg Asp Asp Val
1               5                   10                  15

Pro Arg Ala Val Arg Thr Leu Ala Ala Ala Phe Ala Asp Tyr Pro Ala
            20                  25                  30

Thr Arg His Thr Val Asp Pro Asp Arg His Ile Glu Arg Val Thr Glu
        35                  40                  45

Leu Gln Glu Leu Phe Leu Thr Arg Val Gly Leu Asp Ile Gly Lys Val
    50                  55                  60

Trp Val Ala Asp Asp Gly Ala Ala Val Ala Val Trp Thr Thr Pro Glu
65                  70                  75                  80

Ser Val Glu Ala Gly Ala Val Phe Ala Glu Ile Gly Pro Arg Met Ala
                85                  90                  95

Glu Leu Ser Gly Ser Arg Leu Ala Ala Gln Gln Gln Met Glu Gly Leu
            100                 105                 110

Leu Ala Pro His Arg Pro Lys Glu Pro Ala Trp Phe Leu Ala Thr Val
        115                 120                 125

Gly Val Ser Pro Asp His Gln Gly Lys Gly Leu Gly Ser Ala Val Val
    130                 135                 140

Leu Pro Gly Val Glu Ala Ala Glu Arg Ala Gly Val Pro Ala Phe Leu
145                 150                 155                 160

Glu Thr Ser Ala Pro Arg Asn Leu Pro Phe Tyr Glu Arg Leu Gly Phe
                165                 170                 175

Thr Val Thr Ala Asp Val Glu Val Pro Glu Gly Pro Arg Thr Trp Cys
            180                 185                 190

Met Thr Arg Lys Pro Gly Ala
        195

<210> SEQ ID NO 33
<211> LENGTH: 109
<212> TYPE: DNA
<213> ORGANISM: Artificial Sequence
<220> FEATURE:
<223> OTHER INFORMATION: Oligonucleotide for codon diversifaction of the
      mRuby2 Chormophore Region
<220> FEATURE:
<221> NAME/KEY: unsure
<222> LOCATION: (52)..(53)
<223> OTHER INFORMATION: /note="n = any nucleic acid"
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: unsure
<222> LOCATION: (55)..(56)
<223> OTHER INFORMATION: /note="n = any nucleic acid"
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: unsure
```

```
<222> LOCATION: (58)..(59)
<223> OTHER INFORMATION: /note="n = any nucleic acid"
<220> FEATURE:
<221> NAME/KEY: misc_feature
<222> LOCATION: (58)..(59)
<223> OTHER INFORMATION: n is a, c, g, or t

<400> SEQUENCE: 33
tgtttaaaga aatcaggaat gcctttcggg tacttgataa aagtacggct vnnvnnvnng    60
aacgacgtgg caagaatgtc aaaggcaaat ggcaggggtc ctccctcga              109

<210> SEQ ID NO 34
<211> LENGTH: 117
<212> TYPE: DNA
<213> ORGANISM: Artificial Sequence
<220> FEATURE:
<223> OTHER INFORMATION: Oligo used for inducing a frame-shift near the
      chromophore region of mRuby2

<400> SEQUENCE: 34
agtcatcgag ggaggacccc tgccatttgc ctttgacatt cttgccacgt cgttcgtatg    60
gcagccgtac ttttatcaag tacccgaaag gcattcctga tttctttaaa cagtcct     117

<210> SEQ ID NO 35
<211> LENGTH: 21
<212> TYPE: PRT
<213> ORGANISM: Artificial Sequence
<220> FEATURE:
<223> OTHER INFORMATION: Gene specific primer for RT PCR

<400> SEQUENCE: 35

Cys Thr Thr Gly Thr Ala Cys Ala Gly Cys Thr Cys Gly Thr Cys Cys
1               5                   10                  15

Ala Thr Cys Cys Cys
            20

<210> SEQ ID NO 36
<211> LENGTH: 42
<212> TYPE: DNA
<213> ORGANISM: Artificial Sequence
<220> FEATURE:
<223> OTHER INFORMATION: Deep sequencing primer 1

<400> SEQUENCE: 36
tacacgacgc tcttccgatc tatgcacagg tgaaggagaa gg                      42

<210> SEQ ID NO 37
<211> LENGTH: 42
<212> TYPE: DNA
<213> ORGANISM: Artificial Sequence
<220> FEATURE:
<223> OTHER INFORMATION: Deep sequencing primer 2

<400> SEQUENCE: 37
cagacgtgtg ctcttccgat cctccaccat cttcgtatct cg                      42

<210> SEQ ID NO 38
<211> LENGTH: 41
<212> TYPE: DNA
<213> ORGANISM: Artificial Sequence
<220> FEATURE:
<223> OTHER INFORMATION: Forward primer to extract the coding domains of
      the repaired mNeonGreen

<400> SEQUENCE: 38
```
ataaggatcc ggccaccatg gtgagcaagg gcgaggagga t        41

<210> SEQ ID NO 39
<211> LENGTH: 42
<212> TYPE: DNA
<213> ORGANISM: Artificial Sequence
<220> FEATURE:
<223> OTHER INFORMATION: Reverse primer to extract the coding domains of
      the repaired mNeonGreen

<400> SEQUENCE: 39
tataggaatt cctattatca cttgtacagc tcgtccatgc cc        42

<210> SEQ ID NO 40
<211> LENGTH: 31
<212> TYPE: DNA
<213> ORGANISM: Artificial Sequence
<220> FEATURE:
<223> OTHER INFORMATION: Frame-Shifting Primer for PCR Mutagenesis, 1.F

<400> SEQUENCE: 40
ctttaagtgg acaccactgg aaatggcaag c        31

<210> SEQ ID NO 41
<211> LENGTH: 38
<212> TYPE: DNA
<213> ORGANISM: Artificial Sequence
<220> FEATURE:
<223> OTHER INFORMATION: Frame-Shifting Primer for PCR Mutagenesis, 1.R

<400> SEQUENCE: 41
ccagtggtgt ccacttaaag gtactgatga tggttttg        38

<210> SEQ ID NO 42
<211> LENGTH: 35
<212> TYPE: DNA
<213> ORGANISM: Artificial Sequence
<220> FEATURE:
<223> OTHER INFORMATION: Frame Shifting Primer for PCR Mutagenesis, 2.F

<400> SEQUENCE: 42
ctggtgcagg agaagactta ccccaacgac aaaac        35

<210> SEQ ID NO 43
<211> LENGTH: 28
<212> TYPE: DNA
<213> ORGANISM: Artificial Sequence
<220> FEATURE:
<223> OTHER INFORMATION: Frame-Shifting Primer for PCR Mutagenesis, 2.R

<400> SEQUENCE: 43
taagtcttct cctgcaccag tccgcagc        28

<210> SEQ ID NO 44
<211> LENGTH: 30
<212> TYPE: DNA
<213> ORGANISM: Artificial Sequence
<220> FEATURE:
<223> OTHER INFORMATION: Frame-Shifting Primer for PCR Mutagenesis, 3.F

<400> SEQUENCE: 44
caggtgaagg tggtttccct gctgacggtc        30

<210> SEQ ID NO 45
<211> LENGTH: 29
<212> TYPE: DNA

```
<213> ORGANISM: Artificial Sequence
<220> FEATURE:
<223> OTHER INFORMATION: Frame-Shifting Primer for PCR Mutagenesis, 3.R

<400> SEQUENCE: 45
agggaaacca ccttcacctg ggcctctcc                                29

<210> SEQ ID NO 46
<211> LENGTH: 34
<212> TYPE: DNA
<213> ORGANISM: Artificial Sequence
<220> FEATURE:
<223> OTHER INFORMATION: Frame-Shifting Primer for PCR Mutagenesis, 4.F

<400> SEQUENCE: 46
tcgggtatgg catcagtacc tgccctaccc tgac                          34

<210> SEQ ID NO 47
<211> LENGTH: 33
<212> TYPE: DNA
<213> ORGANISM: Artificial Sequence
<220> FEATURE:
<223> OTHER INFORMATION: Frame-Shifting Primer for PCR Mutagenesis, 4.R

<400> SEQUENCE: 47
ggtactgatg ccatacccga tatgagggac cag                           33

<210> SEQ ID NO 48
<211> LENGTH: 25
<212> TYPE: DNA
<213> ORGANISM: Artificial Sequence
<220> FEATURE:
<223> OTHER INFORMATION: Frame-Shifting Primer for PCR Mutagenesis, 5.F

<400> SEQUENCE: 48
gtccgcagcg gtcagcgagt tggtc                                    25

<210> SEQ ID NO 49
<211> LENGTH: 26
<212> TYPE: DNA
<213> ORGANISM: Artificial Sequence
<220> FEATURE:
<223> OTHER INFORMATION: Frame-Shifting Primer for PCR Mutagenesis, 5.R

<400> SEQUENCE: 49
gcaaccgtaa agttcaagta caaagg                                   26

<210> SEQ ID NO 50
<211> LENGTH: 6
<212> TYPE: PRT
<213> ORGANISM: Artificial Sequence
<220> FEATURE:
<223> OTHER INFORMATION: PAM sequence for SaCas9

<400> SEQUENCE: 50

Asn Asn Gly Arg Arg Thr
1               5

<210> SEQ ID NO 51
<211> LENGTH: 6
<212> TYPE: PRT
<213> ORGANISM: Artificial Sequence
<220> FEATURE:
<223> OTHER INFORMATION: PAM sequence for SaCas9

<400> SEQUENCE: 51
```

Asn Asn Gly Arg Arg Asn
1               5

<210> SEQ ID NO 52
<211> LENGTH: 7
<212> TYPE: PRT
<213> ORGANISM: Artificial Sequence
<220> FEATURE:
<223> OTHER INFORMATION: PAM sequence for St1Cas9

<400> SEQUENCE: 52

Asn Asn Ala Gly Ala Ala Trp
1               5

<210> SEQ ID NO 53
<211> LENGTH: 39
<212> TYPE: DNA
<213> ORGANISM: Artificial Sequence
<220> FEATURE:
<223> OTHER INFORMATION: DNA sequence of mNeonGreen variant

<400> SEQUENCE: 53
tcgctgaccg ctgcgggcag tcgcaggtcg aagaagact                           39

<210> SEQ ID NO 54
<211> LENGTH: 13
<212> TYPE: PRT
<213> ORGANISM: Artificial Sequence
<220> FEATURE:
<223> OTHER INFORMATION: translated protein sequence of mNeonGreen
      variant

<400> SEQUENCE: 54

Ser Leu Thr Ala Ala Gly Ser Arg Arg Ser Lys Lys Thr
1               5                   10

<210> SEQ ID NO 55
<211> LENGTH: 39
<212> TYPE: DNA
<213> ORGANISM: Artificial Sequence
<220> FEATURE:
<223> OTHER INFORMATION: DNA sequence of mNeonGreen variant

<400> SEQUENCE: 55
tcgctgaccg ctgcgagtgt gtccaggtcg aagaagact                           39

<210> SEQ ID NO 56
<211> LENGTH: 13
<212> TYPE: PRT
<213> ORGANISM: Artificial Sequence
<220> FEATURE:
<223> OTHER INFORMATION: translated protein sequence of mNeonGreen
      variant

<400> SEQUENCE: 56

Ser Leu Thr Ala Ala Ser Val Ser Arg Ser Lys Lys Thr
1               5                   10

<210> SEQ ID NO 57
<211> LENGTH: 39
<212> TYPE: DNA
<213> ORGANISM: Artificial Sequence
<220> FEATURE:
<223> OTHER INFORMATION: DNA sequence of mNeonGreen variant

<400> SEQUENCE: 57
tcgctgaccg ctgcggggtg ttgtaggtcg aagaagact                           39

<210> SEQ ID NO 58
<211> LENGTH: 13
<212> TYPE: PRT
<213> ORGANISM: Artificial Sequence
<220> FEATURE:
<223> OTHER INFORMATION: translated protein sequence of mNeonGreen variant

<400> SEQUENCE: 58

Ser Leu Thr Ala Ala Gly Cys Cys Arg Ser Lys Lys Thr
1               5                   10

<210> SEQ ID NO 59
<211> LENGTH: 39
<212> TYPE: DNA
<213> ORGANISM: Artificial Sequence
<220> FEATURE:
<223> OTHER INFORMATION: DNA sequence of mNeonGreen variant

<400> SEQUENCE: 59
tcgctgaccg ctgcgatgat gggcaggtcg aagaagact                          39

<210> SEQ ID NO 60
<211> LENGTH: 13
<212> TYPE: PRT
<213> ORGANISM: Artificial Sequence
<220> FEATURE:
<223> OTHER INFORMATION: translated protein sequence of mNeonGreen variant

<400> SEQUENCE: 60

Ser Leu Thr Ala Ala Met Met Gly Arg Ser Lys Lys Thr
1               5                   10

<210> SEQ ID NO 61
<211> LENGTH: 39
<212> TYPE: DNA
<213> ORGANISM: Artificial Sequence
<220> FEATURE:
<223> OTHER INFORMATION: DNA sequence of mNeonGreen variant

<400> SEQUENCE: 61
tcgctgaccg ctgcgtgtgt ctcgaggtcg aagaagact                          39

<210> SEQ ID NO 62
<211> LENGTH: 13
<212> TYPE: PRT
<213> ORGANISM: Artificial Sequence
<220> FEATURE:
<223> OTHER INFORMATION: translated protein sequence of mNeonGreen variant

<400> SEQUENCE: 62

Ser Leu Thr Ala Ala Cys Val Ser Arg Ser Lys Lys Thr
1               5                   10

<210> SEQ ID NO 63
<211> LENGTH: 39
<212> TYPE: DNA
<213> ORGANISM: Artificial Sequence
<220> FEATURE:
<223> OTHER INFORMATION: DNA sequence of mNeonGreen variant

<400> SEQUENCE: 63
tcgctgaccg ctgcgggcgc caccaggtcg aagaagact                          39

```
<210> SEQ ID NO 64
<211> LENGTH: 13
<212> TYPE: PRT
<213> ORGANISM: Artificial Sequence
<220> FEATURE:
<223> OTHER INFORMATION: translated protein sequence of mNeonGreen
      variant

<400> SEQUENCE: 64

Ser Leu Thr Ala Ala Gly Ala Thr Arg Ser Lys Lys Thr
1               5                   10

<210> SEQ ID NO 65
<211> LENGTH: 39
<212> TYPE: DNA
<213> ORGANISM: Artificial Sequence
<220> FEATURE:
<223> OTHER INFORMATION: DNA sequence of mNeonGreen variant

<400> SEQUENCE: 65
tcgctgaccg ctgcgaagtt ctctaggtcg aagaagact                              39

<210> SEQ ID NO 66
<211> LENGTH: 13
<212> TYPE: PRT
<213> ORGANISM: Artificial Sequence
<220> FEATURE:
<223> OTHER INFORMATION: translated protein sequence of mNeonGreen
      variant

<400> SEQUENCE: 66

Ser Leu Thr Ala Ala Lys Phe Ser Arg Ser Lys Lys Thr
1               5                   10

<210> SEQ ID NO 67
<211> LENGTH: 39
<212> TYPE: DNA
<213> ORGANISM: Artificial Sequence
<220> FEATURE:
<223> OTHER INFORMATION: DNA sequence of mNeonGreen variant

<400> SEQUENCE: 67
tcgctgaccg ctgcgtcgct tatgaggtcg aagaagact                              39

<210> SEQ ID NO 68
<211> LENGTH: 13
<212> TYPE: PRT
<213> ORGANISM: Artificial Sequence
<220> FEATURE:
<223> OTHER INFORMATION: translated protein sequence of mNeonGreen
      variant

<400> SEQUENCE: 68

Ser Leu Thr Ala Ala Ser Leu Met Arg Ser Lys Lys Thr
1               5                   10

<210> SEQ ID NO 69
<211> LENGTH: 39
<212> TYPE: DNA
<213> ORGANISM: Artificial Sequence
<220> FEATURE:
<223> OTHER INFORMATION: DNA sequence of mNeonGreen variant

<400> SEQUENCE: 69
tcgctgaccg ctgcgagtaa gcgcaggtcg aagaagact                              39
```

```
<210> SEQ ID NO 70
<211> LENGTH: 13
<212> TYPE: PRT
<213> ORGANISM: Artificial Sequence
<220> FEATURE:
<223> OTHER INFORMATION: translated protein sequence of mNeonGreen
      variant

<400> SEQUENCE: 70

Ser Leu Thr Ala Ala Ser Lys Arg Arg Ser Lys Lys Thr
1               5                   10

<210> SEQ ID NO 71
<211> LENGTH: 39
<212> TYPE: DNA
<213> ORGANISM: Artificial Sequence
<220> FEATURE:
<223> OTHER INFORMATION: DNA sequence of mNeonGreen variant

<400> SEQUENCE: 71
tcgctgaccg ctgcgcaggc tactaggtcg aagaagact                    39

<210> SEQ ID NO 72
<211> LENGTH: 13
<212> TYPE: PRT
<213> ORGANISM: Artificial Sequence
<220> FEATURE:
<223> OTHER INFORMATION: translated protein sequence of mNeonGreen
      variant

<400> SEQUENCE: 72

Ser Leu Thr Ala Ala Gln Ala Thr Arg Ser Lys Lys Thr
1               5                   10

<210> SEQ ID NO 73
<211> LENGTH: 39
<212> TYPE: DNA
<213> ORGANISM: Artificial Sequence
<220> FEATURE:
<223> OTHER INFORMATION: DNA sequence of mNeonGreen variant

<400> SEQUENCE: 73
tcgctgaccg ctgcgtgcgt gtgtaggtcg aagaagact                    39

<210> SEQ ID NO 74
<211> LENGTH: 13
<212> TYPE: PRT
<213> ORGANISM: Artificial Sequence
<220> FEATURE:
<223> OTHER INFORMATION: translated protein sequence of mNeonGreen
      variant

<400> SEQUENCE: 74

Ser Leu Thr Ala Ala Cys Val Cys Arg Ser Lys Lys Thr
1               5                   10

<210> SEQ ID NO 75
<211> LENGTH: 39
<212> TYPE: DNA
<213> ORGANISM: Artificial Sequence
<220> FEATURE:
<223> OTHER INFORMATION: DNA sequence of mNeonGreen variant

<400> SEQUENCE: 75
tcgctgaccg ctgcgcggat ggggaggtcg aagaagact                    39

<210> SEQ ID NO 76
```

```
<211> LENGTH: 13
<212> TYPE: PRT
<213> ORGANISM: Artificial Sequence
<220> FEATURE:
<223> OTHER INFORMATION: translated protein sequence of mNeonGreen
      variant

<400> SEQUENCE: 76

Ser Leu Thr Ala Ala Arg Met Gly Arg Ser Lys Lys Thr
1               5                   10

<210> SEQ ID NO 77
<211> LENGTH: 39
<212> TYPE: DNA
<213> ORGANISM: Artificial Sequence
<220> FEATURE:
<223> OTHER INFORMATION: DNA sequence of mNeonGreen variant

<400> SEQUENCE: 77
tcgctgaccg ctgcgatttg gacgaggtcg aagaagact                              39

<210> SEQ ID NO 78
<211> LENGTH: 13
<212> TYPE: PRT
<213> ORGANISM: Artificial Sequence
<220> FEATURE:
<223> OTHER INFORMATION: translated protein sequence of mNeonGreen
      variant

<400> SEQUENCE: 78

Ser Leu Thr Ala Ala Ile Trp Thr Arg Ser Lys Lys Thr
1               5                   10

<210> SEQ ID NO 79
<211> LENGTH: 219
<212> TYPE: PRT
<213> ORGANISM: Artificial Sequence
<220> FEATURE:
<223> OTHER INFORMATION: LanYFP

<400> SEQUENCE: 79

Met Ser Leu Pro Ala Thr His Glu Leu His Ile Phe Gly Ser Phe Asn
1               5                   10                  15

Gly Val Asp Phe Asp Met Val Gly Arg Gly Thr Gly Asn Pro Asn Asp
                20                  25                  30

Gly Tyr Glu Glu Leu Asn Leu Lys Ser Thr Lys Gly Ala Leu Gln Phe
            35                  40                  45

Ser Pro Trp Ile Leu Val Pro Gln Ile Gly Tyr Gly Phe His Gln Tyr
        50                  55                  60

Leu Pro Phe Pro Asp Gly Met Ser Pro Phe Gln Ala Ala Met Lys Asp
65                  70                  75                  80

Gly Ser Gly Tyr Gln Val His Arg Thr Met Gln Phe Glu Asp Gly Ala
                85                  90                  95

Ser Leu Thr Ser Asn Tyr Arg Tyr Thr Tyr Glu Gly Ser His Ile Lys
            100                 105                 110

Gly Glu Phe Gln Val Ile Gly Thr Gly Phe Pro Ala Asp Gly Pro Val
        115                 120                 125

Met Thr Asn Ser Leu Thr Ala Ala Asp Trp Cys Val Thr Lys Met Leu
130                 135                 140

Tyr Pro Asn Asp Lys Thr Ile Ile Ser Thr Phe Asp Trp Thr Tyr Thr
145                 150                 155                 160

Thr Gly Ser Gly Lys Arg Tyr Gln Ser Thr Val Arg Thr Asn Tyr Thr
```

```
                    165                 170                 175

Phe Ala Lys Pro Met Ala Ala Asn Ile Leu Lys Asn Gln Pro Met Phe
            180                 185                 190

Val Phe Arg Lys Thr Glu Leu Lys His Ser Lys Thr Glu Leu Asn Phe
        195                 200                 205

Lys Glu Trp Gln Lys Ala Phe Thr Asp Val Met
    210                 215

<210> SEQ ID NO 80
<211> LENGTH: 236
<212> TYPE: PRT
<213> ORGANISM: Artificial Sequence
<220> FEATURE:
<223> OTHER INFORMATION: dLanYFP

<400> SEQUENCE: 80

Met Val Ser Lys Gly Glu Glu Asp Asn Met Ala Ser Leu Pro Ala Thr
1               5                   10                  15

His Glu Leu His Ile Phe Gly Ser Phe Asn Gly Val Asp Phe Asp Met
            20                  25                  30

Val Gly Arg Gly Thr Gly Asn Pro Asn Asp Gly Tyr Glu Glu Leu Asn
        35                  40                  45

Leu Lys Ser Thr Lys Gly Asp Leu Gln Phe Ser Pro Trp Ile Leu Val
    50                  55                  60

Pro Gln Ile Gly Tyr Gly Phe His Gln Tyr Leu Pro Phe Pro Asp Gly
65                  70                  75                  80

Met Ser Pro Phe Gln Ala Ala Met Lys Asp Gly Ser Gly Tyr Gln Val
            85                  90                  95

His Arg Thr Met Gln Phe Glu Asp Gly Ala Ser Leu Thr Ser Asn Tyr
            100                 105                 110

Arg Tyr Thr Tyr Glu Gly Ser His Ile Lys Gly Glu Phe Gln Val Lys
        115                 120                 125

Gly Thr Gly Phe Pro Ala Asp Gly Pro Val Met Thr Asn Ser Leu Thr
    130                 135                 140

Ala Ala Asp Trp Cys Val Thr Lys Met Leu Tyr Pro Asn Asp Lys Thr
145                 150                 155                 160

Ile Ile Ser Thr Phe Asp Trp Thr Tyr Thr Thr Gly Asn Gly Lys Arg
            165                 170                 175

Tyr Gln Ser Thr Ala Arg Thr Thr Tyr Thr Phe Ala Lys Pro Met Ala
            180                 185                 190

Ala Asn Ile Leu Lys Asn Gln Pro Met Phe Val Phe Arg Lys Thr Glu
        195                 200                 205

Leu Lys His Ser Lys Thr Glu Leu Asn Phe Lys Glu Trp Gln Lys Ala
    210                 215                 220

Phe Thr Asp Val Met Gly Met Asp Glu Leu Tyr Lys
225                 230                 235

<210> SEQ ID NO 81
<211> LENGTH: 24
<212> TYPE: DNA
<213> ORGANISM: Artificial Sequence
<220> FEATURE:
<223> OTHER INFORMATION: Primer 1.F

<400> SEQUENCE: 81
caccgcatca tcagtacctt taag                                          24
```

```
<210> SEQ ID NO 82
<211> LENGTH: 24
<212> TYPE: DNA
<213> ORGANISM: Artificial Sequence
<220> FEATURE:
<223> OTHER INFORMATION: Primer 1.R

<400> SEQUENCE: 82
aaaccttaaa ggtactgatg atgc                                              24

<210> SEQ ID NO 83
<211> LENGTH: 24
<212> TYPE: DNA
<213> ORGANISM: Artificial Sequence
<220> FEATURE:
<223> OTHER INFORMATION: Primer 2.F

<400> SEQUENCE: 83
gtggcctggc gacgcctgac cacg                                              24

<210> SEQ ID NO 84
<211> LENGTH: 24
<212> TYPE: DNA
<213> ORGANISM: Artificial Sequence
<220> FEATURE:
<223> OTHER INFORMATION: Primer 2.R

<400> SEQUENCE: 84
aaaccgtggt caggcgtcgc cagg                                              24

<210> SEQ ID NO 85
<211> LENGTH: 24
<212> TYPE: DNA
<213> ORGANISM: Artificial Sequence
<220> FEATURE:
<223> OTHER INFORMATION: Primer 3.F

<400> SEQUENCE: 85
caccgaaagg agaggcccag gtga                                              24

<210> SEQ ID NO 86
<211> LENGTH: 24
<212> TYPE: DNA
<213> ORGANISM: Artificial Sequence
<220> FEATURE:
<223> OTHER INFORMATION: Primer 3.R

<400> SEQUENCE: 86
aaactcacct gggcctctcc tttc                                              24

<210> SEQ ID NO 87
<211> LENGTH: 24
<212> TYPE: DNA
<213> ORGANISM: Artificial Sequence
<220> FEATURE:
<223> OTHER INFORMATION: Primer 4.F

<400> SEQUENCE: 87
caccgtggtc cctcatatcg ggta                                              24

<210> SEQ ID NO 88
<211> LENGTH: 24
<212> TYPE: DNA
<213> ORGANISM: Artificial Sequence
<220> FEATURE:
<223> OTHER INFORMATION: Primer 4.R
```

```
<400> SEQUENCE: 88
aaactacccg atatgaggga ccac                                          24

<210> SEQ ID NO 89
<211> LENGTH: 24
<212> TYPE: DNA
<213> ORGANISM: Artificial Sequence
<220> FEATURE:
<223> OTHER INFORMATION: Primer 5.F

<400> SEQUENCE: 89
caccgcgctg accgctgcgg acgc                                          24

<210> SEQ ID NO 90
<211> LENGTH: 24
<212> TYPE: DNA
<213> ORGANISM: Artificial Sequence
<220> FEATURE:
<223> OTHER INFORMATION: Primer 5.R

<400> SEQUENCE: 90
aaacgcgtcc gcagcggtca gcgc                                          24

<210> SEQ ID NO 91
<211> LENGTH: 708
<212> TYPE: DNA
<213> ORGANISM: Artificial Sequence
<220> FEATURE:
<223> OTHER INFORMATION: mNeonGreen2

<400> SEQUENCE: 91
atggtgagca agggcgagga ggataacatg gcctctctcc cagcgacaca tgagttacac    60
atctttggct ccatcaacgg tgtggacttt gacatggtgg gtcagggcac cggcaatcca   120
aatgatggtt atgaggagtt aaacctgaag tccaccaagg gtgacctcca gttctcccca   180
tggattctgg tccctcatat cgggtatggc ttccatcagt acctgcccta ccctgacggg   240
atgtcgcctt ccaggccgc catggtagat ggctccggat accaagtcca tcgcacaatg   300
cagtttgaag atggtgcctc ccttactgtt aactaccgct acacctacga gggaagccac   360
atcaaaggag aggcccaggt gaagggggact ggtttccctg ctgacggtcc tgtgatgacc   420
aactcgctga ccgctgcgga tgcgtgctgg tcgaagaaga cttaccccaa cgacaaaacc   480
atcatcagta cctttaagtg gagttacacc actggaaatg gcaagcgcta ccggagcact   540
gcgcggacca cctacacctt tgccaagcca atggcggcta actatctgaa gaaccagccg   600
atgtacgtgt tccgtaagac ggagctcaag cactccaaga ccgagctcaa cttcaaggag   660
tggcaaaagg cctttaccga tgtgatgggc atggacgagc tgtacaag              708

<210> SEQ ID NO 92
<211> LENGTH: 236
<212> TYPE: PRT
<213> ORGANISM: Artificial Sequence
<220> FEATURE:
<223> OTHER INFORMATION: mNeonGreen2

<400> SEQUENCE: 92

Met Val Ser Lys Gly Glu Glu Asp Asn Met Ala Ser Leu Pro Ala Thr
1               5                   10                  15

His Glu Leu His Ile Phe Gly Ser Ile Asn Gly Val Asp Phe Asp Met
            20                  25                  30

Val Gly Gln Gly Thr Gly Asn Pro Asn Asp Gly Tyr Glu Glu Leu Asn
```

```
                35                  40                  45
Leu Lys Ser Thr Lys Gly Asp Leu Gln Phe Ser Pro Trp Ile Leu Val
 50                  55                  60

Pro His Ile Gly Tyr Gly Phe His Gln Tyr Leu Pro Tyr Pro Asp Gly
 65                  70                  75                  80

Met Ser Pro Phe Gln Ala Ala Met Val Asp Gly Ser Gly Tyr Gln Val
                 85                  90                  95

His Arg Thr Met Gln Phe Glu Asp Gly Ala Ser Leu Thr Val Asn Tyr
            100                 105                 110

Arg Tyr Thr Tyr Glu Gly Ser His Ile Lys Gly Glu Ala Gln Val Lys
        115                 120                 125

Gly Thr Gly Phe Pro Ala Asp Gly Pro Val Met Thr Asn Ser Leu Thr
    130                 135                 140

Ala Ala Asp Ala Cys Trp Ser Lys Lys Thr Tyr Pro Asn Asp Lys Thr
145                 150                 155                 160

Ile Ile Ser Thr Phe Lys Trp Ser Tyr Thr Thr Gly Asn Gly Lys Arg
                165                 170                 175

Tyr Arg Ser Thr Ala Arg Thr Thr Tyr Thr Phe Ala Lys Pro Met Ala
            180                 185                 190

Ala Asn Tyr Leu Lys Asn Gln Pro Met Tyr Val Phe Arg Lys Thr Glu
        195                 200                 205

Leu Lys His Ser Lys Thr Glu Leu Asn Phe Lys Glu Trp Gln Lys Ala
    210                 215                 220

Phe Thr Asp Val Met Gly Met Asp Glu Leu Tyr Lys
225                 230                 235

<210> SEQ ID NO 93
<211> LENGTH: 4
<212> TYPE: PRT
<213> ORGANISM: Artificial Sequence
<220> FEATURE:
<223> OTHER INFORMATION: Amino acid within mNeonGreen2

<400> SEQUENCE: 93

Asp Ala Cys Trp
1

<210> SEQ ID NO 94
<211> LENGTH: 711
<212> TYPE: PRT
<213> ORGANISM: Artificial Sequence
<220> FEATURE:
<223> OTHER INFORMATION: mRuby2-TagBFP2-Puromycin

<400> SEQUENCE: 94

Met Val Ser Lys Gly Glu Glu Leu Ile Lys Glu Asn Met Arg Met Lys
 1               5                  10                  15

Val Val Met Glu Gly Ser Val Asn Gly His Gln Phe Lys Cys Thr Gly
             20                  25                  30

Glu Gly Glu Gly Asn Pro Tyr Met Gly Thr Gln Thr Met Arg Ile Lys
         35                  40                  45

Val Ile Glu Gly Gly Pro Leu Pro Phe Ala Phe Asp Ile Leu Ala Thr
     50                  55                  60

Ser Phe Met Tyr Gly Ser Arg Thr Phe Ile Lys Tyr Pro Lys Gly Ile
 65                  70                  75                  80

Pro Asp Phe Phe Lys Gln Ser Phe Pro Glu Gly Phe Thr Trp Glu Arg
                 85                  90                  95
```

Val Thr Arg Tyr Glu Asp Gly Gly Val Thr Val Met Gln Asp Thr
              100                 105                 110

Ser Leu Glu Asp Gly Cys Leu Val Tyr His Val Gln Val Arg Gly Val
          115                 120                 125

Asn Phe Pro Ser Asn Gly Pro Val Met Gln Lys Lys Thr Lys Gly Trp
      130                 135                 140

Glu Pro Asn Thr Glu Met Met Tyr Pro Ala Asp Gly Gly Leu Arg Gly
145                 150                 155                 160

Tyr Thr His Met Ala Leu Lys Val Asp Gly Gly His Leu Ser Cys
              165                 170                 175

Ser Phe Val Thr Thr Tyr Arg Ser Lys Lys Thr Val Gly Asn Ile Lys
          180                 185                 190

Met Pro Gly Ile His Ala Val Asp His Arg Leu Glu Arg Leu Glu Glu
      195                 200                 205

Ser Asp Asn Glu Met Phe Val Val Gln Arg Glu His Ala Val Ala Lys
210                 215                 220

Phe Ala Gly Leu Gly Gly Met Asp Glu Leu Tyr Lys Ala Glu Ala
225                 230                 235                 240

Ala Ala Lys Glu Ala Ala Ala Lys Glu Ala Ala Ala Lys Ala Val Ser
          245                 250                 255

Lys Gly Glu Glu Leu Ile Lys Glu Asn Met His Met Lys Leu Tyr Met
      260                 265                 270

Glu Gly Thr Val Asp Asn His His Phe Lys Cys Thr Ser Glu Gly Glu
      275                 280                 285

Gly Lys Pro Tyr Glu Gly Thr Gln Thr Met Arg Ile Lys Val Val Glu
290                 295                 300

Gly Gly Pro Leu Pro Phe Ala Phe Asp Ile Leu Ala Thr Ser Phe Leu
305                 310                 315                 320

Tyr Gly Ser Lys Thr Phe Ile Asn His Thr Gln Gly Ile Pro Asp Phe
              325                 330                 335

Phe Lys Gln Ser Phe Pro Glu Gly Phe Thr Trp Glu Arg Val Thr Thr
          340                 345                 350

Tyr Glu Asp Gly Gly Val Leu Thr Ala Thr Gln Asp Thr Ser Leu Gln
      355                 360                 365

Asp Gly Cys Leu Ile Tyr Asn Val Lys Ile Arg Gly Val Asn Phe Thr
370                 375                 380

Ser Asn Gly Pro Val Met Gln Lys Lys Thr Leu Gly Trp Glu Ala Phe
385                 390                 395                 400

Thr Glu Thr Leu Tyr Pro Ala Asp Gly Gly Leu Glu Gly Arg Asn Asp
              405                 410                 415

Met Ala Leu Lys Leu Val Gly Gly Ser His Leu Ile Ala Asn Ala Lys
          420                 425                 430

Thr Thr Tyr Arg Ser Lys Lys Pro Ala Lys Asn Leu Lys Met Pro Gly
      435                 440                 445

Val Tyr Tyr Val Asp Tyr Arg Leu Glu Arg Ile Lys Glu Ala Asn Asn
450                 455                 460

Glu Thr Tyr Val Glu Gln His Glu Val Ala Val Ala Arg Tyr Cys Asp
465                 470                 475                 480

Leu Pro Ser Lys Leu Gly His Lys Leu Asn Gly Ser Gly Ala Thr Asn
              485                 490                 495

Phe Ser Leu Leu Lys Gln Ala Gly Asp Val Glu Glu Asn Pro Gly Pro
          500                 505                 510

Met Thr Glu Tyr Lys Pro Thr Val Arg Leu Ala Thr Arg Asp Asp Val

|      |      | 515  |      |      | 520  |      |      | 525  |      |      |      |
|---|---|---|---|---|---|---|---|---|---|---|---|

Pro Arg Ala Val Arg Thr Leu Ala Ala Phe Ala Asp Tyr Pro Ala
530                     535             540

Thr Arg His Thr Val Asp Pro Asp Arg His Ile Glu Arg Val Thr Glu
545                 550                 555                 560

Leu Gln Glu Leu Phe Leu Thr Arg Val Gly Leu Asp Ile Gly Lys Val
            565                 570                 575

Trp Val Ala Asp Asp Gly Ala Ala Val Ala Val Trp Thr Thr Pro Glu
        580                 585                 590

Ser Val Glu Ala Gly Ala Val Phe Ala Glu Ile Gly Pro Arg Met Ala
    595                 600                 605

Glu Leu Ser Gly Ser Arg Leu Ala Ala Gln Gln Met Glu Gly Leu
    610                 615                 620

Leu Ala Pro His Arg Pro Lys Glu Pro Ala Trp Phe Leu Ala Thr Val
625                 630                 635                 640

Gly Val Ser Pro Asp His Gln Gly Lys Gly Leu Gly Ser Ala Val Val
            645                 650                 655

Leu Pro Gly Val Glu Ala Ala Glu Arg Ala Gly Val Pro Ala Phe Leu
            660                 665                 670

Glu Thr Ser Ala Pro Arg Asn Leu Pro Phe Tyr Glu Arg Leu Gly Phe
        675                 680                 685

Thr Val Thr Ala Asp Val Glu Val Pro Glu Gly Pro Arg Thr Trp Cys
        690                 695                 700

Met Thr Arg Lys Pro Gly Ala
705                 710

<210> SEQ ID NO 95
<211> LENGTH: 250
<212> TYPE: DNA
<213> ORGANISM: Artificial Sequence
<220> FEATURE:
<223> OTHER INFORMATION: sequenced region within the parental original
      mRuby2 sequence

<400> SEQUENCE: 95
ccaccaattc aaatgcacag gtgaaggaga aggcaatccg tacatgggaa ctcaaaccat      60
gaggatcaaa gtcatcgagg gaggacccct gccatttgcc tttgacattc ttgccacgtc     120
gttcatgtat ggcagccgta cttttatcaa gtacccgaaa ggcattcctg atttctttaa     180
acagtccttt cctgagggtt ttacttggga aagagttacg agatacgaag atggtggagt     240
cgtcaccgtc                                                            250

TARGETED IN SITU PROTEIN DIVERSIFICATION BY SITE DIRECTED DNA CLEAVAGE AND REPAIR

The present invention relates to a method for producing a panel of cells (i.e. a cell library) expressing various different mutant variants of a protein of interest, wherein only one of said mutant variants is expressed per cell from a single gene copy. The present invention also relates to a method or cell library for identifying a mutant variant of a protein of interest having a different or modified biological activity as compared to the corresponding wild-type protein of interest. According to the present invention the identified mutant variant of a protein of interest may be applied for white biotechnology.

White biotechnology (i.e. biotechnology that is applied to industrial production) holds many promises for sustainable development. White biotechnology uses living cells and enzymes to synthesize products that are easily degradable, require less energy and create less waste during their production as compared to conventional products. For example, several enzymes are widely used in food manufacturing and as active ingredients in washing powders to reduce the amount of artificial surfactants. Also enzymes that break down fat have been designed for use in detergents. In addition, transgenic microorganisms are used to produce medical products such as antibodies or human insulin in large-scale fermentation tanks. The benefits of white biotechnology are manifold: they do not rely on fossil resources, are more energy efficient as compared to conventional processes and their substrates, products and waste are biologically degradable, which all helps to decrease their environmental impact. Using alternative substrates and energy sources, white biotechnology is bringing many innovations to the chemical, textile, food, packaging and health care industries.

Proteins have become important tools in white biotechnology, e.g. in industrial processes and medicine, but they rarely come to use in their native form. Often, many rounds of iterative improvements are necessary to generate highly performing mutant variants of a given enzyme, antibody, or other protein of interest. In the absence of detailed knowledge on structure-function relationships, diversification of proteins by mutagenesis and screening has become the method of choice to evolve proteins with useful properties.

A range of techniques have been implemented to perform both site-directed and random mutagenesis, often combining both at some stage. Site-directed mutagenesis can be achieved with modified PCR techniques (QuickChange Kit, Stratagene; Kunkel, 1985, Proc Natl Acad Sci USA. 82(2): 488-492; Vandeyar, Gene 65(1): 129-133.) and is useful if knowledge on the function of a given protein already exists. It is used to substitute individual amino acids with a range of other amino acids, keeping the number of variants to be tested rather low. In addition, selecting individual amino acids for mutagenesis depends on very precise knowledge on the functional importance of the various amino acid residues of the protein of interest.

Random mutagenesis aims at exploring sequence space in proteins without a preconceived idea of possible functional sites. A number of such techniques exist including, for example, chemical or physical mutagenesis or error-prone PCR methods. Chemical or physical mutagenesis uses DNA modifying substances or UV light (Bridges, 1985, Proc. Natl. Acad. Sci. USA 82: 4193-4197) to damage DNA. Repair of such errors results in altered nucleotides being incorporated and can in turn result in amino acid substitutions in encoded proteins. Substances used for this purpose include alkylating compounds as ethyl-methanesulfonate (Lai, 2004, Biotechnol. Bioeng. 86: 622-627), de-aminating substances such as nitrous acid (Myers, 1985, Science 229: 242-247), or base analogues such as 2-aminopurine (Freese, 1959, J. Mol. Biol. 1: 87-105). The disadvantages of these chemical or physical mutagenesis techniques are that they affect the whole cell and all genes of the genome, not only the genes of interest. Thus, toxicity and altered cell homeostasis seriously affect screening results. Moreover, these techniques show strong mutational bias, i.e. they have a strong preference for mutating specific nucleotides (Myers, 1985, 1985, Science 229: 242-247; Lai, 2004, Biotechnol. Bioeng. 86: 622-627). Therefore these techniques are predominantly used for gene inactivation studies.

The currently preferred methods for gene diversification are variations of error-prone PCR (Leung, 1989, Technique 1: 11-15). In this method the gene of interest is replicated in vitro by a polymerase, which is forced to introduce mistakes by a variety of means. Errors accumulate with each round of PCR. This technique is useful in sampling sequence space of a gene of interest. However, it also shows mutational bias, as this kind of mutagenesis does not allow a codon to be diversified in a manner to encode all possible amino acids. This is because many amino acid exchanges require up to three nucleotide substitutions per codon, while error PCR most likely only introduces one nucleotide exchange per codon at best. As a consequence, depending on the starting codon, an amino acid can typically only be converted to between three and seven other amino acids, leaving the function of the majority of possible amino acids at a given position unexplored (Wong, 2006, Journal of Molecular Biology, 355(4): 858-871). Moreover, it is hard to mutate neighboring amino acid residues or short stretches of residues in a gene. Thus, synergistic effects and epistatic interactions between close-by mutations cannot be sampled. Another disadvantage of this method is that the procedure is performed in vitro and any diversified library subsequently needs to be introduced into the cells or organisms of interest for screening of desired phenotypes. While libraries can be efficiently transformed into *Escherichia coli* for propagation and screening, mammalian cells pose a number of problems for this approach. The problem mostly arises from the need to have single variants (i.e. single mutant variants) of a library expressed in a given cell to allow unambiguous assessment of its function. Unfortunately, the major transfection methods for mammalian cells, calcium-phosphate mediated transfection or liposome-mediated transfection, lead to massive co-transfection of DNA constructs into single cells. While this aspect is frequently used to advantage in research application, it poses a severe problem for screening and functionally assessing individual mutant variants of a library. Viral transfection could in principle help to overcome this co-transfection problem, as viral particles can be titrated not to exceed a multiplicity of infection of one. However, cloning of diversified gene libraries into large viral shuttle plasmids such as used for lentivirus production is very time-consuming and is also known to be extremely inefficient. This inefficiency leads to a large loss in the richness of generated libraries. In addition, infected cells express transgenes at very different levels, which conceals the functional activity of the mutated proteins.

Accordingly, at present targeted protein diversification is inefficient. In particular, the production of a library of cells that produce different variants of a protein of interest having different amino acid residues at a defined position is time consuming and labor-intensive. The work and resources required even increase if it is desired to obtain a cell library wherein only one variant of a protein of interest is expressed per cell. However, such a library would have substantial advantages as it would enable fast and comprehensive screening of protein variants with beneficial properties.

Thus, the technical problem underlying the present invention is the provision of an improved method for protein diversification. In particular, an object of the present invention is the provision of means and methods for efficiently producing a panel of cells (i.e. a library of cells) that produce different variants of a protein, wherein one variant of the protein is expressed per cell.

The technical problem is solved by provision of the embodiments as provided herein and as characterized in the claims.

Accordingly, the present invention relates to a method for producing a protein library, particularly a method for producing a panel of cells expressing mutant variants of a protein of interest, wherein one of said mutant variants of said protein of interest is expressed per cell from a single gene copy. The method comprises the following steps:

a) inducing a double-strand break (DSB) or a single-strand nick in the genome of cells at or in close proximity to a target site for mutagenesis in the gene encoding for said protein of interest, wherein said gene encoding for said protein of interest is comprised in the genome of the cells in a single copy, and wherein said single copy of the gene encoding for said protein of interest comprises an inactivating mutation at or in close proximity to said target site for mutagenesis;

b) preferably, providing to the cells (of step a)) a library of different donor nucleic acid templates for the repair of the induced DSB or single-strand nick via homologous recombination, wherein the different donor nucleic acid templates of said library comprise different mutations at the position corresponding to said target site for mutagenesis and remove said inactivating mutation by homology directed repair (HDR), particularly homologous recombination:

c) selecting and/or enriching cells in which the inactivating mutation has been removed; and d) providing a panel of cells selected in step c), which is a panel of cells expressing different mutant variants of said protein of interest, wherein one of said different mutant variants of said protein of interest is expressed per cell from a single gene copy.

The presence of a DSB or single-strand nick within genomic DNA triggers intracellular repair mechanisms, such as non-homologous end joining (NHEJ). Therefore, even without step b), different mutants of a desired protein can be obtained by the method of the present invention. Indeed, repair by NHEJ introduces many kinds of random deletions or insertions; and thus, can lead to the diversification of a protein of interest. Accordingly, one aspect of the present invention relates to a method for producing a panel of cells expressing mutant variants of a protein of interest, wherein one of said mutant variants of said protein of interest is expressed per cell from a single gene copy, wherein and method comprises the following steps:

i) inducing a double-strand break (DSB) or a single-strand nick in the genome of cells at or in close proximity to a target site for mutagenesis in the gene encoding for said protein of interest, wherein said gene encoding for said protein of interest is comprised in the genome of the cells in a single copy, and wherein said single copy of the gene encoding for said protein of interest comprises an inactivating mutation at or in close proximity to said target site for mutagenesis;

(ii) selecting and/or enriching cells in which the inactivating mutation has been removed by a cellular DNA repair process; and iii) providing a panel of cells selected in step c), which is a panel of cells expressing different mutant variants of said protein of interest, wherein one of said different mutant variants of said protein of interest is expressed per cell from a single gene copy.

All descriptions and definitions that are provided below with regard to step a) of the method of the invention apply, mutatis mutandis, to step i) described above. In addition, all descriptions and definitions that are provided below with regard to step c) of the method of the invention apply, mutatis mutandis, to step ii) described above. In line with this, all descriptions and definitions that are provided below with regard to step d) of the method of the invention apply, mutatis mutandis, to step iii) described above.

However, as explained in more detail below, the degree of diversification of a desired protein can considerably be increased if the DSB or single-strand nick is repaired by homology directed repair (HDR). Therefore, the method of the present invention preferably comprises step b), wherein HDR repair is induced by the provision of donor nucleic acid templates.

Accordingly, the present invention relates to a production method (i.e. to a method for producing a panel of cells expressing mutant variants of a protein of interest). In this method a DSB or a single-strand nick (preferably a DSB) is induced (i.e. introduced) near the target site for mutagenesis. This DSB or single-strand nick is preferably repaired by homology-directed repair (HDR), particularly homologous recombination. The use of different nucleic acid templates in step (b) advantageously enables the generation of several different mutant variants of the protein of interest within one step. In addition, cells wherein the protein of interest has successfully been modified (in particular mutated) can easily be selected, since during introduction of the desired mutation (preferably via HDR) an inactivating mutation (e.g. a frame-shift mutation) within the protein of interest is removed. Accordingly, only cells wherein successful mutation of the protein of interest has been occurred express the active protein of interest, and therefore, can easily be selected (or enriched). By using this protein library generation method several variants of a protein of interest can be prepared, which are separately expressed in distinct cells, for example mammalian cells. Accordingly, with the herein provided method a panel of cells (i.e. a cell library) is prepared comprising cells each expressing a different mutant variant of a protein of interest. In particular, with the herein provided generation method a panel of cells (e.g. mammalian cells) is provided, wherein a single mutant variant of a protein of interest is expressed per cell. Said panel of cells is a useful tool for selecting and/or identifying mutant variants of a protein of interest with improved characteristics. For example, the resulting panel of cells may be used for downstream analysis such as phenotypic analysis in comparison to cells that express the original protein of interest from a single copy and optionally from the same promoter. Thus, the present invention provides an efficient and cost-effective method for protein diversification. The ease, efficiency, cellular context and lack of mutation bias of this approach may advantageously expedite protein engineering.

In addition, in the production method of the present invention the combination of targeted single-strand nicks or DSB and corresponding repair thereof (preferably by HDR) introduces diversity of a protein of interest at the desired degree of bias. This offers the unprecedented opportunity to sequentially scan the impact of stretches of amino acids in a given protein within the context of a living cell. Thus, the herein provided means and methods facilitate identification of new protein variants with improved characteristics, which may significantly expand applicability of white biotechnology approaches. For example, the herein provided means and methods may lead to the identification of new enzyme variants that can be used in the industrial production or of new antibody variants that can be used for the treatment and/or prevention of diseases. As described below, also new variants of growth factors may be obtained by the means and methods provided herein.

The use of the production method of the present invention provides a number of advantages over existing techniques. For example, by using the production method of the present invention the protein of interest can be rapidly diversified with a single transfection. In addition, the further analysis and processing of selected protein variants is facilitated as within the resulting panel of cells, each cell contains a single protein variant. Furthermore, the resulting cells stably express the protein variants once the transfected (e.g. CRISPR) plasmids are diluted out. Moreover, due to the use of an inactivating mutation that is removed during mutagenesis, cells expressing a protein that underwent diversification can be easily identified and separated from cells expressing the parental (i.e. wild-type) protein. The production method of the present invention also offers a huge degree of flexibility as regards to the nature of the introduced mutation. For example, at least stretches of up to 12 clustered amino acid residues can undergo saturated mutagenesis in parallel. In addition, the herein provided production method has essentially no mutational bias, as all possible variants can be generated. However, if desired, potential bias can be inserted as well, depending on the design of the homology of the donor nucleic acid templates. However, the herein provided production method is highly specific, since no unwanted mutations are created within in the genome of the cells. For example, the donor nucleic acid templates can easily be designed in a way that critical residues within the protein of interest remain unchanged while the surrounding residues are modified. In addition, by using the herein provided production method, mutant variants that can successfully be expressed in a living cell are directly selected (and/or enriched). Furthermore, all reagents used for the herein provided production method are very cost efficient.

A further advantage of the herein provided production method is that it results in a panel of cells comprising cells each carrying only one single copy (i.e. one allele) of the gene encoding for a variant of the protein of interest. The presence of a second copy (as it is the case in the methods of the prior art) leads to cells expressing more than one mutant variant of the protein of interest. This significantly alters the downstream analysis. Accordingly, employing one single gene copy has the advantage of ensuring that the generated panel of cells only comprises cells that express a single mutant variant of the protein of interest per cell.

Thus, the present invention advantageously allows for the simple and rapid generation of richly diversified protein libraries even in mammalian cells, with a single variant per cell. The diversification is preferably achieved using the CRISPR/Cas9 system and HDR (particularly homologous recombination). For example, the production method of the present invention may be realized as follows. An inactivating mutation, e.g. a reading frame-shift, may be introduced at or in close proximity to the target site of mutagenesis within a protein of interest. For this purpose the protein of interest may be transformed stably in single copy number into cells, e.g. mammalian cells. Subsequently, a DSB or single-strand nick (preferably a DSB) may be introduced in close proximity of the target site for mutagenesis, e.g. by using the CRISPR system. Said single-strand nick or DSB is repaired by a cellular repair mechanism, preferably by using the cellular HDR system. In order to induce HDR specially tailored oligonudeotides (i.e. donor nucleic acid templates) serve as repair templates and comprise homology arms and the desired diversified sequence. HDR advantageously leads to insertion of the desired diversification and removes the inactivating mutation, e.g. restores the reading frame.

For example, with the herein provided production method mutant variants of the protein of interest that are directly selectable (i.e. positively selectable) can be prepared. An example for a protein that is directly selectable is a fluorescent protein. If the protein of interest is directly selectable, mutant variants with improved characteristics can easily be selected (and/or enriched), e.g. by selecting (and/or enriching) mutant variants with increased fluorescence. For engineering of proteins that are not directly selectable (e.g. non-fluorescent proteins), a fluorescent protein may be tagged in frame downstream (i.e. onto the C-terminus) of the protein of interest. In this case, removal of the inactivating mutation (e.g. the frame-shift mutation) by HDR or NHEJ (preferably HDR) also restores expression of the fluorescent protein, and allows harvesting (i.e. selecting and/or enriching) all diversified protein variants by fluorescence sorting.

As mentioned above, the production method of the present invention allows for generating a panel of cells expressing mutant variants of a protein of interest. Specifically, it allows for generating a panel of cells, comprising cells each expressing a particular mutant variant from a single gene copy. Thus, said panel of cells comprises cells each expressing a different mutant variant of a protein of interest.

In one aspect of the present invention, the herein provided production method further comprises the step of generating the cells as used in step a). In the herein provided production method, the single copy of the gene encoding for the protein of interest (i.e. the gene of interest) may be an endogenous gene copy. However, it is preferred in the herein provided production method that the single copy of the gene encoding for the protein of interest is an exogenous gene copy (i.e. that it does not naturally occur in the employed cells). If in the herein provided production method said single copy of the gene encoding for the protein of interest is exogenous, generation of the cells of step a) comprises introducing the single copy of said gene encoding for the protein of interest in the genome of cells. Methods for introducing an exogenous single copy of the gene encoding for a protein of interest into the genome are commonly known in the art and involve, e.g., site-specific homologous recombination systems. For example, integration of a single copy of a gene of interest into cells may be accomplished through standard antibiotic selection, Flp-In or Jump-in recombination, lentiviral transfection and selection, or through Cas9 targeted cutting and recombination with homologous domains, such as in the AAVS1 locus.

In one aspect of the present invention generation of the cells used in step a) comprises introducing said inactivating mutation in said single copy of the gene encoding for the protein of interest. Said inactivating mutation may be, e.g. a frame-shift mutation. Such a frame-shift mutation may be introduced, e.g. by adding or removing 1, 2, 3 or 4 bases within the coding reading frame of the gene of interest. Thus, the frame-shift may be caused by a deletion that is larger than necessary for producing a frame-shift, e.g. by the deletion of nucleotides encoding several amino acids. Deletion of such a large region can be advantageous and it increases homology to the repair template, which may increase the recombination rate. For example, by inactivating the gene of interest with a frame-shift caused by a larger deletion (e.g. a removal of the nucleotides that encode all the targeted amino acids plus 1-2 bases), directly after an induced DSB the chromosomal free-ends would share direct homology with the donor nucleic acid template. There would be no intermediate original DNA that might impair homologous recombination reaction. However, the frame-shift may also be produced by removing 4 base pairs downstream of a selected (or introduced) PAM site, thereby removing one amino acid and generating a frame-shift. If the single gene encoding said protein of interest is exogenous, said inactivating mutation may be introduced prior or after introduction of the single copy of said gene encoding for the protein of interest into the genome of the cells. In principle, any mutagenesis methods known in the art may be employed to introduce an inactivating mutation in the gene of interest before integrating the same into cells. Non-limiting examples for such mutagenesis methods are, for example, targeted restriction enzyme digestion and ligation or PCR-based site-directed mutagenesis methods (Quick Change Kit, Stratagene; Kunkel, 1985, Proc Natl Aced Sci USA. 82(2): 488-492). In the context of the present invention the inactivating mutation may also be introduced after a copy of the gene of interest (without the inactivating mutation) has been incorporated into the genome of cells. This may be achieved by genetic engineering methods known in the art. Such genetic engineering methods include, e.g. CRISPR/Cas mediated gene editing by using suitable donor nucleic acid templates that incorporate the frame-shift. Such methods are commonly known in the art and described, e.g. in Ran, 2013, Nature Protocols 8 (11): 2281-2308).

If said single copy of the gene encoding for the protein of interest is endogenous, generation of the cells as used in step a) may comprise introducing said inactivating mutation in the gene encoding for the protein of interest in the genome of the cells by using a site-specific homologous recombination system. Site-specific homologous recombination systems such as the CRISPR/Cas9 system are commonly known in the art and described, e.g. in Ran, 2013, Nature Protocols 8 (11): 2281-2308.

The herein provided production method produces a panel of cells expressing mutant variants of a protein of interest, wherein one of said mutant variants of said protein of interest is expressed per cell from a single gene copy. This means that in step a) of the herein provided production method the gene encoding for the protein of interest is present in the cells in a single copy. Accordingly, generation of the cells of step a) may comprise inactivation (preferably deletion) of copies of the gene encoding for the protein of interest, in order to obtain one single copy of the gene encoding for the protein of interest per cell. In many cell culture lines and plants, there are more than two alleles. Therefore, in order to get a single copy at the end, all other alleles (but one) must be inactivated (preferably deleted) in order to generate the cells as used in step a). Thus, if said gene encoding for the protein of interest is an endogenous gene that is present in the genome in more than one copies, then generation of the cells of step a) may comprise inactivation (preferably deletion) of endogenous copies of said gene encoding for the protein of interest to obtain one single copy of said gene encoding for the protein of interest per cell. Methods for the inactivation or deletion of a particular gene copy (i.e. of a particular allele) are commonly known in the art. For example, deletion of one gene copy by using the CRISPRICas9 system is described in Ran, 2013, Nature Protocols 8 (11): 2281-2308). Alternatively, cells comprising the gene of interest in one single copy may be obtained by using haploid cell cultures, e.g. as described in WO 2013/079670 A1.

Step a) of the herein provided method comprises inducing a DSB or a single-strand nick (preferably a DSB) in the genome of cells. Said DSB or single-strand nick is preferably performed by using a site-specific nuclease or a site-specific nickase, respectively. Therefore, generation of the cells of step a) may comprise introducing into the cells a nucleic acid sequence encoding a site-specific nuclease or a site-specific nickase. In addition, generation of the cells of step a) may further comprise introducing a corresponding recognition site for said site-specific nuclease or said site-specific nickase, respectively, in the single copy of the gene of interest.

For example, if the site-specific nuclease is Cas9 or Cpf1 or the site-specific nickase is Cas9, said recognition sequence preferably contains a protospacer-adjacent motif (PAM) immediately downstream of the cleavage site. The PAM target sequences of various CRISPR nucleases and their variants (e.g. 5'-NGG for SpCas9, 5'-NNGRRT for SaCas9, 5'-TTN for Cpf1) abundantly exist in the mammalian genome. Therefore, most of genes can be targeted by using the herein provided methods without introducing a PAM sequence. However, in the event that there is no PAM sequence immediately downstream of the desired cleavage site, a PAM sequence (e.g. 5'-NGG for SpCas9, 5'-NNGRRT for SaCas9, 5'-TTN for Cpf1) may be introduced into the protein of interest downstream of the desired cleavage site. Thus, depending on the used site-specific nuclease or nickase, if not present within the gene of interest at the desired position, a recognition site for cleavage by said site-specific nuclease or nickase (e.g. a PAM sequence if Cas9 or Cpf1 is used, or a specific recognition site of a zinc finger nuclease, transcription activator-like effector nuclease or megaTAL endonuclease) may be engineered into the gene of interest together with the frame-shift.

The generation of the cells of step a) may further comprise introducing into the cells means that target the site-specific nuclease or the site-specific nickase to the recognition site. For example, a guide RNA or a polynucleotide encoding said guide RNA may be introduced into the cells of step a). A guide RNA can be a short, synthetic chimeric tracr/crRNA (a "single-guide RNA" or sgRNA). A guide RNA may also comprise two short, synthetic tracr/crRNAs (a "dual-guide RNA" or dgRNA). For some site-specific nucleases (e.g. Cpf1) a short, synthetic crRNA can serve as guide RNA In one aspect of the herein provided methods, Cas9 is targeted to said recognition site via a sgRNA or via a dgRNA. Cpf1 may be targeted to said recognition site via a crRNA.

Thus, generating the cells of step a) may comprise exogenously introducing into the cells the nucleotide sequence encoding the protein of interest in one single copy. For example, the cells may be transformed, transfected or transduced with the nucleotide sequence encoding the protein of interest resulting in expression of one single copy of the gene encoding the protein of interest Means and methods for the transfection, transformation or transduction of cells are commonly known in the art, and include, e.g. liposome mediated transfection, Ca2+-phosphate mediated transfection, and viral vector mediated delivery (see, e.g. Green, Sambrook, 2012, Molecular Cloning. A laboratory manual. Cold Spring Harbor Laboratory Press). Preferably, the resulting cells stably express the protein of interest. As mentioned above, generating the cells of step a) may further comprise introducing a site-specific nuclease or nickase; or a polynucleotide encoding a site-specific nuclease or nickase; into the cells, e.g. via transfection, transformation or transduction. In addition, generating the cells of step a) may further comprise introducing a guide RNA; or a polynucleotide encoding a guide RNA; into the cells, e.g. via transfection, transformation or transduction. Finally, generating the cells of step a) may comprise introducing a recognition site (e.g. PAM sequence) downstream of the desired cleavage site of the site-specific nuclease or nickase.

Alternatively, for step a) cells may be used that already express the protein of interest (from a single copy of the corresponding gene). The protein of interest may already comprise an inactivation (e.g. frame-shift) mutation and/or a recognition site (e.g. a PAM sequence) downstream of the desired cleavage site. Said cells may already comprise a site-specific nuclease or nickase; or a polynucleotide encoding said site-specific nuclease or nickase. Said cells may also already comprise a guide RNA; or a polynucleotide encoding said guide RNA The "target site for mutagenesis in the gene encoding for the protein of interest" is the position within the nucleic acid sequence of the single copy of the gene encoding for the protein of interest (i.e. the gene of interest) in the cells of a), which corresponds to the position that is envisaged to be diversified/mutagenized in order to generate mutant variants of the protein of interest. Accordingly, the target site for mutagenesis can in principle be any defined position within the coding sequence of a gene of interest at which a mutation should be introduced. For example, if a particular amino acid is to be mutated within the protein of interest, then the target site for mutagenesis may be the triplet of nucleotides encoding said amino acid to be mutated. If several amino acids are to be mutated, then the target site of mutagenesis may be the nucleotide sequence encoding said amino acids.

The position of the induced DSB or single-strand nick may either be (directly) at the predefined target site for mutagenesis within the single copy of the gene encoding for the protein of interest or in close proximity thereto. The term in "close proximity to the target site for mutagenesis" is defined herein below. For example, if a frame-shift has been induced by the deletion and/or introduction (e.g. deletion) of amino acids, the DSB or single-strand nick may be at a position 1-100 bp upstream or downstream of said deletion and/or introduction.

Step a) of the method of present invention comprises or consists of inducing (i.e. introducing) a DSB or a single-strand nick (also referred to as single-strand break). Said DSB or single-strand nick is induced "in the genome of cells"; which means that the DSB or single-strand nick is induced in the genomic DNA of cells. Said genomic DNA may be endogenous genomic DNA. However, said genomic DNA may also be derived from a plasmid that has been inserted into the genomic DNA, e.g. by stable transfection, transformation of transduction.

As known in the art, a DSB is the interruption of both DNA strands of a DNA double helix. A DSB may either be blunt-ended (i.e. both strands are cut at the same position) or may comprise sticky ends (i.e. both strands are cut at different positions, which results in short single-stranded, complementary sequences at both ends of the DSB). As also known in the art a single-strand nick (or single-strand break) is the interruption of a single DNA strand of a DNA double helix. "Interruption" in the context of DSBs and single-strand nicks relates to the break of (a) phophodiester bond(s) between two nucleotides in both strands or in only one of the two strands of the double helix, respectively. Preferably, a DSB is induced (i.e. introduced) in the genome of the cells of step a).

In context of the present invention said DSB or said single-strand nick may be induced in a distance of less than 120 base pairs, preferably less than 30 base pairs or most preferably less than 10 base pairs to said target site for mutagenesis. Similarly, said inactivating mutation may be in a distance of less than 120 base pairs, preferably less than 30 base pairs or most preferably less than 10 base pairs to said target site for mutagenesis. Thus, the distance between the inactivating mutation (e.g. the frame-shift) and the DSB or single-strand break may be 0-120 base pairs (corresponding to 0-40 amino acids).

The DSB or a single-strand nick may in principle be achieved by any method known in the art to generate a site-specific DSB or a site-specific single-strand nick, respectively. Preferably, a DSB is induced (i.e. introduced) by a site-specific nuclease (also called "sequence-specific nuclease") and the inactivated single copy of the gene encoding for the protein of interest in step a) preferably comprises a corresponding recognition site for said site-specific nuclease. In line with this, a single-strand nick is preferably induced by a site-specific nickase (also called "sequence-specific nickase") and the inactivated single copy of the gene encoding for the protein of interest in step a) preferably comprises a corresponding recognition site for said site-specific nickase. Accordingly, the cells used in step a) of the present invention may comprise a site-specific nuclease or a site-specific nickase; or a polynucleotide encoding a site-specific nuclease or a site specific nickase. In one aspect of the invention the genome of the cells of step a) does not comprise any additional recognition sites for the site-specific nuclease or the site-specific nickase employed. This has the advantage that any further modification to the genomic DNA of the cells is prevented. A polynucleotide encoding the site-specific nuclease or the site-specific nickase may either be encoded on a vector (e.g. a plasmid vector) comprised in the cells of step a) or may be stably incorporated in the genome of the cells. Means and methods for transiently transform or transfect cells with a (plasmid) vector or for stably integrating a polynucleotide into the genome of a cell are known in the art. Transient transfection of plasmids can be conveniently achieved using calcium-phosphate precipitation of DNA or liposome-mediated transfection. A guide to employ such techniques is provided in Green, Sambrook, 2012, Molecular Cloning. A laboratory manual. Cold Spring Harbor Laboratory Press. Calcium phosphate transfection is described, e.g. in Kingston, 2003, Curr Protoc Cell Biol. Chapter 20: Unit 20.3. Transfection Using DEAE-Dextran is described, e.g. in Gulick, 2003, Curr Protoc Cell Biol. Chapter 20: Unit 20.4T. Transfection by electroporation is described, e.g. in Potter, 2011, Curr Protoc Cell Biol. Chapter 20: Unit 20.5. Transfection of cultured eukaryotic cells using cationic lipid reagents is described, e.g. in Hawley-Nelson, 2003, Curr Protoc Cell Biol. Chapter 20: Unit 20.6. The polynucleotide encoding for the site-specific nuclease or for the site-specific nickase may in particular be operable fused to a constitutive (i.e. constitutively active) promoter having activity in the employed cells, i.e. the site-specific nuclease or nickase may be expressed under control of a constitutive (i.e. constitutively active) promoter. Non-limiting examples for constitutive promoter systems known in the art are CMV, ubiquitin promoter, and CAG promoter. For instance, in one aspect the site-specific nuclease or nickase is expressed under control of a CMV promoter. Alternatively, the site-specific nuclease or nickase may also be expressed under control of an inducible promoter, i.e. the polynucleotide encoding the site-specific nuclease or nickase may be operable fused to an inducible promoter. Non-limiting examples for inducible promoter systems are known in the at and include, e.g. the Tet on/off system, heat shock promoters, and light inducible promoters). Usage of an inducible promoter system has the advantage that the expression of the site-specific nuclease or the site-specific nickase; and thereby also the induction of a DSB or a single-strand nick, respectively, can be timely controlled. For instance, such inducible system allows for stopping the expression after a time that is sufficient to ensure that a DSB or the single-strand nick has been introduced. Accordingly, the expression may, for example, be stopped after 24-48 h hours. An inducible expression system also allows for starting expression of the site-specific nuclease or the site-specific nickase at defined time point. This may be advantageous if the site-specific nuclease or nickase is stably expressed in the employed cells.

Preferably, the site-specific nuclease or the site-specific nickase is expressed from a plasmid comprised in the cells of step a). This plasmid may be removed from the cells. For example, removal of the plasmid may be achieved by diluting the plasmid out. Diluting out means that in subsequent cell division cycles the newly generated cells will progressively lose all of the transfected plasmids coding for the nuclease/nickase, as these plasmids are episomal and are not amplified in mammalian cells. However, as mentioned above, the cells in step a) may also stably express the site-specific nuclease or the site-specific nickase.

The site-specific nuclease employed in the context of the method of the present invention can be any known site-specific nuclease. In particular, the term "site-specific nuclease" (or "sequence-specific nuclease") relates to any enzyme that can cut both strands of a DNA double-strand at a defined target site so as to introduce a DSB in the DNA double strand. Similarly, the site-specific nickase employed in the context of the method of the present invention can be any known site-specific nickase. The term "site-specific nickase" (or "sequence-specific nickase") relates to any enzyme that can cut one strand of a DNA double-strand at a defined target site so as to introduce a single-strand nick in the DNA double strand.

In context of the invention zinc finger nucleases (ZFN) or a transcription activator-like effector nucleases (TALEN) may be used as site-specific nuclease or as site-specific nickase, respectively, because these molecules have been previously used for HDR-mediated genome editing (Li, 2011, Nature 475: 217-221; Bedell, 2012, Nature 491: 114-118; Genovese, 2014, Nature 510: 235-240). Another site-specific nuclease that is useful in the context of the present invention is a megaTAL endonuclease, which has been shown to be particularly suitable for gene editing as it has high target specificity and off-target cleavage is minimized, see, e.g. Boissel, 2014, Nucleic Acids Res. 42(4): 2591-2601. However, clustered regularly interspaced short palindromic repeat (CRISPR)-associated (Cas) effector proteins, such as Cas9 or Cpf1, provide a much more simple and generalizable genome editing method. Thus, in the context of the present invention it is preferred that the site-specific nuclease or nickase is Cas9 or that the site-specific nuclease is Cpf1. Most preferably, a Cas9 nuclease (also called "CRISPRCas9 nuclease") is used as site-specific nuclease or as site-specific nickase in the production method of the present invention.

A ZFN comprises a zinc-finger DNA binding domain, which should be designed for each target gene, and a FokI nuclease. Similarly, a TALEN comprises a DNA binding domain, which should be designed for each target gene, and a FokI nuclease. The FokI nuclease, when combined with a zinc-finger DNA binding domain or a DNA binding domain, has the activity to introduce a single-strand nick or a double strand break into the DNA at a defined target site. Indeed, as ZFNs and TALENs can introduce a single-strand nick into the DNA at a defined target side, they are often referred as zinc finger nickase (ZFNickase) and transcription-activator-like effector nickases (TALE nickase), respectively. Therefore, as described above, a ZFN or a TALEN may be used in the present invention as site-specific nuclease or as site-specific nickase. Cas9 nucleases primarily induce a DSB. However, modified Cas9 nucleases have been described, wherein the nuclease function of the protein is altered into a nicking function. In other words, the naturally occurring Cas9 nuclease that cleaves both strands of a double-stranded target DNA can be altered into a nickase that cleaves (i.e. nicks) only one of the strands. Several Cas9 nickases are known in the art and described, e.g. in Tsai, 2016, Nature Reviews Genetics 17.5: 300-312. Means and methods of modifying a Cas9 protein in order to obtain a site-specific nickase are well known in the art, and include for example the introduction of amino acid replacements into Cas9 that render one of the nuclease domains inactive. More specifically, aspartate can for example be replaced against alanine at position 10 of the *Streptococcus pyogenes* Cas9 as shown in Cong, 2013, Science, 339: 819-823.

The use of a modified Cas9 protein having nicking function provides the advantage that the thus introduced DNA damage in the genome is more likely to be repaired via homologous recombination, instead of by non-homologous end joining. Therefore, Cas9 may be used as site-specific nuclease or as site-specific nickase in the methods of the present invention. Cpf1 may be used as site-specific nuclease in the herein provided methods.

The nucleotide and amino acid sequences of the FokI nuclease are commonly known in the art. The amino acid sequence of the FokI nuclease is shown herein as SEQ ID NO: 19. Preferably, the FokI nuclease employed herein as site-specific nuclease has site-specific nuclease activity and comprises an amino acid sequence that has at least 80%, preferably at least 85%, more preferably at least 90%, even more preferably at least 95%, even more preferably at least 98%, even more preferably at least 99%, and most preferably 100% sequence identity to the amino acid sequence of SEQ ID NO: 19.

The site specific nuclease activity can be tested in vitro by using a plasmid or linear dsDNA containing the gene sequence targeted. The targeted DNA is mixed with the site-specific nuclease and digestion is allowed to proceed for 1 hour, and successful cleavage can be visualized by gel electrophoresis.

If in the herein provided methods the FokI nuclease employed as site-specific nickase, then it is preferred that said FokI nuclease has site-specific nickase activity and comprises an amino acid sequence that has at least 80%, preferably at least 85%, more preferably at least 90%, even more preferably at least 95%, even more preferably at least 98%, even more preferably at least 99%, and most preferably 100% sequence identity to SEQ ID NO: 19

Methods for testing site-specific nickase activity are commonly known in the art and described, e.g. in McConnell, 2009, Proceedings of the National Academy of Sciences of the United States of America. 106(13): 5099-5104. In brief, target fragments for the nickase assay are generated by PCR, with 200 bp flanking the nicking site upstream and downstream. The nicking reaction is allowed to proceed for 1 h at 37° C. in a 10 µL reaction containing 50 mM Tris (pH 7.5), 100 mM NaCl, 10 mM $MgCl_2$, and 1 mM DTT. After the digestion, 2 µL of 5× stop solution [0.1 M Tris·HCl (pH 7.5), 0.25 M EDTA, 5% SDS] is added, and samples are denatured at 95° C. for 5 min with deionized formamide, 0.1% xylene cyanol, and 0.1% bromophenol blue, quick-chilled, and then resolved by electrophoresis on a 6% polyacrylamide denaturing gel. Gels are dried and analyzed by phosphorimaging.

The megaTAL endonuclease, which is a fusion of a meganuclease with a TAL effector, is a new class of DNA targeting endonucleases with high activity and specificity. The nucleotide and amino acid sequences of the megaTAL endonuclease are commonly known in the art and shown, e.g. in Boissel, 2014, Nucleic Acids Res. 42(4): 2591-2601. Preferably, the megaTAL endonuclease employed herein as site-specific nuclease has site-specific nuclease activity and comprises an amino acid sequence that has at least 80%, preferably at least 85%, more preferably at least 90%, even more preferably at least 95%, even more preferably at least 98%, even more preferably at least 99%, and most preferably 100% sequence identity to the amino acid sequence of SEQ ID NO: 20. The site specific nuclease activity can be tested in vitro as described above.

The nucleotide and amino acid sequences of Cfp1 nucleases are commonly known in the art and shown, e.g., in http://www.ncbi.nlm.nih.gov/protein/U2UMQ6.1 or http://www.addgene.orgibrowse/sequence/124373/. The amino acid sequences of the AsCpf1 and the LbCpf1 are shown herein as SEQ ID NOs: 21 and 22, respectively. For example, the Cpf1 nuclease that is used in context of the invention preferably has site-specific nuclease activity and an amino acid sequence that has at least 80%, preferably, at least 85%, more preferably at least 90%, even more preferably at least 95%, even more preferably at least 98%, even more preferably at least 99%, and most preferably 100% identity to the amino acid sequence of SEQ ID NO: 21 or 22. The site specific nuclease activity can be tested in vitro as described above.

A Cas9 nuclease is an enzyme of the CRISPR/Cas9 family. Non-limiting examples for Cas9 nucleases are known in the art. In the context of the invention any (DSB inducing) Cas9 nuclease can be employed in order to induce a DSB. In line with this, any (single-strand break inducing) Cas9 nuclease may be used in order to induce a single-strand nick. The Cas9 nuclease used herein is preferably derived from a bacterial species. Non-limiting examples for Cas9 nucleases that may be used herein are the SpCas9 nuclease from *Streptococcus pyogenes*, the St1Cas9 nuclease from *Streptococcus thermophilus*, and the SaCas9 nuclease from *Staphylococcus aureus*. The amino acid sequences of these proteins are known in the art and shown, e.g. in http://www.ncbi.nlm.nih.gov/protein/500000239?report=genbank&log$=protalign&blast_rank=1&RID=T6UUUEV90 1R or http://www.ncbi.nlm.nih.gov/protein/J7RUA5.1. The amino acid sequences of SpCas9, St1Cas9 and SaCas9 are provided herein as SEQ ID NOs: 23, 24 and 25, respectively. Preferably, the Cas9 nuclease employed herein has site-specific nuclease activity and comprises an amino acid sequence that has at least 80%, preferably at least 85%, more preferably at least 90%, even more preferably at least 95%, even more preferably at least 98%, more preferably at least 99%, and most preferably 100% sequence identity to the amino acid sequence of any of the known Cas9 nucleases, e.g. of SpCas9, St1Cas9, or SaCas9 as shown in SEQ ID NOs: 23, 24 or 25, respectively. The site-specific nuclease activity can be tested in vitro as described above. If in the herein provided methods the Cas9 nuclease employed as site-specific nickase, then it is preferred that said Cas9 nuclease has site-specific nickase activity and comprises an amino acid sequence that has at least 80%, preferably at least 85%, more preferably at least 90%, even more preferably at least 95%, even more preferably at least 98%, more preferably at least 99%, and most preferably 100% sequence identity to the amino acid sequence of any of the known Cas9 nucleases, e.g. of SpCas9, St1Cas9, or SaCas9. The site-specific nickase activity can be tested in vitro as described above.

Thus, in the context of the present invention the site-specific nuclease may be selected from the group consisting of a Cas9 nuclease, a Cpf1 nuclease, a ZFN, a TALEN, and a megaTAL endonuclease. Using Cas9 as nuclease or nickase has the advantage that it solely requires the expression of the Cas9 protein in combination with one short, synthetic chimeric tracr/crRNA (a "single-guide RNA", sgRNA) or two short, synthetic tracr/crRNAs (a "dual-guide RNA", dgRNA) that define target specificity. Similarly, Using Cpf1 as nuclease has the advantage that it solely requires the expression of the Cpf1 protein in combination with one short, synthetic crRNA that defines the target specificity. Therefore, using Cas9 or Cpf1 as a site-specific nuclease or nickase represents a considerable simplification in the generation of target-specific single- or double-strand breaks (Cas9) or double strand breaks (Cpf1). Therefore, it is preferred in context of the present invention that the site-specific DNA nuclease is Cas9 or Cpf1, or that the site-specific nickase is Cas9. Most preferably, the site-specific nuclease or the site-specific nickase is Cas9 (i.e. a Cas9 nuclease).

Beside SpCas9, St1Cas9 and SaCas9 several other Cas9 orthologs are known, which may be used in context of the present invention. These Cas9 orthologs include those derived from *Neisseria meningitides* and *Francisella novicida*. The sequences of several known Cas9 nucleases that may be applied in the methods of the present invention are known in the art, and shown, e.g. in WO 2014/131833. Herein, the Cas9 nuclease may also be a SpCas9 mutant such as eSpCas9 (Ian, 2016, Science, 351: 84-88) or SpCas9-HF1 (Kleinstiver, 2016, Nature, 529: 490-495), which can induce more specific cleavages than the original SpCas9. Furthermore, there are SpCas9 mutants that recognize different PAMs (Kleinstiver, 2015, Nature 523(7561): 481-485), or that have altered PAM specificities (e.g. the VQR and EQR variants as described in Kleinstiver, 2015, Nature 523(7561): 481-485), which may also be applied in the herein provided methods. Also other known Cas9 variants such as split Cas9, intein-Cas9, engineered Cas9, or the dimeric RNA-guided FokI-dCas9 nuclease (RFN) may be used as in the herein provided methods. These Cas9 variants are described, e.g., in Zetsche, 2015, Nat Biotechnol. 33(2): 139-142; Truong, 2015, Nucleic Acids Res. 43(13): 6450-6458; Tsai, 2014, Nat Biotechnol. 32(6): 569-576. When one of these Cas9 variants is used in the herein provided methods, the experiments have to be adapted as commonly known in the art. In particular, split Cas9 and RFN require multiple plasmids and templates respectively, and intein- Cas9 requires the addition of 4-hydroxytamoxifen. However, these are trivial variations commonly known to the skilled artisan.

The specificity of the herein provided methods may be further enhanced by using Cas9 variants with minimum or no off-target effects while retaining comparable on-target cleavage activity (Kleinstiver, 2016, Nature, 529: 490-495; Slaymaker, 2016, Science 351, 84-88). However, in context of the present invention it is preferred that the Cas9 nuclease is SpCas9, St1Cas9 or SaCas9. Most preferably, the Cas9 nuclease is SpCas9.

Because ZFNs and TALENs achieve specific DNA binding via protein domains, individual target sites have to be inserted for each nuclease. Alternatively, one needs to customize the specific nuclease for a given sequence (Heidenreich, 2016, Nature Reviews Neurosciences, 17: 36-44). By contrast, Cas9 is guided by a specificity-determining guide-RNA sequence (CRISPR RNA (crRNA)) that is associated with a trans-activating crRNA (tracrRNA) and forms Watson-Crick base pairs with the complementary DNA target sequence, resulting in site-specific double strand breaks (Heidenreich, 2016, Nature Reviews Neurosciences, 17: 36-44). A simple two-component system (consisting of Cas9 and a fusion of the tracrRNA-crRNA duplex to a "single-guide RNA", sgRNA) or a simple three-component system (consisting of Cas9, a tracrRNA molecule and a crRNA molecule, wherein the two RNA molecules are forming a "dual-guided RNA", i.e. a dgRNA) can be used to achieve DNA cleavage at any genomic locus of interest Cpf1, a single-RNA-guided nuclease, which only uses a crRNA and does not use a tracrRNA, can also be used for the induction of a site-specific DSB. Hence, different Cas proteins can be targeted to specific DNA sequences simply by changing the short specificity-determining part of the guide RNA, which can be easily achieved in one cloning step.

Thus, in the event the herein provided methods use Cas9 as site-specific nuclease, the cells of step a) may further comprise:
(i) at least one guide RNA consisting of at least one target sequence specific CRISPR RNA (crRNA) molecule and at least one trans-activating crRNA (tracrRNA) molecule; ("dual-guide RNA", dgRNA)
(ii) a polynucleotide encoding the RNA molecules of (i);
(iii) at least one guide RNA, which is a chimeric RNA molecule comprising at least one target sequence specific crRNA and at least one tracrRNA or ("single-guide RNA", sgRNA); and/or
(iv) a polynucleotide encoding the chimeric RNA of (iii).

Said guide RNA targets the site-specific nuclease (e.g. Cas9 or Cpf1) or the site-specific nickase (e.g. Cas9) to the site of the desired DSB or single-strand nick. For example, if a frame-shift has been induced by the deletion and/or introduction (e.g. deletion) of amino acids, the guide RNA (e.g. the sgRNA) may target the site-specific nuclease or nickase to the desired position of the DSB or singe-strand nick, respectively, which may be at a position 1-100 bp (corresponding to 1-33 amino acids) upstream or downstream of said deletion and/or introduction. Genome editing by using a site-specific DNA nuclease (such as Cas9 or Cpf1) and a guide RNA is commonly known in the art and described, e.g., in "CRISPR-Cas: A Laboratory Manual", 2016, edited by Jennifer Doudna, ISBN 978-1-621821-31-1.

In a preferred aspect of the herein provided methods, the cells of step a) comprise a polynucleotide (e.g. a plasmid vector) encoding at least one sgRNA. This polynucleotide may comprise a sequence encoding a sequence that is complementary to the target sequence (or complementary to a part of the target sequence) of about 20 nucleotides in length followed by a guide RNA scaffold sequence of about 76 nucleotides in length. This scaffold sequence encodes the direct repeat (DR) sequence and the tracrRNA.

As described above, in one embodiment of the invention, the site-specific nuclease is Cpf1. In this embodiment, the genome editing machinery may further comprise:
(i) at least one guide RNA comprising a target sequence specific crRNA molecule; or
(ii) a polynucleotide encoding the RNA molecules of (i).

In the context of the present invention the polynucleotide encoding the Cas9 or Cpf1 nuclease and the polynucleotide encoding the guide RNA may be comprised in one single nucleic acid sequence, for example in one plasmid vector. Alternatively, separate nucleic acid sequences, e.g. separate plasmid vectors, encoding either the Cas9/Cpf1 nuclease or the guide RNA may be present in (or delivered to) the cells of step a). However, also a pre-assembled Cas9 protein-guide RNA ribonucleoprotein complex (RNP) may be comprised in (or delivered to) the cells of step a) of the herein provided production method.

As mentioned, the Cas9 nuclease, when combined with a guide RNA comprising a target sequence specific crRNA molecule and a tracrRNA molecule, has the activity to introduce single or double strand breaks, preferably double strand breaks, into the DNA at a defined target site. In a preferred aspect of the present invention a plasmid vector encoding a Cas9 nuclease (e.g. SpCas9) as well as a sgRNA is present in (or delivered to) the cells of step a). In another preferred aspect of the invention the Cas9 nuclease is stably expressed in cells, while the sgRNA is delivered to the cells, e.g. via a plasmid vector encoding the sgRNA.

As indicated herein above and below, the cells of step a) of the herein provided production method preferably comprise a recognition site for the used site-specific nuclease or the used site-specific nickase at or in close proximity to the target site for the DSB or single-strand nick. If Cas9 used as site-specific nuclease or site-specific nickase, or if Cpf1 is used as site-specific nuclease, a particular recognition site (i.e. a protospacer-adjacent motif, PAM) is preferably immediately downstream of the target site for the DSB or single-strand nick. Herein, the "target site for the DSB or single-strand nick" is the position within a polynucleotide where the DSB or the single-strand nick is induced. The PAM sequences of various CRISPR nucleases and their variants are commonly known in the art (e.g. 5'-NGG for SpCas9, 5'-NNGRRT (SEQ ID NO: 50) or 5'-NNGRR(N) (SEQ ID NO: 51) for SaCas9, 5'-NNAGAAW (SEQ ID NO: 52) for St1Cas9, 5'-TTN for Cpf1).

and abundantly exist in the mammalian genome. Therefore, most of the genes can be targeted by using the Cas9 nuclease or the Cpf1 nuclease without artificially introducing a PAM sequence. However, if within the wild-type gene of interest no PAM sequence for the applied site-specific nuclease or nickase is immediately downstream of the desired target site for the DSB or single-strand nick, the PAM sequence may be exogenously introduced. If, immediately downstream of the target site for the DSB or single-strand nick, a part of the desired PAM sequence is already present, the full PAM sequence may be generated by exogenously introducing the missing nucleotides of the PAM sequence (i.e. by exogenously introducing the nucleotides of the PAM sequence that are not endogenously present at the desired position within the gene of interest).

The recognition site (e.g. PAM sequence) may or may not be present in the mutant variants of the gene encoding the protein of interest that are comprised in the cells selected in c) and/or provided in d). For example, said recognition site may be removed during introduction of the DSB or single-strand nick and cellular repair, such as HDR or NHEJ. In particular, the donor nucleic acid templates as provided in step b) may be configured to remove the recognition site from the gene of interest. For example, the donor nucleic acid templates may not comprise a sequence corresponding to the recognition site at the position corresponding to the recognition site within the gene of interest. Accordingly, in one aspect of the present invention the recognition site may not be present in the mutant variants of the gene encoding the protein of interest that are comprised in the cells that are selected and/or enriched in step c). This would avoid repeated cutting by Cas9 or Cpf1.

Exogenous introduction of a recognition site or parts thereof can be achieved by introducing said recognition site or said part thereof into the gene of interest before introducing the gene of interest into the genome of the cells. If the gene of interest is an endogenous protein, an exogenous recognition site or parts thereof may be incorporated by genetic engineering methods known in the art, in particular homologous recombination.

In a preferred aspect of the present invention the cells in step a) comprise a gene of interest, wherein a recognition site (e.g. a PAM sequence) for the applied site-specific nuclease or site-specific nickase is immediately downstream or upstream of the target site for the DSB or the single-strand nick, respectively. As mentioned above, it is preferred in the herein provided methods that the site-specific nuclease or the site-specific nickase is Cas9. It is further preferred in the herein provided methods that the cells in step a) express a sgRNA or a dgRNA targeting said Cas9 nuclease to said recognition site (e.g. to said PAM sequence). For example, the PAM site may be 1-100 bp downstream or upstream of the desired cutting site (e.g. the desired site for the DSB or single-strand nick).

As indicated above, if a ZRN, a TALEN or a megaTAL endonuclease is used as site-specific nuclease/nickase, one needs to customize the specific nuclease for a given sequence. TALENs can be custom-designed to target specific DNA sequences, for example 12 base stretches, to achieve a certain degree of specificity. The TALEN is assembled from protein modules, each recognizing a specific base. For example, for recognizing a 12base DNA stretch, twelve protein modules with correct base recognition need to be fused. Designing the correct TALEN for a sequence is routinely performed in the prior art, and can be done, e.g. by applying online tools. In addition, guidance on design and targeting by TALENs can be found in the internet, e.g. in the TALEN targeter tutorial (https://talent.cac.cornell.edu/tutorials/talentargeterupdated and under http://www.e-talen.org/E-TALEN/designtalens.html. Furthermore, design and assembly of custom TALEN and other TAL effector-based constructs for DNA targeting is also described in the scientific literature, e.g. by Cermak, 2011, Nucleic Acids Res. 39(12): e82).

The DSB in step a) of the herein provided generation method may also be induced (i.e. introduced) by two single-strand nicks in each of the two strands of the gene encoding for said protein of interest Said two single-strand nicks may be introduced by the same nickase or by two different nickases. The single copy of the gene encoding for said protein of interest in the cells of step a) may accordingly comprise two recognition sites (e.g. PAM sequences). If the same nickase is used for both single-strand nicks, both recognition sites may be identical. If two different nickases are used for both single-strand nicks, the recognition sites may differ from each other. The first and/or the second nickase may be a Cas9 nuclease that has site-specific nicking activity. For example, using a Cas9 nuclease allows introducing two nicks with a single enzyme. This can be achieved by providing two different guide RNAs (e.g. two different sgRNAs) which mediate targeting of the enzyme to the respective recognition site. For Cas9 nucleases, two different sgRNAs targeting the Cas9 nuclease to two different target sites and at least one PAM sequence may be used to induce a desired DSB (see, e.g., Tsai, Shengdar Q., and J. Keith Joung. "Defining and improving the genome-wide specificities of CRISPR-Cas9 nucleases." Nature Reviews Genetics 17.5 (2016): 300-312). The Cas9 nuclease and/or the two guide RNAs (e.g. two different sgRNAs) may be expressed from separate plasmids or, preferably, from the same plasmid. PAM sequences that serve as recognition site for Cas9 nucleases that have nicking activity are known in the art and are. For example, the PAM sequence for Cas9n (a D10A mutant of Cas9) is 5'-NGG The presence of a DSB or single-strand nick within the genomic DNA triggers intracellular repair mechanisms. Typically, if a single-strand nick is present and if a repair template is available, such a break is repaired by homology directed repair (HDR), particularly by homologous recombination; while a double strand break is typically repaired by either non-homologous end joining (NHEJ) or HDR. However, also in case of a single-strand nick repair via NHEJ may occur, however at a much lower frequency than by HDR. Generally, after introducing single- or double-strand breaks, HDR can be induced if a donor nucleic acid template is present; see, e.g., Heidenreich, 2016, Nature Reviews Neurosciences, 17: 36-44; Cong, 2013, Science, 339: 819-23; Doudna, 2014, Science, 346: 1258096; Hsu, 2014, Cell 157: 1262-78. HDR enables precise genome editing including accurate insertion, deletion or replacement of a desired sequence at the target site for mutagenesis. In contrast, repair by NHEJ introduces any kind of random deletions or insertions, also known as so called "INDEL mutations". The number and type of inserted nucleotides of such INDEL mutations can hardly be controlled. Similarly, INDEL mutations are limited to insertions and/or deletions of one or more nucleotides; and thus, do not offer a similar degree of diversification of a protein of interest as provided by HDR. Therefore, according to a prioritized aspect of the present invention, it is envisaged that the DSB or single-strand nick is at least preferentially repaired by HDR. This is achieved by providing the cells with a library of donor nucleic acid templates. Therefore, it is not necessary in the methods of the present invention to repress (i.e. inhibit) NHEJ to induce HDR. Indeed, a certain rate of NHEJ may be desired in order to further diversify the mutant variants of the protein of interest.

Independent of whether the method of the invention comprises step b) or not, NHEJ may contribute to the diversification of the protein of interest. In cases in which NHEJ lead to removal of the inactivating mutation as comprised in the single copy of the gene of interest in step a), also cells expressing such mutant variants of the protein of interest may be selected in step c), and may thus also form part of the panel of cells provided in step d). Accordingly, in one aspect of the invention the panel of cells provided in step d) may further comprises cells, in which repair of the DSB or the single-strand nick occurred by NHEJ. The cells, in which repair of the DSB or the single-strand nick occurred by NHEJ may comprise at least one random mutation that removed the inactivating mutation, wherein said random mutation preferably comprises an insertion and/or a deletion of one or more nucleotides directly adjacent to the position at which the DSB or single-strand nick is introduced in step a). As mentioned above, such random mutations are also referred to as INDEL mutations.

If desired, during step a) and b) the cells may be cultured under conditions that increase the rate of homologous recombination versus NHEJ. For example, said conditions may be inhibition or inactivation of an enzyme involved in NHEJ, expression of a protein that inhibits NHEJ, adding substances inhibiting NHEJ, slowing down replication fork progression, and/or triggering a cell cycle arrest in G2/M (see, e.g., Wu, 2005, Proceedings of the National Academy of Sciences of the United States of America 102.7: 2508-2513). A potential enzyme involved in NHEJ that may be inhibited is KU70 and/or DNA ligase IV. The protein that inhibits NHEJ may be a protein complex comprising or consisting of E1B55K and E4orf6. The substance inhibiting NHEJ may be selected from the group consisting of Sa7-pyrazine, ESCR7, L755507, Brefeldin A and L189 (CAS 64232-83-3) (see, e.g., Yu, 2015, Cell stem cell 16.2: 142-147 or http://www.tocris.com/pdfs/5342.pdf). Due to such culturing conditions, the rate of homologous recombination versus NHEJ may be increased by at least 1-fold, preferably at least 3-fold and most preferably at least 15-fold. Enzymes mediating NHEJ such as DNA ligase IV or KU70 may be completely knocked out in suitable cell lines or be replaced with versions of the respective protein in which destabilizing amino acid sequences are fused to N- or C-termini of the proteins. Stabilizing drugs may keep such enzymes functional while removal of drugs make the protein subject to rapid degradation, see e.g. Egeler, 2011, Journal of Biol Chemistry 286: 31328-31336. The protein diversification protocols of the current application may then be performed under conditions in which enzymes of NHEJ are transiently removed by degradation. After protein diversification ligand may be added again and result in stabilization of newly expressed enzymes mediating NHEJ.

In step b) of the herein provided production method the cells are provided with a library of donor nucleic acid templates. Said donor nucleic acid templates remove the inactivating mutation within the gene encoding the protein of interest. Thus, said nucleic acid templates are configured to remove said inactivating mutation. Or, in other words, the nucleic acid sequence of the donor nucleic acid templates are configured in a manner that upon HDR (particularly homologous recombination) of the DSB or single-strand nick using the provided donor nucleic acid templates, the inactivating mutation in the gene encoding for the protein of interest is removed.

Said different donor nucleic acid templates may comprise or be double-stranded DNA molecules. For example, said different donor nucleic acid templates may be comprised in a vector, e.g. a plasmid vector. In this case, each of said different donor nucleic acid templates may be comprised in a separate vector. In addition or alternatively, said different donor nucleic acid templates may comprise or be single-stranded oligonucleotides. For example, said single-stranded oligonucleotides may be locked nucleic acids (LNAs) and/or may comprise phosphorothioate modifications.

The term "locked nucleic acid(s)" of "LNA(s)" is commonly known in the art. A LNA is a nucleotide, wherein the ribose moiety is modified with an extra bridge connecting the 2' oxygen and 4' carbon. The bridge "locks" the ribose in the 3'-endo (North) conformation, which is often found in the A-form duplexes. The locked conformation improves hybridization properties of oligonucleotides, target specificity and resistance to nucleases.

The term "phosphorothioate modification" is commonly known to the skilled artisan and means that the phosphorothioate bond substitutes a sulfur atom for a non-bridging oxygen in the phosphate backbone of an oligonucleotide. This modification renders the internucleotide linkage resistant to nuclease degradation.

Each of said different donor nucleic acid templates comprises homologous nucleic acid sequences being homologous to the regions flanking the target site for mutagenesis. These homologous nucleic acid sequences are flanking the region encoding the desired mutation. For example, if the donor nucleic acid templates are comprised in plasmids, the length of the homologous sequences may be at least 800 nucleotides (i.e. at least 400 nucleotides on both sides of the desired mutation), preferably at least 1600 (i.e. at least 800 nucleotides on both sides of the desired mutation) and most preferably at least 2000 (i.e. at least 1000 nucleotides on both sides of the desired mutation). If the donor nucleic acid templates are ssODNs, the length of the homologous sequence may be around 40 nucleotides (i.e. 20 nucleotides on both sides of the desired mutation) to around 200 nucleotides (i.e. 100 on both sides of the desired mutation), preferably around 60 nucleotides (i.e. 30 nucleotides on both sides of the desired mutation) to around 120 nucleotides (i.e. 60 nucleotides on both sides of the desired mutation), and most preferably, around 80 nucleotides (i.e. 40 nucleotides on both sides of the desired mutation) to around 100 nucleotides (i.e. 50 nucleotides on both sides of the desired mutation). Accordingly, each of said different donor nucleic acid templates may comprise a first homologous nucleic acid sequence upstream of said position corresponding to said target site for mutagenesis with a length of at least 20 nucleotides, e.g. 20 to 500 nucleotides, 20 to 300 nucleotides, 20 to 100 nucleotides, 30 to 60 nucleotides, or 40 to 50 nucleotides; and may further comprise a second homologous nucleic acid sequence downstream of said position corresponding to said target site for mutagenesis with a length of at least 20 nucleotides, e.g. 20 to 500 nucleotides, 20 to 300 nucleotides, 20 to 100 nucleotides, 30 to 60 nucleotides, or 40 to 50 nucleotides.

The first homologous nucleic acid sequence may be directly upstream of said position corresponding to the target site for mutagenesis or may be within the 10 nucleic acids that are directly upstream of said position corresponding to the target site for mutagenesis. Similarly, the second homologous nucleic acid sequence may be directly downstream of said position corresponding to the target site for mutagenesis or may be within the 10 nucleic acids that are directly downstream of said position corresponding to the target site of mutagenesis.

The homologous sequences within the donor nucleic acid templates may have at least 80% sequence identity, preferably at least 95% sequence identity, and most preferably at least 99% identity to the regions flanking the target site for mutagenesis.

As mentioned above, in accordance with the present invention the donor nucleic acid templates also comprise different mutations at the position corresponding to the target site for mutagenesis. In particular, each donor nucleic acid template comprises a desired mutation that is to be generated in the protein of interest (at the target site for mutagenesis). Said different mutations at the position corresponding to the target site for mutagenesis are one or more nucleotide substitutions, deletions, or insertions, i.e. one or more nucleotide substitutions, deletions, or insertions as compared to the nucleotide sequence encoding the wild-type (i.e. non-modified) protein of interest. For example, a combination of nucleotides endogenous to the protein of interest and mutated nucleotides may result in a different amino acid sequence at the target site for mutagenesis. Alternatively, the nucleotides newly inserted into the target site for mutagenesis may encode for one or more amino acid residues that are different as compared to the amino acid residues that are present at the corresponding position of the wild-type (i.e. non-modified) protein of interest.

In the context of the present invention the donor nucleic acid templates remove the inactivating mutation (of the gene encoding the protein of interest) by HDR, particularly by homologous recombination. Within the donor nucleic acid templates the nucleic acid sequence removing said inactivating mutation may be the corresponding wild-type sequence of the gene encoding for the protein of interest, and/or may remove a frame-shift mutation within the gene encoding the protein of interest.

Typically, in the herein provided methods one batch of donor nucleic acid templates is used that comprises the diversity programmed into it, flanked by the homology arms. Usually, all donor nucleic acid templates are synthesized in one batch and share the same homology arms, but they are constituting millions of different donor molecules. In particular, due to different "donor nucleic acid sequences" the library of donor nucleic acid templates comprises at least 2, at least 5, at least 10, at least 15, at least 20, at least 100, at least 1000, at least 10000, or at least 1000000 different donor nucleic acid templates. Thus, one aspect of the present invention relates to the herein provided methods, wherein the library of different donor nucleic acid templates comprises at least two different donor nucleic acid templates, preferably at least 5 different donor nucleic acid templates, more preferably at least 10 different donor nucleic acid templates, even more preferably at least 15 different donor nucleic acid templates, even more preferably at least 20 different donor nucleic acid templates, even more preferably at least 100 different donor nucleic acid templates, even more preferably at least 1000 different donor nucleic acid templates, even more preferably at least 10000 different donor nucleic acid templates, or even more preferably at least 1000000 different donor nucleic acid templates. As mentioned above, the donor nucleic acid templates comprise different mutations. Preferably, there is one mutation per donor nucleic acid molecule. The "mutation" within each donor nucleic acid template is a nucleotide or a nucleotide sequence that is different as compared to the corresponding sequence within the gene of interest. The "mutation" within each donor nucleic acid template is also called "sequence of diversification". Said "mutation" or "sequence of diversification" preferably results in one or more amino acid substitution(s), replacement(s) and/or insertion(s) within the protein of interest. Said sequence of diversification can encode one or more specific amino acid(s), and/or can comprise a degenerate codon. For example, the degenerated code within the sequence of diversification may be NNN, NNK/NNS, NNB and/or the MAX system. As known in the art, N stands for any nucleotide of the DNA, i.e. adenine (A), guanine (G), cytosine (C) or thymine (T). B stands for any nucleotide apart from adenine. Therefore, the degenerated code NNB decreases the likelihood for introducing a stop codon (i.e. TAA, TGA). As also known in the art, in degenerated codes K stands for guanine (G) or thymine (T), excluding adenine (A) or cytosine (C); and S stands for cytosine (C) or guanine (G), excluding adenine (A) or thymine (T). The MAX system is also known in the art and described, e.g., in Hughes, 2003, J. Mol. Biol. 331: 973-979. In this system, up to 20 primers are generated (one for each amino acid) at each site to be targeted. These are annealed to a fully randomized template (NNN for targeted residues), and ligated to form the unbiased library.

The donor nucleic acid templates may also be designed to leave (a) particular amino acid(s) unchanged, wherein the flanking amino acid(s) (i.e. the amino add(s) surrounding the unchanged amino acid) is/are modified. Thus, the degenerate codon within the donor nucleic acid templates may be interleaved with (an) amino acid(s) from the original amino acid sequence of the protein of interest. For example, some amino acids within the target site for mutagenesis may be considered critical, and therefore, are not to be diversified.

The library of different donor nucleic acid templates comprises donor nucleic acid templates that differ in the mutation they comprise at the position corresponding to the target site for mutagenesis. For example, the different donor nucleic acid templates may differ in the amino acid(s) they encode at the position corresponding to the target site for mutagenesis. In addition or alternatively, the different donor nucleic acid templates may differ in the amount of different amino acids they encode at the position corresponding to the target site for mutagenesis. For example, within the library of different donor nucleic acid templates some donor nucleic acid templates may encode for 1 amino acid at the position corresponding to the target site for mutagenesis, whereas others encode for at least 2, at least 3, at least 4, at least 5, at least 6, at least 7, at least 8, at least 9, at least 10, at least 11, and/or at least 12 amino acids (e.g. 3 to 5 amino acids) at the position corresponding to the target site for mutagenesis.

For example, in the inactivated gene of interest (i.e. the gene of interest comprising the inactivating mutation) the condon for at least one amino acid may have been deleted. In this scenario, the donor nucleic acid templates may be configured to replace the deleted amino add(s), to remove the frame-shift, and to randomize at least one amino acid (e.g. 1 or 2 amino acids) flanking the replaced amino acid(s).

In the herein provided production method step b) may be performed prior to step a); or preferably simultaneously with step a). If steps a) and b) are performed simultaneously, the site-specific nuclease or nickase may also cut some of the donor nucleic acid templates. This does not significantly perturb the methods of the present invention. However, if desired, cutting of the donor nucleic acid templates can be obviated by several methods commonly known to the skilled artisan. For example, if the donor nucleic acid templates are double strand DNA (dsDNA), e.g. comprised in a plasmid, a silent or at least neutral mutation may be introduced into the PAM sequence of the donor nucleic acid templates. If the donor nucleic acid templates are ssODNs, cutting of the ssODNs may be obviated by having the sgRNA sequence and the corresponding ssODN sequence at the same strand.

In step a) of the production method of the present invention a DSB or a single-strand nick is induced at or in close proximity to a target site for mutagenesis in the gene encoding for the protein of interest (i.e. the gene of interest). In this context the cells comprise only a single and inactivated copy of the gene of interest (i.e. only a single and inactivating allele of the gene of interest) in their genome. Specifically, the single copy of the gene of interest is inactivated by comprising at least one inactivating mutation at or in close proximity to a target site for mutagenesis at which the amino acid sequence should be diversified (particularly mutagenized).

Thus, the single copy of the gene encoding for the protein of interest comprises an inactivating mutation at or in close proximity to the target site for mutagenesis. Said inactivating mutation may be at or in close proximity to the site at which the DSB or single-strand nick is introduced. For example, 1-21 nucleotides (corresponding to 1-7 amino acids) downstream of a selected (or introduced) PAM site, 4 base pairs may have been removed, removing one amino acid and generating a frame-shift.

A gene comprising an inactivating mutation can also be referred to as an inactivated gene or a gene that is inactivated by mutation. Thus, an inactivating mutation comprised in the gene of interest is preferably any alteration/modification within the nucleic acid sequence of the gene that at least inhibits or more preferably prevents the expression of the corresponding protein. In other words, the inactivating mutation may inhibit or preferably prevent the expression of the protein of interest as compared to the protein that is encoded by the corresponding wild-type gene that lacks the inactivating mutation. The inactivating mutation may also lead to the expression of a protein that is less active as compared to the corresponding wild-type protein. Or, in other words, the protein that is expressed from the inactivated gene of interest (i.e. the protein of interest that is encoded by the gene of interest having the inactivating mutation) may have less activity as compared to the wild-type protein of interest (i.e. the protein encoded by the gene of interest without the inactivating mutation). For example, the less active protein may have not more than 70%, preferably not more than 50%, more preferably not more than 30%, even more preferably not more than 10%, and most preferably 0% of the activity of the corresponding wild-type protein of interest. Such a less active protein may have a less enzymatic activity (if the protein of interest is an enzyme) or less binding activity to a particular epitope (if the protein of interest is an antibody) as compared to the corresponding wild-type protein. If the protein of interest is a fluorescent protein, such a less active protein may have less (or preferably no) fluorescence. However, the protein of interest is not limited to enzymes, antibodies and fluorescent proteins. Therefore, depending on the protein of interest, the less active protein may have, e.g., less binding affinity to an affinity material or to a molecular structure (e.g. to DNA, RNA, a protein, or a peptide), less activity in terms of inducing a chemical reaction that can be observed in vivo (e.g. a color reaction), or less drug and/or antibiotic resistance.

In the context of the present invention less activity of the protein of interest that is caused by the inactivating mutation can be used in step c) for selecting and/or enriching those cells wherein said inactivating mutation has been removed, e.g. by homologous recombination. For the example, in the event that the inactivating mutation causes less fluorescence activity, fluorescent cells (and/or highly fluorescent cells) can be selected and/or enriched in step c). Therefore, fluorescence-activated cell sorting (FACS) techniques may be used. A non-limiting example of how such FACS techniques may be performed is presented in the appended examples.

Examples for inactivating mutations comprise mutations that lead to a frame-shift in said gene of encoding for the protein of interest (i.e. a mutation that causes an alteration of the reading frame of the gene of interest), a mutation that introduces a premature stop codon in said gene encoding for the protein of interest or introduces in said gene encoding for the protein of interest a mutation resulting in an inactivating amino acid substitution. Said inactivating amino acid substitution may inhibit or prevent activity (e.g. enzymatic activity or binding activity) of the corresponding protein, or may preferably inhibit or more preferably prevent expression of the corresponding protein. Most preferably, the inactivating mutation is a frame-shift mutation within the gene (i.e. nucleotide sequence) encoding for the protein of interest.

From a molecular perspective an inactivating mutation may be a base pair substitution, an insertion of one or more nucleotides or a deletion of one or more nucleotides. For example, said inactivating mutation is or comprises a base pair substitution, a base pair insertion, a base pair deletion, a stop codon, or an inactivating amino acid substitution. Said inactivating amino acid substitution may lead, e.g., to a misfolded protein and/or to a catalytically inactive protein. A skilled person knows which mutation is required to achieve any of the above mentioned types of inactivating mutations.

As mentioned above, the inactivating mutation in the single copy of the gene encoding for the protein of interest is at or in close proximity to the target site for mutagenesis. The term in "close proximity to the target site for mutagenesis" as used herein refers to any distance to the target site for mutagenesis that still allows for designing donor nucleic acid templates for introducing the desired mutation(s) at the target site for mutagenesis and removing the inactivating mutation. Thus, the term "in close proximity to the target site of mutagenesis" may refer to a distance of not more than 100 nucleotides, preferably not more than 80 nucleotides, more preferably not more than 60 nucleotides, even more preferably not more than 40 nucleotides, even more preferably not more than 30 nucleotides, and most preferably not more than 10 nucleotides. Similarly the inactivating mutation may also be positioned directly at the target site for mutagenesis.

In the context of the present invention the inactivating mutation may prevent a selectable activity of the protein of interest (e.g. fluorescence activity). In this case, step c) of the herein provided production method may comprise or be selection and/or enrichment of cells having said selectable activity (e.g. having fluorescence activity). Preferably, the inactivating mutation prevents expression of the protein of interest. In this case, expression of the protein of interest indicates successful removal of the inactivating mutation; and thus, advantageously indicates successful mutagenesis of the protein of interest. In this case step c) of the herein provided production method may comprise or be selection and/or enrichment of cells expressing said protein of interest. If the protein of interest is not directly selectable (i.e. is not selectable due to its inherent properties, such as fluorescence, cells expressing the protein of interest may be selected and/or enriched by using antibodies specifically binding to said protein of interest.

For example, FACS and antibodies specifically binding to the protein of interest may be used to select and/or enrich cells that express the protein of interest Such a method is particularly useful if the protein of interest is displayed at the cell surface. This can be achieved by commercial vectors e.g. pDisplay. In particular, targeting sequences to send mutant variants of the protein of interest to the cell surface can simply be added to the gene cassette encoding the protein of interest before insertion into the cell genome in single copy number. Such techniques have become very powerful and allow efficient functional presentation of proteins (such as Fab fragments, single chain antibodies or whole IgGs) on the surface of cells, such as mammalian cells, e.g. HEK293 cells. Protocols for efficient display and screening have become standard of the art and are provided, e.g. by Ho, 2008, Methods in Molecular Biology, 525: pp 337-352; and Zhou, 2012, Methods in Molecular Biology, 907: 293-302.

Alternatively, if the protein of interest is a binding molecule such an antibody, cells expressing mutant variants of the protein of interest can be identified via a panning approach. For this purpose specific surfaces may be conjugated with the desired antigen. Cells expressing the antibody library and expressing it on the cell surface may be incubated on this surface. Cells expressing effective antibodies will bind to the surface. After washing away non-binding cells, stringency can be increased by additional washes with increasing amounts of added soluble antigen. After several rounds of washes, the remaining cells bound to the surface can be harvested by a suitable method, e.g trypsinization, and allowed to recover.

Alternatively, the panning approach can be reverted by adsorbing an antibody to a surface, and presenting the protein of interest on the surface of cells. This panning could be used to enrich cells.

One could also generate a fusion protein comprising the protein of interest and an immune tag, e.g. a myc epitope or HA tag, as selectable marker (instead of or in addition to a fluorescent protein or a drug resistance protein).

It may be desired (e.g. if the protein of interest is a fluorescent protein) that the protein of interest is a monomer. Therefore, the gene of interest may have been modified in order to prevent dimer or multimer formation of the expressed protein of interest.

Alternatively, the gene encoding for the protein of interest may be comprised in the genome of the cells as a fusion gene, wherein said fusion gene comprises a marker gene downstream of the gene encoding the protein of interest A marker gene (also called "selectable marker gene") is a gene that confers a trait suitable for artificial selection. The marker gene encodes a marker (also called "marker protein"). A "positive marker" is a selectable marker that confers selective advantage to the host organism, or is selectable due to its inherent properties, such as fluorescence. A "negative marker" (also called "counter-selectable marker") is a selectable marker that eliminates or inhibits growth of the host organism that is not to be selected.

In the above-described fusion gene, the marker gene and the gene encoding for the protein of interest are in frame. In particular, in the fusion gene the coding sequences of the protein of interest and a marker gene are operable fused to each other so that they are expressed in one mRNA molecule that allows for the expression of a respective fusion protein. Said fusion protein comprises the protein of interest and the marker protein that are operable linked/fused to each other. Particularly, said fusion protein comprises the protein of interest and, at its C-terminus, the marker protein.

It is preferred in the context of the invention that the inactivating mutation in the protein of interest that is comprised in said fusion gene also prevents expression of the marker gene. In this case, cells wherein the inactivating mutation has been removed; and thus, diversification of the protein of interest has been occurred; can easily be selected by selecting and/or enriching cells expressing the marker gene. Thus, in one aspect of the herein provided production method step c) comprises or is selection and/or enrichment of cells expressing the protein encoded by the marker gene. Preferably, expression of the protein encoded by the marker gene is directly selectable (i.e. is selectable due to its inherent properties, e.g. due to its fluorescence). For example, the protein encoded by the marker gene may be a fluorescent protein. In this case, selecting and/or enriching in step c) preferably comprises isolation of cells that express said fluorescent protein. Several methods for selectively isolating a population of cells are known in the art. For example, isolation of cells may be achieved by or may comprise FACS or microfluidic cell sorting. It may be desired (e.g. if the marker gene encodes a fluorescent protein) that the marker protein (e.g. the protein encoded by the marker gene) is a monomer. Therefore, as mentioned above, the marker gene may have been modified in order to prevent dimer or multimer formation of the expressed marker protein.

Selection and/or enrichment of cells expressing the above described fusion gene (i.e. the fusion gene comprising the gene encoding the protein of interest and a marker gene) may also be achieved by using other mechanisms than sorting by fluorescence. For example, expression of the protein encoded by the marker gene may confer drug resistance, may confer antibiotic resistance, may complement an auxotrophy, may confer a detectable enzymatic activity, or may be an immune epitope. These properties of the marker protein may be used in order to select and/or enrich in step c) cells in which the inactivating mutation has been removed.

For example, a protein encoded by the marker gene and confers enzymatic activity may be, e.g. a β-lactamase, or a protease such as enterokinase, or TEV. Several drugs (e.g. antibiotics) as well as genes encoding proteins that confer resistance to said drugs are known. For example, puromycin inhibits protein synthesis by disrupting peptide transfer on ribosomes causing premature chain termination during translation. The pac gene encodes for puromycin N-acetyl-transferase and is a potential puromycin resistance gene. Hygromycin B is an aminoglycosidic antibiotic that inhibits protein synthesis by disrupting translocation and promoting mistranslation at the 80S ribosome. The hyg gene encoding aminocyclitol phosphotransferase confers resistance to hygromycin B. Zeocin causes cell death by intercalating into and cleaving DNA. The Sh ble gene product binds Zeocin, preventing it from binding DNA; and thus, confers resistance. Blasticidin is a translational inhibitor in both prokaryotic and eukaryotic cells. Resistance to blasticidin is conferred by the product of the bsd gene. G-418 interferes with the function of 80S ribosomes and protein synthesis in eukaryotic cells. The neor gene confers resistance to G-418. If the protein encoded by the marker gene confers drug resistance, antibiotic resistance or completes an auxotrophy, selecting and/or enriching in step c) preferably comprises culturing the cells under selective conditions.

In context of the present invention, expression of the protein of interest may also be negatively selectable. Or, in other words, non-expression of the protein encoded by the marker gene may indicate expression of the protein of interest. Thus, the protein encoded by the marker gene may be expressed in the presence of the inactivating mutation and the marker gene may not be expressed in cells in which the inactivating mutation has been removed. Herein, "not expressed" includes that the protein is not expressed in frame. Thus, herein the marker gene is considered to be not expressed, if a reading frame that is different from the reading frame of the marker gene is transcribed. Thus, one aspect of the present invention relates to the herein provided production method, wherein the protein encoded by the marker gene is expressed in presence of said inactivating mutation in said gene encoding for the protein of interest, and wherein said marker gene is not expressed or not expressed in frame in cells in which said inactivating mutation in said gene encoding for the protein of interest is removed. In this case, step c) of the herein provided production method preferably comprises or is selection and/or enrichment of cells that do not express the protein encoded by the marker gene. In order to achieve expression of the protein of interest when the protein encoded by the marker gene is not expressed, a few systems are known in the art. For example, the protein encoded by the marker gene may be the thymidine kinase (HSVtk). This protein acts as a conditional lethal marker in mammalian cells since it is able to phosphorylate certain nucleoside analogs like ganciclovir, converting them into toxic DNA replication inhibitors.

The above described fusion gene (i.e. the fusion gene comprising the gene encoding the protein of interest and a marker gene) may comprise a linker nucleic acid sequence between said gene encoding for the protein of interest and said marker gene. Said linker nucleic acid sequence may comprise or consist of a nucleic acid sequence that encodes a self-cleaving peptide. Several self-cleaving peptides are commonly known in the art. For example, the self-cleaving peptide may be selected from the group consisting of the T2A peptide, the P2A peptide, the E2A peptide, and the F2A peptide. The amino acid sequences of 2A peptides, particularly of T2A, P2A, E2A and F2A are shown herein below as SEQ ID NOs: 1-4.

The linker nucleic acid sequence may also comprise or consist of a nucleic acid sequence that encodes a target site of a site-specific protease. For example, said target site of a site-specific protease may be selected from the group consisting of the target site of the TEV protease having an amino acid sequence as shown in SEQ ID NO: 5, the target site of Genenase I having an amino acid sequence as shown in SEQ ID NO: 6, the target site of Enterokinase having an amino acid sequence as shown in SEQ ID NO: 7, and the target site for Human Rhinovirus (HRV) 3C Protease having an amino acid sequence as shown in SEQ ID NO: 8. Although less preferred, the target site of a site specific protease may also be the target site for Factor Xa having an amino acid sequence as shown in SEQ ID NO: 9, and the target site for Thrombin having an amino acid sequence as shown in SEQ ID NO: 10. If the linker nucleic acid sequence comprises or consists of a nucleic acid sequence that encodes a target site of a site-specific protease, then the cells (i.e. the cells of any one of steps a) to d) of the herein provided production method) may further express the corresponding site-specific protease cleaving said target site. Said site-specific protease may be selected from the group consisting of a TEV protease, Genenase I, Enterokinase, Human Rhinovirus (HRV) 3C Protease, Factor Xa, and Thrombin.

Preferably, after steps a) and b) of the herein provided production method, cells that have undergone diversification produce the marker protein fused to the protein of interest. The marker gene is expressed at the same level as the gene of interest, and when a fluorescent protein is used as marker protein, said fluorescent protein can serve as an estimate of protein concentration. Thus, for binding assay utilizing the protein of interest, the binding can be calibrated to the expression level. In addition, cells expressing a fluorescent marker gene can be rapidly collected with FACS or microfluidic sorting, a more rapid process than antibiotic selection.

If the marker gene encodes a positive or negative selectable marker protein, several possibilities exist to obtain a cell population consisting of just diversified variants. If both positive and negative markers are used together via multiple cleavable peptide linkers such as T2A or F2A, negative selection can be used to eliminate the non-frame-shifted variants, with a gene such as herpes simplex virus type 1 thymidine kinase, and selected against with ganciclovir. Once the cells are isogenic, and subjected to the diversification via the production method of the present invention, the unwanted remaining frame-shift variants can be removed with a positive selection gene such as hygromycin phosphotransferase and hygromicin B. However, as described herein above, other selection markers will be also useable.

In step c) of the method of the present invention cells are selected and/or enriched (e.g. enriched) in which the inactivating mutation has been removed. Selection and/or enrichment of the cells in which the inactivating mutation has been removed can even be improved by performing at least 1 (e.g. 1 to 10, such as 3) further rounds of selection. For example, the cells selected/enriched in step c) may be grown and the desired fraction (e.g. the 1-30% of the cells, which show highest protein expression, e.g. the 5% of the cells, which show highest protein expression) may be selected and grown. This procedure can be repeated 1 to 10 times, e.g. 3 times. If the protein of interest is or is fused to a fluorescent protein, the 1-30% of the cells, which show highest protein expression can be selected, e.g., by selecting the 1-30% of the cells that show highest fluorescence, e.g. by FACS.

The cells selected in step c) comprise or consist of cells in which repair of the DSB or single-strand nick as induced in step a) gave rise to the removal of the inactivating mutation in the gene encoding for the protein of interest. Removal of the inactivating mutation preferably means that the sequence of the inactivated single copy encoding the protein of interest is modified in a manner that a mutant variant of the protein of interest is expressed. As detailed below, said mutant variant has at least 80% sequence identity to the protein of interest. Thus, a completely different protein (e.g. resulting from the transcription of a reading frame that is different from the reading frame of the gene encoding the protein of interest) is not considered as a mutant variant of the protein of interest. As mentioned above, the inactivating mutation may also lead to the expression of a variant of the protein of interest with a decreased or activity or with no activity at all. In this case, removal of the inactivating mutation may recover activity of the protein of interest at least in some of the mutant variants of the protein of interest. However, as in the herein provided methods several different mutant variants of the protein of interest are produced, many of these mutant variants will usually still be non-functional in terms of the protein activity one seeks to improve. For example, removal of the inactivating mutation may lead to the expression of a mutant variant of the protein of interest that has at least 80%, more preferably at least 90%, even more preferably at least 95%, even more preferably at least 98%, even more preferably at least 99%, and even more preferably at least 100% of the activity of the corresponding protein of interest Most preferably, the mutant variant has more than 100% (e.g. at least 101%, at least 110%, at least 120%, or at least 150%) of the activity of the protein of interest.

In step d) of the herein provided production method a panel of cells expressing different mutant variants of the protein of interest are provided. The amino acid sequence of the protein of interest is encoded by the gene of interest without the inactivating mutation. Or, in other words, the protein of interest (also called herein "wild-type protein of interest") is the protein that would be encoded by the gene encoding the protein of interest in the cells of step a), if the gene would not comprise the inactivating mutation. Although the protein of interest is also called "wild-type protein of interest" it may, in principle, also be a known mutant variant of a particular protein. For example, mutant variants of a protein with improved properties may be known in the art and it may be desired to test whether further mutations within this known mutant variant result in a protein with even better performance.

Thus, the protein of interest may be any protein that is to be mutated within the herein provided means and methods. For example, the protein of interest may be a fluorescent protein, an antibody, an enzyme, a growth factor, a cytokine, a peptide hormone, a transcription factor, a RNA binding protein, a cytoskeletal protein, an ion channel, a G-protein coupled receptor, a kinase, a phosphatase, a chaperone, a transporter, or a transmembrane protein. Preferably, the protein of interest is an enzyme, an antibody or a fluorescent protein. If said protein of interest is a fluorescent protein, it may be a fluorescent protein selected from the group consisting of mNeonGreen, mRuby2/3, dTomato, TagRFP, Citrine, Venus, YPet, mTFP1, EGFP, Kusabira Orange, mOrange, mApple, mCerulean3, mTurquoise2, mCardinal, EosFP, Dronpa, Dreiklang and infrared iRFP. If the protein of interest is a fluorescent protein it is preferably mNeonGreen2. If the protein of interest is an antibody, then the target site for mutagenesis is preferably in a CDR coding region of the nucleic acid sequence encoding the heavy or the light chain of said antibody. If the protein of interest is an enzyme, then the target site for mutagenesis is preferably in the nucleic acid region encoding the active center of the enzyme or a regulatory subunit of said enzyme.

The mutant variant of the protein of interest is a protein that has a related but not identical amino acid sequence to the protein of interest. In particular, the amino acid sequence of the mutant variant of interest may have at least 80%, even more preferably at least 85%, even more preferably at least 90%, even more preferably at least 95%, even more preferably 98% and most preferably at least 99% sequence identity to the amino acid sequence of the protein of interest. In one aspect of the production method of the present invention said different mutant variants of the protein of interest expressed in the cells of the panel of cells provided in step d) comprise one or more amino acid exchanges, insertions of one or more amino acids, and/or deletions of one or more amino acids compared to the protein of interest. For example, said one or more amino acid exchanges may be at least 1, e.g. at least 2, at least 3, or at least 5 amino acid exchanges. Similarly, said insertions of one or more amino acids may be insertions of at least 1, e.g. of at least 2, at least 3, or at least 5 amino acids. In line with this, said deletions of one or more amino acids may be deletions of at least 1, e.g. of at least 2, at least 3, or at least 5 amino acids.

Preferably, the mutant variant of the protein of interest has an amino acid sequence that is identical to the amino acid sequence of the protein of interest, except of one or more amino acid substitutions (i.e. exchanges), insertions of one or more amino acids, and/or deletions of one or more amino acids as compared to the protein of interest. These substitutions, insertions and/or deletions of one or more amino acids are at the target site for mutagenesis. The number of amino acids that are substituted, inserted and/or deleted may be between 1 and 25 amino acids, preferably between 1 and 20 amino acids, more preferably between 1 and 15 amino acids, even more preferably between 1 and 12 amino acids, even more preferably between 1 and 5 amino acids, and most preferably between 3 and 5 amino acids.

The panel of cells provided in step d) of the herein provided production method is preferably enriched for cells that comprise at the target site for mutagenesis different mutations that are comprised in the different donor nucleic acid templates at the position corresponding to the target site for mutagenesis in the gene encoding for the protein of interest. The position that corresponds to the target site for mutagenesis may, for example, be determined by sequence alignments as described elsewhere herein and/or as known in the art. Preferably, the cells that are enriched in the panel of cells are cells, in which HDR of said DSB or single-strand nick (preferably DSB) occurred via homologous recombination with a donor nucleic acid template of the library of different donor nucleic acid templates provided in step b). In other words, the panel of cells that is provided in step d) of the method of the present invention is preferably enriched for cells expressing different mutant variants of the protein of interest that are encoded by mutated variants of the gene of interest. In particular, as mentioned above, in step a) of the herein provided production method the gene of interest comprises an inactivating mutation, i.e. the protein of interest is less active and/or less expressed. Preferably, the protein of interest is not expressed at all. In step b) of the herein provided production method HDR is induced by the provision of donor nucleic acid templates, which, in turn, leads to removal of the inactivating mutation. Consequently, activity and/or expression of the protein of interest is recovered. In addition, HDR leads to introduction of the mutations comprised in the donor nucleic acid templates into the protein of interest. A mutation is introduced into the gene of interest at the target site for mutagenesis. Accordingly, the panel of cells provided in d) preferably comprises or is enriched for cells in which HDR of the induced DSB or single-strand nick occurred using a donor nucleic acid template of the provided library of different donor nucleic acid templates. It is envisaged that in the panel of cells provided in step d) at least 4%, preferably at least 6%, more preferably at least 8%, even more preferably at least 12%, even more preferably at least 15%, even more preferably at least 20%, even more preferably at least 30%, even more preferably at least 40%, even more preferably at least 50% and most preferably at least 60% of the cells comprise at the target site for mutagenesis one of the mutations that are comprised in the different donor nucleic acid templates.

As in the herein provided methods a library of different donor nucleic acid templates is employed, the resulting panel of cells comprises different mutant variants of the protein of interest. Thus, in the herein provided production method said panel of cells provided in step d) comprises (or preferably is) a pool of cells that express different mutant variants of said protein of interest, wherein one of said different mutant variants is expressed per cell from a single gene copy. Accordingly, the produced panel of cells comprises different cells that differ in the particular mutant variant of the protein of interest that is expressed. Said different cells may be cultured as a pool. Alternatively, said different cells may be cultured separately. Separate culturing of the cells may facilitate purification and/or analysis of a single mutant variant of the protein of interest. Therefore, in one aspect of the herein provided production method said panel of cells provided in step d) is a library of cells in which the cells expressing different mutant variants are cultured separately. In this aspect of the invention, the herein provided production method may further comprise between steps c) and d) the step of separating from the cells selected and/or enriched in step c) the cells expressing different mutant variants.

In accordance with the present invention the nucleic acid and/or amino acid sequence of one or more mutant variant(s) of the protein of interest (that are comprised in the produced panel of cells) may be determined. Analysis of the nucleotide or amino acid sequence of a mutant variant of the protein of interest is useful for determining the generated mutation and/or cloning the desired mutant variant. Thus, in one aspect of the present invention the herein provided production method further comprises determining the nucleic acid sequence of one or more of the genes encoding for said different mutant variants of the protein of interest comprised in the cells selected and/or enriched in step c) and/or provided in d); or determining the amino acid sequence of one or more of said different mutant variants of the protein of interest comprised in the cells selected and/or enriched in step c) and/or provided in d).

The panel of cells (also called "cell library" or "cell population") preferably comprises 100,000 to billions of cells. For example, for FACS usually a few hundred million cells (e.g. 100,000,000 to 300,000,000 cells) are used. For panning, a liter-scale suspension cell culture, e.g. with about 500,000 cells per ml, may be used. Thus, for panning billions of cells may be applied. The cells employed in the methods of the present invention may in principle be any cells in which cellular repair, such as HDR (particularly homologous recombination), can occur. Such cells are well known in the art. In all diploid organisms (even if the diploidy is only transient, as in replicating bacteria or replicating haploid yeast), HDR can in principle be induced. For instance, in the herein provided means and methods the cells may be any prokaryotic cells (e.g. in which HDR, particularly homologous recombination, can occur) or any eukaryotic cells (e.g. in which HDR, particularly homologous recombination can occur). For example, the cells employed in the context of the present invention may be selected from the group consisting of yeast cells, non-mammalian vertebrate cells (e.g. in which HDR, particularly homologous recombination, can occur), plant cells (e.g. in which HDR, particularly homologous recombination, can occur), insect cells (e.g. in which HDR, particularly homologous recombination, can occur) or mammalian cells (e.g. in which HDR, particularly homologous recombination, can occur). Preferably, mammalian cells or non-mammalian vertebrate cells are employed. Most preferably, mammalian cells are employed. Particularly preferred non-mammalian vertebrate cells are DT-40 cells, which are cells of a B-cell line derived from an avian leukosis virus induced bursal lymphoma in a white leghorn chicken. Particularly preferred mammalian cells that may be employed in the context of the present invention are HEK 293 cells (sometimes also referred to as Human Embryonic Kidney 293 cells, HEK-293, 293 cells, 293 T cells or HEK cells), lymphoma cell lines (e.g. NSO, Sp2/0-Ag14), leukemia cell lines, Jurkat cells, Chinese hamster ovary (CHO) cells, HeLa cells, PC12 cells, antibody producing hybridoma cell lines, immortalized human B-cell lines, or other immortalized human cell lines known in the art.

In the herein provided production method the culturing periods may be adjusted to the respective cell type used. During the culturing period after induction of HDR (i.e. the culturing period after steps a) and b)) expression of the mutant variant of the protein of interest takes place. Subsequently, cells comprising the protein of interest (e.g. in form of a fusion protein comprising the protein of interest and a marker protein) can be selected and/or enriched in step c) of the herein provided production method. For example, when the cells are mammalian cells, the cells may be cultured for at least 48 hours, preferably at least 72 hours and most preferably at least 96 hours after steps a) and b). As mentioned herein, steps a) and b) are preferably performed simultaneously. Therefore, the above mentioned culturing period may be after the simultaneously performed steps a) and b).

The panel of cells produced in the herein provided production method may comprise cells expressing a mutant variant (of the protein of interest) that has an improved first activity and/or a new activity as compared to the wild-type protein of interest. Accordingly, after provision of a panel of cells in step d) of the herein provided method, a further step e) may be performed in order to specifically enrich mutant variants having an improved first activity and/or a new activity. Thus, one aspect of the present invention relates to the herein provided production method, wherein said mutant variants of the protein of interest are improved in a first activity and/or have a new activity compared to the wild-type protein of interest, wherein said method further comprises:

e) selecting and/or enriching from the panel of cells a second panel of cells that express mutant variants of the protein of interest that are improved in a first activity and/or have a new activity.

Alternatively, an improved first activity and/or new activity may be directly used in step c) of the herein provided production method in order to particularly select and/or enrich cells expressing a mutant variant having said improved first activity and/or new activity. For example, if the protein of interest is a fluorescent protein, then cells expressing mutant variants of the protein of interest that have an improved fluorescence (e.g. an improved first activity) may selectively be enriched in step c) of the herein provided method.

Thus, a further aspect of the present invention relates to the herein provided production method, wherein said mutant variants of said protein of interest are improved in a first activity and/or have a new activity compared to the wild-type protein of interest and wherein step c) comprises selecting and/or enriching mutant variants of the protein of interest that are improved in a first activity and/or have a new activity compared to the wild-type protein of interest.

The herein provided production method advantageously enables screening for mutant variants (of a protein of interest) having a different or modified activity as compared to the protein of interest. Thus, the present invention provides a screening method, i.e. a method for identifying a mutant variant of a protein of interest having a different or modified (e.g. biological) activity compared to the wild-type protein of interest, wherein said method comprises:

a) selecting and/or enriching from the panel of cells resulting from the production method of the invention a second panel of cells that express mutant variants of the protein of interest that are improved in a first activity and/or have a new activity; and b) determining the amino acid sequence of the mutant variants of the protein of interest expressed by said second panel and/or determining the nucleic acid sequence of the genes encoding for the mutant variants of the protein of interest expressed by said second panel.

As described above, an improved first activity and/or new activity may be directly used in step c) of the herein provided production method in order to particularly select and/or enrich cells expressing a mutant variant having an improved first activity and/or new activity. Thus, the present invention provides a further screening method, i.e. a method for identifying a mutant variant of a protein of interest having a different or modified (e.g. biological) activity compared to the wild-type protein of interest, wherein said method comprises:

a) the production method as provided herein,
  wherein step c) comprises selecting and/or enriching
    mutant variants of the protein of interest that are improved in a first activity and/or have a new activity compared to the wild-type protein of interest; and b) determining the amino acid sequence of at least one of the mutant variants of the protein of interest that are improved in a first activity and/or have a new activity compared to the wild-type protein of interest; and/or determining the nucleic acid sequence of at least one of the genes encoding for the mutant variants of the protein of interest that are improved in a first activity and/or have a new activity compared to the wild-type protein of interest.

The herein provided production method or the herein provided screening method may further comprise expression and optionally collecting said protein of interest having a different or modified biological activity compared to the wild-type protein of interest. There are several methods known in the art that may be used for selecting and/or enriching cells expressing mutant variants with an improved first activity and/or that have a new activity as compared to the wild-type protein of interest. For example, selecting and/or enriching of mutant variants of the protein of interest that are improved in a first activity and/or have a new activity compared to the wild-type protein of interest may be performed by using FACS, magnetic-activated cell sorting, microfluidic cell sorting and/or bead-based cell isolation.

As described above, the terms "protein of interest" and "wild-type protein of interest" are used interchangeably herein, and refer to the protein that is to be mutated in the herein provided methods. Therefore, the term "wild-type protein of interest" also refers to a known mutant of a particular protein, if further modification of this known mutant is desired. Herein, a "first activity" refers to any activity of the protein of interest that is newly identified or known in the art. Herein the term "new activity" refers to any additional activity that is different from the "first activity". Thus, the "new activity" may be any activity that is newly identified or known in the art, provided that is differs from the "first activity". A different or modified activity is preferably an increased activity. For example, a mutant variant of a protein of interest that has an increased activity may have at least 101%, preferably at least 110%, more preferably at least 120%, or most preferably at least 150% of the activity of the wild-type protein of interest.

For example, in one aspect of the herein provided production method or screening methods, said protein of interest is a fluorescent protein, and said first activity and/or said new activity (e.g. the first activity) is fluorescence. Methods for the sorting of cells depending on their fluorescence are commonly known in the art and include, e.g. FACS. In another aspect of the herein provided production method or screening methods the protein of interest is an antibody, and said first activity and/or said new activity (e.g. the first activity) is antigen binding. A potential "new activity" of said antibody may be cross-reactivity e.g. to the corresponding antigen within another organism. An antibody that is directed against a human antigen and shows cross-reactivity to the corresponding antigen of a non-human animal may be desired, e.g. in order to facilitate pre-clinical animal studies. In another aspect of the herein provided production method or screening methods said protein of interest is an enzyme, and said first activity and/or said new activity (e.g. the first activity) is an enzymatic activity of said enzyme. Methods for identifying within a pool of proteins those that have desired activities are commonly known in the art, and described, e.g., in Wojcik, 2015, Int J. Mol. Sci. 16: 24918-24945; and Xiao, 2015, Ind. Eng. Chem. Res. 54: 4011-4020.

As described above, in the herein provided means and methods the protein of interest may be an antibody. For example, the present invention provides a number of advantages in engineering and selecting of Fab fragments, single chain antibodies or whole IgGs with new specificities or higher affinities than naturally occurring variants.

For this purpose genes coding for Fab fragments, single chain antibodies or for light and heavy chain IgGs may be inserted into cells at single copy number. A frame-shift or another inactivating mutation may be inserted near the target site for mutagenesis as described herein above and below. In this example, the target site for mutagenesis are preferably located within the regions encoding the CDRs (complementarity determining regions), i.e. regions of the antigen binding domains. However, the target site for mutagenesis may also be located within other sites that affect antibody function. If necessary (e.g. if humanized antibody genes are to be diversified in human cell lines), codons may be differentiated from endogenous antibody gene sequences to ensure that only the heterologous gene is diversified.

Libraries will initially be screened for efficient restoration of the reading-frame and/or for the generation of a fused marker gene (e.g. a fluorescent protein or a resistance marker). For efficient presentation and follow-up screening of the antibody library, surface display techniques may be used to localize the new antibody variant on the cell surface. Targeting sequences to send antibody variants to the cell surface can simply be added to the gene cassette encoding the protein of interest before insertion into the cell genome in single copy number. Such techniques have become very powerful and allow efficient functional presentation of e.g. Fab fragments, single chain antibodies or whole IgGs on the surface of cells, such as mammalian cells, e.g. HEK293 cells. Protocols for efficient display and screening have become standard of the art and are provided, e.g. by Ho, 2008, Methods in Molecular Biology, 525: pp 337-352; and Zhou, 2012, Methods in Molecular Biology, 907: 293-302. Screening of such surface displayed antibody libraries may occur by FACS sorting.

For this purpose, a fluorophore-conjugated antigen may be used to label cells displaying antibodies that exhibit an affinity to this specific antigen. FACS sorting allows for the harvesting these cells. In sequential rounds of screening the stringency can be increased, as cells can be washed with increasing amounts of unlabeled antigen, followed by additional FACs sorts. This will allow the identification of variants with a particularly high affinity for a given antigen.

Alternatively, desired antibodies can be identified via a panning approach. For this purpose specific surfaces may be conjugated with the desired antigen. Cells expressing the antibody library and expressing it on the cell surface may be incubated on this surface. Cells expressing effective antibodies will bind to the surface. After washing away non-binding cells, the stringency can be increased by additional washes with increasing amounts of added soluble antigen. After several rounds of washes, the remaining cells bound to the surface can be harvested by a suitable method, e.g trypsination, and allowed to recovery.

Genes coding for selected antibody variants can be isolated by preparing PolyA-RNA from these cells, performing RT-PCR to transcribe the genes into cDNAs and subcloning them into suitable vectors for further analysis.

As described above, the herein provided production method advantageously enables efficient production of a cell library (i.e. a panel of cells) without any non-desired mutational bias. Thus, in the produced cell library amino acids have been inserted, deleted and/or substituted randomly, according to their codon prevalence. However, a desired mutational bias can be programmed by using donor nucleic acid templates that have been specifically designed to induce the desired mutational bias. Thus, the herein provided cell library either comprises mutant variants that are randomly modified at a particular site, without any mutational bias; or that are randomly modified at a particular site, with a desired mutational bias that has been generated by using particular donor nucleic acid templates. Consequently, the herein provided cell library has a high degree of variation.

For example, by using the herein provided production method even targeting a small region, e.g. a region of only 8 amino acids, would result in a potential library of over 25 billion variants. Generating a library from such a large pool means fewer duplicates.

In contrast, methods for mutagenesis of the prior art, e.g. Error Prone PCR, cannot offer bias-free codon usage, and more importantly, will contain large amounts of redundancy due to the PCR replication process (i.e. multiple copies of variant would make up a large percentage of the library), resulting in wasting of screening effort. For example, Error Prone PCR is described in Firth, 2005, Bioinformatics 21(15): 3314-3315. According to this study in a library of 10 million variants, only around 100,000 variants have 6 or more mutations, and there are 5.5 million duplicates in total.

The cell library as produced by the production method provided herein significantly differs from the cell libraries of the prior art, e.g. the cell library as disclosed in EP 2 319 918 A1. In this document, diversified sequences are cloned into lentiviral plasmids to generate lentiviruses, which then infect cells and become stably integrated in these cells. In EP 2 319 918 A1 lentiviruses are integrated at different sites in the genome, which leads to the fact that (due to different neighboring regulatory sequences) the expression of the lentivirus-encoded protein within the different cells suffers from strong fluctuations. In contrast, in the cell library as produced by the method provided herein expression of the diversified (i.e. mutated) protein of interest always takes place from the same genomic locus, which ensures high reproducibility and comparability of the expressed protein within different cells. In addition, cloning of DNA libraries into large lentiviral plasmids (as done in EP 2 319 918 A1) is very inefficient and leads to a great loss of diversity of the produced variants (i.e. mutants) of the protein of interest. Thus, the cell library provided by the inventive method comprises much more different variants of a protein of interest. Moreover, only small proteins can be diversified by the lentivirus-based method as disclosed in EP 2 319 918 A1.

By using the herein provided production method if 6 amino acid positions are randomized a library of 10 million variants can be generated as demonstrated by the following calculation:

$$p=(1-(1-1/n)^s)$$

where
p is Coverage
s is Samples
n is Variants $$p=(1-(1-1/20^6)^{10000000})$$

$p=14.47\%$, or 9.26 million ($p*n$) different variants from a pool of 10 million.

Accordingly, in the herein provided cell library the amount of different mutant variants per cell population is higher as compared to cell libraries of the prior art. Therefore, the provided cell library is advantageous over the cell libraries known in the art as it provides a more efficient tool for screening for mutant variants of a protein of interest with improved properties. Thus, a further aspect of the present invention relates to a cell library obtained by the herein provided methods.

In accordance with the present invention, the herein provided cell library may be used for the identification of a mutant variant of a protein of interest having a different or modified biological activity compared to the wild-type protein of interest. The identified mutant variant of the protein of interest may be applied for white biotechnology. For example, the identified mutant variant may be an antibody that is used in therapy, i.e. for the treatment and/or prevention of a disease. The identified mutant variant may also be an enzyme that is used in industrial production, e.g. of biodegradable plastic. A modified variant of an enzyme (e.g. of a cellulase) may also be used in the production of textiles or paper. Alternatively, an identified mutant variant of an enzyme may be used for the production of biofuel. For example, biotechnologically produced ethanol can be used as substitute for gasoline. The protein of interest may also be a cytokine or a growth factor engineered to be useful in therapy.

The means for realizing the herein provided methods may be part of a kit, which may be used to generate the herein provided panel of cells (i.e. library of cells). Thus, the invention relates to a kit comprising:
(i) cells comprising a gene of interest in a single copy;
(ii) a library of different donor nucleic acid templates as defined herein; and/or
(iii) a site-directed nuclease or nickase; or a polynucleotide encoding a site-specific nuclease or nickase.

In the kit of the present invention the gene of interest may comprise an inactivating mutation as described herein. The kit of the present invention may further comprises (a) reaction buffer(s), storage solutions, wash solutions and/or remaining reagents or materials required for the conduction of the methods as described herein. Furthermore, parts of the kit of the invention can be packaged individually in vials or bottles or in combination in containers or multicontainer units. In addition, the kit may contain instructions for use. The manufacture of the kit of the present invention follows preferably standard procedures, which are known to the person skilled in the art. As mentioned above, the kit provided herein is useful for performing the herein provided methods, particularly for producing the cell library of the present invention.

In context of the present invention, the term "identity" or "percent identity" means that amino acid or nucleotide sequences have identities, e.g. of at least 80%, preferably at least 90%, more preferably at least 95%, even more preferably at least 98%, and even more preferably at least 99% identity to the sequences shown herein, wherein the higher identity values are preferred upon the lower ones. In accordance with the present invention, the term "identity/identities" or "percent identity/identities" in the context of two or more nucleic acid or amino acid sequences, refers to two or more sequences that are the same, or that have a specified percentage of amino acid residues or nucleotides that are the same (e.g., at least 80%, at least 90%, at least 95%, at least 98%, or at least 99% identity with the amino acid sequences of, e.g., any one of SEQ ID NOs: 19-25), when compared and aligned for maximum correspondence over a window of comparison, or over a designated region as measured using a sequence comparison algorithm as known in the art, or by manual alignment and visual inspection. Preferably the described identity exists over all amino acids or nucleotides in length.

Those having skills in the art will know how to determine percent identity between/among sequences using, for example, algorithms such as those based on the CLUSTALW computer program (Thompson, 1994, Nucl Acids Res, 2: 4673-4680) or FASTDB (Brutlag, 1990, Comp App Biosci, 6: 237-245), as known in the art. Also available to those having skills in this art are the BLAST and BLAST 2.0 algorithms (Altschul, 1997, Nucl Acids Res 25: 3389-3402; Altschul, 1993, J Mol Evol, 36: 290-300; Altschul, 1990, J Mol Biol 215: 403-410). For example, BLAST 2.0, which stands for Basic Local Alignment Search Tool BLAST (Altschul, 1997, loc. cit; Altschul, 1993, loc. cit; Altschul, 1990, loc. cit.), can be used to search for local sequence alignments. BLAST, as discussed above, produces alignments of both nucleotide and amino acid sequences to determine sequence similarity. Because of the local nature of the alignments, BLAST is especially useful in determining exact matches or in identifying similar sequences. Analogous computer techniques using BLAST (Altschul, 1997, loc. cit; Altschul, 1993, loc. cit.: Altschul, 1990, loc. cit) are used to search for identical or related molecules in nucleotide databases such as GenBank or EMBL.

The term "target sequence specific CRISPR RNA" or "crRNA", as used herein, is commonly know in the art and described, e.g. in Ran, 2013, Nature Protocols 8 (11): 2281-2308. crRNAs typically contain a sequence complementary to the target sequences (or complementary to a part of the target sequence) of between 10 and 30, preferably between 15 and 25 (e.g. about 20) nucleotides length, flanked by two direct repeats (DR) of a length of between 21 to 46 nucleotides. The 3' located DR of the crRNA is complementary to and hybridizes with the corresponding tracrRNA, which in turn binds to the Cas9 protein. The preferred DR sequence for use with the SpCas9 or SaCas9 nuclease is the sequence as shown in SEQ ID NO: 11 (i.e. GTTTTAGAGCTA). DR sequences functioning together with Cas9 nucleases of other bacterial species may be identified by bioinformatic analysis of sequence repeats occurring in the respective Crispr/Cas operons and by experimental binding studies of the Cas9 nuclease and tracrRNA together with putative DR sequence flanked target sequences, as shown by Deltcheva, 2011, Nature, 471: 602-607.

As used herein, the term "trans-activating crRNA" or "tracrRNA)" is commonly known in the art and described, e.g., in Hsu, 2014, Cell 157: 1262-78, Yang, 2014, Nature Protocols, 9:1956-1968 and Heidenreich, 2016, Nature Reviews Neurosciences, 17: 36-44. The term "tracrRNA" refers to a small RNA, that is complementary to and base pairs with a crRNA, thereby forming an RNA duplex. The tracrRNA may also be complementary to and base pair with a pre-crRNA, wherein this pre-rRNA is then cleaved by an RNA-specific ribonuclease, to form a crRNA/tracrRNA hybrid. In particular, the "tracrRNA" contains a sequence complementary to the palindromic repeat of the crRNA or of the pre-crRNA. Therefore, it can hybridize to a crRNA or pre-crRNA with direct repeat. The crRNA/tracerRNA hybrid is the so-called "guide RNA", which acts as a guide for the Cas9 nuclease, which cleaves the invading nucleic acid. The preferred tracrRNA sequence for use with the SpCas9 or SaCas9 nuclease is shown herein in SEQ ID NO: 12 (i.e. TAGCAAGTTAAAATAAGGCTAGTCCGTTTT).

Chimeric RNA molecules comprising at least one target sequence specific crRNA and at least one tracrRNA (i.e. single-guide RNAs, sgRNAs) that target a desired target sequence (e.g. a desired target site for mutagenesis) can easily be designed by using routine techniques. For example, the sgRNA may comprise a sequence of at least 17 nucleotides in length (e.g. of about 19 base pairs) that has homology to sequences adjacent to a PAM site (e.g. NGG for SpCas9). Additionally, the sgRNA preferably has no significant homology to the sequences in the genome of the cell (beside the gene of interest). For example, such a chimeric RNA may be e.g. as shown by Jinek, Science, 337: 816-821. A further method to obtain a single-guide RNA is described in Ran, 2013, Nat Protoc 8 2281-2308. In particular, single-guide RNAs may be designed by unbiased genome-wide analysis to minimize the potential off-target cleavages by Cas9 (Ran, 2013, Nat Protoc 8 2281-2308). Therefore, an online tool may be used (e.g. the CRISPR design tool, http://crispr.mitedu/).

The skilled person readily knows how a dual-guide RNA (i.e. a guide RNA comprising at least one target sequence specific CRISPR RNA (crRNA) molecule and at least one tracrRNA molecule) that targets a desired target sequence (e.g. a desired target site for mutagenesis) can be designed. For example, such a dual-guide RNA may be designed by designing a crRNA and tracrRNA separately. A crRNA may be designed by a sequence that is complementary to the target sequence with a part or the entire DR sequence. A tracrRNA may be synthesized as shown by Jinek, Science, 337: 816-821.

The generation of guide RNAs for a Cpf1 nuclease is commonly known in the art. For example, such a guide RNA may be designed as described by Zetsche, 2015, Cell, 163: 759-71). It is envisaged that the crRNA contains a sequence that is complementary to the target sequence (or complementary to a part of the target sequence) of 10-30, preferably 15-25 nucleotides in length. Preferably, the crRNA for Cpf1 comprises a sequence that is complementary to the target sequence (or complementary to a part of the target sequence) of about 20 nucleotides in length followed by a nucleotide sequence having a length of about 19 nucleotides. This 19 nucleotide sequence is a short stem-loop structure in direct repeat. Cpf1 does not require an additional tracrRNA.

Herein "homology directed repair" or "HDR" refers to a mechanism in cells to repair a DSB or a single-strand nick, which is usually performed by homologous recombination; see, e.g., Cong, 2013, Science 339 819-23; Pardo, 2009, Cellular and Molecular Life Sciences 66 (6): 1039-1056; Bolderson, 2009, Clinical Cancer Research, 15: 6314-6320. Therefore, the term "homology directed repair" or "HDR" preferably refers to homologous recombination. The HDR repair mechanism can only be used by the cell when there is a homologues piece of DNA (i.e. a donor nucleic acid template) present in the nucleus. When the homologue DNA piece is absent, another process called non-homologous end joining (NHEJ) can take place instead. The highly error-prone NHEJ pathway induces insertions and deletions (INDELS) of various lengths that can result in frame-shift mutations and, consequently, gene knockout. By contrast, the HDR pathway directs a precise recombination event between a homologous DNA donor template (i.e. a donor nucleic acid template) and the damaged DNA site, resulting in accurate correction of the single or double strand break. Therefore, HDR can be used to introduce specific mutations or transgenes into the genome. The donor nucleic acid template (usually a ssODN) has to contain a region with sequence homology with the region to be repaired. While homologous recombination appears to be the dominant way for HDR, there is evidence that a second alternative mechanism may be involved in HDR, in particular when using single stranded oligonucleotides (ssODN) as repair templates to insert the library. The teaching by Aarts and te Riel (2010, J. Cell. Mol. Med. 14(6B): 1657-1667) shows that oligo-mediated HDR may involve annealing of the homology region of the oligonucleotide to the target region in the genome within the context of a replication fork. The work suggests that an Okazaki-fragment like priming may be involved, during which the oligonucleotide is physically incorporated into the gene target site during replication fork progression.

The term "homologous recombination" refers to a mechanism of genetic recombination in which two DNA strands comprising similar nucleotide sequences exchange genetic material. Cells use homologous recombination for the repair of damaged DNA, in particular for the repair of single and double strand breaks. The mechanism of homologous recombination is well known to the skilled person and has been described, for example by Paques, 1999, Microbiol Mol Biol Rev, 63: 349404.

In accordance with the methods of the invention, the site-specific nuclease or nickase (e.g. the Cas9 nuclease) may be present in or may be introduced into the cells of step a). For example, the site-specific nuclease or nickase may be present or introduced as a protein. Alternatively the site-specific nuclease or nickase (e.g. the Cas9 nuclease) may be introduced in form of a polynucleotide encoding said protein. It will be appreciated that the polynucleotide encodes said site-specific nuclease or nickase (e.g. Cas9 nuclease), and/or said guide RNA(s) in expressible form such that expression in the cells of step a) results in a functional site-specific nuclease or nickase and functional guide RNA(s). Means and methods to ensure expression of a functional polypeptide or RNA are well known in the art. For example, the coding sequences may be comprised in a vector, such as for example a plasmid, cosmid, virus, bacteriophage or another vector used conventionally e.g. in genetic engineering. Preferably, the vector is a plasmid vector. The coding sequences inserted in the vector can e.g. be synthesized by standard methods, or isolated from natural sources. The coding sequences may further be ligated to transcriptional regulatory elements and/or to other amino acid encoding sequences. Such regulatory sequences are well known to those skilled in the art and include, without being limiting, regulatory sequences ensuring the initiation of transcription, internal ribosomal entry sites (IRES) (Owens, 2001, Proc Natl Acad Sei, USA, 98: 1471-1476) and optionally regulatory elements ensuring termination of transcription and stabilization of the transcript. Non-limiting examples for regulatory elements ensuring the initiation of transcription comprise a translation initiation codon, transcriptional enhancers such as e.g. the SV40-enhancer, insulators and/or promoters, such as for example the cytomegalovirus (CMV) promoter, SV40-promoter, RSV-promoter (Rous sarcoma virus), the lacZ promoter, chicken beta-actin promoter, CAG-promoter (a combination of chicken beta actin promoter and cytomegalovirus immediate-early enhancer), the gai10 promoter, human elongation factor 1a-promoter, AOX1 promoter, GAL1 promoter CaM-kinase promoter, the lac, trp or tac promoter, the lacUV5 promoter, or the *Autographa californica* multiple nuclear polyhedrosis virus (AcMNPV) polyhedral promoter. Non-limiting examples for regulatory elements ensuring transcription termination include the V40-poly-A site, the tk-poly-A site or the SV40, lacZ or AcMNPV polyhedral polyadenylation signals. Additional regulatory elements may include translational enhancers, Kozak sequences and intervening sequences flanked by donor and acceptor sites for RNA splicing. Moreover, elements such as origin of replication, drug resistance gene or regulators (as part of an inducible promoter) may also be included.

Herein, the terms "polynucleotide", "nucleic acid", "nucleic acid sequence" or "nucleotide sequence" are used interchangeably herein and refer to DNA, such as cDNA or genomic DNA, and RNA. The polynucleotides used in accordance with the present invention may be of natural as well as of (semi) synthetic origin. Thus, the polynucleotides may, for example, be nucleic acid molecules that have been synthesized according to conventional protocols of organic chemistry. The person skilled in the art is familiar with the preparation and the use of polynucleotides (see, e.g., Sambrook and Russel "Molecular Cloning, A Laboratory Manual", Cold Spring Harbor Laboratory, N.Y. (2001)). The polynucleotides used in accordance with the invention may comprise or consist of nucleic acid mimicking molecules known in the art. They may contain additional non-natural or derivatized nucleotide bases, as will be readily appreciated by those skilled in the art. Nucleic acid mimicking molecules or nucleic acid derivatives according to the invention include, without being limiting, a phosphorothioate nucleic acid, a phosphoramidate nucleic acid, a morpholino nucleic acid, a hexitol nucleic acid (HNA), a peptide nucleic acid (PNA), and a locked nucleic acid (LNA).

Herein the term "gene" refers to a locus (or region) of DNA which is made up of nucleotides and is the molecular unit of heredity within the genome of an organism. However, herein the term "gene" is not limited to a nucleotide sequence that is present in the genome of an organism. Herein, the term "gene" is directed to each nucleotide sequence encoding for a protein. Thus, herein the term "gene" also includes an artificially produced nucleotide sequence, such as a nucleotide sequence without introns. Accordingly, herein the term "gene" also refers to a cDNA sequence. Thus, herein the terms "gene of interest" or "gene encoding (for) the protein of interest" are used interchangeably and refer to the nucleotide sequence encoding the protein of interest. Said nucleotide sequence is preferably a cDNA encoding the protein of interest. It is indicated that the terms "encode" or "encoding" are used interchangeably with the terms "encode for" or "encoding for", respectively. In addition, herein the term "gene copy" refers to a copy of a nucleotide sequence. Thus, the term "a single gene copy" refers to a single copy of a particular nucleotide sequence; and means that said nucleotide sequence is unique within the genome of the particular cell(s).

Herein the term "donor nucleic acid template" (also called "DNA donor template", see, e.g. Heidenreich, 2016, Nature Reviews Neurosciences, 17: 36-44) refers to a nucleic acid sequence that serves as a template in the process of HDR, preferably in the process of homologous recombination, and that carries the modification that is to be introduced into the target sequence. By using this donor nucleic acid template as a template, the genetic information, including the modification(s), is copied into the gene of interest. For example, a donor nucleic acid template can be identical to a part of the gene of interest, with the exception of 1 to 36 nucleotides that differ; and thus, may result in the introduction or substitution of 1 to 12 amino acids upon homologous recombination. The donor nucleic acid template may also be configured that homologous recombination leads to a deletion of amino acids, e.g. of 1 to 12 amino acids. Herein, a donor nucleic acid template is preferably a single-stranded nucleic acid molecule (i.e. a ssODN). However, also plasmid vectors can be used as donor nucleic acid templates, i.e. (plasmid based) double-stranded DNA may be used as donor nucleic acid templates.

A donor nucleic acid template comprises a "donor nucleic acid sequence" that carries the mutation (i.e. the modification to the gene of interest) to be inserted. A donor nucleic acid template further comprises regions that are homologous to the target sequence of the donor nucleic acid template. In this regard, the "target sequence of the donor nucleic acid template" is a sequence region within the gene of interest that surrounds the target site for mutagenesis. Herein, the term "regions homologous to the target sequence of the donor nucleic acid template" refers to the so-called "homology arms". The homology arms are regions having sufficient sequence identity to ensure specific binding to the target sequence of the donor nucleic acid template. The regions homologous to the target sequence of the donor nucleic acid template (homology arms) flank the "donor nucleic acid sequence" that carries the mutation (i.e. the modification) to be inserted into the gene of interest. Or, in other words, the homology arms are localized at the 5' and 3' ends of the donor nucleic acid sequence. Accordingly, the donor nucleic acid templates used in the herein provided methods comprise a first homology arm, followed by the donor nucleic acid sequence, which is followed by a second homology arm. The homology arms are preferably >30 nucleotides, more preferably 30-150 nucleotides, even more preferably 30-80 (e.g. 40-55) nucleotides flanking the donor nucleic acid sequence (i.e. the sequence carrying the mutation) at both sides.

Preferably, the "regions homologous to the target sequence of the donor nucleic acid template" have a sequence identity with the corresponding target sequence of the donor nucleic acid template of at least 95%, preferably at least 97%, more preferably at least 98%, even more preferably at least 99%, even more preferably at least 99.9% and most preferably 100%. The above defined sequence identities are defined only with respect to the "target sequences of the donor nucleic acid template" that serve as binding sites for the homology arms. Thus, the overall sequence identity between the entire donor nucleic acid template and the "target sequence of the donor nucleic acid template" can differ from the above defined sequence identities, due to the presence of the part of the donor nucleic acid template that is to be inserted into the gene of interest at the target site for mutagenesis (i.e. the donor nucleic acid sequence).

Donor nucleic acid templates that induce HDR (particularly homologous recombination) at a desired target site for mutagenesis can easily be designed by using routine techniques, e.g. as described in Ran, 2013, Nat Protoc 8 2281-2308.

As mentioned, in the context of the present invention a donor nucleic acid template may be a single-stranded oligodeoxynucleotide (ssODN). The term "oligodeoxynucleotide (ODN)" is commonly known in the art and relates to a nucleic acid polymer made up of a sequence of desoxynucleotide residues. An ODN is a single-strand ODN (ssODN) if it does not hybridized with a second, different (i.e. complementary or partially complementary) oligonucleotide strand. Nonetheless, it will be appreciated that the ssODN may fold back onto itself, thus forming a partial or complete double stranded molecule consisting of one oligodeoxynucleotide strand. However, it is preferred that the ssODN does not fold back to form a partial or complete double stranded molecule but instead is single-stranded over its entire length. An ODN in accordance with the present invention refers to both oligodeoxynucleotide and polydesoxynucleotides and is between 30 and 600 nucleotides in length, preferably between 50 and 500 nucleotides in length, even more preferably between 70 and 350 nucleotides in length, and most preferably between 90 and 150 nucleotides in length. For example, to insert a short sequence (such as a nucleotide sequence having a length of 1 to 36 nucleotides), an about 90-150 nucleotides long ssODN may be used. In this regard, the ssODN preferably comprises homology arms that are >30 nucleotides, more preferably 30-150 nucleotides, even more preferably 40-55 nucleotides (e.g. about 50 nucleotides), flanking the donor nucleic acid sequence (i.e. the sequence carrying the mutation) at both sides.

As described herein above and below, by using the herein provided means and methods, exogenous recombinant genes can be stably introduced into mammalian cell lines in single copy numbers and diversified in vivo, e.g. by using the CRISPRICas9 system and homologous recombination repair. By exemplary using the fluorescent protein mNeonGreen the appended examples show that sites of interest can be targeted with CRISPR and large libraries of diversified amino acid sequences of varying lengths can be inserted by homologous repair. For this purpose a reading frame-shift may be introduced selectively near the sites of targeting that result in a non-fluorescent protein. As demonstrated in the appended examples, cut and repair leads to insertion of the desired diversification and restores the reading frame. Analysis of mutants (e.g. by FACS) allows screening large numbers of variants and sequence space. As demonstrated in the appended examples, the herein provided methods already resulted in the engineering of mNeonGreen2, a green fluorescent variant of increased brightness. As also shown in the appended examples, this approach can be extended to non-fluorescent protein targets where the fusion of a fluorescent protein or selection marker can be used to collect diversified proteins for further functional analysis.

As described above, in the context of the present invention the protein mNeonGreen2 has been engineered. This protein advantageously has increased brightness as compared to mNeonGreen. Therefore, the present invention also relates to mNeonGreen2. Accordingly, one aspect of the present invention relates to a polypeptide that is selected from the group consisting of:
(a) a polypeptide comprising an amino acid sequence encoded by a nucleic acid molecule having the nucleic acid sequence as depicted in SEQ ID NO: 91;
(b) a polypeptide comprising an amino acid sequence as depicted in SEQ ID NO: 92;
(c) a polypeptide encoded by a nucleic acid molecule encoding a polypeptide comprising an amino acid sequence as depicted in SEQ ID NO: 92;
(d) a polypeptide having at least 80% homology, preferably at least 85%, more preferably at least 90%, even more preferably at least 95%, even more preferably at least 98%, and even more preferably at least 99% identity to the polypeptide of any one of (a) to (c), whereby said polypeptide comprises the amino acids "D A C W" at the position corresponding to positions 147-150 of mNeonGreen as shown in SEQ ID NO: 28; and
(e) a polypeptide comprising an amino acid sequence encoded by a nucleic acid molecule being degenerate as a result of the genetic code to the nucleotide sequence of a nucleic acid molecule as defined in (a) or (c).

mNeonGreen2 as provided herein has fluorescence activity. Indeed, overall brightness, as determined by the product of quantum yield and extinction co-efficient, of mNeonGreen2 is brighter than that of mNeonGreen (e.g. as shown in SEQ ID NO: 28). For example, the overall brightness of the herein provided mNeonGreen2 is at least 1%, preferably at least 2%, more preferably at least 4%, even more preferably at least 6%, and most preferably at least 8% or at least 10% brighter than that of mNeonGreen (e.g. as shown in SEQ ID NO: 28).

One aspect of the present invention relates to the following items.

1. A method for producing a panel of cells expressing mutant variants of a protein of interest, wherein one of said mutant variants of said protein of interest is expressed per cell from a single gene copy, said method comprising:
   a) inducing a double-strand break (DSB) or a single-strand nick in the genome of cells at or in close proximity to a target site for mutagenesis in the gene encoding for said protein of interest, wherein said gene encoding for said protein of interest is comprised in the genome of the cells in a single copy, and wherein said single copy of the gene encoding for said protein of interest comprises an inactivating mutation at or in close proximity to said target site for mutagenesis;
   b) providing to the cells of step a) a library of different donor nucleic acid templates for the repair of the induced DSB or single-strand nick via homologous recombination, wherein the different donor nucleic acid templates of said library comprise different mutations at the position corresponding to said target site for mutagenesis and remove said inactivating mutation by homology directed repair (HDR), particularly homologous recombination;
   c) selecting and/or enriching cells in which the inactivating mutation has been removed; and
   d) providing a panel of cells selected in step c), which is a panel of cells expressing different mutant variants of said protein of interest, wherein one of said different mutant variants of said protein of interest is expressed per cell from a single gene copy.
2. The method of item 1, wherein said panel of cells provided in d) is enriched for cells that comprise at said target site for mutagenesis different mutations that are comprised in the different donor nucleic acid templates at the position corresponding to said target site for mutagenesis.
3. The method of item 2, wherein in the cells that are enriched in said panel of cells are cells, in which repair of said DSB or single-strand nick occurred via homologous recombination with a donor nucleic acid template of said library of different donor nucleic acid templates.
4. The method of any one of items 1 to 3, wherein in said panel of cells provided in d) at least 4%, preferably at least 20%, most preferably at least 60% of the cells comprise at said target site for mutagenesis one of the mutations that are comprised in the different donor nucleic acid templates.
5. The method of any one of items 1 to 4, wherein said panel of cells provided in d) further comprises cells, in which repair of the DSB or the single-strand nick occurred by non-homologous end joining (NHEJ).
6. The method of item 5, wherein the cells, in which repair of the DSB or the single-strand nick occurred by NHEJ comprise at least one random mutation that removed the inactivating mutation, wherein said random mutation preferably comprises an insertion and/or or a deletion of one or more nucleotides directly adjacent to the position at which the DSB or single-strand nick is introduced in step a).
7. The method of any one of items 1 to 6, wherein said inactivating mutation is introduced in said single copy of the gene encoding the protein of interest.
8. The method of any one of items 1 to 7, wherein said inactivating mutation prevents expression of said protein of interest.
9. The method of any one of items 1 to 8, wherein said inactivating mutation is or comprises a base pair substitution, a base pair insertion, a base pair deletion, a stop codon, or an inactivating amino add substitution.
10. The method of any one of items 1 to 9, wherein said inactivating mutation prevents a selectable activity of the protein of interest.
11. The method of item 10, wherein step c) comprises or is selection and/or enrichment of cells having said selectable activity.
12. The method of any one of items 1 to 11, wherein said inactivating mutation introduces a frame-shift in said gene encoding for the protein of interest, introduces a premature stop codon in said gene encoding for the protein of interest or introduces in said gene encoding for the protein of interest a mutation resulting in an inactivating amino acid substitution.
13. The method of any one of items 1 to 12, wherein step c) comprises or is selection of cells expressing said protein of interest.
14. The method of item 12 or 13, wherein said gene encoding for said protein of interest is comprised in the genome of said cells as a fusion gene, wherein said fusion gene comprises a marker gene downstream of said gene encoding the protein of interest
15. The method of item 14, wherein said inactivating mutation in said gene encoding for the protein of interest prevents expression of said marker gene.
16. The method of item 14 or 15, wherein the expression of the protein encoded by said marker gene is directly selectable.
17. The method of any one of items 14 to 16, wherein step c) comprises or is selection of cells expressing the protein encoded by said marker gene.
18. The method of any one of items 14 to 17, wherein the protein encoded by said marker gene is a fluorescent protein.
19. The method of item 18, wherein said selecting and/or enriching in step c) comprises isolation of cells that express said fluorescent protein.
20. The method of item 19, wherein said isolation of cells is or comprises fluorescence-activated cell sorting (FACS) or microfluidic cell sorting.
21. The method of any one of items 14 to 17, wherein the expression of the protein encoded by said marker gene confers antibiotic resistance, confers drug resistance, complements an auxotrophy or confers a detectable enzymatic activity.
22. The method of item 21, wherein said selecting and/or enriching in step c) comprises culturing the cells under selective conditions.
23. The method of item 14, wherein the protein encoded by said marker gene is expressed in presence of said inactivating mutation in said gene encoding for the protein of interest, and wherein said marker gene is not expressed or not expressed in frame in cells in which said inactivating mutation in said gene encoding for the protein of interest is removed.
24. The method of item 14 or 23, wherein expression of the protein of interest is negatively selectable.

25. The method of any one of items 14, 23 or 24, wherein step c) comprises or is selection and/or enrichment of cells that do not express the protein encoded by said marker gene.

26. The method of any one of items 14 and 23 to 25, wherein said protein encoded by the marker gene is thymidine kinase (HSVtk).

27. The method of any one of items 14 to 26, wherein said fusion gene further comprises a linker nucleic acid sequence between said gene encoding for the protein of interest and said marker gene.

28. The method of item 27, wherein said linker nucleic acid sequence comprises or consists of a nucleic acid sequence that encodes a self-cleaving peptide.

29. The method of item 28, wherein said self-cleaving peptide is selected from the group consisting of T2A peptide, P2A peptide, E2A peptide, and F2A peptide.

30. The method of item 27, wherein said linker nucleic acid sequence comprises or consists of a nucleic acid sequence that encodes a target site of a site-specific protease.

31. The method of item 30, wherein said target site of a site-specific protease is selected from the group consisting of the target site of TEV protease having an amino acid sequence as shown in SEQ ID NO: 5, the target site of Genenase I having an amino acid sequence as shown in SEQ ID NO: 6, the target site of Enterokinase having an amino acid sequence as shown in SEQ ID NO: 7, and the target site for Human Rhinovirus (HRV) 3C Protease having an amino acid sequence as shown in SEQ ID NO: 8.

32. The method of item 30 or 31, wherein said cells further express the corresponding site-specific protease cleaving said target site.

33. The method of item 30 or 32, wherein said site-specific protease is selected from the group consisting of TEV protease, Genenase I. Enterokinase, Human Rhinovirus (HRV) 3C Protease, Factor Xa, and Thrombin.

34. The method of any one of items 1 to 33, wherein the single copy of the gene encoding for the protein of interest is an exogenous gene copy.

35. The method of any one of items 1 to 34, wherein the single copy of the gene encoding for the protein of interest is an endogenous gene copy.

36. The method of any one of items 1 to 35, wherein said method further comprises the step of generating the cells as used in a).

37. The method of item 36, wherein said generating comprises introducing said inactivating mutation in said single copy of the gene encoding for the protein of interest.

38. The method of item 36 or 37, wherein said single copy of the gene encoding for the protein of interest is exogenous, and wherein said generating comprises introducing the single copy of said gene encoding for the protein of interest in the genome of cells.

39. The method of item 38, wherein said introducing of an exogenous single copy of the gene encoding for the protein of interest into the genome involves site-specific homologous recombination systems.

40. The method of item 38 or 39, wherein said inactivating mutation is introduced prior or after introduction of the single copy of said gene encoding for the protein of interest into the genome of the cells.

41. The method of item 38 or 39, wherein said generating comprises introducing said inactivating mutation in the gene of interest prior or after introduction of the single copy of said gene encoding for the protein of interest in the genome of cells.

42. The method of item 36 or 37, wherein said single copy of the gene encoding for the protein of interest is endogenous, and wherein said generating comprises introducing said inactivating mutation in the gene encoding for the protein of interest in the genome of the cells by using a site-specific homologous recombination system.

43. The method of any one of items 36, 37 and 42, wherein said gene encoding for the protein of interest is an endogenous gene that is present in the genome in more than one copies, and wherein said generation comprises inactivation of endogenous copies of said gene encoding for the protein of interest to obtain one single copy of said gene encoding for the protein of interest per cell.

44. The method of any one of items 36 to 43, wherein said generating comprises introducing into the cells a nucleic acid sequence encoding a site-specific nuclease or a site-specific nickase.

45. The method of item 44, wherein said generating further comprises introducing into the cells a corresponding recognition sequence for said site-specific nuclease or said site-specific nickase in the single copy of the gene of interest.

46. The method of item 44 or 45, wherein said generating further comprises introducing into the cells means that target said site-specific nuclease or said site-specific nickase to said recognition site.

47. The method of any one of items 1 to 46, wherein said DSB is induced.

48. The method of any one of items 1 to 47, wherein said DSB is induced by a site-specific nuclease and wherein the single copy of the gene encoding for said protein of interest in the cells of step a) comprises a corresponding recognition site for said site-specific nuclease.

49. The method of item 48, wherein said site-specific nuclease is expressed under control of a constitutive or an inducible promoter.

50. The method of item 48 or 49, wherein said site-specific nuclease is encoded on a plasmid.

51. The method of item 50, wherein said method further comprises between step c) and d) or after step d) removing the plasmid encoding for said site-specific nuclease from the selected and/or provided cells.

52. The method of any one of items 33 to 36, wherein said recognition site for said site-specific nuclease in said gene encoding for the protein of interest is endogenously present in said single copy of the gene encoding for said protein of interest or is fully or partially exogenously introduced.

53. The method of any one of items 48 to 52, wherein said recognition site for said site-specific nuclease is fully or partially exogenously introduced, and wherein the exogenously introduced sequence is not present in the mutant variants of the gene encoding the protein of interest that are comprised in the cells selected in c) or provided in d).

54. The method of any one of items 48 to 53, wherein said site-specific nuclease is selected from the group consisting of a Cas9 nuclease, a Cpf1 nuclease, a zinc finger nuclease (ZNF), a transcription activator-like nuclease (TALEN) and a megaTAL endonuclease.

55. The method of any one of items 48 to 53, wherein said site-specific nuclease is a CRISPR/Cas9 nuclease.

56. The method of item 54 or 55, wherein said Cas9 nuclease is selected from the group consisting of SpCas9 from *Streptococcus pyogenes*, St1Cas9 from *Streptococcus* thermophiles, SaCas9 from *Staphylococcus aureus*, Cas9 VQR variant, Cas9 EQR variant, Split Cas9, Intein-Cas9, engineered Cas9, and dimeric RNA-guided FokI-dCas9 nuclease (RFN).

57. The method of any one of items 54 to 56, wherein the cells in step a) express a sgRNA targeting said Cas9 nuclease to said recognition site.
58. The method of any of items 54 to 57, wherein said corresponding recognition site for said Cas9 nuclease comprises a PAM site that is recognized by said Cas9 nuclease.
59. The method of any one of items 1 to 47, wherein said double-strand break is induced by two single-strand nicks on different strand within the gene encoding for said protein of interest.
60. The method of item 59, wherein said two single strand nicks are introduced by one or more nickases, and wherein the single copy of the gene encoding for said protein of interest in the cells of step a) comprises a first recognition site for a first site-specific nickase and a second recognition site for a second site-specific nickase.
61. The method of item 59, wherein said first and said second site-specific nickase is identical.
62. The method of any one of items 60 to 61, wherein said first and/or said second nickase are (a) Cas9 nickase(s).
63. The method of item 62, wherein the cells in step a) comprise a first sgRNA that targets said first site-specific nickase to said first recognition site and said second site-specific nickase to said second recognition site.
64. The method of item 63, wherein the first recognition sequence and/or the second recognition sequence comprise a PAM sequence.
65. The method of any one of items 1 to 46, wherein said single-strand nick is induced by a site-specific nickase, and wherein the single copy of the gene encoding for said protein of interest comprises a corresponding recognition site for said site-specific nickase.
66. The method of item 65, wherein said recognition site for said site-specific nickase in said gene encoding for the protein of interest is endogenously present in said gene encoding for the protein of interest or is fully or partially exogenously introduced.
67. The method of item 65 or 66, wherein said recognition site for said site-specific nickase is fully or partially exogenously introduced, and wherein the exogenously introduced sequence is not present in the mutant variants of the gene encoding the protein of interest that are comprised in the cells selected in c) or provided in d).
68. The method of any one of items 65 to 67, wherein said site-specific nickase is a Cas9 nickase.
69. The method of item 68, wherein the corresponding recognition sequence for said Cas9 nickase is a PAM sequence that is recognized by said CRISPR/Cas9 nickase.
70. The method of any one of items 1 to 69, wherein said cells are prokaryotic cells or eukaryotic cells.
71. The method of any one of items 1 to 69, wherein said cells are yeast cells, non-mammalian vertebrate cells, plant cells, insect cells or mammalian cells.
72. The method of any one of items 1 to 69, wherein said cells are mammalian cells.
73. The method of item 71 or 72, wherein said mammalian cells are selected from the group consisting of HEK 293 cells, lymphoma cell lines (e.g. NSO or Sp2/0-Ag14), leukemia cell lines, Jurkat cells, Chinese hamster ovary (CHO) cells, HeLa cells, PC12 cells, antibody producing hybridoma cell lines, immortalized human B-cell lines, and immortalized human cell lines.
74. The method of item 71, wherein said non-mammalian vertebrate cells are DT40 chicken cells.
75. The method of any one of items 1 to 74, wherein said DSB or said single-strand nick is induced in a distance of less than 100 base pairs, preferably less than 30 base pairs or most preferably less than 10 base pairs to said target site for mutagenesis.
76. The method of any one of items 1 to 75, wherein said inactivating mutation is in a distance of less than 100 base pairs, preferably less than 30 base pairs or most preferably less than 10 base pairs to said target site for mutagenesis.
77. The method of any one of items 1 to 76, wherein said different donor nucleic acid templates comprise or are double-stranded DNA molecules.
78. The method of item 77, wherein each of said different donor nucleic acid templates is comprised in a separate vector.
79. The method of any one of items 1 to 78, wherein said different donor nucleic acid templates comprise or are single-stranded oligonucleotides.
80. The method of item 79, wherein said single-stranded oligonucleotides are locked nucleic acids and/or comprise phosphorothioate modifications.
81. The method of any one of items 1 to 80, wherein each of said different donor nucleic acid templates comprises homologous nucleic acid sequences being homologous to said gene encoding the protein of interest.
82. The method of item 81, wherein said homologous nucleic acid sequences comprise 20 to 100 nucleotides, preferably 30 to 60 nucleotides, and most preferably 40 to 50 nucleotides.
83. The method of any one of items 1 to 82, wherein each of said different donor nucleic acid templates comprises a first homologous nucleic acid sequence upstream of said position corresponding to said target site of mutagenesis with a length of at least 20 nucleotides, e.g. 20 to 500 nucleotides, 20 to 300 nucleotides, 20 to 100 nucleotides, 30 to 60 nucleotides, or 40 to 50 nucleotides and further comprises a second homologous nucleic acid sequence downstream of said position corresponding to said target site of mutagenesis with a length of at least 20 nucleotides, e.g. 20 to 500 nucleotides, 20 to 300 nucleotides, 20 to 100 nucleotides, 30 to 60 nucleotides, or 40 to 50 nucleotides.
84. The method of any one of items 81 to 83, wherein homologous means at least 80% sequence identity, preferably at least 95% sequence identity and most preferably at least 99% identity.
85. The method of any one of items 1 to 84, wherein said different mutations at the position corresponding to said target site for mutagenesis are one or more nucleotide substitutions, deletions, or insertions.
86. The method of any one of items 1 to 85, wherein said different mutant variants of the protein of interest expressed in the cells of the panel of cells provided in d) comprise one or more amino acid exchanges, insertions of one or more amino acids and/or deletions of one or more amino acids compared to the protein of interest
87. The method of item 86, wherein said one or more amino acid exchanges are at least 1, e.g. at least 2, at least 3, or at least 5 amino acid exchanges.
88. The method of item 86, wherein said insertions of one or more amino acids are insertions of at least 1, e.g. at least 2, at least 3, or at least 5 amino acids.

89. The method of item 86, wherein said deletions of one or more amino acids are deletions of at least 1, e.g. at least 2, at least 3, or at least 5 amino acids.
90. The method of any one of items 1 to 89, wherein said nucleic acid sequence removing said inactivating mutation is the corresponding wild-type sequence of the gene encoding for the protein of interest, and/or removes a frame-shift mutation within the gene of the protein of interest
91. The method of any one of items 1 to 90, wherein step b) is performed prior to step a) or preferably simultaneously with step a).
92. The method of any one of items 1 to 91, wherein during step a) and b) the cells are cultured under conditions that increase the rate of homologous recombination versus NHEJ.
93. The method of item 92, wherein said conditions are inhibition or inactivation of an enzyme involved in NHEJ, expression of a protein that inhibits NHEJ, adding substances inhibiting NHEJ, slowing down replication fork progression or triggering a cell cycle arrest in G2/M.
94. The method of item 93, wherein the enzymes involved in NHEJ is KU70 or DNA ligase IV, and wherein the enzyme involved in NHEJ is inhibited.
95. The method of item 93, wherein the protein that inhibits NHEJ is a protein complex comprising or consisting of E1B55K and E4orf6.
96. The method of item 93, wherein said substance inhibiting NHEJ is selected from the group consisting of Scr7-pyrazine, ESCR7, L755507, Brefeldin A and L189 (CAS 64232-83-3).
97. The method of any one of items 92 to 96, wherein the rate of homologous recombination versus NHEJ is increased by at least 1-fold, preferably at least 3-fold, and most preferably at least 15-fold.
98. The method of any one of items 1 to 97, wherein the cells are mammalian cells and are cultured for at least 48 hours, preferably at least 72 hours and most preferably at least 96 hours between step a) and/or b) and c).
99. The method of any one of items 1 to 98, wherein said panel of cells provided in d) is a pool of cells that express different mutant variants of said protein of interest, wherein one of said different mutant variants is expressed per cell from a single gene copy.
100. The method of any one of items 1 to 98, wherein said panel of cells provided in d) is a library of cells in which the cells expressing different mutant variants are cultured separately.
101. The method of item 100, wherein said method further comprises between steps c) and d) the step of separating from the cells selected in step c) the cells expressing different mutant variants.
102. The method of any one of items 1 to 101, wherein said method further comprises determining the nucleic acid sequence of one or more of the genes encoding for said different mutant variants of the protein of interest comprised in the cells selected and/or enriched in step c) and/or provided in d); or determining the amino acid sequence of one or more of said different mutant variants of the protein of interest comprised in the cells selected and/or enriched in step c) and/or provided in d).
103. The method of any one of items 1 to 102, wherein said protein of interest is a fluorescent protein, an antibody, an enzyme, a growth factor, a cytokine, a peptide hormone, a transcription factor, a RNA binding protein, a cytoskeletal protein, an ion channel, a G-protein coupled receptor, a kinase, a phosphatase, a chaperone, a transporter, or a transmembrane protein.
104. The method of any one of items 1 to 102, wherein said protein of interest is a fluorescent protein selected from the group consisting of mNeonGreen, mRuby2/3, dTomato, TagRFP, Citrine, Venus, YPet, mTFP1, EGFP; Kusabira Orange, mOrange, mApple, mCerulean3, mTurquoise2, mCardinal, EosFP, Dronpa, Dreiklang and infrared iRFP,
105. The method of any one of items 1 to 102, wherein said protein of interest is an antibody, and wherein said target site for mutagenesis is in a CDR coding region of the nucleic acid sequence encoding the heavy or the light chain of said antibody.
106. The method of any one of items 1 to 102, wherein said protein of interest is an enzyme, and wherein said target site for mutagenesis is in the nucleic acid region encoding the active center of the enzyme or a regulatory subunit of said enzyme.
107. The method of any one of items 1 to 106, wherein said mutant variants of the protein of interest are improved in a first activity and/or have a new activity compared to the wild-type protein of interest, wherein said method further comprises:
  e) selecting and/or enriching from the panel of cells a second panel of cells that express mutant variants of said protein of interest that are improved in said first activity and/or have said new activity.
108. The method of any one of items 1 to 106, wherein said mutant variants of said protein of interest are improved in a first activity and/or have a new activity compared to the wild-type protein of interest, and wherein step c) comprises selecting and/or enriching mutant variants of the protein of interest that are improved in a first activity and/or have a new activity compared to the wild-type protein of interest.
109. A method for identifying a mutant variant of a protein of interest having a different or modified activity compared to the wild-type protein of interest, wherein said method comprises:
  a) selecting and/or enriching from the panel of cells resulting from any one of items 1 to 106 a second panel of cells that express mutant variants of said protein of interest that are improved in said first activity and/or have said new activity; and
  b) determining the amino acid sequence of the mutant variants of the protein of interest expressed by said second panel and/or determining the nucleic acid sequence of the genes encoding for the mutant variants of the protein of interest expressed by said second panel.
110. A method for identifying a mutant variant of a protein of interest having a different or modified activity compared to the wild-type protein of interest, wherein said method comprises:
  a) the method for producing a panel of cells expressing mutant variants of a protein of interest of any one of items 1 to 106,
    wherein step c) comprises selecting and/or enriching mutant variants of the protein of interest that are improved in a first activity and/or have a new activity compared to the wild-type protein of interest; and
  b) determining the amino acid sequence of at least one of the mutant variants of the protein of interest that are improved in a first activity and/or have a new activity compared to the wild-type protein of interest; and/or determining the nucleic acid sequence of at least one of the genes encoding for the mutant variants of the protein of interest that are improved in a first activity and/or have a new activity compared to the wild-type protein of interest 111. The method of item 109 or 110, wherein said method further comprises expression and optionally collecting said protein of interest having a different or modified biological activity compared to the wild-type protein of interest 112. The method of any one of items 107 to 111, wherein said selecting and/or enriching mutant variants of the protein of interest that are improved in a first activity and/or have a new activity compared to the wild-type protein of interest comprises FACS cell sorting, magnetic-activated cell sorting, microfluidic cell sorting and/or bead-based cell isolation.

113. The method of any one of items 107 to 112, wherein said protein of interest is a fluorescent protein, and said first activity and/or said new activity is fluorescence.

114. The method of any one of items 107 to 112, wherein said protein of interest is an antibody, and said first activity and/or said new activity is antigen binding.

115. The method of any one of items 107 to 112, wherein said protein of interest is an enzyme, and said first activity and/or said new activity is an enzymatic activity of said enzyme.

116. A cell library obtained by the method of any one of items 1 to 115.

117. Use of the cell library of item 116 for the identification of a mutant variant of a protein of interest having a different or modified biological activity compared to the wild-type protein of interest 118. The use of item 117, wherein the identified mutant variant of the protein of interest is applied for white biotechnology.

119. The method of any one of items 1 to 115, the cell library of item 116, or the use of item 117 or 118, wherein the protein of interest is any one of the proteins selected from a growth factor, a cytokine, a peptide hormone, a transcription factor, a RNA binding protein, a cytoskeletal protein, a ion channel, a G-protein coupled receptor, a kinase, a phosphatase, a chaperone, a transporter, and a transmembrane protein.

Herein, a number of documents including patent applications and scientific publications are cited. The disclosure of these documents, while not considered relevant for the patentability of this invention, is herewith incorporated by reference in its entirety.

The figures show:

FIG. 1: Scheme of an exemplary but not limiting embodiment of the method for protein library generation of the present invention. An expression cassette for a gene of interest, in this case the gene coding for the fluorescent protein mNeonGreen, is transformed stably into the genome of a suitable cell line in single-copy number. Insertion into unique FRT-sites within the genome of engineered cell lines is a suitable means. A frameshift had been introduced into mNeonGreen near the site to be targeted for mutagenesis. The frameshift prevents expression of mNeonGreen and of another selectable marker protein fused to the 3' end of mNeonGreen, in this case the fluorescent protein mKate2. Transfection of Cas9/sgRNA first generates a targeted cleavage in the genomically-integrated target gene mNeonGreen adjacent to the frame-shift. The co-transformed ssDNA library (Oligo Library) contains homologous regions neighbouring the cut-site of mNeonGreen, and enables homology-directed repair. Upon integration into the mNeonGreen gene, the frameshift is repaired and a diversified library of desired randomness inserted at the target site.

Figure 2:
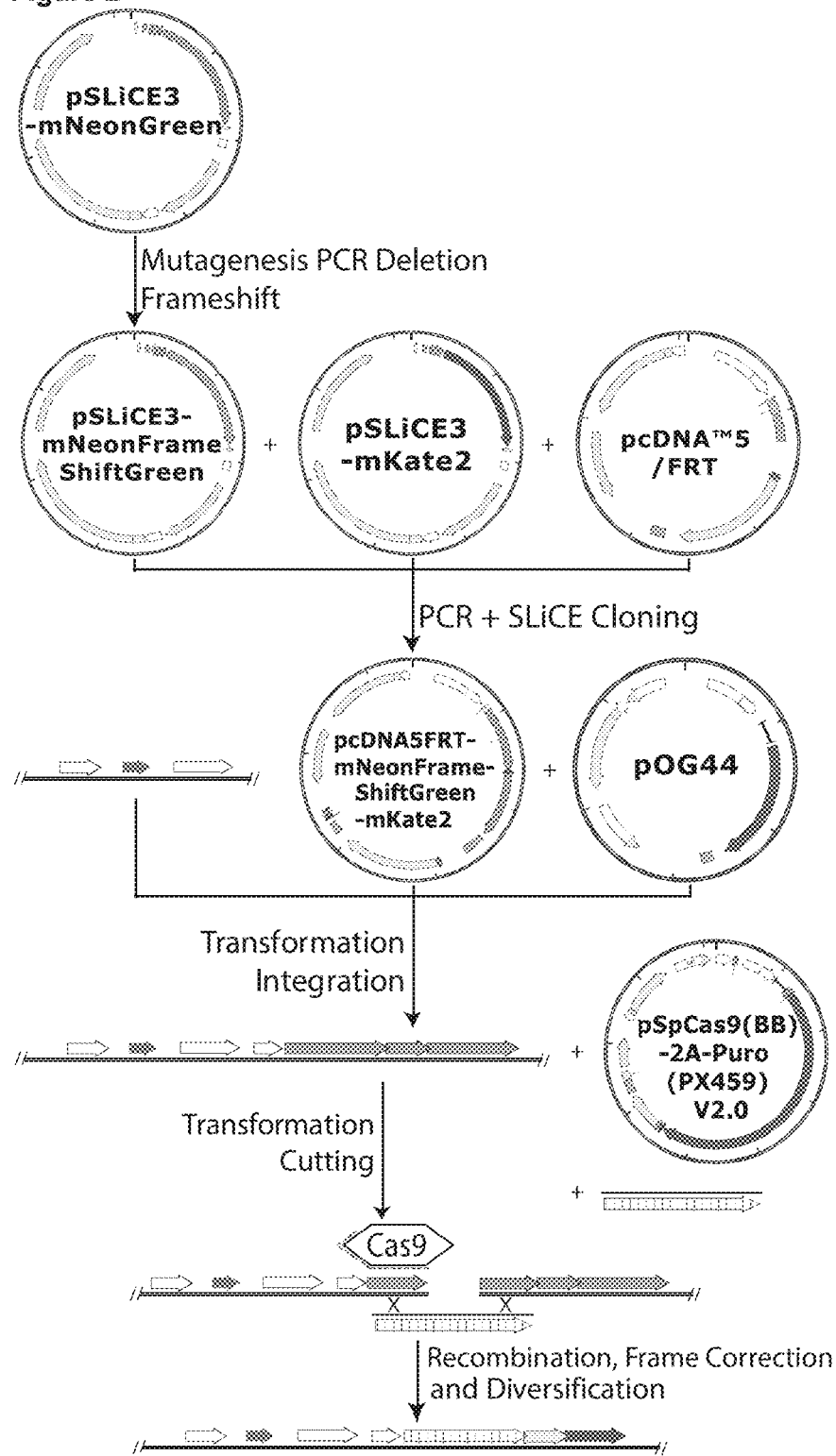

FIG. 2: Plasmids and cloning schemes. The gene for mNeonGreen is inserted into the bacterial expression plasmid pSLICE3 (derived from pRSETB) and a frameshift is introduced using PCR techniques close to the target site within mNeonGreen. mKate2 is fused downstream of fameshifted mNeonGreen as a second marker gene, and the cassette is inserted into the mammalian expression plasmid pcDNA5FRT. pcDNA5FRT-mNeonFrameshift-mKate2 is transfected into suitable cell lines (e.g. HEK 293 cells) harboring a singe FRT site in the genome. The expression cassette for mNeonFrameshift-mKate2 is integrated in single copy number into the unique FRT site. Cells stably expressing the cassette are selected. Expression plasmids coding for Cas9 and suitable guide RNAs (sgRNAs) are transfected into the cells. Upon cutting by Cas9 co-transfected oligonucleotide libraries with corresponding homology arms enable homology-directed repair, thereby correcting the frame-shift within mNeonGreen and inserting the desired randomized stretch of diversified sequence into the selected target site within the gene.

FIG. 3: The histogram of brightness of live cells from a) a 3-residue (residues 148-150 of mNeonGreen) library, and b) from a 5-residue (residues 145-149 of mNeonGreen) library over the course of 4 rounds of screening. The initial sort (filled with dashed lines) displays a very low median fluorescence. Subsequent rounds of FACS sorts (grey open circles to closed black circles) display marked improvements in brightness, as low-fluorescence mNeonGreen-variants are eliminated from the population. (FITC A: Green Emission Fluorescence Channel).

Figure 4:
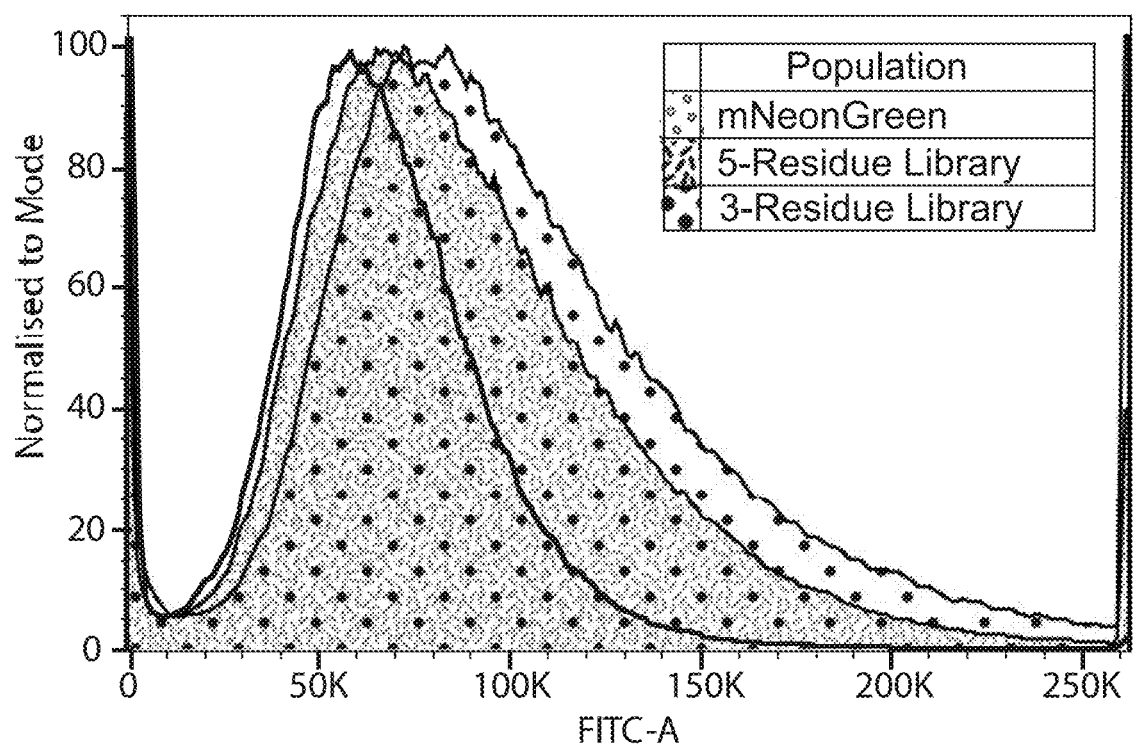

FIG. 4: The histogram of brightness of live cells after the final round of FACS sorting of the 3-residue and 5-residue libraries, together with a population of parental mNeonGreen expressing cells for comparison.

FIG. 5: Fluorescence microscopy images of stably transformed HEK 293 cells expressing mNeonGreen (a), a member of the 3-residue library (b) and a member of the 5-residue library (c). Emission was 530/20 nm. All fluorescence was equally distributed throughout the cytosol and nucleus of cells without any signs of aggregation.

FIG. 6: Amino acid sequences of diversified mNeonGreen variants after an initial round of FACS sorting. A stretch of 3 amino acids (residues 147-149) had been diversified using the technique. The figure shows the DNA sequence (left) and the translated protein sequence (right) of 10 selected variants. The diversified stretch of amino acids is between hyphens. The parental amino sequence of the target site in mNeonGreen is DWC.

Figure 7:
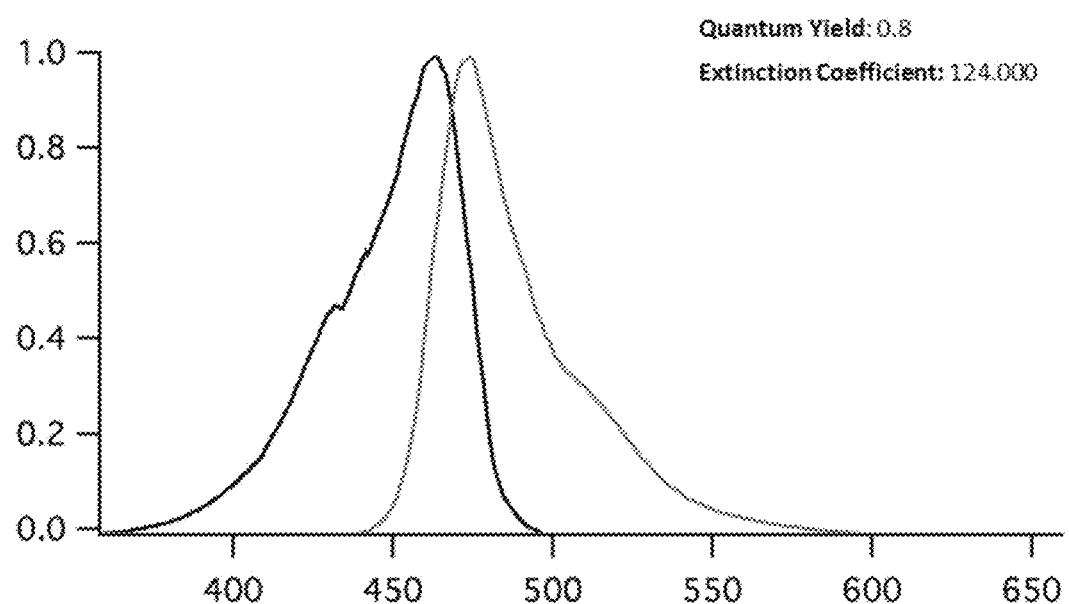

FIG. 7: Characterization of mNeonGreen2. Graph shows excitation and emission spectrum of recombinant mNeonGreen2 purified from E. coli. The quantum yield of the variant was determined to be 0.8. The extinction co-efficient was 124.000 M$^{-1}$ cm$^{-1}$, higher than that of parental mNeonGreen (116.000). Thus, in overall brightness, as determined by the product of quantum yield and extinction co-efficient, mNeonGreen 2 is up to 10% brighter than parental mNeonGreen.

FIG. 8: Target selection within mNeonGreen. Structure (top) and primary amino acids sequence (bottom) of mNeonGreen are shown. 5 regions chosen for diversification were marked in black in the structure and are numbered and underlined in the amino acid sequence. Residues that block dimer and tetramer formation are marked with grey shading in the amino acid sequence. These residues were left unaltered while residues around were diversified. At each site, a nearby NGG PAM site was identified for Cas9 targeting, and primers were designed to generate the appropriate sgRNAs with help of the plasmid pSpCas9(BB)-2A-Puro.

FIG. 9: List of primers used to generate sgRNAs to target sites within mNeonGreen as indicated in FIG. 7.

Figure 10:
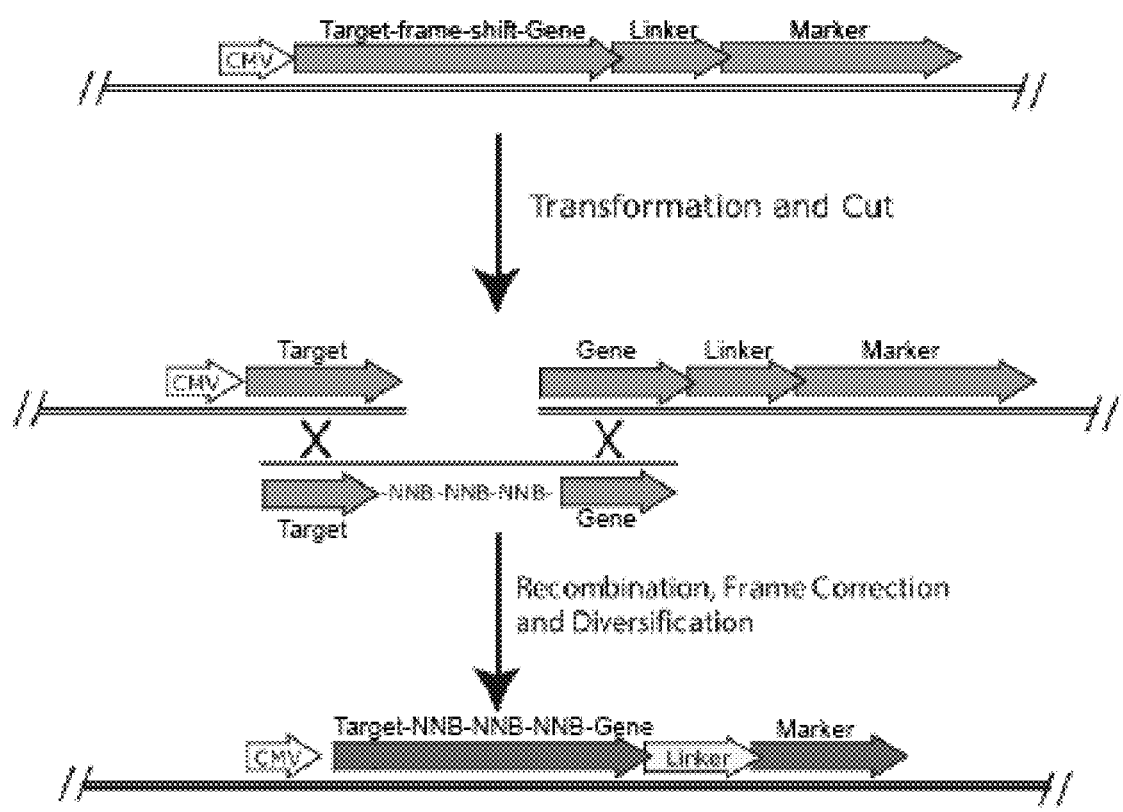

FIG. 10: A generalized scheme on how to execute the invention

Figure 11:
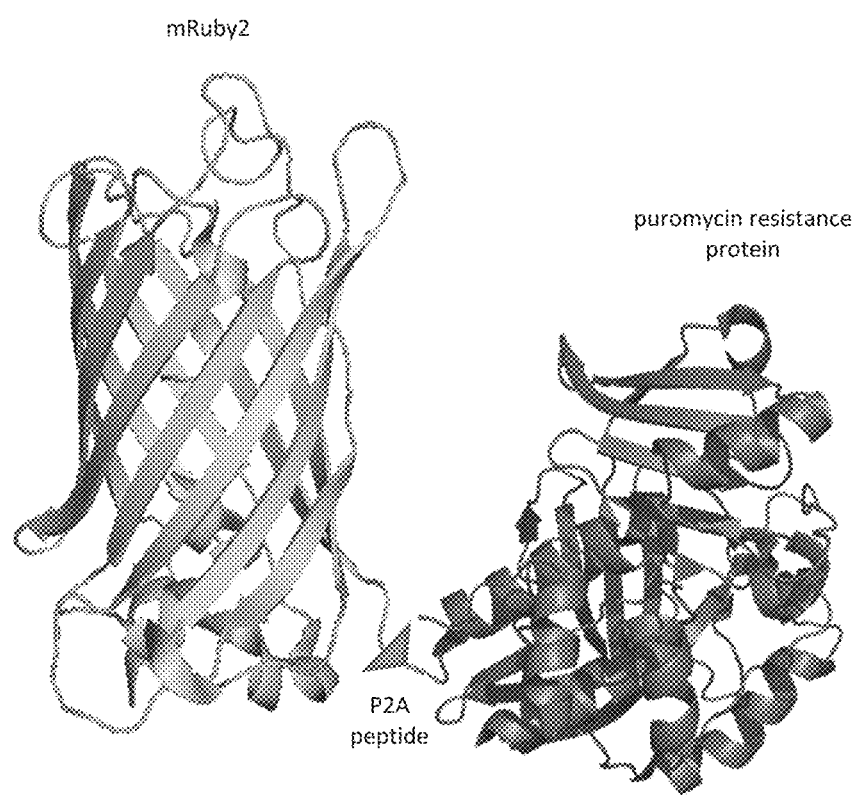

FIG. 11: Another alternative construct design for the mutation and screening procedure. A marker protein, N-acetyltransferse puromycin resistance protein, is fused via a P2A peptide to the C-terminal end of the fluorescent protein mRuby2. When a frameshift introduced near the target site within mRuby2 is repaired, puromycine resistance is generated and diversified mRuby2 libraries can be harvested and enriched using drug selection. The cells that are transfected with Cas9/sgRNA are treated with puromycin for two consecutive days in order to eliminate those that do not property express the target fluorescent protein library.

Figure 12:
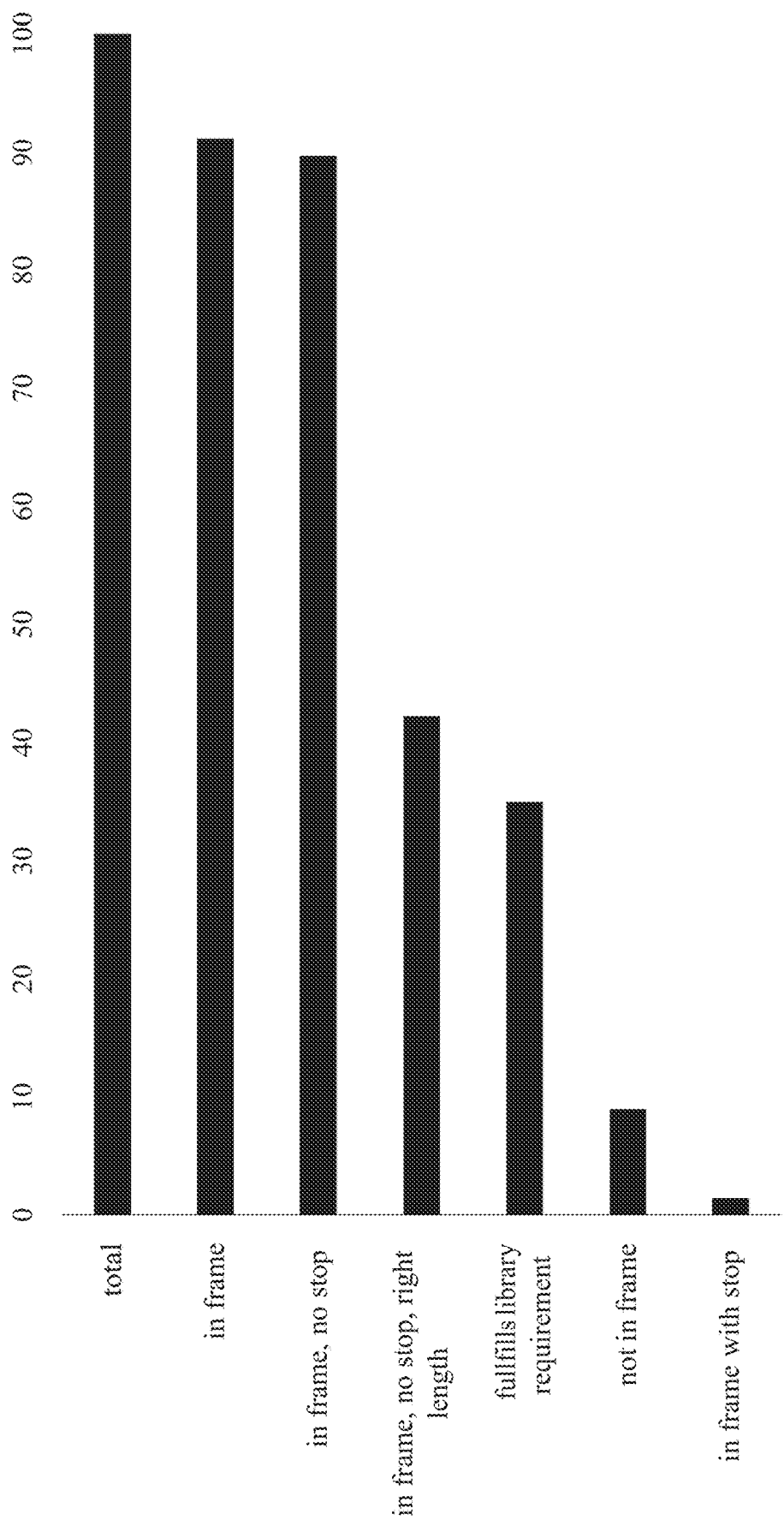

FIG. 12: Next Generation Sequencing results of a 3-residue amino acid library inserted into the chromophore region of mRuby2 (diversifying amino acid residues residues 67-69 of mRuby2) after selection using puromycine for two days. X-axis indicates the percentages of observed mutation types (0-100%). The total library size is 7292 sequences. in-fame numbers all observed mutant sequences that are in frame relative to wild-type mRuby2 gene (6639 sequences). in-frame, no stop amounts sequences in-frame and without an early stop codon (6537 sequences). In-frame, no stop, right length symbolizes all sequences that are in-frame, without an early stop codon and same in length with the wild type mRuby2 gene (3077). fulfills library requirements indicates the number of sequences displaying the correct library inserted in frame (2550). not in-frame indicates sequences that are not in-frame relative to the wild-type mRuby2 gene (653). in-frame with stop indicates the number of the mutant sequences with an early stop codon relative to the wild type mRuby2 gene (102). The effect of puromycin treatment is demonstrated by the low abundance of "not in-frame and in-frame with stop" sequences in the library.

Figure 13:
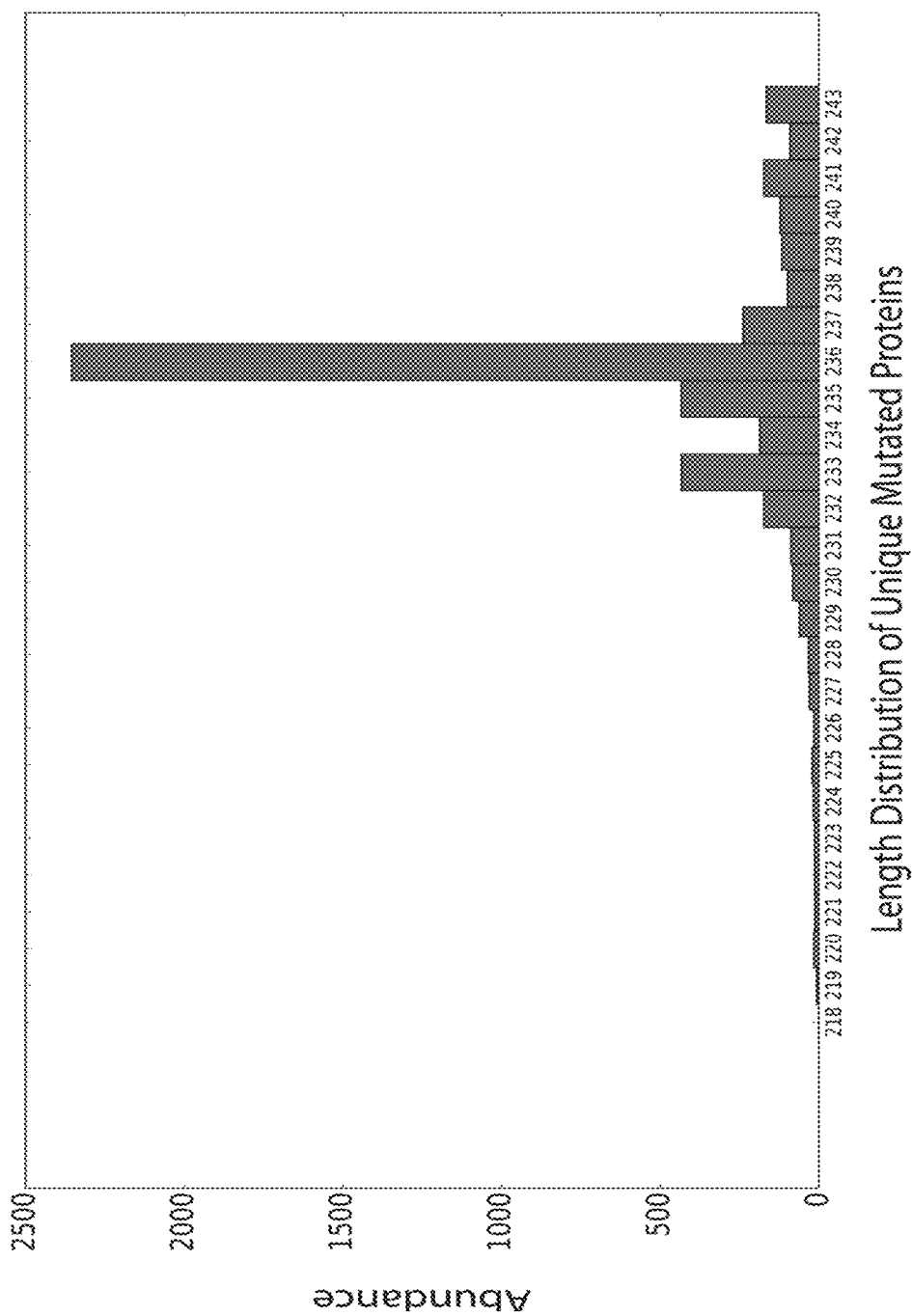

FIG. 13: Length distribution of translated diversified library proteins as verified by next generation sequencing. Only unique sequences were considered. Axes indicate the length distribution of the observed diversified mRuby2 proteins and their relative abundance. The parental mRuby2 protein is 236 amino acids in length. It can be seen that there are INDEL (insertion-deletion) events, most likely by non-homologous end joining that lead to protein variants in which mutagenesis also varied the length of the diversified stretch of amino acids, thereby increasing the diversity of the library additionally.

Figure 14:
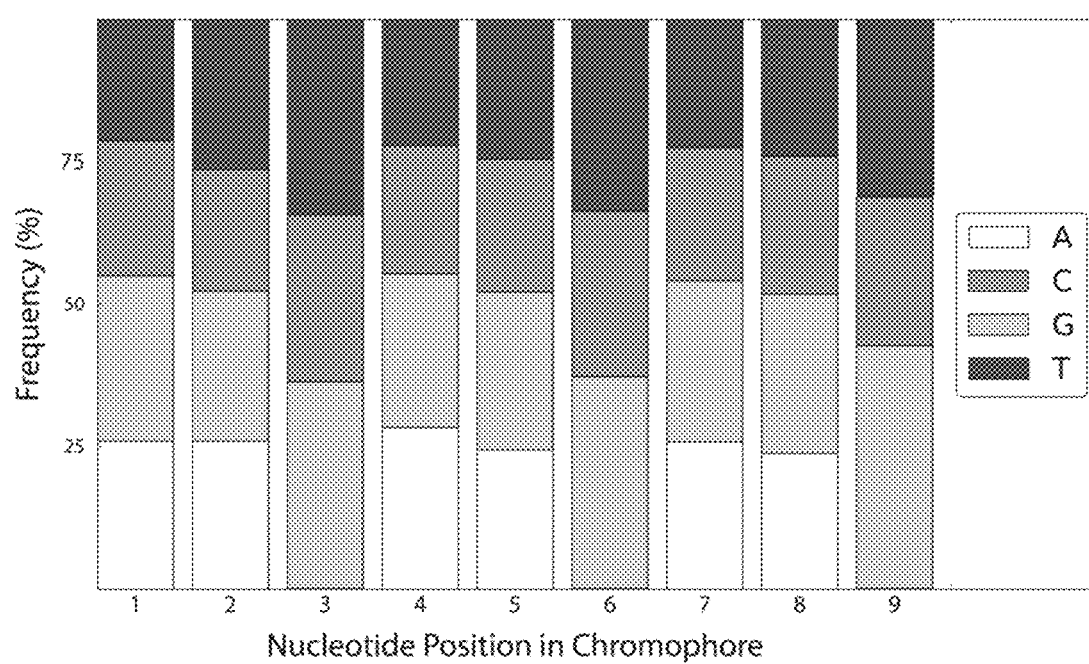

FIG. 14. Next gen sequencing analysis of nucleotide frequency for each position within the diversified 3-amino acid residue stretch in the chromophore region of mRuby2 (amino acids 67-69). Donor single stranded oligonucleotides incorporated a library bearing three codons of the pre-conceived synthesis type NNB (where N is any nucleotide, B is any nucleotide apart from A (adenine). This design eliminates the generation of the TAA and TGA stop codons. Apart from this pre-programmed bias disfavoring stop codons, the nucleotides are distributed nearly equally, hence randomly, over the mutated positions, which indicates that the proposed method generates highly heterogeneous and complex libraries with designed bias.

FIG. 15: Targeted mutagenesis of mRuby2 at amino acid residues 43-47. a) Structure of mRuby2. The black stretch on the beta sheet indicates region diversified using Cas9. It is a 5-amino acid region corresponding to residues 43-47. The original primary sequence of this modified region in parental mRuby2 is 043, T44, M45, R46, and I47. b) The basic structure of the expression cassette for mRuby2 used for mutagenesis. For this series of experiments the fluorescent protein TagBFP2 was fused to mRuby2 in addition to the selection marker puromycin R. The use of a second fluorophore allows FACs sorting with an additional wavelength.

Figure 16:
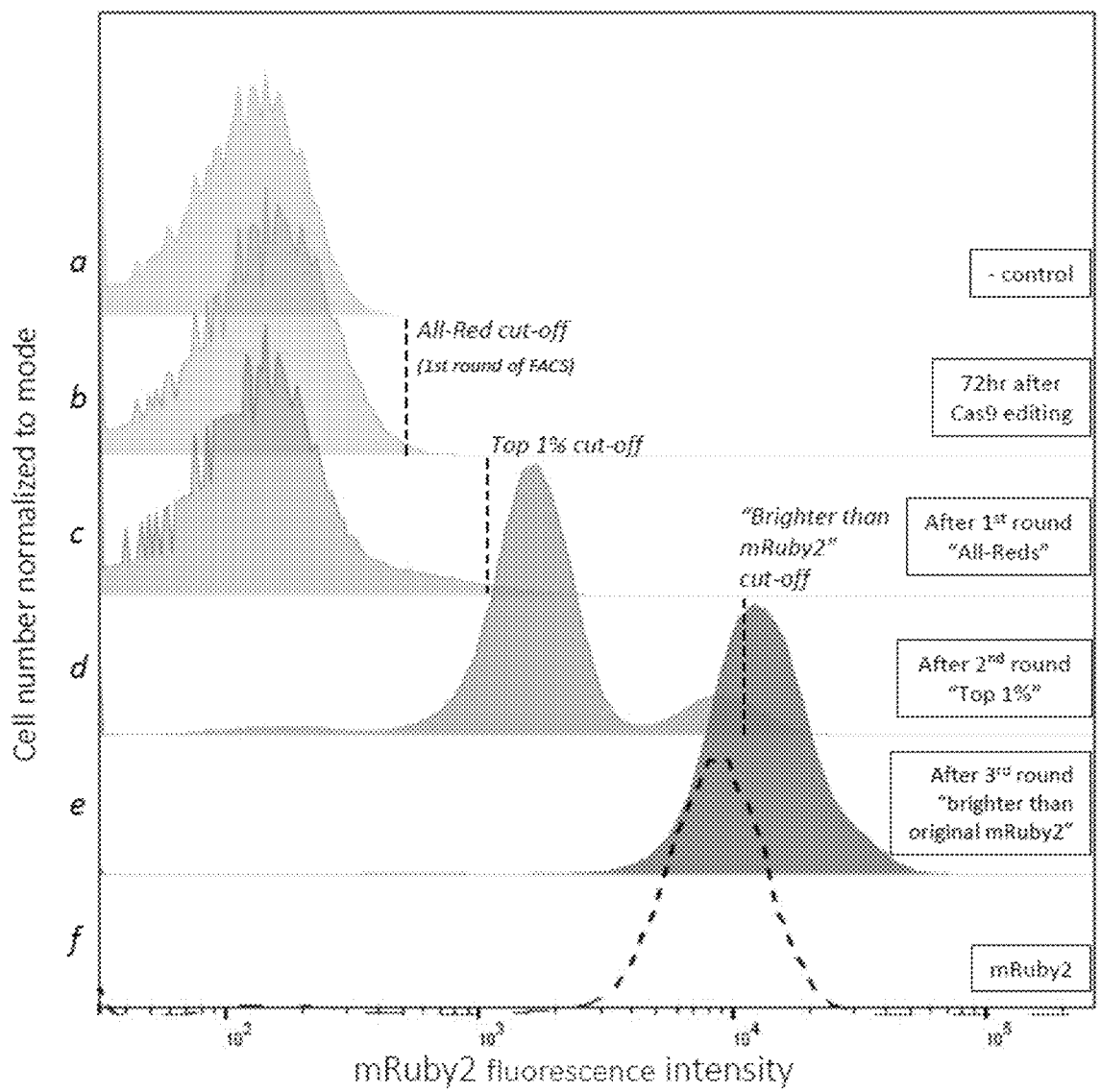

FIG. 16: Fluorescence histograms showing evolution of mRuby2 brightness after Cas9 editing and consecutive rounds of FACS sorting. mRuby2 was diversified in a region ranging from from amino acids 43 to 47. Vertical dashed lines indicate the cut-off gates for FACS rounds. a) control indicates the cells that express the frame-shifted mRuby2 vector before editing. b) Fluorescence histograms of cell populations 72 h after start of Cas9 editing. Selection started with a population of 100 million cells. Cells that appeared red above an arbitrary cut-off line were sorted, propagated, amplified and used for a new round of FACS-sorting. c) 2nd round of FACS sorting. A 1% cut-off was used to select bright cells. d) 3rd round of sorting. Cell populations that appeared brighter than an mRuby2-control population were selected. e) Histogram of cell populations after the third round of selection and amplification. f) Histogram of control population expressing parental mRuby2.

Figure 17:
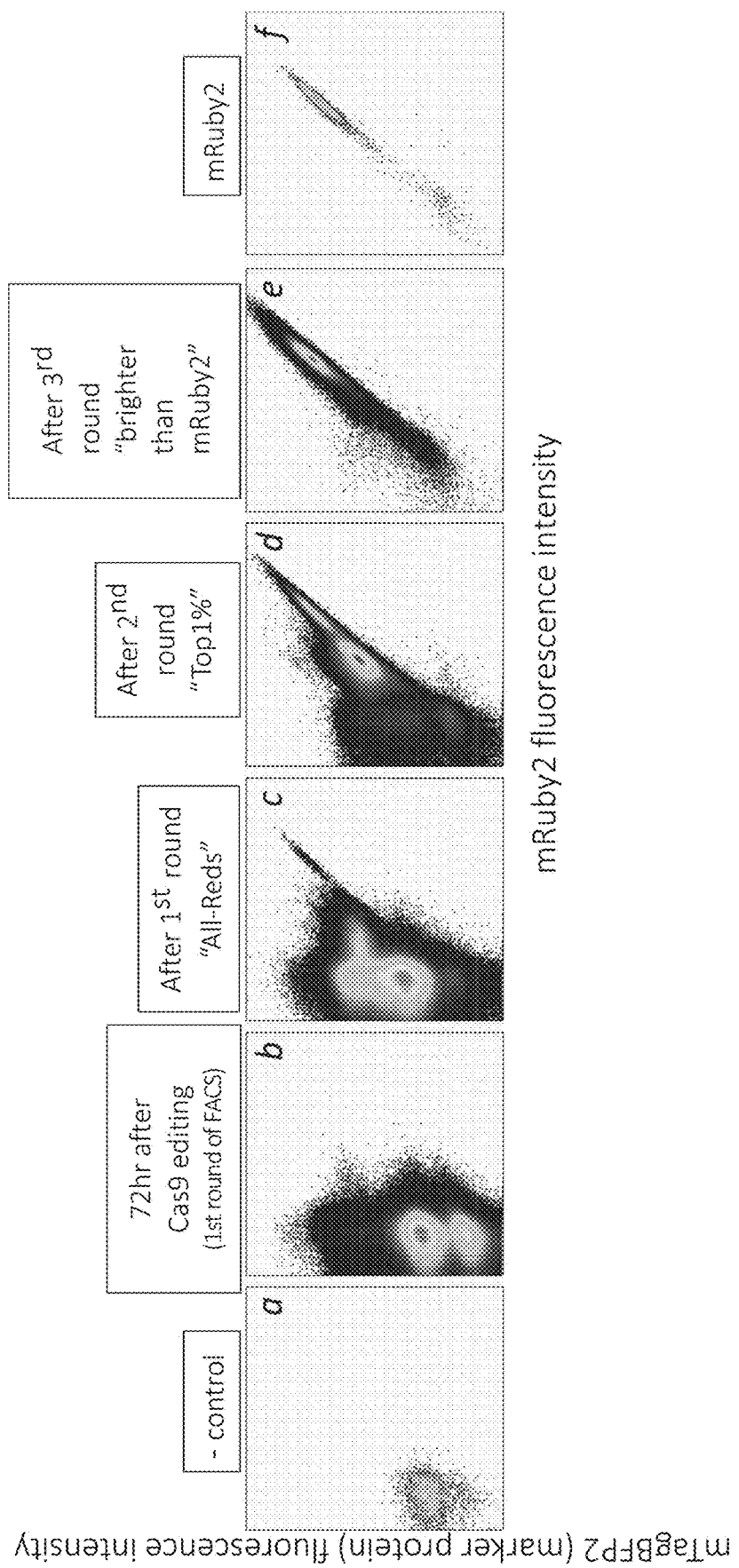

FIG. 17: Fluorescence dot plot representation showing evolution of fluorescence intensity of mRuby2, with reference to the fused marker protein "mTagBFP2", after Cas9 editing and three consecutive rounds of FACS sorting. a-f) Similar to FIG. 16.

Figure 18:
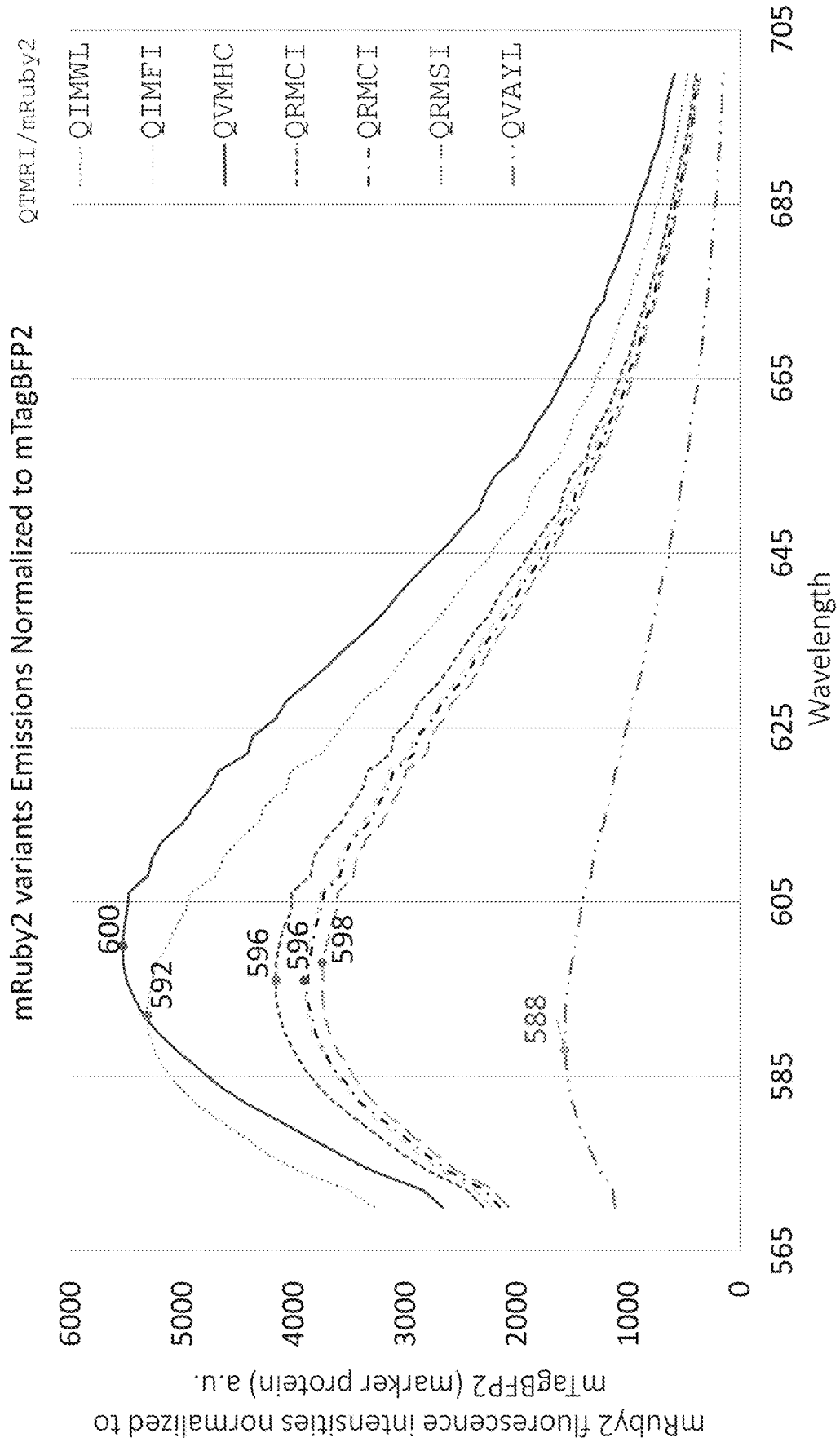

FIG. 18: Emission fluorescence graphs of 7 fluorescent recombinant proteins after first round of FACS sorting. The amino acid sequence of the diversified region is indicated on the right for each protein. After sorting for fluorescence, mRNA was isolated from cells, reverse transcribed and cDNAs cloned into the bacterial expression vector pRSETB. After expression in bacteria fluorescent proteins were extracted using standard procedures in the field and recombinant proteins were analyzed using a fluorescence spectrometer. Fused Tag-BFP2 was used as a standard to normalize protein levels. The data demonstrate that protein variants form these cell lines can be conveniently extracted and transferred to other systems for analysis. The numbers on the lines indicate the emission peak wavelength (in nm). The sequence QTMRI at the top right indicates the parental mRuby2 sequence.

FIG. 19: DNA and protein sequences of the 7 different mRuby2 variants as shown in FIG. 18. Dark grey shading highlights the DNA sequences at the diversified region of the variants. Light grey shading highlights a codon that was modified by a silent mutation introduced by the repair template in order to eliminate the recurrent binding of the sgRNA and multiple re-cuts. AAA represents the unchanged parental sequence. This indicates that the diversification in this case is a result of non-homologous end joining (NHEJ), whereas AAG is introduced via homology template-based repair. Thus, NHEJ can significantly contribute to the diversification of proteins. The very right panel shows the corresponding amino acid sequences at the diversified regions of the variants. mRuby2 indicates the parental sequence. Two lowercase "aa" within the mRuby2 DNA sequence indicate two nucleotides that had been deleted to effect the frame-shift for the inactivation of the parental mRuby2 protein. It was subsequently repaired in the variants and reading frame restored after Cas9 editing, both through homology directed repair and occasionally through NHEJ.

Figure 20:
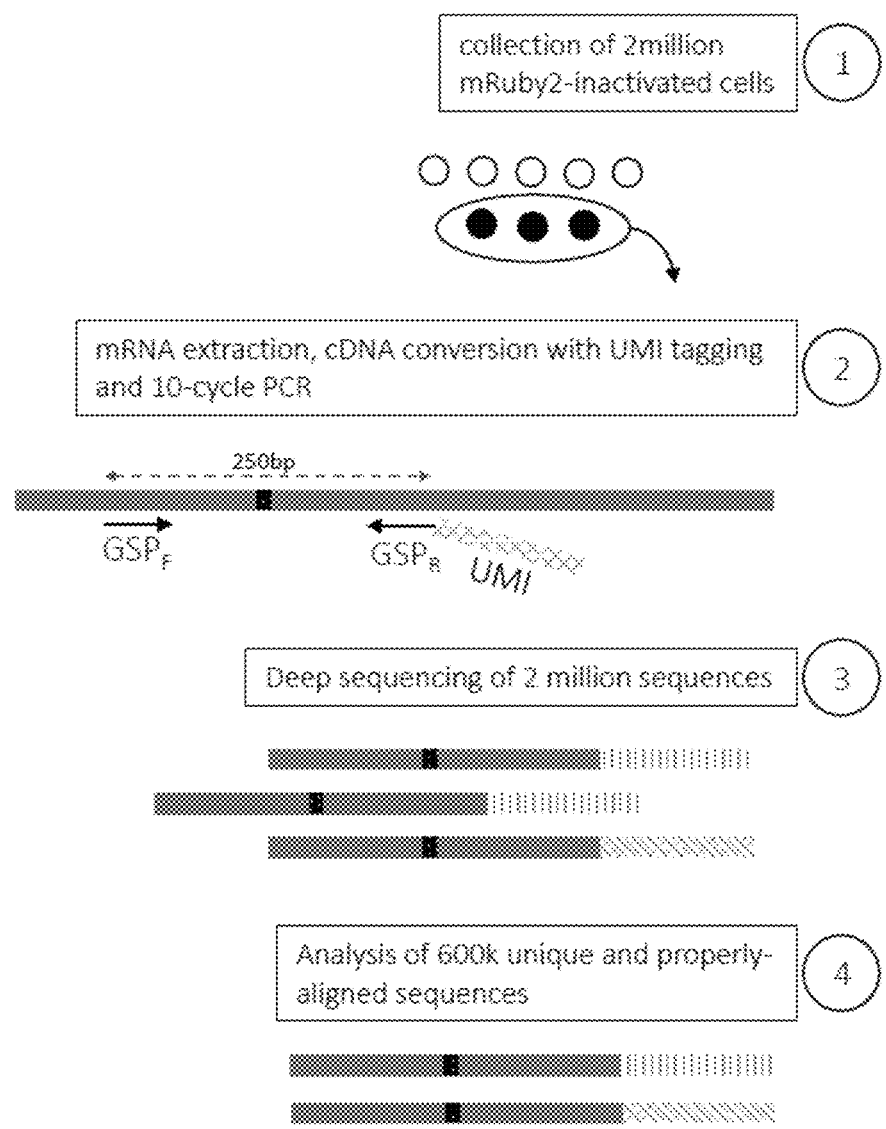

FIG. 20: Scheme for illustration of experimental proceedings for results presented in FIG. 21. The objective was to determine the overall rate of homology directed repair and to assess if any pharmacological treatments could influence this rate. a) Scheme for the targeted Cas9-editing of the mRuby2 DNA. In this particular case a frameshift was introduced with a repair template into parental mRuby2. The guide RNA and the repair template (SSODN HDR template) were co-delivered and generated the frame-shifted mRuby2. HA-L: Homology Arm-Left; HA-R: Homology Arm-Right and ssODN: single-stranded Oligonucleotide. Dotted black strip indicate the frame-shifted region. b) Outline for the Next-Generation Sequencing analysis of HDR-inducing strategies, schemed as four consecutive steps. About two million cells in which mRuby2 was inactivated were sorted to obtain dark cells (1). mRNA form this population was isolated, reverse transcribed and subjected to next generation sequencing (2). Two million sequences surrounding the frame-shifted site were obtained by deep sequencing (3). Finally, sequences were aligned, duplicates removed and the remaining 600.000 results analyzed. UMI: Unique Molecular Identifier, stretch of 15 random nucleotides. GSP: Gene Specific Primer. Line patterns represent UMI variants. The region sequenced is 250 bp.

Figure 21:
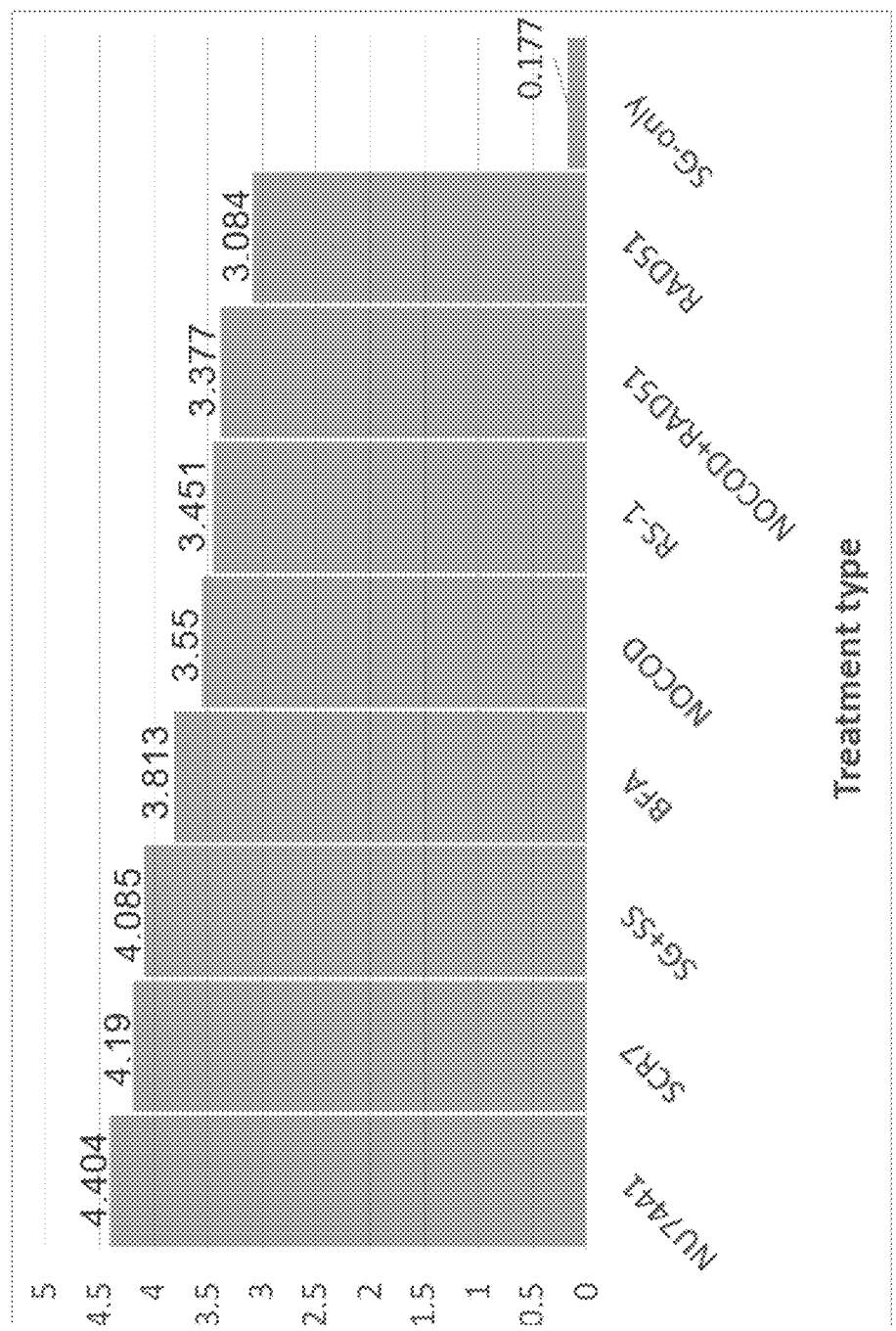

FIG. 21: Effects of 8 different pharmacological interventions on rate of homology directed repair (HDR) of mRuby2 as analyzed by next generation sequencing. Experimental details are illustrated in FIG. 20. Rate of homology directed repair is indicated on the X-axis. Treatments with pharmaceutical compounds were applied to cells during the 72 h period for Cas9 editing. In all cases the same sgRNA was applied and the same repair template (apart from SG-only). NU7441: treatment with NU7441; SCR7: treatment with SCR7; SG+SS: control experiment, sgRNA and HDR template were applied with no additional pharmacological treatment; BFA: treatment with BrefeldinA; NOCOD: treatment with Nocodazole; RS-1: treatment with RS-1; NOCOD+ RAD51: treatment with Nocodazole and RAD51 mRNA at the same time; RAD51: treatment with RAD51 mRNA. SG-only: only guide sgRNA, but no homology template was applied.

The present invention is further described and/or illustrated by reference to the following non-limiting examples.

Example 1: Protein Diversification and Targeted Mutagenesis of mNeonGreen

Schematic Overview of the Protein Library Generation

The basic setup of the performed experiments is schematically depicted in FIGS. 1 and 2. Specifically, in a first step a vector (referred to as pcDNA5-FRT-NGFS) was generated that comprises a single copy of the mNeonGreen gene under control of a CMV promoter. The single mNeonGreen gene copy that was introduced in this vector by cloning comprised an inactivating frame-shift mutation in the mNeonGreen gene that prevents expression of the mNeonGreen protein from said vector. The frame-shift mutation was introduced into the gene by site-directed mutagenesis prior to cloning of the gene into the vector. Specifically, a frame-shift mutation was introduced at a specific target site by deleting 4 base pairs at a pre-defined position to produce a frame-shift version of the mNeonGreen nucleotide sequence as shown in SEQ ID NO: 26. This pre-defined position is at the site that was selected as the target site for introducing different mutations with the steps described further below.

In the next step a stable cell line was generated in which a single copy of the pcDNA5-FRT-NGFS vector was integrated into the genome of the cells. Specifically, this was achieved by using Flp-In recombination into the Flp-In-293 Cell Line (Thermofisher). Accordingly, a stable cell line comprising a single copy of the inactivated mNeonGreen variant (referred to as NGFS) under control of a CMV promoter was generated.

The generated cell line was subsequently used to generate a panel of cells (in other words a library of cells) that express different mutant variants of mNeonGreen. The mutant variants were generated by a recombination based approach in which first a double-strand break (DSB) was introduced in the genome of the cell at a position in close proximity to the inactivating frame-shift mutation within the single copy of the NGFS gene. In particular, in this case, the cut was introduced 1 bp upstream of the deletion site. In this example, the CRISPR/Cas9 system was used to introduce the site-specific DSB. To this end the stable cell line was transformed with a vector encoding a Cas9 nuclease (i.e. SpCas9). The same vector also encoded a sgRNA targeting the Cas9 nuclease to the site at which the DSB was introduced. Together with the vector encoding the Cas9 nuclease and the sgRNA also a library of oligonucleotides was co-transformed into the cell line. The oligonucleotides of this library had a sequence that allowed them to serve as a donor nucleic acid template for the repair of the introduced DSB via homologous recombination. To function as a donor nucleic acid template for homologous recombination the oligonucleotides comprised sequences being homologous to the regions flanking the DSB. In addition, the oligonucleotides comprised mutated codons for 3 or 5 amino acids. The library of oligonucleotides comprised different oligonucleotides with different mutations at the respective 3 (residues 147-149 of mNeonGreen) or 5 amino acid (residues 146-150 of mNeonGreen) target sites, which allowed for basically covering all possible codons. Similarly, the oligonucleotides did not have the inactivating mutation that introduced the frame-shift. Therefore, the oligonucleotides were configured to remove the frame-shift mutation by homologous recombination.

Results and Discussion

The basic concept of the method for generating cells expressing mutant variants of a protein of interest (i.e. for generating a library of cells expressing different mutant variants of a protein) that was employed is summarized in FIGS. 1 and 2. Specifically, the Flp-recombinase system was used to insert a single copy of a protein-coding gene into a mammalian cell line. In the context of the present example the fluorescent protein mNeonGreen (Shaner, 2013, Nature methods 10.5: 407-409) was engineered. In order to distinguish members of the library from parental mNeonGreen an inactivating mutation in form of a fame-shift was inserted into the reading frame of mNeonGreen that prevents correct expression of the target protein, and of potential C-terminal fusion proteins. A Cas9/sgRNA system was designed to cut specifically near the site of the frame-shift. In particular, the cut was introduced 1 bp upstream of the site of the deletion. For the repair of the double stand break, oligonucleotides (i.e. a donor nucleic acid templates) with appropriate homology arms on both ends were co-transfected into cells and acted as a repair template. These repair templates contained besides the homologous sequences stretches of diversified DNA sequence that are to be fused in frame into the target site (i.e. the target site for mutagenesis) within mNeonGreen. The degree of diversification and the length of the diversified stretches of DNA and protein was designed in advance when synthesizing the repair templates. Subsequent recombination of the repair template at the site of double strand break lead to insertion of the desired diversification and also repaired the frame-shift in mNeonGreen, restoring expression. Thus, the still fluorescent cells subsequently harbored a diversified gene-variant that is properly folding and functional.

In detail, HEK293 cells containing the frame-shift/deletion of mNeonGreen were transformed with a targeted Cas9/sgRNA vector, together with either a library of repair templates with three diversified amino acids or a library of repair templates with five diversified amino acids. These repair templates led to the introduction of the either three or five diversified amino acids into the chosen site into the mNeonGreen gene. The library was encoded by the nucleotides NNB, where N stands for any of the four nucleotides, whereas B encodes any nucleotide apart from A. This was used to decrease the likelihood for introducing stop codons (TAA, TGA). However, any preference or bias for nucleotides can in principle be incorporated. As target for a 3 amino acid library the amino sequence NSLTAAD*WCRSK (SEQ ID NO: 30) was initially chosen within mNeonGreen. The asterisk indicates the site of double strand break right after the codon coding for aspartate 147. Underlined amino acids illustrates the residues replaced by the 3-residue library. Flanking the diversified libraries, these oligonucleotide repair templates encode 48 or 45 base pairs of homology respectively, to each side of the mNeonGreen at the Cas9 cut site. Lastly, this variable domain within the repair template encoded the missing base pair to restore the correct reading frame, and express the remaining C-terminal domain correctly. Following transfection, daily inspection with fluorescence microscopy showed the initiation of green fluorescence in cells 48 h post-transfection, with further increase in brightness and number of cells expressing a fluorescent mNeonGreen variant maximizing at 96 h post-transfection. This delay is due to the required sequential expression of first Cas9, followed by specific genomic DNA cleavage, then homologous repair, and then the CMV-promoter driven expression of the mNeonGreen variants. The control reaction, using a template that just repaired the frame-shift back to parental mNeonGreen showed an efficiency of 5%, the percentage of fluorescent cells was detected via cytometry.

At this stage, the cells underwent FACS for brightness. The FITC channel was used on a FACSAria III sorter (BD), which fitted the spectral profile of mNeonGreen well. All cells displaying this signal were collected, including those above the baseline, in order to maximize the library size for later sequencing. Sorted cells were grown for 3 further rounds of screening, with the top 5% of cells at each round kept and grown. As shown in FIG. 3, the initial selection of cells from the diversified variants showed broad distribution of fluorescence intensity, with a very low average intensity. This low level of average fluorescence is due to the large number of variants that adversely affect the fluorescent protein structure.

To verify the correct insertion of diversified residues at the intended site, cells were collected after the first round of FACS sorting for genomic DNA extraction. Diversified mNeonGreen genes were extracted by PCR and cloned into an E. coli expression vector. After transformation, a random selection of bacterial colonies were picked and the variants sequenced. Sequencing results for a number of clones are shown in FIG. 6. The variants had been diversified at the intended site of interest. Moreover, no codon bias was observed when inspecting the sequences of diversity.

Each further round of sorting increased the mean fluorescence of the library population, as dim variants (i.e. variants showing low levels of fluorescence intensity) were eliminated. FIG. 4 shows the results after the final third round of sorting, and includes a comparison with parental mNeonGreen. The mean brightness of both library populations indicates higher fluorescence of our sorted diversified variants than the parental mNeonGreen.

Images of cells obtained in the final round of FACS sorting are shown in FIG. 5. Cells are evenly fluorescent with no indication of aggregation of sequestering into organelles. After final rounds of FACs sorting genes coding for brighter variants of mNeonGreen were extracted by RT-PCR, transcribed into cDNA and cloned into bacterial expression vectors. One such mNeonGreen variants, tentatively named mNeonGreen2 (SEQ ID NOs: 91 and 92), was purified and characterized in more detail (FIG. 7)

An outline of further target sites within mNeonGreen to be diversified using this approach is seen in FIG. 8. It is expected that diversification of these target sites can lead to further brighter variants of mNeonGreen. Finally, all these diversified sites may be combined to obtain an utrabright variant of mNeonGreen, using the protocols as presented here within this application.

FIG. 9 shows the sequences of sgRNAs used to target Cas9 to other sites within mNeonGreen as indicated in FIG. 8.

Materials and Methods

Construction of mNeonGreen Substrate Plasmid Comprising mNeonGreen with an Inactivating Mutation The coding region of mNeonGreen (Allele Biotechnology; nucleic acid sequence see SEQ ID NO: 27; amino acid sequence see SEQ ID NO: 28) in the plasmid pSLiCE3-NeonGreen (Shaner, 2013, Nature methods 10.5: 407-409), was subjected to site-directed mutagenesis with the primers 5'-TCGCTGACCGCTGCGGACGCAGGTCGAAGAA-GACTTACC-3'-forward (SEQ ID NO: 13) and 5'-GTCCGCAGCGGTCAGCGAGTTGGTC-3'-reverse (SEQ ID NO: 14) to delete 4-base pairs. In particular, positions 442-445 of the nucleotide sequence of mNeonGreen have been deleted. The deletion was 1 bp downstream of the cutting site and 3 bp upstream of the selected PAM site. The selected PAM site was at positions 448-450 of the nucleotide sequence of mNeonGreen. Or, in other words, base pairs 442, 443, 444 and 445 were deleted, positions 446 and 447 remained (2 bp) and the selected PAM site was at positions 448, 449 and 450. This resulted in the removal of one amino acid and the introduction of a frame-shift that lead to a non-fluorescent protein that we termed NGFS. The nucleic acid sequence of the mutated coding region of mNeonGreen is shown in SEQ ID NO: 29.

After the mutagenesis PCR the coding domain of the NGFS was subsequently amplified with the following primers:

```
(forward primer, SEQ ID NO: 15)
5'-TCGCTGACCGCTGCGGACGCAGGTCGAAGAAGACTTACC-3';
and (reverse primer, SEQ ID NO: 16)
5'-CGGCCGCCACTGTGCTGGATCTATTATCACTTGTACAGCTCGT
CCATGC-3'.
```

The above-mentioned primers included overlaps with the pcDNA5-FRT vector (Thermofisher), and SLiCE cloning (Methods Mol Biol. 2014; 1116: 235-244) was used to ligate the PCR-generated coding domain fragment into AflII-Not1 cut pcDNA5-FRT (Thermofisher) vector resulting in the construct pcDNA5-FRT-NGFS. The sequence of this construct was verified by DNA sequencing.

Construction of sgRNA/Cas9 Plasmid

The plasmid pSpCas9(BB)-2A-Puro (Ran, 2013, Nat Protoc. 8(11): 2281-2308) was double cut with the restriction enzyme BbsI (NEB), gel purified (NucleoSpin Gel and PCR Clean-up, Macherey-Nagel), and ligated with the pre-annealed primers 5'-CACCGCGCTGACCGCTGCGGACGC-3' (forward, SEQ ID NO: 17) and 5'-AAACGCGTCCGCAGCGGTCAGCGC-3' (reverse, SEQ ID NO: 18) to generate a nucleic acid sequence that encodes a sgRNA sequence that targets the NGFS sequence upstream of the 4-base pair deletion. In particular, The 4-bp deletion was within the 20 bp recognition sequence for NGFS. The sgRNA encoding sequence was introduced in the plasmid pSpCas9(BB)-2A-Puro in a manner that it is expressed from a U6 promoter. The final construct, termed pSpCas9(BB)-2A-Puro-NGFS was confirmed via sequencing. The pSpCas9(BB)-2A-Puro-NGFS can be used to express the Cas9 nuclease and a corresponding sgRNA for targeting the Cas9 nuclease to a defined site upstream of the 4-base pair deletion in the NGFS gene sequence.

Construction/Design of Donor Nucleic Acid Template Library

A repair template (i.e. a donor nucleic acid template) of 105 base pairs of synthesized ssDNA termed NSFS-R (see SEQ ID NO: 30), consisting of 50 bp of homology on either side of the NGFS deletion and that also comprised the 4 bp that were deleted in the NGFS sequence, was used to test the efficiency of the Cas9 system. Two libraries of donor nucleic acid templates were also generated, again consisting of 50 bp homology flanks, and degenerate NNB codons, to replace the deleted amino acid and frameshift, and to randomize either 1 or 2 amino acids flanking the deletion. These libraries were termed NGFS-3M and NGFS-5M, referring to the number of randomized amino acids in each.

All cloning steps were performed in E. coli XL1-Blue (Agilent), on LB plates and LB media supplemented with ampicillin, and grown at 37° C.

Stable Cell Line Generaton

The Flp-In-293 Cell Line (Thermofisher), was grown in DMEM, supplemented with 10% FBS, 100 U/mL Penicillin, 100 μg/mL Streptomycin and 2.5 mM L-glutamine, and was co-transformed with pcDNA5-FRT-NGFS and the pOGG44 plasmid which comprises a gene encoding for the Flp-recombinase (Thermofisher) using Lipofectamine 3000, following the standard protocol. Cells were subjected to Hygromycin selection at 100 μM until the generation of isogenic colonies, which were pooled and maintained with standard protocols. The result was a stable cell line that comprises a single copy of the NGFS gene. Notably, the used Flp-In strategy ensures that only a single copy of the NGFS gene was incorporated in the genome by ensuring that a single pcDNA5-FRT-NGFS vector is integrated (by Flp catalyzed recombination) at a predefined target site in the Flp-In-293 Cell Line. The basic principle of Flp-In recombination is known in the art and, for example, described in https://www.thermofisher.com/ddehomerefenesprtocolsproteinsexpression-isolation-and-analysis/protein-expression-protocop-in-system-for-generating-constitutive-expression-ceines.html.

HEK293 Cas9 Expression, Provision of Donor Repair Template Library and FACS Sorting Cells were grown to 80% confluency on 10 cm plates before co-transformation with pSpCas9(BB)-2A-Puro-NGFS, and each of the library of donor nucleic acid templates, NGSF-3M, NGFS-5M and NGFS-R. Cells were inspected via fluorescence microscopy (Axiovert 135TV, Zeiss), and after 96 hours, maximal fluorescence was observed, and the cells were prepared for FACS cell sorting (FACSAria III, BD Biosciences). All cells exhibiting fluorescence on the FITC channel were sorted and expanded.

At the first round, the NSFS-3M and NGFS-5M sorted cells were grown until reaching confluency on 10 cm plates, at which time 5 million cells were taken for genomic DNA extraction using the DNeasy Blood & Tissue Kit (Qiagen). The remaining cells were grown for subsequent rounds of FACS, with the top 5% in brightness selected and expanded at each round. After the final round, genomic DNA was isolated from best performing variants, i.e. the variants with the highest fluorescence.

DNA Analysis and Confirming Mutation of the Target Gene and Protein Expression and Analysis.

Genomic DNA isolated at the steps described above was used as the template to extract the coding domains of the repaired mNeonGreen, using the primers 5'-ATAAGGATCCGGCCACCATGGT-GAGCAAGGGCGAGGAGGAT-3' forward (SEQ ID NO: 38) and 5'-TATAGGAATTCCTATTATCACTTGTA-CAGCTCGTCCATGCCC-3' reverse (SEQ ID NO: 39) that included overlaps with the EcoRV-cut vector pSUCE3. SLiCE cloning followed by heat-shock transformation of E. coli XL1-Blue led to the generation of fluorescent colonies. In the case of the initial round of NGFS-3M and NGFS-5M sorting, a wide variance of fluorescent intensities was observed, and colonies were picked for plasmid preparation (NudeoSpin Plasmid, Macherey-Nagel), for sequencing and subsequent expression in the E. coli strain BL-21 (NEB).

Briefly, 4 ml starter cultures of transformed BL21 grown in LB+ampicillin with shaking at 37° C. were used to inoculate 200 ml of auto-inductive Studier media grown at RT with shaking for 48 h. The cells were harvested and lysed with lysozyme, a freeze-thaw cycle, and 10 m sonication, before ultracentrifugation. The 10-His-tagged proteins were purified on NI-NTA resin (Jena Bioscience), and washed with 25 mM Imidizole, and eluted with 250 mM Imidizole. The fluorescent protein concentrations were determined via the Bradford assay, after thermal denaturation in 3M Guanadine HCl at 95 C for 5 m. Using an excitation of 480 nm, the quantum yield was determined via the integrated fluorescence spectrum of a dilution spectrum of between 0.01 and 0.1 absorbance units, calibrated to the emission of Fluorescein in 0.1 N NaCl (QE 0.95).

Example 2: Possible Variations of the Method for Diversification and Targeted Mutagenesis The means and methods of the present invention allow for the complex, saturated mutagenesis of peptide sequences within target proteins. A schema of the general procedure is provided in FIG. 10.

The process first involves the generation of a stable, singe copy integration of a gene-of-interest (GOI) into a cultured cell line. The singe copy integration process can be accomplish through a variety of means, including standard antibiotic selection, Flp-In and Jump-In recombination, lentiviral transfection and selection, or through Cas9 targeted cutting and recombination with homologous domains, such as in the AAVS1 locus. The description below is focused on the Flp-In system for generating stable single copy cell lines, without being limited thereto.

The GOI receives a frame-shift mutation, located at a site targeted for diversification. The site is also suitable of being targeted for a cleavage by a site-specific nuclease. The GOI can be a fluorescent protein or a non-fluorescent protein. If desired, the protein product coded by the GOI can be fused to a variety of markers genes, such as an additional fluorescent reporter or drug resistance gene. If fused, these markers may be direct fusions, or linked by cleavable or self-cleaving peptide linkers. Due to the frame-shift in the GOI the markers will initially not expressed correctly. The frame-shift can be produced during the cloning of the GOI via site-directed-mutagenesis, or can be generated directly in cell lines containing the GOI-marker fusion, via a nuclease process as described below.

For introducing targeted double strand breaks in the gene of interest CRISPR/Cas9 is preferably used as nuclease because it is very efficient and programmable to target many possible locations within a gene. However, other enzymes and means to induce single-strand nicks, or preferably double strand breaks, such as zinc finger nucleases (ZNFs), or transcription activator-like effector nucleases (TALENs) would also be applicable. If not present at the correct site within the gene of interest, target sites for cleavage by CRISPR (PAM site) or target sites for TALEN or zinc finger nucleases can be engineered into the gene of interest together with the frame-shift. Upon cut and repair, such site will be removed from the diversified gene.

Increases in efficiency of the cut/repair protocol can be achieved by several means. Transfection protocols and methods to deliver sgRNA and Cas9 or other nucleases into cells can be optimized. Furthermore, the efficiency of homologous recombination repair can be enhanced by inhibiting non-homologous end joining (NHEJ), via methods such as co-expressing E1B55K and E4orf6, or suppressing KU70 and DNA ligase IV using the inhibitor Scr7.

Upon targeted cleavage of the genomic DNA in the GOI, single stranded DNA is used as a template (i.e. as donor nucleic acid template) for repair via homologous recombination. The oligonucleotides contain the degenerate codons required for diversification, and frame-shift-correcting base pairing. The sequence of diversification is flanked by region between 30 and 80 base pairs in length that are homologous to the regions flanking the cleavage site. The sequence of diversification can include specific amino acids and also degenerate codons including NNN, NNK/NNS, NNB or the MAX system for the expression of all possible amino acids. Degenerate codons may be interleaved with amino acids from the original peptide sequence that may be considered critical and should not be diversified. The number of degenerate or specific codons can also be varied, shortening or increasing the final protein length.

After the diversification, cells that have undergone the process correctly will produce the fused marker gene. This gene will be expressed at the same level as the GOI, and when a fluorescent protein is used, it can serve as an estimate of protein concentration. Thus, for binding assay utilizing the GOI, the binding can be calibrated to the expression level. Cells expressing a fluorescent marker gene can be rapidly collected with FACS or microfluidic sorting, a more rapid process than antibiotic selection.

If the fusion marker is a positive or negative resistance gene, several possibilities exist to obtain a cell population consisting of just diversified variants. If both positive and negative marker are used together via multiple cleavable peptide linkers such as T2A or F2A, an original GOI can be converted by the process described above to a frame-shift variant and negative selection can be used to eliminate the non-frame-shifted variants, with a gene such as herpes simplex virus type 1 thymidine kinase, and selected against with ganciclovir. Once these cells are isogenic, and subjected to the diversification via the process described above, the unwanted remaining frame-shift variants can be removed with a positive selection gene such as hygromycin phosphotransferase and hygromicin B. However, other selection markers will be also useable.

Application of the herein provided production method is exemplarily be illustrated describing the diversification of the gene coding for mNeonGreen, the brightest known monomeric fluorescent protein to date. By using the herein provided method, various proteins, such as mNeonGreen can be diversified, and sorted for brighter variants via FACS. Monomeric mNeonGreen had been engineered from the tetrameric fluorescent protein LanYFP. The red fluorescent maker gene mKate2 may be fused onto the C-terminal end of mNeonGreen. As it will be always fluorescent after frame-shift correction, it can be used to collect successfully diversified variants of mNeonGreen, even if they are dim or non-fluorescent. mKate2 may also be used to correct for differing protein expression levels during sorting. An overview for exemplified experimental processes, is shown in FIG. 10.

Based on the predicted crystal structure, and research published on the development of mNeonGreen, five regions may be targeted for complex saturated mutagenesis. An example for a target selection within mNeonGreen is shown in FIG. 8. A list of primers that may be used to generate sgRNAs to target sites within mNeonGreen is indicated in FIG. 9. By using the herein provided methods it can be achieved, e.g. that at each locus, 5 amino acids undergo saturated mutagenesis, for a possible 3.2 million combinatorial variants per locus. In addition, it is possible to perform the herein provided methods in a way that at some sites certain residues within the sequence to be diversified remain unaltered. For example, those residues may be left unchanged that have been previously introduced to block dimer and tetramer formation to generate momomeric mNeonGreen. Keeping them unaltered prevents reformation of dimer interfaces. This exemplified application of the herein provided methods is a demonstration of the extraordinary flexibility in mutagenesis that the invention enables.

After the initial sort for all red-fluorescing variants, indicating successful recombination, mNeoGen sequencing may be used to accurately report the scope of the diversification via sequencing the diversified region, e.g. using the Illumina MiSeq NextGen sequencing platform.

Each set of variants may undergo multiple rounds of screening to select the best performing fluorescent protein variants. The final variants may undergo characterization, before DNA shuffling to generate a final set of combined variants to be compared with the wild-type protein of interest here exemplarily progenitor mNeonGreen.

Materials and Methods

The materials and methods that may be used in order to diversify a fusion gene, e.g. comprising mNeonGreen and mKate2 are shown below.

Olio Annealing and Cloning into Backbone Vectors:
1. Digest 1 ug of pSpCas9(BB)-2A-Puro with BbsI for 30 min at 37° C.:

| 1 ug | Plasmid (pSpCas9(BB)-2A-Puro) |
|------|-------------------------------|
| 1 ul | Bbsi |
| 1 ul | Alkaline Phosphatase |
| 2 ul | 10 × buffer Buffer |
| X ul | ddH$_2$O |
| 20 ul | total |

2. Gel purify digested plasmid.

3. Phosphorylate and anneal each pair of oligos:

| | | |
|---|---|---|
| 1 ul | oligo 1 with (100 mM) | |
| 1 ul | oligo 2 with (100 mM) | |
| 1 ul | 10 × T4 Ligation Buffer (NEB) | |
| 6.5 ul | ddH$_2$O | |
| 0.5 ul | T4 PNK (NEB) | |
| 10 ul | total | |

Anneal in a thermocyder using the following parameters:

| | |
|---|---|
| 37° C. | 30 min |
| 95° C. | 5 min and then ramp down to 25° C. at 5° C./min |

4. Set up ligation reaction and incubate at room temperature for 10 min:

| | |
|---|---|
| X ul | Bbsi digested plasmid from step 2 (50 ng) |
| 1 ul | phosphorylated and annealed oligo duplex from step 3 (1:200 dilution) |
| 5 ul | 2 × Quickligation Buffer (NEB) |
| X ul | ddH$_2$O |
| 10 ul | subtotal |
| 1 ul | Quick Ligase (NEB) |
| 11 ul | total |

5. Transform plasmid into XL1-Blue

6. Check clones with sequencing, Midiprep to amplify vector

Frame-Shifting Primers for PCR Mutagenesis

```
1.F
                                        (SEQ ID NO: 40)
CTTTAAGTGGACACCACTGGAAATGGCAAGC

1.R
                                        (SEQ ID NO: 41)
CCAGTGGTGTCCACTTAAAGGTACTGATGATGGTTTTG

2.F
                                        (SEQ ID NO: 42)
CTGGTGCAGGAGAAGACTTACCCCAACGACAAAAC

2.R
                                        (SEQ ID NO: 43)
TAAGTCTTCTCCTGCACCAGTCCGCAGC

3.F
                                        (SEQ ID NO: 44)
CAGGTGAAGGTGGTTTCCCTGCTGACGGTC

3.R
                                        (SEQ ID NO: 45)
AGGGAAACCACCTTCACCTGGGCCTCTCC

4.F
                                        (SEQ ID NO: 46)
TCGGGTATGGCATCAGTACCTGCCCTACCCTGAC

4.R
                                        (SEQ ID NO: 47)
GGTACTGATGCCATACCCGATATGAGGGACCAG

5.F
                                        (SEQ ID NO: 48)
GTCCGCAGCGGTCAGCGAGTTGGTC

5.R
                                        (SEQ ID NO: 49)
GCAACCGTAAAGTTCAAGTACAAAGG
```

PCR Mutagenesis

1. PCR pSlice3-NeonGreen

| | |
|---|---|
| 1 uL | Plasmid |
| 1 ul | Primer F 10 × dilution |
| 1 ul | Primer R 10 × dilution |
| 1 ul | dNTPs |
| 1 ul | Herculase II |
| 10 ul | 5 × Herculase Buffer |
| 35 ul | ddH$_2$O |
| 50 ul | total |

95 C/30 s denaturation, 60 C/30 s annealing, 72 C/3m extension

2. Dpn1 digest

| | |
|---|---|
| 2.5 uL in 50 uL | PCR reaction mixture |
| 37° C. | 60 min |

3. Analytical Gel+PCR cleanup

FRT Vector Generation

1. PCR NeonGreen-Frameshift

| | |
|---|---|
| 1 uL | pSlice3-NeonGreenFrameshift |
| 1 ul | Primer F 10 × dilution |
| 1 ul | Primer R 10 × dilution |
| 1 ul | dNTPs |
| 1 ul | Herculase II |
| 10 ul | 5 × Hemlase Buffer |
| 35 ul | ddH$_2$O |
| 50 ul | total |

95 C/30 s denaturation, 60 C/30 s annealing, 72 C/30 s extension

2. PCR mKate2

| | |
|---|---|
| 1 uL | pSlice3-mKate2 |
| 1 ul | Primer F 10 × dilution |
| 1 ul | Primer R 10 × dilution |
| 1 ul | dNTPs |
| 1 ul | Herculase II |
| 10 ul | 5 × Herculase Buffer |
| 35 ul | ddH$_2$O |
| 50 ul | total |

95 C/30 s denaturation, 60 C/30 s annealing, 72 C/30 s extension

3. Digest 1 ug of pcDNA5FRT-APMA-ap-IRES-H2BGFP with AflII and NotI for 3 h at 37° C.:

| | |
|---|---|
| 1 ug | Plasmid |
| 1 ul | AflII |
| 1 ul | NotI |

-continued

| | |
|---|---|
| 2 ul | 10 × Buffer |
| X ul | ddH$_2$O |
| 20 ul | total |

4. Gel purify digested DNA.
5. SLICE ligate the DNA fragments for 30 min at 37° C.:

| | |
|---|---|
| 1 ul | Cut Plasmid from step 3 |
| 3 ul | Fragment from step 1 |
| 3 ul | Fragment from step 2 |
| 1 ul | T4 ligation buffer |
| 1 ul | SLiCE reagent |
| 1 ul | ddH$_2$O |
| 10 ul | total |

6. Transformation
7. Check clones with sequencing

Stable Cell Line Generation
1. Grow 3×30 mm plates of Flp-In-293 Cell to 80% confluency
2. Transform with 10:1 pOG44 to pcDNA5-FRT-NGFS plasmid with Lipofectamine 3000
3. Grow at 30 C overnight without antibiotics
4 Select with hygromicin at 30, 60 an 120 μg/ml until colonies form.

Library Generation
1. Grow 4×10 cm plates of each mNeonGreen-mKate2 variant to 80% confluency
2. Transform with pSpCas9(BB)-2A-Puro-NGFS1-5 plasmid with Lipofectanmine 3000 using 100 pM/ul template diluted 1000× to final volume of media (100 nM)
3. Grow for 96 hours before FACS FACS Round 1
1. Treat cells with Trypsin
2. Resuspend at 2 million cells/ml
3. Record 1 million events for each cell line, including NeonGreen-mKate2 control line
4. Sort for all cells displaying mKate2 fluorescence, as determined from the mNeonGreen-mKate2 control line.
   PE-TexasRed or PE-Cy5 for mKate2, use the one with the best signal
   2 ml medium per 15 ml falcon, bring 4 tubes per construct.
   Change collection tubes every 400 k cells
5. Expect approximately 1.6 million cells per construct. (at 5% efficiency)
6. Grow in 2×10 cm plates until confluent
7. For each library variant, trypsinate cells, pool, wash and take 5 million cells for genomic extraction with the DNeasy Kit Store DNA at −80 C.
8. Seed remaining cells for FACS on 2×10 cm plates FACS Round 2 and Subsequent Rounds
1. Treat cells with Trypsin
2. Resuspend at 2 million cells/ml
3. Record 1 million events for each cell line, including mNeonGreen-mKate2 control line
4. Sort for all cells on the FITC channel
   Plot FITC by Forward Scattering
   Take top 10% of cells by brightness, calibrated for size
   2 ml medium per 15 ml falcon, bring 4 tube per cell line.
   Change collection tubes every 400 k cells
5. Expect approximately 1.6 million cells per construct.
6. Grow in 2×10 cm plates until confluent Example 3: In, Situ Targeted Mutagenesis of the Fluorescent Protein mRuby2 and Subsequent Deep Sequencing Analyses of the Variants Here in this Example 3, the Flp-recombinase system was used to insert a single copy of a protein-coding gene into a mammalian cell line. In the context of the present example, the fluorescent protein mRuby2 (Lam, 2012, Nature methods 9.10: 1005-1012) (SEQ ID NO: 31) fused with a puromycin resistance gene (puromycinR) (SEQ ID NO: 32) at its C-terminal via a P2A peptide (SEQ ID NO: 2) was engineered. In order to distinguish members of the library from parental mRuby2, an inactivating mutation in form of a fame-shift was inserted into the reading frame of mRuby2 that prevents the correct expression of the target protein, and of the C-terminal fusion protein puromycinR. The mutant library generation procedure comprises two adjacent steps. Briefly, in the first step, Cas9/mRuby2-P2A-puroR double-stable cells are transfected first with in vitro-transcribed frame-shifting ssODNs that lead to a specific frame-shift due to a 2-nucleotide deletion within the chromophore region. Subsequently, the frame-shifted, hence dark cells are selected via FACS. On the following second step, the dark cells that express the frame-shifted mRuby2-P2A-puroR cassette are transfected with randomization another in vitro-transcribed sgRNA that binds to the frame-shifted mRuby2 together with ssODNs that lead to the generation of the mRuby2 mutant library. C-terminal end-fused puromycin resistance gene enables the positive selection and enrichment of the cells that properly express the mRuby2 library and to eliminate the frame-shifted parental cells. The puromycin antibiotic treatment is performed at the end of the second step. The experimental details are presented in the methods section.

The schematic demonstration of the construct design of the fluorescent protein to be diversified is depicted in FIG. 11.

A second mRuby2 construct incorporated the blue fluorescent protein TagBFP2 in addition to the puromycin resistance gene as C-terminal markers (SEQ ID NO: 94). This allowed FACS sorting with an additional blue laser line. The construct is schematized in FIG. 15.

Results and Discussion

In detail, initially a plasmid vector (referred to as pcDNA5-FRT-mRuby2-P2A-puromycinR) was generated that comprises a single copy of a marker protein, N-acetyltransferse puromycin resistance protein, which is fused with a P2A peptide to the C-terminal of the fluorescent protein mRuby2 and expressed under control of a CMV promoter. In parallel, a HEK293 cell line stably expressing Cas9 gene fused to a Neomycin resistance gene was also generated.

In the next step, a double-stable cell line was generated using the Cas9-stabilized cells, in which a single copy of the pcDNA5-FRT-mRuby2-P2A-puromycinR plasmid vector was integrated into its genome. Specifically, this was achieved by using Flp-In recombination into the Flp-In-293 Cell Line (Thermofisher). At the end, a double-stable cell line comprising a single copy of the mRuby2-P2A-puromycin gene cassette and expressing Cas9-NeomycinR gene was generated.

The generated double-stable cell line was employed in a 2-step mutagenesis protocol, which eventually leads to the generation of a panel of cells that express different mutant variants of mRuby2. The library generation procedure comprises two adjacent steps. In the first step, the mRuby2+/

Cas9+ double-positive cells are transfected first with ssODNs that introduce a specific frame-shift via a 2-nucleotide deletion within the chromophore region of mRuby2. Subsequently the cells that are mRuby2-frame-shifted, hence dark, were selected via FACS. In the following second step, the dark cells that express the frame-shifted mRuby2-P2A-puromycinR proteins are transfected with randomization ssODNs that repair the frame-shift and lead to the generation of the mutant cell library. Both in the first and second steps, the mutants were generated by a recombination-based approach, which in this example it was the CRISPR/Cas9 system that introduced the site-specific double strand break (DSB).

In the first step, a DSB was introduced in the genome of the cell at the position that corresponds to the last nucleotide of the codon of Met-67, which is a part of the chromophore region of the mRuby2. This first DSB led to a frame-shift mutation within the single copy of the mRuby2-P2A-puromycinR cassette. To this end, in order to inactivate the mRuby2 protein, mRuby2/Cas9 double-stable cell line was transfected with the specific in vitro-transcribed sgRNA also a frameshifting ssODN donor template was co-transfected into the cell line. The oligonucleotides had a sequence that allowed them to serve as a donor nucleic acid template for the repair of the introduced DSB via homology-directed repair. To function as a donor nucleic acid template for homology-directed repair the oligonucleotides contained sequences being homologous to the regions flanking the DSB. In addition, the oligonucleotides also contained a frame-shifting sequence for a 2 nucleotide deletion at the immediate upstream of the chromophore region of the mRuby2.

Two days after the frame-shifting ssODN transfection, the cells underwent FACS to harvest cells expressing frame-shifted variants of mRuby2. The TexasRed channel was used on a FACSAria III sorter (BD), which fitted the spectral profile of mRuby2. All cells displaying ground-zero signal, which was off-set based on the basal signal of a HEK293 cell line that did not express mRuby2, were collected as frame-shifted dark cells. FACS sorting data showed that the percentage of dark cells within the entire population was 40%, which in fact indicates the mutation efficiency. Sorted cells were grown for four more days for the application of the second step of the mutagenesis protocol. On the fourth day after sorting of the dark cells, half of the cells were frozen as stock, and the other half were employed in the second step.

In the second step, a DSB was introduced in the genome of the cell at the position that corresponds to the immediate upstream of the chromophore region of the mRuby2 gene. This second DSB and the following homology-directed repair via the co-delivered ssODN library, led to the correction of the frame-shift and also to generation of the mutant mRuby2 cell library. To function as a donor nucleic acid template for homology directed repair the single-stranded oligonucleotides (ssODNs) comprised sequences being homologous to the regions flanking the DSB. In addition, the oligonucleotides contained diversified codons replacing the amino acids Met67-Try68-Gly69 that comprises the chromophore region of mRuby2 protein. For codon diversification in the oligos the synthesis scheme NNB was used, whereby N stands for any nucleotide, and B stands for any nucleotide apart from A (adenine). As the onligonucleotides bound the reverse strand, the diversified codons were coded by the sequence VNN, where V stands for any nucleotide but T (thymidine) (see SEQ ID NO: 33). Thus, when read on the opposite strand the sequence generated would be NNB.

The ssODNs consisted of 109 nucleotides in total. There were 50-base homology regions on both 5' and 3' sites of the ssODNS, and 9 randomized nucleotides in between (SEQ ID NO: 34). An NNB codon consists of any of the four nucleotides in the first and second nucleotide position (NN) and excluding only the A nucleotide in the third position (B). The experimental details are presented in the methods section. The oligonucleotides were also configured so that to remove the frame-shift mutation within mRuby2 by homology directed repair. 24 hrs after transfection with suitable sgRNA and repair oligonucleotides, the media was refreshed and 2 ug/µL puromycin was applied to the cells for 3 consecutive days by supplementing the medium every day with fresh puromycin. During the first two days of application, significant cell death was observed, and on the 3rd day, there was no significant cell death, and the puromycin treatment ended. The puromycin treatment led to the positive selection of the in-frame mutants and to eliminate the parental frame-shifted cells, together with the ones that possess an undesired early stop codon; eventually this antibiotic treatment enabled enrichment of the cells that contain the desired library.

Finally, the entire library was directly used for deep sequencing with MiSeq Next Generation Sequencing System (Illumina). In order to collect the entire mutant gene library, total RNA isolation was performed using the RNeasy Mini Kit (Qiagen). After collection of the total RNA, by using a gene specific primer (SEQ ID NO: 35), mRuby2 sequences were reverse transcribed into cDNA libraries and then purified with Machery Nagel Gel&PCR cleanup kit. These cDNA libraries were then amplified through 10 cycles of PCR in order to be ready for deep sequencing. Only the small region of interest of the mRuby2 sequences was PCR amplified. The amplified sequence stretch corresponds to the region between the nucleotide positions 86-313 within the wild type mRuby2 DNA sequence. The 10-cycle-PCR was performed using forward and reverse primers, both having adapter flanking sequences that enable the binding of the library amplicons to the flows of Illumina MiSeq platform (SEQ ID NO: 36 and SEQ ID NO: 37).

As shown in FIG. 12, 91% of the sequences are in-frame, which indicates that the puromycin selection worked efficiently and eliminated most of the cells that contain a frame-shifted mRuby2-P2A-puromycinR cassette and/or early stop codons. On the other hand, it also showed that there are sequences that do not perfectly fulfill the library requirements as they introduced additional insertions or deletions of nucleotides and codons, presumably due to homology directed repair. We however thought that this additional variation in the length of the diversified target sequence is a welcome side effect of the protocol and may be useful in detecting interesting phenotypes. The percentage of the sequences that perfectly depict the library length as introduced by the oligonucleotides is 35%. Deep sequencing data shown in FIG. 13, document that there is a length distribution among the mutated proteins, which ranges from 218 to 243 amino acids. Nevertheless, the dominant protein length observed is 236, which is in fact the length of the wild type mRuby2 protein. These data demonstrate that the proposed mutagenesis system is able to generate protein libraries with a remarkable accuracy in terms of protein length.

The chromophore region of the mRuby2, which consists of three codons and nine nucleotides, had been mutated with single-stranded DNA oligonucleotides having 50-base homology arms on both 5' and 3' sides and three consecutive NNB codons in between these homology arms (where N is any nucleotide, B is any nucleotide apart from A (adenine). This design eliminates the generation of the TAA and TGA stop codons. In FIG. 14, it is shown that the A nucleotide is not observed in third positions of neither of the codons. In addition to that, the nucleotides are distributed nearly equally, hence randomly, over the mutated positions, which indicates that the proposed method generates highly heterogeneous and complex libraries with intended pre-programmed bias.

In a second parental construct, mRuby2 was fused to both the blue fluorescent protein TagBFP2 and the puromycin resistance gene (FIG. 15). This construct was used to diversify amino acids 43-47. Based on the crystal structure information, the residues Q43, T44, M45, R46, I47 are part of a chromophore-interacting region and thus were of interest as a target for diversification. Initially, the mRuby2-TagBFP2-Puromycin coding expression cassette shown in FIG. 15, was inserted in the genome of HEK293 cells as a single copy. This was achieved by using Flp-In recombination into the Flp-In-293 Cell Line as described above. The single mRuby2-TagBFP2-Puromycin gene copy that was introduced comprised an inactivating frame-shift mutation in the mRuby2 gene that prevents expression of the mRuby2 protein from the cassette. The frame-shift mutation was introduced into the gene by site-directed mutagenesis prior to cloning of the gene into the vector. Specifically, a frame-shift mutation was introduced at a specific target site by deleting 2 base pairs at a pre-defined position to produce a frame-shift version of the mRuby2 nucleotide sequence. The generated cell line was subsequently used to generate the library of cells that express different mutant variants of mRuby2. In particular, in this case, the cut was introduced 6 bp downstream of the deletion site.

The procedure for generation of the mutant library and directed evolution of the mRuby2 protein involves two adjacent steps. Briefly, in the first step, Cas9/mRuby2-P2A-puroR double-stable cells are co-transfected with in vitro-transcribed sgRNA that binds to close proximity of the DNA region to be modified, and with the ssODNs that lead to the diversification of the region-of-interest. This ssODN is 115 bases long. The 5' 50 bases and the 3' 50 bases are the homology arms, and the 15 bases in the middle are incorporated the library bearing five codons of the NNB. In addition to the leading to the diversification of the region-of-interest, the homology template also corrects the previously introduced frameshift back into frame with its homology arms. 72 hr after the transfection, the cells were sorted with the FACSAria III sorter (BD), hence the second step begins (FIGS. 16, 17).

The second step, the selection and the enrichment of the new fluorescent variants, involves 4 consecutive processes of sorting of in-frame, yet fluorescent cells were selected via FACS. As shown in FIG. 16, 3 iterative rounds of FACS were applied to gradually select and enrich the brighter variants. Approximately 100 million cells were processed in the first round of FACS and as a result, around 250 k fluorescent cells were collected at the end of $1^{st}$ round. After round 1, mRNA was collected from harvested cells and reverse transcribed to DNA, cloned into the bacterial expression vector pRSETB and transformed into E. coli BL21. 7 different mRuby2 protein variants were purified form E. coli using $Ni^{2+}$-affinity columns and emission spectra were taken on a fluorescence spectrometer (FIG. 18). Sequences of the diversified variants are shown in FIG. 19. All of the variants have diversification of residues 43-47, as intended. Judging from the introduction or missing of a silent mutation within the sgRNA binding area, 5 of the 7 variants were diversified using HDR, while the other ones were the result of NHEJ (FIG. 19).

The cell populations after round 1 of FACS sorting (FIGS. 16, 17) were then further processed through 2 additional rounds of FACS to increase the yield of cells with higher fluorescence intensities. Between each round of FACS sessions, the collected cells were cultured in a 10 cm plate, until the plate become fully confluent. When the plate become confluent, the enriched cells were further processed through another FACS session.

We were also interested in determining whether any pharmacological treatments or other conditions would change the ratio of HDR versus other mechanisms such as NHEJ for the repair and diversification of proteins of interest (FIGS. 20, 21). In order to test the effectivities of various strategies on inducing the HDR pathway, we assessed different treatment approaches. Deep sequencing technique was utilized for the analysis of the HDR activity. The experimental outline is schematized in FIG. 20. For this experiment, a frame-shifting ssODN template was introduced into the cells expressing the intact simple coding sequence of mRuby2, inserted as a single copy in HEK293 cells as previously described. The ssODN was co-delivered with the sgRNA that binds to the close proximity of the region that the frameshift was introduced. The frameshift was effected by a 2 nucleotide deletion immediately upstream of the PAM site. The length of the ssODN was 100 bases, which was complementary to the immediate 5' and 3' ends of the intended 2-nucleotide deletion.

8 different strategies were assessed and compared with the—control, which is the transfection of cells with only the sgRNA but no HDR ssODN template. In all of the cases, same sgRNA was utilized and in all of the cases, except the—control, same ssODN HDR template was utilized. In all of the cases, except the ones that utilizes Nocodazole; the treatment agent, the sgRNA and the HDR templates were co-delivered. 24 hours after co-delivery, the cell media were replaced excluding the agents. In cases that utilizes Nocodazole, the cells were pretreated for 18 h with Nocodazole before the co-delivery of the sgRNA, ssODN and the treatment reagent. At the end of 18 h, the cells were synchronized and the transfection was performed. 72 hr after the transfections, the cells were processed through the FACS sorter. All cells displaying ground-zero signal in mRuby2 channel, and the cells with any degree of signal from zero to top in blue channel were collected as edited cells. This entire population collected represents any possible edits including the frameshift introduced with HDR template and NHEJ-caused variations. 2 million cells were sorted in total, and subsequently, the entire library was directly used for deep sequencing with MiSeq Next Generation Sequencing System (Illumina). In order to collect the entire mutant gene library, total RNA isolation was performed using the RNeasy Mini Kit (Qiagen). After collection of the total RNA, by using a gene specific primer, mRuby2 sequences were reverse transcribed into cDNA libraries and then purified with Machery Nagel Gel&PCR cleanup kit. These cDNA libraries were then amplified through 10 cycles of PCR in order to be ready for deep sequencing. Only the small region of interest of the mRuby2 sequences was PCR amplified (SEQ ID NO: 95). The amplified sequence stretch corresponds to the region between the nucleotide positions 75-324 within the parental original mRuby2 DNA sequence. The 10-cycle-PCR was performed using forward and reverse primers, both having adapter flanking sequences that enable the binding of the library amplicons to the flows of Illumina MiSeq platform. Results of the different treatments and effects on the rate of HDR are shown in FIG. 21.

Materials and Methods

FRT Vector Generation

1. PCR mRuby2

| 1 uL  | pSlice3-mRuby2       |
|-------|----------------------|
| 1 ul  | Primer F 10 × dilution |
| 1 ul  | Primer R 10 × dilution |
| 1 ul  | dNTPs                |
| 1 ul  | Herculase II         |
| 10 ul | 5 × Herculase Buffer |
| 35 ul | ddH$_2$O             |
| 50 ul | total                |

95 C/30 s denaturation, 60 C/30 s annealing, 72 C/30 s extension

2. PCR P2A-puromycin resistance gene

| 1 uL  | pSlice3-P2A-puromycin resistance gene |
|-------|----------------------------------------|
| 1 ul  | Primer F 10 × dilution                 |
| 1 ul  | Primer R 10 × dilution                 |
| 1 ul  | dNTPs                                  |
| 1 ul  | Herculase II                           |
| 10 ul | 5 × Herculase Buffer                   |
| 35 ul | ddH$_2$O                               |
| 50 ul | total                                  |

95 C/30 s denaturation, 60 C/30 s annealing, 72 C/30 s extension

3. Digest 1 ug of pcDNA5FRT-APMA-ap-IRES-H2BGFP with AflII and NotI for 3 h at 37° C.:

| 1 ug  | Plasmid       |
|-------|---------------|
| 1 ul  | AflII         |
| 1 ul  | NotI          |
| 2 ul  | 10 × Buffer   |
| X ul  | ddH$_2$O      |
| 20 ul | total         |

4. Gel purify digested DNA.
5. SLiCE ligate the DNA fragments for 30 min at 37° C.:

| 1 ul  | Cut Plasmid from step 3 |
|-------|--------------------------|
| 3 ul  | Fragment from step 1     |
| 3 ul  | Fragment from step 2     |
| 1 ul  | T4 ligation buffer       |
| 1 ul  | SLiCE reagent            |
| 1 ul  | ddH$_2$O                 |
| 10 ul | total                    |

6. Transformation
7. Check clones with sequencing

Stable Cell Line Generation

Generation of stable FRT-mRuby2-P2A-puromycinR expressing cell line
1. Grow 3×30 mm plates of Flp-In-293 Cell to 80% confluency
2. Transfect with 10:1 pOG44-pcDNA5-FRT-mRuby2-P2A-puromycinR plasmids with Lipofectamine 3000
3. Grow at 30 C overnight without antibiotics
4. Select with hygromicin at 30, 60 and 120 µg/ml until colonies form.

Generation of stable Cas9-expressing FRT-mRuby2-P2A-puromycinR positive cell line
1. Grow 3×30 mm plates of FRT-mRuby2-P2A-puromycinR expressing cell line to 80% confluency
2. Transfect with 10:1 pSpCas9 plasmid vector containing Cas9 nuclease from Streptococcus pyogenes fused to Neomycin resistance gene, with Lipofectamine 3000
3. Grow at 37 C overnight without antibiotics
4. Select with G418 antibiotic at 600 µg/ml until colonies form Library Generation The library generation protocol comprises two adjacent steps. In the first step, cells are transfected first with ssODNs that lead to a specific frame-shift due to a 2-nucleotide deletion within the chromophore region. On the following second step, the cells that express the frame-shifted proteins are transfected with randomization ssODNs that lead to the generation of the library.

The protocol is as follows:
First step:
1. Cells are trypsinized and are plated in a 10 cm cell culture plate with 70-80% confluency.
2. On the following day of plating, 10 ug sgRNA+10 ug frameshifting ssODNs (mixed in 200 uL Optimem) and 7.5 uL Lipofectamine MessengerMax Reagent (in a separate tube of 200 uL Optimem) are mixed. Afterwards, these two 200 uL solutions are mixed into one and incubated RT for 15 mins. The total solution is then applied to the 10 cm plate.
3. On the following day, the medium is refreshed and incubated one more day. Two days after the transfection, the frame-shifted dark cells are sorted out via FACS and expanded into a 10 cm plate, which takes 4 days to reach to a confluency of 60-70% confluency.
4. After reaching 70% confluency, the plate is divided into two separate 10 cm plate. One of the plates is frozen as stock and the other plate incubated for overnight to introduce the randomization and library generation process.

Second step:
5. On the following day, the region of interest within the frameshifted-mRuby2-expressing cells are transfected with NNB-containing randomization ssODNs by using the same transfection parameters mentioned above by using Lipofectamine MessengerMax. 24 h after transfection, the media are refreshed. The cells then transferred into a 15 cm plate, and 24 h after replating, 2 ug/uL puromycin was applied on to the cells for 3 consecutive days via refreshing the medium every day with fresh puromycin. During the first two days of application, significant cell death is observed, and on the 3rd day, no significant cell death was observed, and the puromycin treatment is ended. The puromycin treatment leads to the positive selection of the in-frame mutants together with the ones that do not possess an early stop codon, which lead to the enrichment of the cells that incorporate the desired library.

cDNA Library Generation and Next Generation Sequencing Preparation
1. total RNA isolation is done according to the datasheet of the RNeasy Mini Kit (Qiagen)
2. cDNA conversion is done according to the RevertAid H Minus First Strand cDNA Synthesis Kit (Thermo Fisher) with using the mRuby2 specific reverse primer with the SEQ ID NO: 4 at 42 C 50 minutes.

3. 10 cycle Next Generation Sequencing PCR is performed with the primer pairs with the SEQ ID NO: 5 and SEQ ID NO: 6 in 24 separate PCR tubes by using the entire cDNA library. The reaction conditions in a single PCR reaction tube is as follows:

| | |
|---|---|
| 2 uL | cDNA |
| 1 ul | Primer F 10 × dilution |
| 1 ul | Primer R 10 × dilution |
| 1 ul | dNTPs |
| 1 ul | Herculase II |
| 10 ul | 5 × Herculase Buffer |
| 34 ul | ddH2O |
| 50 ul | total |

95 C/10 s denaturation, 60 C/10 s annealing, 72 C/10 s extension

4. PCR purification
5. MiSeq (Illumina) deep sequencing

Example 4: Modifying an Antibody Using the Method for Diversification and Targeted Mutagenesis As described above, in the herein provided means and methods the protein of interest may be an antibody. For example, the present invention provides a number of advantages in engineering and selecting of Fab fragments, single chain antibodies or whole IgGs with new specificities or higher affinities than naturally occurring variants.

For this purpose genes coding for Fab fragments, single chain antibodies or for light and heavy chain IgGs will be inserted into cells at single copy number. A frame-shift or another inactivating mutation will be inserted near the target site for mutagenesis. In this example, the target site for mutagenesis will preferably be located within the regions encoding the CDRs (complementarity determining regions), i.e. regions of the antigen binding domains. However, the target site for mutagenesis may also be located within other sites that affect antibody function.

If necessary (e.g. if humanized antibody genes are to be diversified in human cell lines), codons will be differentiated from endogenous antibody gene sequences to ensure that only the heterologous gene is diversified.

Libraries will initially be screened for efficient restoration of the reading-frame and/or for the generation of a fused marker gene (e.g. a fluorescent protein or a resistance marker). For efficient presentation and follow-up screening of the antibody library, surface display techniques will be used to localize the new antibody variant on the cell surface. Targeting sequences to send antibody variants to the cell surface will simply be added to the gene cassette encoding the protein of interest before insertion into the cell genome in single copy number. Such techniques have become very powerful and allow efficient functional presentation of, e.g. Fab fragments, single chain antibodies or whole IgGs on the surface of cells, such as mammalian cells, e.g. HEK293 cells. Protocols for efficient display and screening have become standard of the art and are provided, e.g. by Ho, 2008, Methods in Molecular Biology, 525: pp 337-352; and Zhou, 2012, Methods in Molecular Biology, 907: 293-302.

Screening of such surface displayed antibody libraries may occur by FACS sorting. For this purpose, a fluorophore-conjugated antigen may be used to label cells displaying antibodies that exhibit an affinity to this specific antigen. FACS sorting allows for the harvesting these cells. In sequential rounds of screening the stringency can be increased, as cells can be washed with increasing amounts of unlabeled antigen, followed by additional FACs sorts. This will allow the identification of variants with a particularly high affinity for a given antigen.

Alternatively, desired antibodies can be identified via a panning approach. For this purpose specific surfaces may be conjugated with the desired antigen. Cells expressing the antibody library and expressing it on the cell surface may be incubated on this surface. Cells expressing effective antibodies will bind to the surface. After washing away non-binding cells, the stringency can be increased by additional washes with increasing amounts of added soluble antigen. After several rounds of washes, the remaining cells bound to the surface can be harvested by a suitable method, e.g trypsination, and allowed to recovery.

Genes coding for selected antibody variants can be isolated by preparing PolyA-RNA from these cells, performing RT-PCR to transcribe the genes into cDNAs and subcloning them into suitable vectors for further analysis.

The present invention refers to the following nucleotide and amino acid sequences:

```
SEQ ID NO: 1:
The amino acid sequence for the 2A peptide T2A:
E G R G S L L T C G D V E E N P G P SEQ ID NO: 2:
The amino acid sequence for the 2A peptide P2A:
A T N F S L L K Q A G D V E E N P G P SEQ ID NO: 3:
The amino acid sequence for the 2A peptide E2A:
Q C T N Y A L L K L A G D V E S N P G P SEQ ID NO: 4:
The amino acid sequence for the 2A peptide F2A:
V K Q T L N F D L L K L A G D V E S N P G P SEQ ID NO: 5:
Target site of TEV Protease: indeed, X can be any amino acid
Glu, X, X, Tyr, X, Gln, Gly/Ser SEQ ID NO: 6:
Target site of Genenase I:
Pro-Gly-Ala-Ala-His-Tyr
```

-continued

SEQ ID NO: 7:
Target site of Enterokinase:
Asp-Asp-Asp-Asp-Lys

SEQ ID NO: 8:
Target site of Human Rhinovirus (HRV) 3C Protease:
Leu-Glu-Val-Leu-Phe-Gln-Gly-Pro SEQ ID NO: 9:
Target site of Factor Xa:
Ile-(Glu or Asp)-Gly-Arg SEQ ID NO: 10:
Target site of Thrombin:
Leu-Val-Pro-Arg-Gly-Ser SEQ ID NO: 11:
Preferred direct repeat (DR) sequence for use with the SpCas9 or SaCas9
nuclease:
GTTTTAGAGCTA SEQ ID NO: 12:
Preferred tracrRNA sequence for use with the SpCas9 or SaCas9 nuclease:
TAGCAAGTTAAAATAAGGCTAGTCCGTTTTT SEQ ID NO: 13:
Forward primer for site-directed mutagenesis:
5'-TCGCTGACCGCTGCGGACGCAGGTCGAAGAAGACTTACC-3'-forward SEQ ID NO: 14:
Reverse primer for site-directed mutagenesis:
5'-GTCCGCAGCGGTCAGCGAGTTGGTC-3'-reverse SEQ ID NO: 15:
Forward amplification primer:
5'-TCGCTGACCGCTGCGGACGCAGGTCGAAGAAGACTTACC-3'

SEQ ID NO: 16:
Reverse amplification primer:
5'-CGGCCGCCACTGTGCTGGATCTATTATCACTTGTACAGCTCGTCCATGC-3'

SEQ ID NO: 17:
Pre-annealed forward primer:
5'-CACCGCGCTGACCGCTGCGGACGC-3'

SEQ ID NO: 18:
Pre-annealed reverse primer:
5'-AAACGCGTCCGCAGCGGTCAGCGC-3'

SEQ ID NO: 19:
Amino acid sequence of the FokI nuclease:
GSQLVKSELE EKKSELRHKL KYVPHEYIEL IEIARNSTQD

RILEMKVMEF FMKVYGYRGK HLGGSRKPDG AIYTVGSPID YGVIVDTKAY

SGGYNLPIGQ ADEMQRYVEE NQTRNKHINP NEWWKVYPSS VTEFKFLFVS

GHFKGNYKAQ LTRLNHITNC NGAVLSVEEL LIGGEMIKAG TLTLEEVRRK

FNNGEINF

SEQ ID NO: 20:
Amino acid sequence of the megaTAL endonuclease:
VDLRTLGYSQQQQEKIKPKVRSTVAQHHEALVGHGFTHAHIVALSQHPAALGTVAVTY

QHIITALPEATHEDIVGVGKQWSGARALEALLTDAGELRGPPLQLDTGQLVKIAKRGG

VTAMEAVHASRNALTGAPLNLTPDQVVAIASNGGGKQALETVQRLLPVLCQDHGLTPD

QVVAIASHDGGKQALETVQRLLPVLCQDHGLTPDQVVAIASNIGGKQALETVQRLLPV

LCQDHGLTPDQVVAIASNGGGKQALETVQRLLPVLCQDHGLTPDQVVAIASNGGGKQA

LETVQRLLPVLCQDHGLTPDQVVAIASNIGGKQALETVQRLLPVLCQDHGLTPDQVVA

IASHDGGKQALETVQRLLPVLCQDHGLTPDQVVAIASNIGGKQALETVQRLLPVLCQD

HGLTPDQVVAIASHDGGKQALETVQRLLPVLCQDHGLTPDQVVAIASHDGGKQALETV

QRLLPVLCQDHGLTPDQVVAIASNGGGKQALETVQRLLPVLCQDHGLTPDQVVAIASN

-continued

```
NGGKQALETVQRLLPVLCQDHGLTPDQVVAIASHDGGKQALETVQRLLPVLCQDHGLT

PDQVVAIASNIGGKQALETVQRLLPVLCQDHGLTPDQVVAIASNNGGKQALETVQRLL

PVLCQDHGLTPDQVVAIASHDGGKQALETVQRLLPVLCQDHGLTPDQVVAIASNGGGK

QALESIVAQLSRPDPALAALTNDHLVALACLGGRPAMDAVKKGLPHAPELIRRVNRRI

GERTSHRVAISRVGGSDLTYAYLVGLYEGDGYFSITKKGKYLTYELGIELSIKDVQLI

YKIKKILGIGIVSFRKRNEIEMVALRIRDKNHLKSKILPIFEKYPMFSNKQYDYLRFR

NALLSGIIYLEDLPDYTRSDEPLNSIESIINTSYFSAWLVGFIEAEGCFSVYKLNKDD

DYLIASFDIAQRDGDILISAIRKYLSFTTKVYLDKTNCSKLKVTSVRSVENIIKFLQN

APVKLLGNKKLQYKLWLKQLRKISRYSEKIKIPSNY
```

SEQ ID NO: 21:
Amino acid sequence of AsCpf1:

```
   1  mtqfegftnl yqvsktlrfe lipqgktlkh iqeqgfieed karndhykel kpiidriykt
  61  yadqclqlvq ldwenlsaai dsyrkektee trnalieeqa tyrnaihdyf igrtdnltda
 121  inkrhaeiyk glfkaelfng kvlkqlgtvt ttehenallr sfdkfttyfs gfyenrknvf
 181  saedistaip hrivqdnfpk fkenchiftr litavpslre hfenvkkaig ifvstsieev
 241  fsfpfynqll tqtqidlynq llggisreag tekikglnev lnlaiqknde tahiiaslph
 301  rfiplfkqil sdrntlsfil eefksdeevi qsfckyktll rnenvletae alfnelnsid
 361  lthifishkk letissalcd hwdtlrnaly erriseltgk itksakekvq rslkhedinl
 421  qeiisaagke lseafkqkts eilshahaal dqplpttlkk qeekeilksq ldsllglyhl
 481  ldwfavdesn evdpefsarl tgiklemeps lsfynkarny atkkpysvek fklnfqmptl
 541  asgwdvnkek nngailfvkn glyylgimpk qkgrykalsf eptektsegf dkmyydyfpd
 601  aakmipkcst qlkavtahfq thttpillsn nfiepleitk eiydlnnpek epkkfqtaya
 661  kktgdqkgyr ealckwidft rdflskytkt tsidlsslrp ssqykdlgey yaelnpllyh
 721  isfqriaeke imdavetgkl ylfqiynkdf akghhgkpnl htlywtglfs penlaktsik
 781  lngqaelfyr pksrmkrmah rlgekmlnkk lkdqktpipd tlyqelydyv nhrlshdlsd
 841  earallpnvi tkevsheiik drrftsdkff fhvpitlnyq aanspskfnq rvnaylkehp
 901  etpiigidrg ernliyitvi dstgkileqr slntiqqfdy qkkldnreke rvaarqawsv
 961  vgtikdlkqg ylsqviheiv dlmihyqavv vlenlnfgfk skrtgiaeka vyqqfekmli
1021  dklnclvlkd ypaekvggvl npyqltdqft sfakmgtqsg flfyvpapyt skidpltgfv
1081  dpfvwktikn hesrkhfleg fdflhydvkt gdfilhfkmn rnlsfqrglp gfmpawdivf
1141  eknetqfdak gtpfiagkri vpvienhrft gryrdlypan elialleekg ivfrdgsnil
1201  pkllenddsh aidtmvalir svlqmrnsna atgedyinsp vrdlngvcfd srfqnpewpm
1261  dadangayhi alkgqlllnh lkeskdlklq ngisnqdwla yiqelrn
```

SEQ ID NO: 22:
Amino acid sequence of LbCpf1:

```
   1  MSKLEKFTNC YSLSKTLRFK AIPVGKTQEN IDNKRLLVED EKRAEDYKGV
  51  KKLLDRYYLS FINDVLHSIK LKNLNNYISL FRKKTRTEKE NKELENLEIN
 101  LRKEIAKAFK GNEGYKSLFK KDIIETILPE FLDDKDEIAL VNSFNGFTTA
 151  FTGFFDNREN MFSEEAKSTS IAFRCINENL TRYISNMDIF EKVDAIFDKH
 201  EVQEIKEKIL NSDYDVEDFF EGEFFNFVLT QEGIEVYNAI IGGFVTESGE
 251  KIKGLNEYIN LYNQKTKQKL PKFKPLYKQV LSDRESLSFY GEGYTSDEEV
 301  LEVFRNTLNK NSEIFSSIKK LEKLFKNFDE YSSAGIFVKN GPAISTISKD
```

-continued

```
 351   IFGEWNVIRD KWNAEYDDIH LKKKAVVTEK YEDDRRKSFK KIGSFSLEQL

401   QEYADADLSV VEKLKEIIIQ KVDEIYKVYG SSEKLFDADF VLEKSLKKND

451   AVVAIMKDLL DSVKSFENYI KAFFGEGKET NRDESFYGDF VLAYDILLKV

501   DHIYDAIRNY VTQKPYSKDK FKLYFQNPQF MGGWDKDKET DYRATILRYG

551   SKYYLAIMDK KYAKCLQKID KDDVNGNYEK INYKLLPGPN KMLPKVFFSK

601   KWMAYYNPSE DIQKIYKNGT FKKGDMFNLN DCHKLIDFFK DSISRYPKWS

651   NAYDFNFSET EKYKDIAGFY REVEEQGYKV SFESASKKEV DKLVEEGKLY

701   MFQIYNKDFS DKSHGTPNLH TMYFKLLFDE NNHGQIRLSG GAELFMRRAS

751   LKKEELVVHP ANSPIANKNP DNPKKTTTLS YDVYKDKRFS EDQYELHIPI

801   AINKCPKNIF KINTEVRVLL KHDDNPYVIG IDRGERNLLY IVVVDGKGNI

851   VEQYSLNEII NNFNGIRIKT DYHSLLDKKE KERFEARQNW TSIENIKELK

901   AGYISQVVHK ICELVEKYDA VIALEDLNSG FKNSRVKVEK QVYQKFEKML

951   IDKLNYMVDK KSNPCATGGA LKGYQITNKF ESFKSMSTQN GFIFYIPAWL

1001   TSKIDPSTGF VNLLKTKYTS IADSKKFISS FDRIMYVPEE DLFEFALDYK

1051   NFSRTDADYI KKWKLYSYGN RIRIFRNPKK NNVFDWEEVC LTSAYKELFN

1101   KYGINYQQGD IRALLCEQSD KAFYSSFMAL MSLMLQMRNS ITGRTDVDFL

1151   ISPVKNSDGI FYDSRNYEAQ ENAILPKNAD ANGAYNIARK VLWAIGQFKK

1201   AEDEKLDKVK IAISNKEWLE YAQTSVKH
```

SEQ ID NO: 23:
Amino acid sequence of SpCas9:

```
    1   mdkkysigld igtnsvgwav itdeykvpsk kfkvlgntdr hsikknliga llfdsgetae 61   atrlkrtarr rytrrknric ylqeifsnem akvddsffhr leesflveed kkherhpifg 121   nivdevayhe kyptiyhlrk klvdstdkad lrliylalah mikfrghfli egdlnpdnsd 181   vdklfiqlvq tynqlfeenp inasgvdaka ilsarlsksr rlenliaqlp gekknglfgn 241   lialslgltp nfksnfdlae daklqlskdt ydddldnlla qigdqyadlf laaknlsdai 301   llsdilrvnt eitkaplsas mikrydehhq dltllkalvr qqlpekykei ffdqskngya 361   gyidggasqe efykfikpil ekmdgteell vklnredllr kqrtfdngsi phqihlgelh 421   ailrrqedfy pflkdnreki ekiltfripy yvgplargns rfawmtrkse etitpwnfee 481   vvdkgasaqs fiermtnfdk nlpnekvlpk hsllyeyftv yneltkvkyv tegmrkpafl 541   sgeqkkaivd llfktnrkvt vkqlkedyfk kiecfdsvei sgvedrfnas lgtyhdllki 601   ikdkdfldne enedilediv ltltlfedre mieerlktya hlfddkvmkq lkrrrytgwg 661   rlsrklingi rdkqsgktil dflksdgfan rnfmqlihdd sltfkediqk aqvsgqgdsl 721   hehianlags paikkgilqt vkvvdelvkv mgrhkpeniv iemarenqtt qkgqknsrer 781   mkrieegike lgsqilkehp ventqlqnek lyylyqngr dmyvdqeldi nrlsdydvdh 841   ivpqsflkdd sidnkvltrs dknrgksdnv pseevvkkmk nywrqllnak litqrkfdnl 901   tkaergglse ldkagfikrq lvetrqitkh vaqildsrmn tkydendkli revkvitlks 961   klvsdfrkdf qfykvreinn yhhahdayln avvgtalikk ypklesefvy gdykvydvrk 1021   miakseqeig kataykffys nimnffktei tlangeirkr plietngetg eivwdkgrdf 1081   atvrkvlsmp qvnivkktev qtggfskesi lpkrnsdkli arkkdwdpkk yggfdsptva 1141   ysvlvvakve kgkskklksv kellgitime rssfeknpid fleakgykev kkdliiklpk 1201   yslfelengr krmlasagel qkgnelalps kyvnflylas hyeklkgspe dneqkqlfve
```

```
1261  qhkhyldeii eqisefskrv iladanldkv lsaynkhrdk pireqaenii hlftltnlga 1321  paafkyfdtt idrkrytstk evldatlihq sitglyetri dlsqlggd SEQ ID NO: 24:
Amino acid sequence of St1Cas9:
   1  msdlvlgldi gigsvgvgil nkvtgeiihk nsrifpaaqa ennlvrrtnr qgrrlarrkk 61  hrrvrlnrlf eesglitdft kisinlnpyq lrvkgltdel sneelfialk nmvkhrgisy 121  lddasddgns svgdyaqivk enskqletkt pgqiqleryq tygqlrgdft vekdgkkhrl 181  invfptsayr sealrilqtq qefnpqitde finryleilt gkrkyyhgpg neksrtdygr 241  yrcsgetldn ifgiligkct fypdefraak asytaqefnl lndlnnltvp tetkklskeq 301  knqiinyvkn ekamgpaklf kyiakllscd vadikgyrid ksgkaeihtf eayrkmktle 361  tldieqmdre tldklayvlt lnteregiqe alehefadgs fsqkqvdelv qfrkanssif 421  gkgwhnfsvk lmmelipely etseeqmtil trlgkqktts ssnktkyide kllteeiynp 481  vvaksvrqai kivnaaikey gdfdniviem aretneddek kaiqkiqkan kdekdaamlk 541  aanqyngkae lphsvfhghk qlatkirlwh qqgerclytg ktisihdlin nsnqfevdhi 601  lplsitfdds lankvlvyat anqekgqrtp yqaldsmdda wsfrelkafv resktlsnkk 661  keyllteedi skfdvrkkfi ernlvdtrya srvvlnalqe hfrahkidtk vsvvrgqfts 721  qlrrhwgiek trdtyhhhav daliiaassq lnlwkkqknt lvsysedqll dietgelisd 781  deykesvfka pyqhfvdtlk skefedsilf syqvdskfnr kisdatiyat rqakvgkdka 841  detyvlgkik diytqdgyda fmkiykkdks kflmyrhdpq tfekviepil enypnkqine 901  kgkevpcnpf lkykeehgyi rkyskkgngp eikslkyyds klgnhiditp kdsnnkvvlq 961  svspwradvy fnkttgkyei lglkyadlqf ekgtgtykis qekyndikkk egvdsdsefk 1021  ftlykndlll vkdtetkeqq lfrflsrtmp kqkhyvelkp ydkqkfegge alikvlgnva 1081  nsgqckkglg ksnisiykvr tdvlgnqhii knegdkpkld f SEQ ID NO: 25:
Amino acid sequence of SaCas9:
   1  mkrnyilgld igitsvgygi idyetrdvid agvrlfkean vennegrrsk rgarrlkrrr 61  rhriqrvkkl lfdynlltdh selsginpye arvkglsqkl seeefsaall hlakrrgvhn 121  vneveedtgn elstkeqisr nskaleekyv aelqlerlkk dgevrgsinr fktsdyvkea 181  kqllkvqkay hqldqsfidt yidlletrrt yyegpgegsp fgwkdikewy emlmghctyf 241  peelrsvkya ynadlynaln dlnnlvitrd enekleyyek fqiienvfkq kkkptlkqia 301  keilvneedi kgyrvtstgk peftnlkvyh dikditarke iienaelldq iakiltiyqs 361  sediqeeltn lnseltqeei eqisnlkgyt gthnlslkai nlildelwht ndnqiaifnr 421  lklvpkkvdl sqqkeipttl vddfilspvv krsfiqsikv inaiikkygl pndiiielar 481  eknskdaqkm inemqkrnrq tnerieeiir ttgkenakyl iekiklhdmq egkclyslea 541  ipledllnnp fnyevdhiip rsvsfdnsfn nkvlvkqeen skkgnrtpfq ylsssdskis 601  yetfkkhiln lakgkgrisk tkkeylleer dinrfsvqkd finrnlvdtr yatrglmnll 661  rsyfrvnnld vkvksinggf tsflrrkwkf kkernkgykh haedaliian adfifkewkk 721  ldkakkvmen qmfeekqaes mpeieteqey keifitphqi khikdfkdyk yshrvdkkpn 781  relindtlys trkddkgntl ivnnlnglyd kdndklkkli nkspekllmy hhdpqtyqkl 841  klimeqygde knplykyyee tgnyltkysk kdngpvikki kyygnklnah lditddypns
```

-continued 901  rnkvvklslk pyrfdvyldn gvykfvtvkn ldvikkenyy evnskcyeea kklkkisnqa 961  efiasfynnd likingelyr vigvnndlln rievnmidit yreylenmnd krppriikti 1021 asktqsikky stdilgnlye vkskkhpqii kkg SEQ ID NO: 26:
Nucleotide sequence of a frame-shift version of mNeonGreen:
Atggtgagcaagggcgaggaggataacatggcctctctcccagcgacacatgagttacacatctttggctccat caacggtgtggactttgacatggtgggtcagggcaccggcaatccaaatgatggttatgaggagttaaacctga agtccaccaagggtgacctccagttctcccccctggattctggtccctcatatcgggtatggcttccatcagtac ctgccctaccctgacgggatgtcgcctttccaggccgccatggtagatggctccggataccaagtccatcgcac aatgcagtttgaagatggtgcctcccttactgttaactaccgctacacctacgagggaagccacatcaaggag aggcccaggtgaaggggactggtttccctgctgacggtcctgtgatgaccaactcgctgaccgctgcggacgca ggtcgaagaagacttaccccaacgacaaaaccatcatcagtacctttaagtggagttacaccactggaaatggc aagcgctaccggagcactgcgcggaccacctacacctttgccaagccaatggcggctaactatctgaagaacca gccgatgtacgtgttccgtaagacggagctcaagcactccaagaccgagctcaacttcaaggagtggcaaaagg cctttaccgatgtgatgggcatggacgagctgtacaag SEQ ID NO: 27:
Nucleotide sequence of the coding region of mNeonGreen
atggtgagcaagggcgaggaggataacatggcctctctcccagcgacacatgagttacacatctttggctccat caacggtgtggactttgacatggtgggtcagggcaccggcaatccaaatgatggttatgaggagttaaacctga agtccaccaagggtgacctccagttctcccccctggattctggtccctcatatcgggtatggcttccatcagtac ctgccctaccctgacgggatgtcgcctttccaggccgccatggtagatggctccggataccaagtccatcgcac aatgcagtttgaagatggtgcctcccttactgttaactaccgctacacctacgagggaagccacatcaaggag aggcccaggtgaaggggactggtttccctgctgacggtcctgtgatgaccaactcgctgaccgctgcggactgg tgcaggtcgaagaagacttaccccaacgacaaaaccatcatcagtacctttaagtggagttacaccactggaaa tggcaagcgctaccggagcactgcgcggaccacctacacctttgccaagccaatggcggctaactatctgaaga accagccgatgtacgtgttccgtaagacggagctcaagcactccaagaccgagctcaacttcaaggagtggcaa aaggcctttaccgatgtgatgggcatggacgagctgtacaag SEQ ID NO: 28:
Amino acid sequence of mNeonGreen
MVSKGEEDNMASLPATHELHIFGSINGVDFDMVGQGTGNPNDGYEELNLKSTKGDLQFSPWILVPHIGYGFHQY

LPYPDGMSPFQAAMVDGSYQVHRTMQFEDGASLTVNYRYTYEGSHIKGEAQVKGTGFPADGPVMTNSLTAADW

CRSKKTYPNDKTIISTFKWSYTTGNGKRYRSTARTTYTFAKPMAANYLKNQPMYVFRKTELKHSKTELNFKEWQ

KAFTDVMGMDELYK

SEQ ID NO: 29:
The nucleotide sequence of the mutated coding region of mNeonGreen
Atggtgagcaagggcgaggaggataacatggcctctctcccagcgacacatgagttacacatctttggctccat caacggtgtggactttgacatggtgggtcagggcaccggcaatccaaatgatggttatgaggagttaaacctga agtccaccaagggtgacctccagttctcccccctggattctggtccctcatatcgggtatggcttccatcagtac ctgccctaccctgacgggatgtcgcctttccaggccgccatggtagatggctccggataccaagtccatcgcac aatgcagtttgaagatggtgcctcccttactgttaactaccgctacacctacgagggaagccacatcaaggag aggcccaggtgaaggggactggtttccctgctgacggtcctgtgatgaccaactcgctgaccgctgcggacgca ggtcgaagaagacttaccccaacgacaaaaccatcatcagtacctttaagtggagttacaccactggaaatggc aagcgctaccggagcactgcgcggaccacctacacctttgccaagccaatggcggctaactatctgaagaacca -continued gccgatgtacgtgttccgtaagacggagctcaagcactccaagaccgagctcaacttcaaggagtggcaaaagg cctttaccgatgtgatgggcatggacgagctgtacaag SEQ ID NO: 30:
A donor nucleic acid template of 105 base pairs termed NSFS-R
GGTTTCCCTGCTGACGGTCCTGTGATGACCAACTCGCTGACCGCTGCGGACTGGTGCAGGTCGAAGAAGACTTA

CCCCAACGACAAAACCATCATCAGTACCTTT

SEQ ID NO: 31:
Amino acid sequence of mRuby2
MVSKGEELIKENMRMKVVMEGSVNGHQFKCTGEGEGNPYMGTQTMRIKVIEGGPLPFAFDILATSFMYGSRTFI

KYPKGIPDFFKQSFPEGFTWERVTRYEDGGVVTVMQDTSLEDGCLVYHVQVRGVNFPSNGPVMQKKTKGWEPNT

EMMYPADGGLRGYTHMALKVDGGGHLSCSFVTTYRSKKTVGNIKMPGIHAVDHRLERLEESDNEMFVVQREHAV

AKFAGLGGGMDELYK

SEQ ID NO: 32:
Amino acid sequence of the Puromycin Resistance gene
MTEYKPTVRLATRDDVPRAVRTLAAAFADYPATRHTVDPDRHIERVTELQELFLTRVGLDIGKVWVADDGAAVA

VWTTPESVEAGAVFAEIGPRMAELSGSRLAAQQQMEGLLAPHRPKEPAWFLATVGVSPDHQGKGLGSAVVLPGV

EAAERAGVPAFLETSAPRNLPFYERLGFTVTADVEVPEGPRTWCMTRKPGA

SEQ ID NO: 33:
Oligonucleotide for Codon Diversification of the mRuby2 Chromophore Region
(binds reverse strand)
5' TGT TTA AAG AAA TCA GGA ATG CCT TTC GGG TAC TTG ATA AAA GTA CGG CT

VNNVNNVNN GAACGAC GTG GCA AGA ATG TCA AAG GCA AAT GGC AGG GGT CCT CCC

TCG A 3'

SEQ ID NO: 34:
Oligo used for inducing a frame-shift (2 nucleotide deletion) near the
chromophore region of mRuby2
5' AGTCATCGAGGGAGGACCCCTGCCATTTGCCTTTGACATTCTTGCCACGTCGTTCGTATGGCAGCCGTACT

TTTATCAAGTACCCGAAAGGCATTCCTGATTTCTTTAAACAGTCCT 3'

SEQ ID NO: 35:
Gene specific primer for RT PCR
5' CTTGTACAGCTCGTCCATCCC 3'

SEQ ID NO: 36:
Deep sequencing primer 1
5' TACACGACGCTCTTCCGATCTATGCACAGGTGAAGGAGAAGG 3'

SEQ ID NO: 37:
Deep sequencing primer 2
5' CAGACGTGTGCTCTTCCGATCCTCCACCATCTTCGTATCTCG 3'

SEQ ID NO: 38:
Forward primer to extract the coding domains of the repaired mNeonGreen
5'-ATAAGGATCCGGCCACCATGGTGAGCAAGGGCGAGGAGGAT-3' forward SEQ ID NO: 39:
Reverse primer to extract the coding domains of the repaired mNeonGreen
5'-TATAGGAATTCCTATTATCACTTGTACAGCTCGTCCATGCCC-3' reverse SEQ ID NO: 40:
Frame-Shifting Primer for PCR Mutagenesis, 1.F
CTTTAAGTGGACACCACTGGAAATGGCAAGC SEQ ID NO: 41:
Frame-Shifting Primer for PCR Mutagenesis, 1.R
CCAGTGGTGTCCACTTAAAGGTACTGATGATGGTTTTG SEQ ID NO: 42:
Frame-Shifting Primer for PCR Mutagenesis, 2.F
CTGGTGCAGGAGAAGACTTACCCCAACGACAAAAC SEQ ID NO: 43:
Frame-Shifting Primer for PCR Mutagenesis, 2.R
TAAGTCTTCTCCTGCACCAGTCCGCAGC SEQ ID NO: 44:
Frame-Shifting Primer for PCR Mutagenesis, 3.F
CAGGTGAAGGTGGTTTCCCTGCTGACGGTC SEQ ID NO: 45:
Frame-Shifting Primer for PCR Mutagenesis, 3.R
AGGGAAACCACCTTCACCTGGGCCTCTCC SEQ ID NO: 46:
Frame-Shifting Primer for PCR Mutagenesis, 4.F
TCGGGTATGGCATCAGTACCTGCCCTACCCTGAC SEQ ID NO: 47:
Frame-Shifting Primer for PCR Mutagenesis, 4.R
GGTACTGATGCCATACCCGATATGAGGGACCAG SEQ ID NO: 48:
Frame-Shifting Primer for PCR Mutagenesis, 5.F
GTCCGCAGCGGTCAGCGAGTTGGTC SEQ ID NO: 49:
Frame-Shifting Primer for PCR Mutagenesis, 5.R
GCAACCGTAAAGTTCAAGTACAAAGG SEQ ID NO: 50:
PAM sequence for SaCas9
5'-NNGRRT SEQ ID NO: 51:
PAM sequence for SaCas9
5'-NNGRR(N)

SEQ ID NO: 52:
PAM sequence for St1Cas9
5'-NNAGAAW

SEQ ID NOs 53 to 90 are shown in the appended Figures.
SEQ ID NO: 91:
Nucleotide sequence of mNeonGreen2 (diversified sequence is in italic script, underlined and boldface)
ATGGTGAGCAAGGGCGAGGAGGATAACATGGCCTCTCTCCCAGCGACACATGAGTTACACATCTTTGGCTCCAT

CAACGGTGTGGACTTTGACATGGTGGGTCAGGGCACCGGCAATCCAAATGATGGTTATGAGGAGTTAAACCTGA

AGTCCACCAAGGGTGACCTCCAGTTCTCCCCCTGGATTCTGGTCCCTCATATCGGGTATGGCTTCCATCAGTAC

CTGCCCTACCCTGACGGGATGTCGCCTTTCCAGGCCGCCATGGTAGATGGCTCCGGATACCAAGTCCATCGCAC

AATGCAGTTTGAAGATGGTGCCTCCCTTACTGTTAACTACCGCTACACCTACGAGGGAAGCCACATCAAAGGAG

AGGCCCAGGTGAAGGGGACTGGTTTCCCTGCTGACGGTCCTGTGATGACCAACTCGCTGACCGCTGCG

*GATGCGTGCTGG*TCGAAGAAGACTTACCCCAACGACAAAACCATCATCAGTACCTTTAAGTGGAGTTACACCA

CTGGAAATGGCAAGCGCTACCGGAGCACTGCGCGGACCACCTACACCTTTGCCAAGCCAATGGCGGCTAACTAT

CTGAAGAACCAGCCGATGTACGTGTTCCGTAAGACGGAGCTCAAGCACTCCAAGACCGAGCTCAACTTCAAGGA

GTGGCAAAAGGCCTTTACCGATGTGATGGGCATGGACGAGCTGTACAAG

SEQ ID NO: 92:
Amino acid sequence of mNeonGreen2 (diversified sequence is in italic script, underlined and boldface)
M V S K G E E D N M A S L P A T H E L H I F G S I N G V D F D M V G Q G T

G N P N D G Y E E L N L K S T K G D L Q F S P W I L V P H I G Y G F H Q Y

L P Y P D G M S P F Q A A M V D G S G Y Q V H R T M Q F E D G A S L T V N

Y R Y T Y E G S H I K G E A Q V K G T G F P A D G P V M T N S L T A A

*D A C W* S K K T Y P N D K T I I S T F K W S Y T T G N G K R Y R S T A R T

T Y T F A K P M A A N Y L K N Q P M Y V F R K T E L K H S K T E L N F K E

W Q K A F T D V M G M D E L Y K

SEQ ID NO: 93:
Amino acid sequence within mNeonGreen2
Asp Ala Cys Trp

SEQ ID NO: 94:
Amino acid sequence of mRuby2-TagBFP2-Puromycin
MVSKGEELIKENMRMKVVMEGSVNGHQFKCTGEGEGNPYMGTQTMRIKVIEGGPLPFAFDILATSFMYGSRTFI

KYPKGIPDFFKQSFPEGFTWERVTRYEDGGVVTVMQDTSLEDGCLVYHVQVRGVNFPSNGPVMQKKTKGWEPNT

EMMYPADGGLRGYTHMALKVDGGGHLSCSFVTTYRSKKTVGNIKMPGIHAVDHRLERLEESDNEMFVVQREHAV

AKFAGLGGGMDELYKAEAAAKEAAAKEAAAKAVSKGEELIKENMHMKLYMEGTVDNHHFKCTSEGEGKPYEGTQ

TMRIKVVEGGPLPFAFDILATSFLYGSKTFINHTQGIPDFFKQSFPEGFTWERVTTYEDGGVLTATQDTSLQDG

CLIYNVKIRGVNFTSNGPVMQKKTLGWEAFTETLYPADGGLEGRNDMALKLVGGSHLIANAKTTYRSKKPAKNL

KMPGVYYVDYRLERIKEANNETYVEQHEVAVARYCDLPSKLGHKLNGSGATNFSLLKQAGDVEENPGPMTEYKP

TVRLATRDDVPRAVRTLAAAFADYPATRHTVDPDRHIERVTELQELFLTRVGLDIGKVWVADDGAAVAVWTTPE

SVEAGAVFAEIGPRMAELSGSRLAAQQQMEGLLAPHRPKEPAWFLATVGVSPDHQGKGLGSAVVLPGVEAAERA

GVPAFLETSAPRNLPFYERLGFTVTADVEVPEGPRTWCMTRKPGA*

SEQ ID NO: 95:
Nucleotide sequence of the sequenced region within the parental original
mRuby2 sequence
CCACCAATTCAAATGCACAGGTGAAGGAGAAGGCAATCCGTACATGGGAACTCAAACCATGAGGATCAAAGTCA

TCGAGGGAGGACCCCTGCCATTTGCCTTTGACATTCTTGCCACGTCGTTCATGTATGGCAGCCGTACTTTTATC

AAGTACCCGAAAGGCATTCCTGATTTCTTTAAACAGTCCTTTCCTGAGGGTTTTACTTGGGAAAGAGTTACGAG

ATACGAAGATGGTGGAGTCGTCACCGTC

---

The invention claimed is:

1. A method for producing a panel of cells expressing mutant variants of a protein of interest, wherein one of said mutant variants of said protein of interest is expressed per cell from a single gene copy, said method comprising:
   a) inducing a double-strand break (DSB) or a single-strand nick in the genome of cells at or in close proximity to a target site for mutagenesis in the gene encoding for said protein of interest, wherein said gene encoding for said protein of interest is comprised in the genome of the cells in a single copy, and wherein said single copy of the gene encoding for said protein of interest comprises an inactivating mutation at or in close proximity to said target site for mutagenesis;
   b) providing to the cells of step a) a library of different donor nucleic acid templates for the repair of the induced DSB or single-strand nick via homologous recombination, wherein the different donor nucleic acid templates of said library comprise different mutations at the position corresponding to said target site for mutagenesis and remove said inactivating mutation by homology-directed repair (HDR);
   c) selecting and/or enriching cells in which the inactivating mutation has been removed; and
   d) providing a panel of cells selected in step c), which is a panel of cells expressing different mutant variants of said protein of interest, wherein one of said different mutant variants of said protein of interest is expressed per cell from a single gene copy.

2. The method of claim 1, wherein said inactivating mutation prevents expression of said protein of interest.

3. The method of claim 1, wherein said gene encoding for said protein of interest is comprised in the genome of said cells as a fusion gene, wherein said fusion gene comprises a marker gene downstream of said gene encoding the protein of interest; and wherein said inactivating mutation in said gene encoding for the protein of interest prevents expression of said marker gene.

4. The method of claim 1, wherein the protein encoded by said marker gene is a fluorescent protein.

5. The method of claim 1, wherein said double-strand break is performed by using a site-specific nuclease selected from the group consisting of a Cas9 nuclease, a Cpf1 nuclease, a zinc finger nuclease (ZNF), a transcription activator-like nuclease (TALEN) and a megaTAL endonuclease; or wherein said single-strand nick is performed by using a site-specific nickase, and wherein said site-specific nickase is a Cas9 nickase.

6. The method of claim 1, wherein said cells are mammalian cells.

7. The method of claim 1, wherein said method further comprises determining the nucleic acid sequence of one or more of the genes encoding for said different mutant variants of the protein of interest comprised in the cells selected and/or enriched in step c) and/or provided in d); or determining the amino acid sequence of one or more of said different mutant variants of the protein of interest comprised in the cells selected and/or enriched in step c) and/or provided in d).

8. The method of claim 1, wherein said protein of interest is a fluorescent protein, an antibody, an enzyme, a growth factor, a cytokine, a peptide hormone, a transcription factor, a RNA binding protein, a cytoskeletal protein, an ion channel, a G-protein coupled receptor, a kinase, a phosphatase, a chaperone, a transporter, or a transmembrane protein.

9. The method of claim 1, wherein:
 (i) said protein of interest is an antibody, and wherein said target site for mutagenesis is in a CDR coding region of the nucleic acid sequence encoding the heavy or the light chain of said antibody; or
 (ii) said protein of interest is an enzyme, and wherein said target site for mutagenesis is in the nucleic acid region encoding the active center of the enzyme or a regulatory subunit of said enzyme.

10. The method of claim 1, wherein said mutant variants of the protein of interest are improved in a first activity and/or have a new activity compared to the wild-type protein of interest, wherein said method further comprises:
 e) selecting and/or enriching from the panel of cells a second panel of cells that express mutant variants of said protein of interest that are improved in said first activity and/or have said new activity.

11. The method of claim 1, wherein said mutant variants of said protein of interest are improved in a first activity and/or have a new activity compared to the wild-type protein of interest, and wherein step c) comprises selecting and/or enriching mutant variants of the protein of interest that are improved in a first activity and/or have a new activity compared to the wild-type protein of interest.

12. A method for identifying a mutant variant of a protein of interest having a different or modified activity compared to the wild-type protein of interest, wherein said method comprises:
 a) selecting and/or enriching from the panel of cells resulting from claim 1 a second panel of cells that express mutant variants of said protein of interest that are improved in said first activity and/or have said new activity; and
 b) determining the amino acid sequence of the mutant variants of the protein of interest expressed by said second panel and/or determining the nucleic acid sequence of the genes encoding for the mutant variants of the protein of interest expressed by said second panel.

13. A method for identifying a mutant variant of a protein of interest having a different or modified activity compared to the wild-type protein of interest, wherein said method comprises:
 a) the method for producing a panel of cells expressing mutant variants of a protein of interest of claim 1, wherein step c) comprises selecting and/or enriching mutant variants of the protein of interest that are improved in a first activity and/or have a new activity compared to the wild-type protein of interest; and
 b) determining the amino acid sequence of at least one of the mutant variants of the protein of interest that are improved in a first activity and/or have a new activity compared to the wild-type protein of interest; and/or determining the nucleic acid sequence of at least one of the genes encoding for the mutant variants of the protein of interest that are improved in a first activity and/or have a new activity compared to the wild-type protein of interest.

14. The method of claim 10, wherein:
 (i) said protein of interest is an antibody, and said first activity and/or said new activity is antigen binding; or
 (ii) said protein of interest is an enzyme, and said first activity and/or said new activity is an enzymatic activity of said enzyme.

* * * * *